United States Patent
Haider et al.

(10) Patent No.: US 11,464,574 B2
(45) Date of Patent: Oct. 11, 2022

(54) ON-BOARD TOOL TRACKING SYSTEM AND METHODS OF COMPUTER ASSISTED SURGERY

(71) Applicant: Board of Regents of the University of Nebraska, Lincoln, NE (US)

(72) Inventors: Hani Haider, Carter Lake, IA (US); Ibrahim Al-Shawi, Amman (JO); Osvaldo Andres Barrera, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 876 days.

(21) Appl. No.: 16/140,289

(22) Filed: Sep. 24, 2018

(65) Prior Publication Data

US 2019/0090959 A1 Mar. 28, 2019

Related U.S. Application Data

(63) Continuation of application No. 15/354,778, filed on Nov. 17, 2016, now Pat. No. 10,080,617, which is a
(Continued)

(51) Int. Cl.
*A61B 34/20* (2016.01)
*A61B 17/14* (2006.01)
(Continued)

(52) U.S. Cl.
CPC ............ *A61B 34/20* (2016.02); *A61B 1/3132* (2013.01); *A61B 5/061* (2013.01); *A61B 5/1076* (2013.01);
(Continued)

(58) Field of Classification Search
CPC ....... A61B 34/20; A61B 34/37; A61B 1/3132; A61B 5/061; A61B 5/1076; A61B 17/142; A61B 34/76; A61B 17/1703; A61B 2034/2065; A61B 2090/061; A61B 5/00; A61B 2090/064; A61B 2090/3983; A61B 2034/102; A61B 2034/2057; G06K 2209/057; G06T 2207/30004
See application file for complete search history.

(56) References Cited

U.S. PATENT DOCUMENTS 5,928,137 A * 7/1999 Green .................. A61B 1/3132
600/160
6,348,034 B1 * 2/2002 Thompson ............. A61B 1/018
600/101

(Continued)

*Primary Examiner* — Bo Joseph Peng
(74) *Attorney, Agent, or Firm* — Nasr Patent Law LLC; Faisal K. Abou-Nasr

(57) ABSTRACT

A number of improvements are provided relating to computer aided surgery utilizing an on tool tracking system. The various improvements relate generally to both the methods used during computer aided surgery and the devices used during such procedures. Other improvements relate to the structure of the tools used during a procedure and how the tools can be controlled using the OTT device. Still other improvements relate to methods of providing feedback during a procedure to improve either the efficiency or quality, or both, for a procedure including the rate of and type of data processed depending upon a CAS mode.

14 Claims, 71 Drawing Sheets

LID REMOVED

Related U.S. Application Data continuation of application No. 13/842,526, filed on Mar. 15, 2013, now Pat. No. 9,498,231, which is a continuation-in-part of application No. PCT/US2012/044486, filed on Jun. 27, 2012.

(60) Provisional application No. 61/501,489, filed on Jun. 27, 2011.

(51) Int. Cl.
| | | |
|---|---|---|
| *A61B 34/00* | (2016.01) | |
| *A61B 17/17* | (2006.01) | |
| *A61B 34/37* | (2016.01) | |
| *A61B 1/313* | (2006.01) | |
| *A61B 5/06* | (2006.01) | |
| *A61B 5/107* | (2006.01) | |
| *A61B 90/00* | (2016.01) | |
| *A61B 34/10* | (2016.01) | |
| *A61B 5/00* | (2006.01) | |

(52) U.S. Cl.
CPC ........ *A61B 17/142* (2016.11); *A61B 17/1703* (2013.01); *A61B 34/37* (2016.02); *A61B 34/76* (2016.02); *A61B 5/00* (2013.01); *A61B 2034/102* (2016.02); *A61B 2034/2057* (2016.02); *A61B 2034/2065* (2016.02); *A61B 2090/061* (2016.02); *A61B 2090/064* (2016.02); *A61B 2090/3983* (2016.02); *G06T 2207/30004* (2013.01); *G06V 2201/034* (2022.01)

(56) References Cited

U.S. PATENT DOCUMENTS

| | | | | |
|---|---|---|---|---|
| 6,387,043 | B1* | 5/2002 | Yoon | A61B 1/00052 600/104 |
| 8,523,764 | B2* | 9/2013 | Hatcher | A61B 1/0052 600/136 |
| 2005/0020909 | A1* | 1/2005 | Moctezuma de la Barrera | A61B 17/62 600/424 |
| 2006/0281972 | A1* | 12/2006 | Pease | A61B 1/0684 600/109 |
| 2007/0083209 | A1* | 4/2007 | Schenberger | A61B 17/142 606/82 |
| 2007/0236514 | A1* | 10/2007 | Agusanto | G16H 50/50 345/646 |
| 2007/0238981 | A1* | 10/2007 | Zhu | A61B 90/36 600/424 |
| 2008/0009697 | A1* | 1/2008 | Haider | A61B 90/11 600/407 |
| 2008/0013809 | A1* | 1/2008 | Zhu | A61B 34/20 382/128 |
| 2009/0068620 | A1* | 3/2009 | Knobel | A61B 34/20 433/223 |
| 2011/0178765 | A1* | 7/2011 | Atwell | G01B 5/012 702/152 |
| 2011/0257653 | A1* | 10/2011 | Hughes | A61B 34/10 606/79 |
| 2012/0253200 | A1* | 10/2012 | Stolka | A61B 6/547 600/459 |
| 2013/0053648 | A1* | 2/2013 | Abovitz | A61B 90/92 600/249 |

\* cited by examiner

SURGICAL TOOL

OTT ON SURGICAL TOOL

LID REMOVED

| d | | 105 | mm | | |
|---|---|---|---|---|---|
| a | | 94 | deg | | |
| t | | MOD/d | MOL/d | MOD | MOL |
| 1 | | 13.32 | 28.6 | 1398 | 3001 |
| 2 | | 6.65 | 14.3 | 698 | 1502 |
| 3 | | 4.42 | 9.5 | 464 | 1002 |
| 4 | | 3.31 | 7.2 | 347 | 753 |
| 5 | | 2.63 | 5.7 | 277 | 603 |
| 6 | | 2.18 | 4.8 | 229 | 504 |
| 7 | | 1.86 | 4.1 | 195 | 433 |
| 8 | | 1.62 | 3.6 | 170 | 380 |
| 9 | | 1.43 | 3.2 | 150 | 339 |
| 10 | | 1.27 | 2.9 | 134 | 306 |
| 11 | | 1.14 | 2.7 | 120 | 280 |
| 12 | | 1.04 | 2.5 | 109 | 258 |
| 13 | | 0.95 | 2.3 | 99 | 239 |
| 14 | | 0.87 | 2.1 | 91 | 223 |
| 15 | | 0.80 | 2.0 | 84 | 209 |
| 16 | | 0.73 | 1.9 | 77 | 198 |
| 17 | | 0.68 | 1.8 | 71 | 187 |
| 18 | | 0.63 | 1.7 | 66 | 178 |
| 19 | | 0.58 | 1.6 | 61 | 170 |
| 20 | | 0.54 | 1.6 | 57 | 163 |
| 21 | | 0.50 | 1.5 | 53 | 157 |
| 22 | | 0.47 | 1.4 | 49 | 151 |
| 23 | | 0.43 | 1.4 | 46 | 146 |
| 24 | | 0.40 | 1.3 | 42 | 141 |

MOD - Minimum Object Distance

MOL - Maximum Object Length (at MOD)

MOD/d = 1/ (tan(a/2+t) - tan(a/2-t))

MOL/d = 1+ 2 (MOD/d)* tan (a/2-t)

FIG. 11B

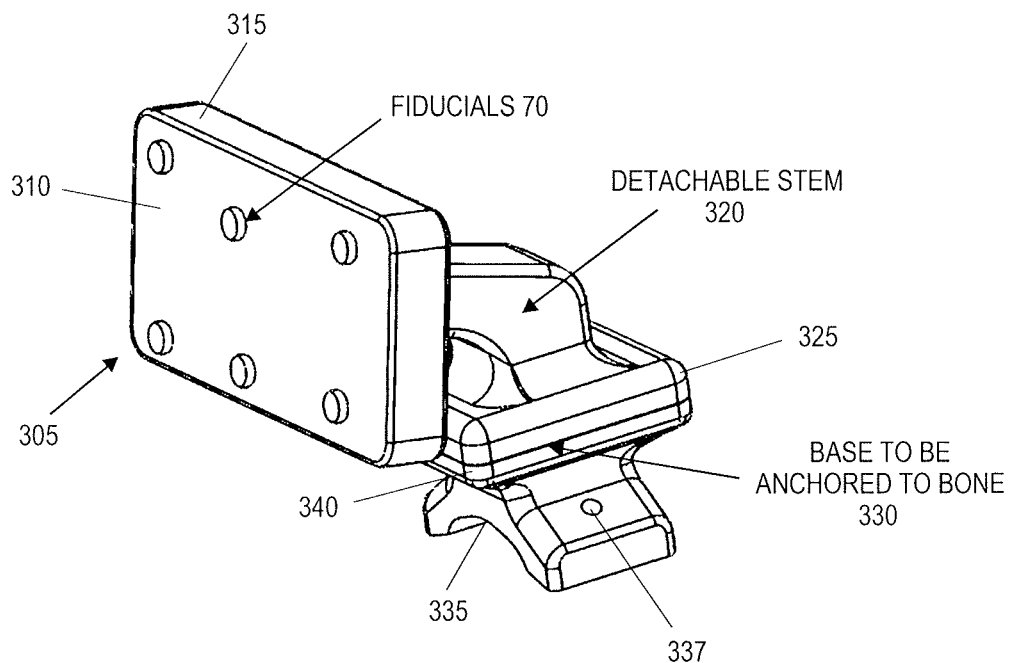
FIG. 16A
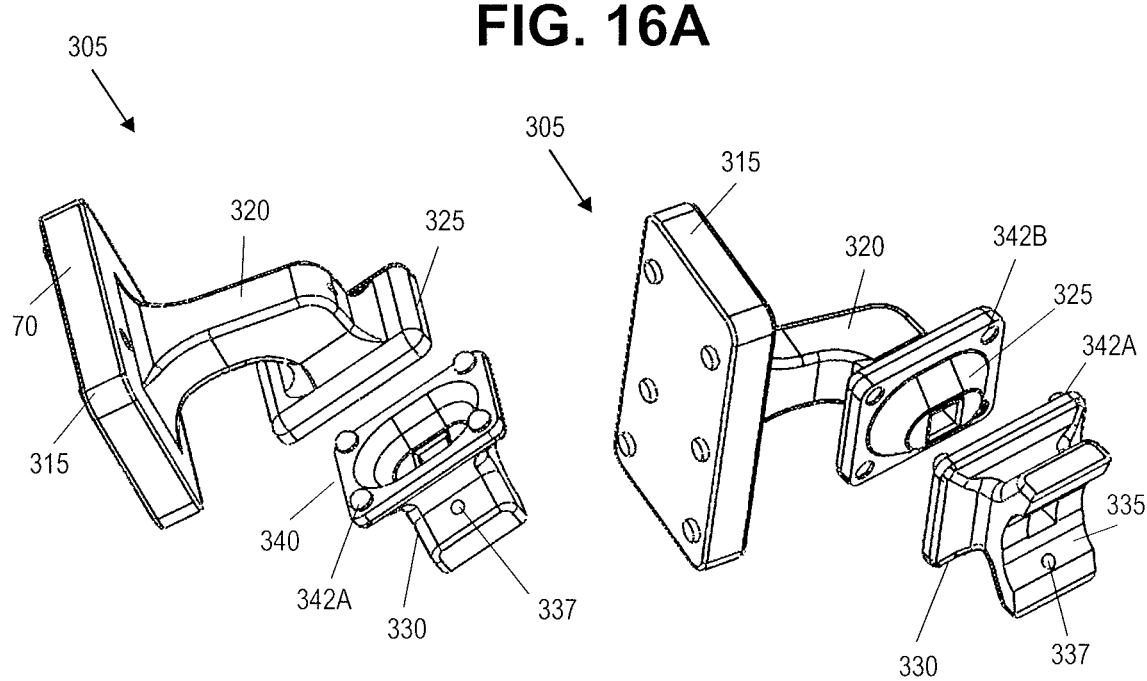
FIG. 16B     FIG. 16C

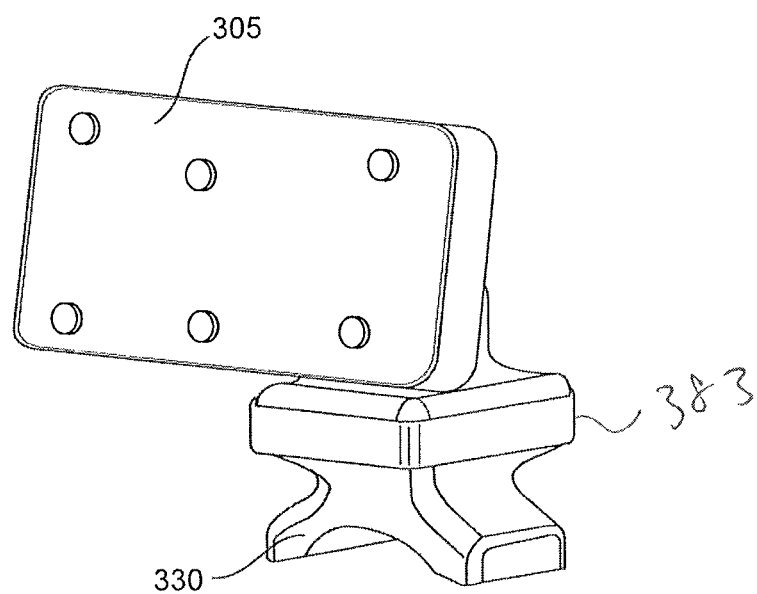
FIG. 26B1a
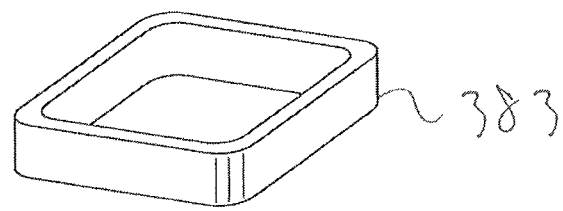
FIG. 26B1b

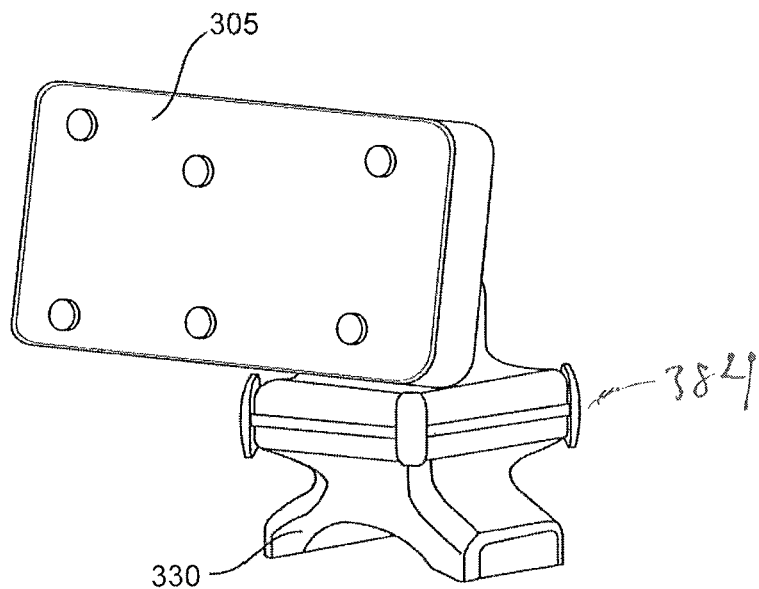
FIG. 26B2a
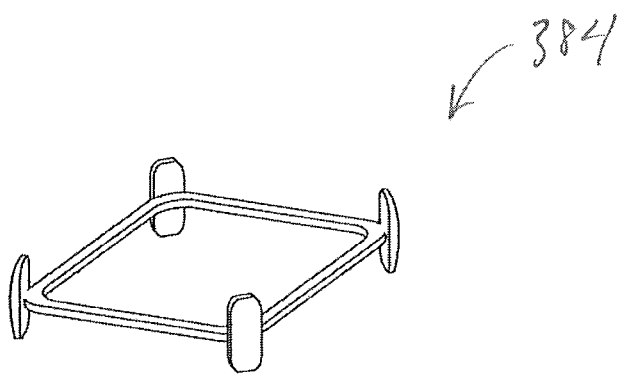
FIG. 26B2b

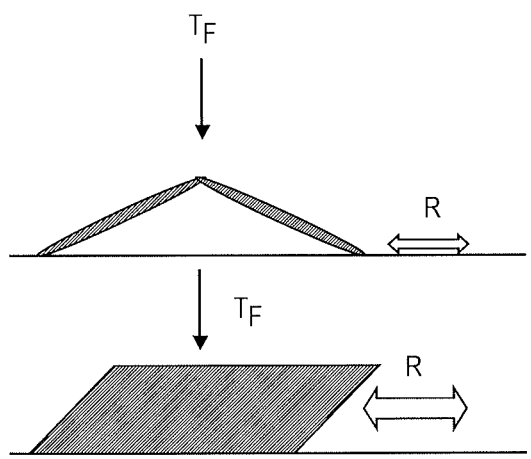
FIG. 37A
FIG. 37B
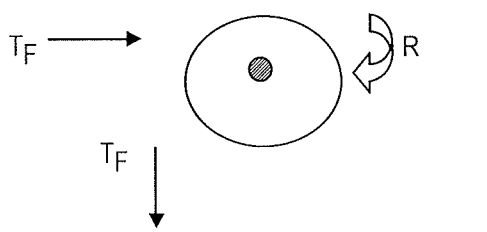
FIG. 37C
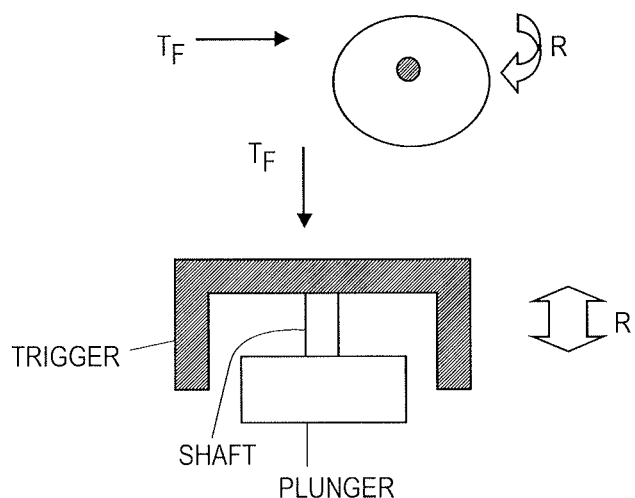
FIG. 37D
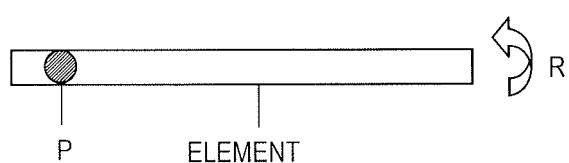
FIG. 37E

LOW PROFILE AT FULL SPEED POSITION

FIG. 39A
PUSH-PULL THROUGH A SOLID ACTUATOR
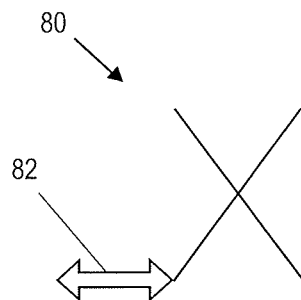
FIG. 39B
PULL / SPRING RETURN - BOWDEN CABLE
"NORMALLY OFF"
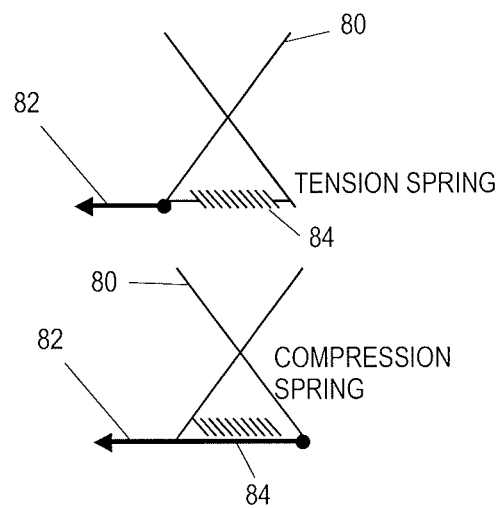
FIG. 39C
THE MOVEMENT OF THE ACTUATOR SHOWN DETERMINES THE HEIGHT OF THE UPPER END OF THE SCISSOR ARMS THEREFORE THE ELEVATION OF THE SCISSOR MECHANISM. THIS HEIGHT WILL PRESS AGAINST, AND WILL BE FELT BY THE USER PLACING HIS OR HER FINGER ON THE TOOL TRIGGER.

MECHANISM IN PUSHED UP POSITION

MECHANISM IN PULLED DOWN POSITION

MECHANISM ON TOOL - REPLACES THE TOOL TRIGGER

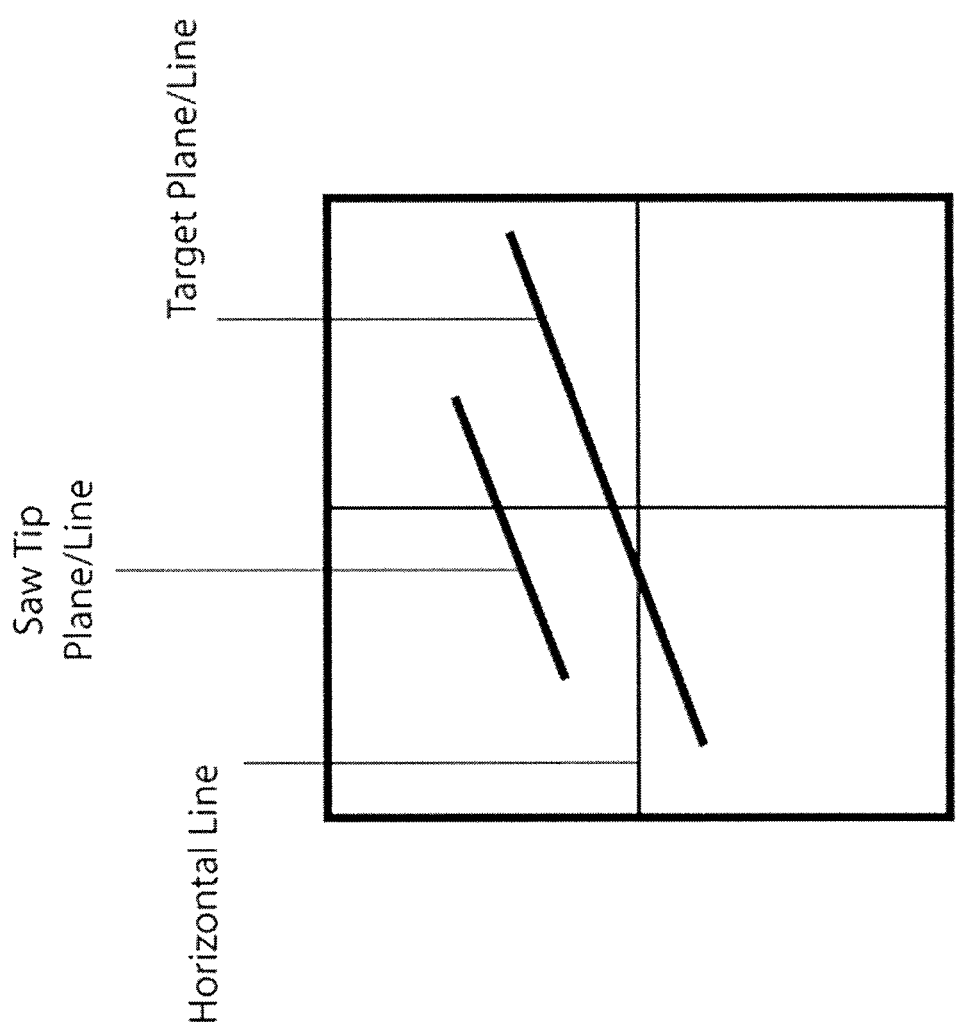

ON-BOARD TOOL TRACKING SYSTEM AND METHODS OF COMPUTER ASSISTED SURGERY

CROSS REFERENCE TO RELATED APPLICATION

This application is a continuation of U.S. patent application Ser. No. 15/354,778, filed Nov. 17, 2016, titled "ON-BOARD TOOL TRACKING SYSTEM AND METHODS OF COMPUTER ASSISTED SURGERY," now U.S. Pat. No. 10,020,617, which is a continuation of U.S. patent application Ser. No. 13/842,526, filed Mar. 15, 2013, titled "ON-BOARD TOOL TRACKING SYSTEM AND METHODS OF COMPUTER ASSISTED SURGERY," now U.S. Pat. No. 9,498,231, which is a continuation-in-part of International Application Number PCT/US2012/044486, filed Jun. 27, 2012, titled "ON-BOARD TOOL TRACKING SYSTEM AND METHODS OF COMPUTER ASSISTED SURGERY," which claims priority to U.S. Provisional Patent Application No. 61/501,489, filed Jun. 27, 2011, titled "SYSTEM FOR COMPUTER ASSISTED NAVIGATION AND CONTROL OF A POWER TOOL," each of which is incorporated by reference in its entirety for all purposes.

STATEMENT AS TO FEDERALLY SPONSORED RESEARCH

This invention was made with Government support under Grant No. W911QY-10-C-0178, awarded by the Army Natick Soldier Systems Center. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to the field of computer assisted surgery. Specifically, the present invention relates to various aspects of a surgical suite in which a tracking system on a tool provides guidance or assistance during a surgical procedure.

BACKGROUND

Many surgical procedures are complex procedures requiring numerous alignment jigs and intricate soft tissue procedures. Preparing and placing the alignment jigs and other preparation is often a significant part of the procedure and involves various errors. For instance, when performing a total knee replacement procedure ("TKR"), the prosthesis must be accurately implanted to ensure that the joint surfaces are properly aligned. If the alignment is inaccurate, the misalignment can compromise the function and eventually lead to failure of the joint, requiring the complex task of replacing one or more portions of the knee prosthesis.

To ensure that the prosthesis is accurately implanted, during a TKR procedure, the surgeon uses a variety of jigs to guide the cutting of the femur, the tibia and sometimes the patella. The jigs are complex and expensive devices that require significant time and skill to locate and attach on the patient during the surgical procedure.

The advent of computer assisted surgery (CAS) provides the promise of simplifying many of the complexities of surgical procedures. To date systems have been developed that utilize separate room based tracking systems designed to monitor the cutting jigs, tools and the patient. In some instances, the computer may be used to guide the surgeon during the process. The placement of the in room camera closer to the tool has been proposed. However, improvements are needed to address the challenges of the line of sight requirements and other real-time and dynamic environment of a surgical procedure.

Although computer assisted surgery holds promise, there are numerous aspects to be addressed to make a system commercially viable and useful to surgeons. There continues to exist numerous aspects of computer assisted surgery that require improvement to improve the efficiency and/or quality of the procedure for processing of CAS data, and more useful outputs to the user.

SUMMARY OF THE DISCLOSURE

In one aspect, a tactile feedback mechanism includes a first platform; a second platform; a scissor linkage formed by a first linkage coupled to a second linkage, the scissor linkage extending between the first platform and the second platform wherein a first end of the first linkage is coupled to the first platform and a second end of the first linkage is coupled to the second platform and the first end of the second linkage is coupled to the first platform and the second end of the second linkage is coupled to the second platform; and at least one position restoration element coupled to the scissor linkage to adjust a force response of the relative movement between the first platform and the second platform. In some aspects the at least one position restoration element is coupled between the first end of the first linkage and the second end of the second linkage. In another aspect, the at least one position restoration element extends along a second platform and is coupled to the scissor linkage to adjust the movement of the second linkage second end relative to the second platform. In one embodiment, the first platform and the second platform are configured for operation alongside, partially covering, partially surrounding, partially over or completely over an on/off and or speed control trigger of a surgical tool. In one embodiment, a trigger cover is placed within the first platform for engagement with the trigger.

In still another configuration of a tactile feedback mechanism, there is provided at least one position restoration element coupled to the scissor linkage to adjust a force response of the relative movement between the first platform and the second platform is coupled so as to extend between the first platform and the second platform. Still further, there may be provided a position restoration element coupled to the scissor linkage and extending along the second platform. In one specific configuration of a tactile feedback mechanism, the position restoration element is a return spring coupled to the second end of the second linkage and there is an override spring coupled to the return spring and also there may be an actuator coupled to the override spring. In another embodiment of a tactile feedback mechanism, the position restoration element is a spring coupled in tension to the movement of the second ends of the scissor linkage relative to the second platform. In still another position restoration element configuration, a spring coupled in compression to the movement of the second ends of the scissor linkage relative to the second platform. In some feedback mechanisms, there is also a shaft extending from an opening in the second platform and coupled to the scissor linkage wherein movement of the scissor linkage produces corresponding movement of the shaft relative to the opening. The alternatives to the shaft include for example, a flexible shaft portion, a cable portion, a hollow shaft portion or a flexible linkage portion.

In still other configurations, an embodiment of a tactile feedback mechanism may be used in conjunction with an embodiment of an on tool tracking (OTT) device configured for use in computer assisted surgery. Such an OTT device would include for example a component or series of components working in cooperation within the on tool tracking device that are adapted and configured to translate the shaft relative movement into a signal used in a computer assisted surgery procedure. In one aspect the component may be an actuator, a solenoid, a motor, a potentiometer, a linear potentiometer, and inductive position sensor, or a linear encoder or other device positioned adjacent to the cable to register and measure displacement of the cable. In one aspect, cable movement relates to a signal indicative of the operation of the trigger of the surgical tool. In still further embodiments, the same component or a different component may also act as an actuator to impart movement to the shaft to influence the relative movement between the first platform and the second platform. These various components and functions are each used in support of being configured to impart movement to or respond to the shaft in response to a signal related to controlling the operation of the surgical tool during a computer assisted surgery procedure.

In another embodiment, there is provided a reference frame for use in a computer assisted surgery procedure with navigation. The reference frame includes a frame having a flat or 3-dimensional surface or cluster of markers bounded or unbounded by perimeter; the stem extending from the frame; a coupling on the stem; a base having a first surface configured to engage a portion of the anatomy within a surgical field related to the procedure and a second surface to engage with the coupling. In some configurations, there may also be provided at least one registration element on the coupling and at least one registration element on the second surface wherein the registration elements are adapted and configured for mating cooperation at one or more repeatable 3D relative positions and orientations when the coupling is engaged to the second surface. In still further configurations, a plurality of registration elements on the coupling; and a plurality of registration elements on the second surface, wherein a portion of the registration elements on the coupling when engaged with a portion of the registration elements on the second surface will orient the frame in a first orientation within the surgical field. In one aspect, movement between the coupling in the second surface to engage other of said plurality of registration elements will position the frame in a second, different orientation within the surgical field. In some aspects, the first and second orientations are known position and are used in surgical preplanning. The reference frame may include other features such as surface for engagement anatomy, and aperture for a fixation element or configurations to mate with particular anatomical targets. In another aspect, there is provided a reference frame according to claim C1, further comprising: a reference frame guide having a frame and a stem extending from the frame, wherein the stem has a curvature or shape configured to engage with an anatomical feature to assist in the placement of the reference frame. In one aspect, the reference frame guide further comprising: one or more engagement elements along the frame for temporary engagement with the perimeter or a portion of the reference frame to permit proper positioning and adjustment of a base associated with the reference frame. In one aspect, the portion of the bony anatomy relates to the placement of the stem in relation to the condyles. In another aspect, the reference frame includes a mount coupling adapted and configured to maintain the relative position and orientation of the coupling and the second surface. In one aspect, the mount coupling is provided in the reference frame such that when the mount coupling is mated to the base the mount coupling is within an interior portion of the reference frame. In another aspect, the mount coupling is provided in the reference frame such that when the mount coupling attached to the reference frame the mount coupling substantially or completely surrounds the area of mating contact between the coupling and the second surface.

In one alternative embodiment, there is provided a method of performing a computer aided surgery procedure within a surgical field. First, step of attaching a first reference frame within the surgical field at a first position; then, attaching a second reference frame within the surgical field at a second position; and thereafter initiating an active step of the procedure using the surgical tool while maintaining positioning information used during the computer aided surgery procedure obtained from both the first and the second reference frames. In one alternative aspect, there is the step of adjusting the position of a surgical tool relative to a section of the anatomy during a step or as part of the procedure while maintaining positioning information used during the computer aided surgery procedure obtained from the first and/or the second reference frames attached to the section of the anatomy. In one alternative embodiment there is also the step of hovering the surgical tool during a step as part of the procedure while maintaining positioning information used during the computer aided surgery procedure obtained from either the first and/or the second reference frames. In still further aspect, there are methods including one or more of the steps of initiating, adjusting or hovering are performed in furtherance of one or more steps of a computer assisted surgery procedure on a knee. In a still further alternative, there are methods including, one or more steps of a computer assisted surgery procedure on a knee comprising: making a single distal condyle cut, or separate distal medial and lateral condyle cuts, making an anterior cut, making a posterior lateral condyle cut, making a posterior medial condyle cut, making an anterior chamfer cut, making a posterior lateral condyle chamfer cut, making a posterior medial condyle chamfer cut making a femoral box cut, drilling one or more holes in a portion of a surgical site and making a tibial proximal cut and associated holes or cuts for knee tibial component fixation anchoring features. In still another alternative embodiment, the method proceeds while maintaining the first reference frame and the second reference frame in the first position and the second position respectively after completion of the attaching steps, altering the orientation of a portion of the reference frame relative to the surgical field and thereafter using position information from the altered orientation for a portion of a computer aided surgery procedure. In still further aspect, the position information relating to the orientations of the first reference frame and the second reference frame in both the initial and the altered orientation are used as part of the preplanning processes for the computer aided surgery.

In another alternative embodiment, there is an on tool tracking and guidance device. In one aspect, the device has a housing having a surface or feature for releasable engagement with a portion of a surgical tool; a first camera and, optionally, a second camera in a stereo-vision arrangement where each of the first camera and the second camera (if provided) provides an image output selected for viewing substantially all or a portion of a surgical field selected for a computer assisted surgery procedure. The OTT device in one aspect may include a simple output device for communicating information to the user about the ongoing OTT CAS processes. In still other aspects, the OTT device may include a separate or onboard projector configured to provide an output at least partially within the surgical field of view. The various embodiments of OTT device is described herein may incorporate a wide variety of capabilities for electronic image processing and image communication capabilities within the housing. Still further, additional embodiments may be configured to receive an output from each of the one, two, or more cameras provided by an embodiment of an OTT device. Additionally or optionally, electronics and processing capabilities of the OTT device may be utilized to perform a wide range of digital processing functions. In one aspect, electronics included with the OTT perform an image processing operation using at least a portion of the output from one or both cameras configured for use in the computer assisted surgery procedure. In one aspect, the camera selected for use with an OTT device may include a field of view from about 70 mm to about 200 mm, or optionally, from about 40 mm to 250 mm from the first and second cameras. Still other ranges and camera configurations may be used in various other embodiments.

In a still further embodiment, the OTT housing surface for releasable engagement with a portion of a surgical tool is shaped to form a complementary curve with the portion of the surgical tool or a modified surgical tool selected for engagement with the housing and, in some instances, part of the surgical tool is modified to accommodate releasable engagement with the housing surface. In one example, the surface for releasable engagement with a portion of a surgical tool is adapted and configured so that when the surface is coupled to the surgical tool at least a portion of an active segment of the surgical tool lies within the horizontal field of view and the vertical field of view.

In still further aspects, the onboard or separate projector may include such attributes as: the output from the projector is projected on or near an active element associated with a surgical tool attached to the housing; the output from the projector is adapted for projection on a portion of the patients anatomy such as the bone and/or surrounding tissue, or on or within the surgical field surface in the surgical scene; an adaptation process gives an adapted projector output that is adjusted for the curvature, roughness or condition of the anatomy. In one aspect, the projector is what is known as a pico projector.

In on embodiment, there is a method for performing a computer assisted surgery procedure using a hand held surgical instrument having an on tool tracking device attached thereto including collecting and processing computer assisted surgery data using the on tool tracking device; assessing the data in real time during the computer assisted surgery procedure; performing CAS related operations using the on tool tracking device selected from at least two of: controlling the operation of the tool, controlling the speed of the tool and providing to the user guidance related to a CAS step; controlling the operation or speed of the tool or providing guidance to the user to adjust the speed of the tool; and providing a user of the surgical instrument an output related to the assessing step. There may also be, in additional or alternative aspects, one or more of displaying, projecting, or indicating an output related to a computer assisted surgery processing step.

There may also be, in additional or alternative aspects, an output comprising one or more of a tactile indication, a haptic indication, an audio indication or a visual indication; the tactile indication comprises a temperature indication; and the haptic indication comprises a force indication or a vibration indication. Still further aspects, the output is the control signal automatically generated to adjust a performance parameter of the surgical tool in response to a result of the assessing step. In other aspects, the performance parameter includes modifying a tool cutting speed or stopping a tool operation. The output of providing a step further comprising electronics to control operation of power tools (modifying cutting speed and/or stopping it). There may also be, in additional or alternative aspects, a determining step that is based upon an evaluation of one or more of: a physical parameter within the surgical field such as position or combination of positions of elements tracked in the field through reference frames attached to them a reference frame input, projected image(s) taken, a motion detected from a sensor, a motion detection from a calculation, the overall progress of a computer aided surgery procedure, and a measured or predicted deviation from a previously prepared computer aided surgery plan. Still further, the determining step selects one of a number of predefined processing modes, such as for example hover mode, site approach mode, and active step mode. In each of these modes there are specific outputs, processing techniques and algorithms applied to the CAS data.

In still further aspects, there are OTT CAS processing mode factors selected from one or more of: a camera frame size; an OTT camera orientation; an adjustment to a camera software program or firmware in accordance with the desired adjustment; adjustments to an OTT camera or other camera image outputs to modify a size of a region of interest within a horizontal field of view, the vertical field of view or both the horizontal and the vertical fields of view of the camera; drive signals for adjustable camera lens adjustment or positioning; image frame rate; image output quality; refresh rate; frame grabber rate; reference frame two; reference frame one; on reference frame fiducial select; off reference frame fiducial select; visual spectrum processing; IR spectrum processing; reflective spectrum processing; LED or illumination spectrum processing; surgical tool motor/actuator speed and direction, overall CAS procedure progress; specific CAS step progress; image data array modification; an OTT pico projector refresh rate; an OTT pico projector accuracy; one or more image segmentation techniques; one or more logic-based extractions of an image portion based on a CAS progress; signal-to-noise ratio adjustment; one or more image amplification process, one or more imaging filtering process; applying weighted averages or other factors for dynamic, real-time enhancement or reduction of image rate, pixel or sub-pixel vision processing; a hand tremor compensation; an instrument-based noise compensation for a saw, a drill or other electrical surgical tool and a vibration compensation process, and any user preferences through the LCD touch screen if one was onboard the OTT device along with any one or more additional OTT CAS processing mode factors, based on information from the OTT each alone or in any combination.

In still other aspects, the output is provided to the user with a projector in the on tool tracking device. In addition, the projector output is automatically or manually adjusted based upon a physical characteristic of the surgical site presented during the display of the projector output. It is to be appreciated that the physical characteristic is one or more of the shape of the portion of the size available to the projector output; the topography in the projector projected field and the orientation of the projector to the portion of the site available for the projector output. Optionally, the projector or a display on the OTT device has an output that includes information visible to the user of the surgical tool while the surgical tool is in use in the surgical site. In still further aspects, the projector or a display on the OTT device output includes information visible to the user of the surgical tool to indicate the position, relative motion, orientation, or other navigation or guidance parameter related to the positioning of the active element of the surgical tool within the surgical field according to the surgical plan. Still the step of providing an output from an OTT device may include displaying the output on a system screen; on a GUI interface on the OTT or a mobile device screen.

In a still further aspect, any of the above steps of outputting a CAS or guidance output to the user is, optionally, changed and an OTT CAS processing technique or output is modified as a result of the user performing one or more steps of a computer assisted surgery procedure on a knee comprising: making one or more distal femur cuts, making a distal femur anterior cut, making a distal femur posterior lateral condyle cut, making a distal femur posterior medial condyle cut, making a distal femur anterior chamfer cut, making a distal femur posterior lateral condyle chamfer cut, making a distal femur posterior medial condyle chamfer cut, making proximal tibial cut or any tibial holes or cuts to cater for any anchors fixation features on a tibial component such as pegs, stems, keels, etc. In still other alternatives, the methods herein of outputting a CAS output to the user is changed as a result of one of the above recited steps performed during a surgical procedure related to one of a shoulder; a hip; an ankle; a vertebra; an elbow or deformity correction or fracture reduction bone osteotomy. Additionally, an OTT CAS processing technique or output is modified as a result of one of the above recited steps performed during a surgical procedure related to one of a shoulder; a hip; an ankle; a vertebra; an elbow or deformity correction or fracture reduction bone osteotomy.

In still another aspects, there is provided a system for performing computer assisted surgery, having a surgical tool having an active element corresponding to the surgical function of the tool; an on tool tracking device coupled to the tool using a housing configured to engage with at least a portion of the surgical tool; at least one camera in the housing configured to obtain imaging information related to the surgical tool and a surgical field; an output device like a graphical screen display, or, optionally a projector in the housing configured to provide a projected output on or near an active element of the surgical tool; a computer having computer readable instructions stored within electronic memory for performing a computer assisted surgical procedure using data at least partially obtained from the on tool tracking device and to provide an output for use during a step of the surgery. When the system includes a projector within the OTT capabilities, the projector further comprising one or more of the following: projection capability to project an output on a portion of the patient's anatomy, a surface within the surgical scene, an electronic device, or other object within the projector output range. In one configuration, the computer is in the housing. In another the computer is separated from the on tool tracking device and connected via a wired or a wireless connection. In still further aspects, the system includes one or more of the computer readable instructions for performing any of the CAS mode select methods described above. In still further aspect, the system may include the on tool tracking device having one or more of the elements described above. The system may adapted and configured for use with one or more reference frames and associated methods described herein. In a still further aspect, the system is adapted and configured for use in combination with a tactile feedback mechanism described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 11A, 11B, 11C and 11D provide additional information relating to variations of camera angle.

FIGS. 16A, 16B and 16C illustrate various views of a reference frame.

FIG. 26B1a illustrates a flexible coupling in use about the upper and lower mount as shown in FIG. 26B.

FIG. 26B1b is an isometric view of the flexible coupling of FIG. 26B 1a.

FIG. 26B2a illustrates a flexible coupling in use about the upper and lower mount of FIG. 26B.

FIG. 26B2b is an isometric view of the flexible coupling of FIG. 26B2a.

FIGS. 37A-44 relate to various alternative tactile feedback mechanisms along with related kinematic responses and design criteria.

FIG. 37A illustrates a bent form that deflects to move an actuator in response to trigger force.

FIG. 37B illustrates a sliding trapezoid form that will deform and restore its shape in response to trigger force.

FIG. 37C illustrates a rotating reader or encoder used to provide a rotating response to the trigger force.

FIG. 37D illustrates a frame moving in response to trigger force to depress a shaft into a base where the movement of the shaft may be registered as an indication of trigger force.

FIG. 37E illustrates a pinned element that may deflect to indicate an amount of trigger force.

FIGS. 39A, 39B and 39C each illustrate a scissor mechanism without a position restoration element (39A), with a tension spring as a position restoration element (39B) and a compression spring as a position restoration element (39C).

FIG. 41 illustrates another scissor mechanism 80 having a surgeon system override capability.

FIG. 42 illustrates a scissor mechanism similar to the schematic mechanism illustrated in FIG. 41.

FIGS. 43 and 44 are charts illustrating the operational characteristics of the scissor mechanism of FIG. 42.

FIG. 47 illustrates the tactile feedback mechanism in an expanded state configured to cover the trigger to prevent or attenuate manual pressing of the trigger and FIG. 48 shows the tactile feedback mechanism collapsed to expose the trigger and allow manual control.

FIGS. 66A, 66B and 67 relate to various CAS displays.

DETAILED DESCRIPTION

Figure 1:
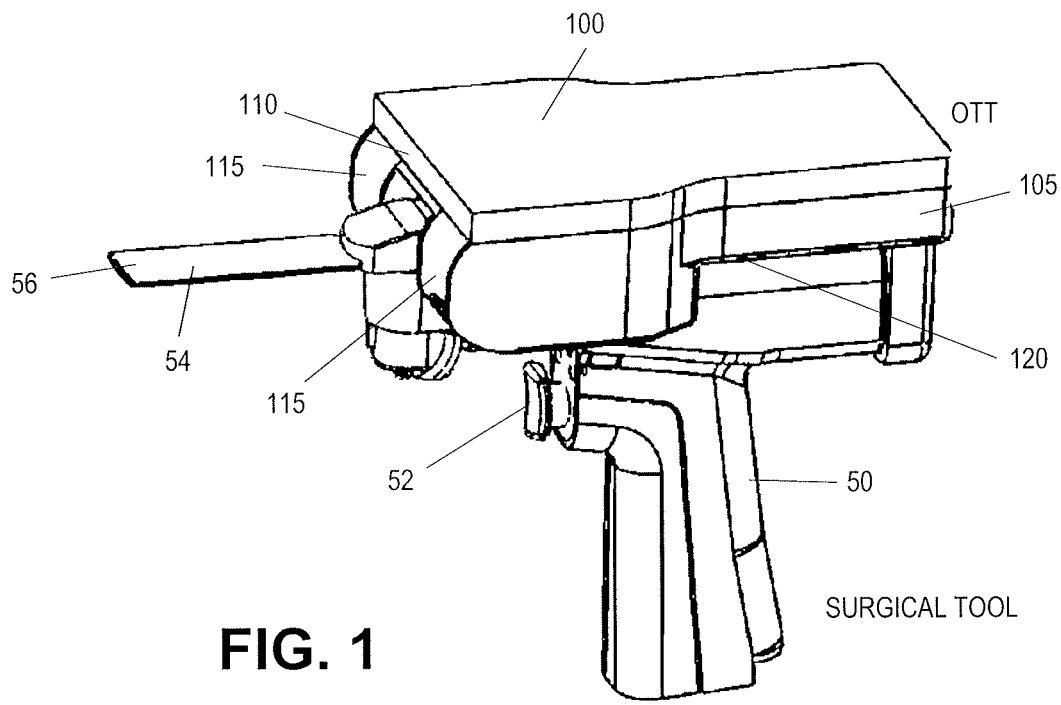
FIG. 1 illustrates an isometric view of an example of an on tool tracking device attached to a surgical instrument.

The present invention is a system for performing computer assisted orthopedic surgery and novel tools for operating that system. The present invention overcomes limitations of current computer assisted surgery systems by optionally combining all elements of computer assisted surgery (tools, displays and tracking) into a single smart instrument. The instrument does not rely on an external navigation system but the tool contains all the tracking equipment on the tool itself in a self-contained assembly. As a result, the overall system is significantly less complicated, less intrusive to the surgeon and easy to integrate into existing practices in orthopedic surgery.

By way of overview, the system is comprised of principal subsystems. The first is the tool itself, which is used to carry a standalone on tool tracking device or modified to contain the subsystems or elements of the subsystems to provide On-Tool Tracking (OTT) functionality. The modifications can be simple, such as an extended chassis to hold the additional components, or complex, such as a modified power system to power the additional subsystems, and/or to stop or control the motor speed or other actuators on the powered tool. The second subsystem is the tracking subsystem, which comprises one or more trackers and one or more tracking elements. The tracker can be a one, two (stereovision) or more cameras that are sensitive to visible light or light from another wavelength. Alternatively, the tracker could be an electromagnetic tracker or other non-camera based system. The tracking element is whatever the tracker tracks. For example, where the tracker is an infrared camera, the tracking element is an infrared LED, or a passive surface reflective of infra-red light emitted from around the camera or elsewhere. Where the tracker is a pair of high-resolution cameras sensitive to visible light, the tracking element could be the specific anatomy of a patient and/or marks made directly on the anatomy including markers or reference frames. The subsystem can utilize one or more trackers, mounted on the tool in various configurations, to track one or more tracking elements. In one aspect, the tracker(s) (used to track the sensors required to track the tool, the patient and the other relevant objects in order to perform an OTT CAS surgery) are located, at least in part, on-board the surgical tool in a self-contained manner. The navigation system navigates when the tracking subsystem senses and calculates the position (location and orientation/pose) of the tracking element(s) relative to the tool.

The third subsystem is an OTT CAS computer system that contains an appropriate CAS planning software and programming to perform the OTT CAS functions of the implementation of the surgical plan. The surgical plan can be produced and expressed through a variety of means but ultimately contains the locations, orientations, dimensions and other attributes of the resections (e.g. cuts, drill holes, volume of tissue to be removed), intended by the operator, in three-dimensional space. The system can also contain a reference dataset from imaging of the patient's anatomy, such as a computed tomography image (dataset) of a patient's anatomy, and 2D or 3D virtual reconstructed models of the patient's anatomy, or morphed models scaled to fit the patient anatomy as a point of reference. The computer system compiles data from the tracking system and the surgical plan to calculate the relative position of boundaries defining the intended resections by the tool. In some configurations, the computer system can be a wholly separate component, in wireless communication with the other components. In other configurations, the computer system is integrated into the other systems. Together, the tracking system and the computer system can determine if the surgeon's location, orientation and movement of the tool (the surgical path) will produce the desired resection. It is important to note that the computer sub system and the tracking sub system work together to establish the three dimensional space of the surgical site. Elements necessary for the tracking sub-system to function can be located in the computer sub-system or some intermediary mode of transmitting tracking data to the computer sub-system.

The final subsystem is an indicator to provide the surgeon with OTT CAS appropriate outputs related to his position, orientation and movement of the tool, as well as the intended resection, and the deviations (errors) between the two, within a real (or semi real) time OTT CAS step. The indicator can be any variety of means to align/locate the surgical path with the intended resection: a panel of lights that sign directions to correct the surgeon, a speaker with audio instructions, a screen, touchscreen or iPhone or iPad or iPod like device (i.e., a so-called "smartphone") on the OTT equipped tool displaying 3D representation of the tool and the patient with added guidance imagery or a digital projection (e.g., by a picoprojector) onto the patient's anatomy of the appropriate location of a resection. The indicator serves to provide an appropriate OTT CAS output to guide the surgeon to make the right resection based on real time (or semi-real time) information.

Looking now to the specific subsystems:

A surgical suite for computer assisted surgery includes a first computer for pre-operative planning use. For example, pre-operative analysis of the patient and selection of various elements and planned alignment of the implant on the modeled anatomy may be performed on the first computer. The suite may also include a second computer, referred to as the OR computer, which is used during a procedure to assist the surgeon and/or control one or more surgical instruments. In addition the suite may include a computer (standalone or collaborating with another computer) mounted on the surgical instrument via an embodiment of an on tool tracking system. Finally, one or more computers are used as dedicated drivers for the communication and medium stage data processing functions interfaced to the cutting instrument tracking system, motor control system, or projection or display system. The first computer is provided in the present instance, but may be omitted in some configurations because the functions of the computer are also implemented on the OR computer, which can be a standalone. Moreover the whole 'pre-surgical planning' may eventually happen instantaneously inside the OR using primarily the OR computer in conjunction with an OTT. Nevertheless, if desired for particular applications, the first computer may be used. The pre-surgical planning and procedure can also be aided by data or active guidance from online web-links. As used herein, the term CAS system or CAS computer refers to those computers or electronic components as provided in any of these combinations to perform CAS function. Furthermore, the micro-processing unit of the system can reside in the on tool tracking instrument. In such a configuration, the computations and user interface can be performed within a computer borne on the surgical tool being used, or in collaboration with the main system computer by wired or wireless communications, and some of which can be done through the sub-system "driver" computers. In collaboration with the main OTT CAS computer by direct wireless communication or indirect through the intermediary driver computers, such system performs error analysis of location of the cutting instrument relative to the ideal cut to be performed, and displays corrective actions and other information on a screen provided as part of the on tool tracker alone or in any combination with an output provided by one or more projectors provided with the OTT for that purpose.

As a result, a surgical suite for OTT CAS may include a tracking/navigation system that allows tracking in real time of the position and orientation in space of several elements, including: (a) the patient's structures, such as the bone or other tissue; (b) the surgical tool, such as the bone saw and/or OTT, which carries the OTT and is controlled by the surgeon based on information from the OR computer or (c) surgeon/assistance specific tools, such as a navigated pointer, registration tools, or other objects as desired. The OR computer or an OTT may also perform some control on the instrument. Based on the location and orientation (pose) of the tool and feedback from an OTT, the system or CAS computer is able to vary the speed of the surgical tool as well as turn the tool off to prevent potential damage. Additionally, the CAS computer may provide variable feedback to a user. The surgical instrument shown in the accompanying description is a surgical saw. It is to be appreciated that many others instruments can be controlled and/or navigated as described herein, such as a drill, reamer, burr, file, broach, scalpel, stylus, or other instrument. Therefore in the following discussion, the OTT enabled CAS system is not limited to the particular tool described, but has application to a wide variety of instruments and procedures.

As discussed further below, one exemplary use of the surgical suite incorporates the use of a virtual model of the portion of the patient upon which a procedure is to be performed. Specifically, prior to a procedure, a three dimensional model of the relevant portion of the patient is reconstructed using CT scans, MRI scans or other techniques. Prior to surgery, the surgeon may view and manipulate the patient model to evaluate the strategy for proceeding with the actual procedure.

One potential methodology uses the patient model as a navigation device during a procedure. For instance, prior to a procedure, the surgeon may analyze the virtual model of a portion of the patient and map out the tissue to be resected during a procedure. The model is then used to guide the surgeon during the actual procedure. Specifically, during the procedure, the on tool tracking device monitors the progress of the procedure. As a result of the OTT CAS processes performed, the progress/results are displayed in real time on the OR computer or on an OTT monitor (e.g. onboard LCD screen) so that the surgeon can see the progress relative to the patient model. Importantly, the surgeon is also provided an OTT projector to provide real type feedback based on OTT CAS processing steps (described in greater detail below).

To provide navigation assistance during an OTT CAS procedure, an on tool tracking device monitors the position of the associated surgical tool within the surgical field. The OTT CAS system may use none, or one or more reference frames including one or more positions sensors or one or more fiducial markers depending upon the requirements of the OTT CAS procedure being undertaken. Any of the above described markers may be utilized in an active or passive configuration. Markers may, optionally, be wired or wireless sensors that are in communication with the system. An active marker emits a signal that is received by the OTT device. In some configurations, the passive markers are (naturally wireless) markers that need not be electrically connected to the OTT CAS system. In general, a passive marker reflects infrared light back to an appropriate sensor on the OTT device. When using passive markers, the surgical field of view is exposed to infrared light that is then reflected back to and received by the OTT, from which the data locations of the passive markers are determined by the OTT CAS, and from such data the location and orientation of the surgical site, and other instruments are computed relative to the OTT and to each other. Some embodiments of an OTT device may be provided with an infrared transmission device and an infrared receiver. The OTT receives emitted light from the active markers and reflected light from the passive markers along with other visual field information reaching the OTT. The OTT CAS system performs calculations and triangulates the three dimensional position and orientation of the tool based on the vision processing of the images including the position of the markers along with other imaging information in the surgical field. Embodiments of the on tool tracking device are operable to detect the position and orientation of the OTT-enabled tool relative to three orthogonal axes. In this way, using information from the OTT device, the OTT CAS system determines the location and orientation of the tool, and then uses that information to determine OTT CAS processing modes and produce appropriate OTT CAS outputs for the user.

As is typical in navigation and other CAS systems, a series of points or surfaces are used to register or correlate the position of the patient's anatomy with the virtual model of the patient. To gather this information, a navigated pointer is used to acquire points at an anatomical landmark or a set of points on a surface within the patient's anatomy. A process referred to as morphing (or kinematic registration) may alternatively be used to register the patient to an approximate (scaled) virtual model of the patient taken from an atlas or database and not originating from actual imaging of that particular patient. During such a process, the surgeon digitizes parts of the patient and some strategic anatomical landmarks. The OTT CAS computer analyzes the data and identifies common anatomical features to thereby identify the location of points on the patient that correspond to particular points on the virtual model.

Accordingly, as set forth above, the on tool tracking device visually monitors the position of several items in real time, including: the position of the associated surgical tool, the position of the patient and the position of items used during a procedure, such as one or more reference frames or one or more markers. Accordingly, the OTT CAS computer processes the OTT CAS data regarding the position of the associated surgical tool, visual field information in OTT image data, the data regarding the position of the patient, and the data regarding the model of the patient. This result of OTT CAS computer processes provide dynamic, real time interactive position and orientation feedback information, which can be viewed by the surgeon on a monitor provided by the OTT device (if provided) or as a displayed output of an OTT projector. Further still, as previously described, prior to a procedure, the surgeon may analyze the patient model and identify the tissue that is to be resected as well as plan for or indicate desired OTT CAS mode for use during an OTT CAS step or during a CAS procedure. This information can then be used during the procedure to guide the surgeon using dynamically adjusted outputs based on the mode of CAS processing and other factors.

FIG. 1 is an isometric view of an on tool tracking device (OTT) 100 arranged for tracking and providing guidance during computer aided surgery using the surgical instrument 50. The OTT 100 has a housing 105 that includes a pair of cameras 115, in an opening for projector output 110. The OTT 100 and also as a housing 105 with a surface 120 adapted and configured to mate with the surgical instrument 50. The surgical instrument 50 includes a trigger 52 for operating a tool 54 having an active element 56. An illustrative embodiment of FIG. 1 the tool 54 is a saw and the active element 56 is the serrated edge of a saw blade at the distal end thereof.

Figure 2:
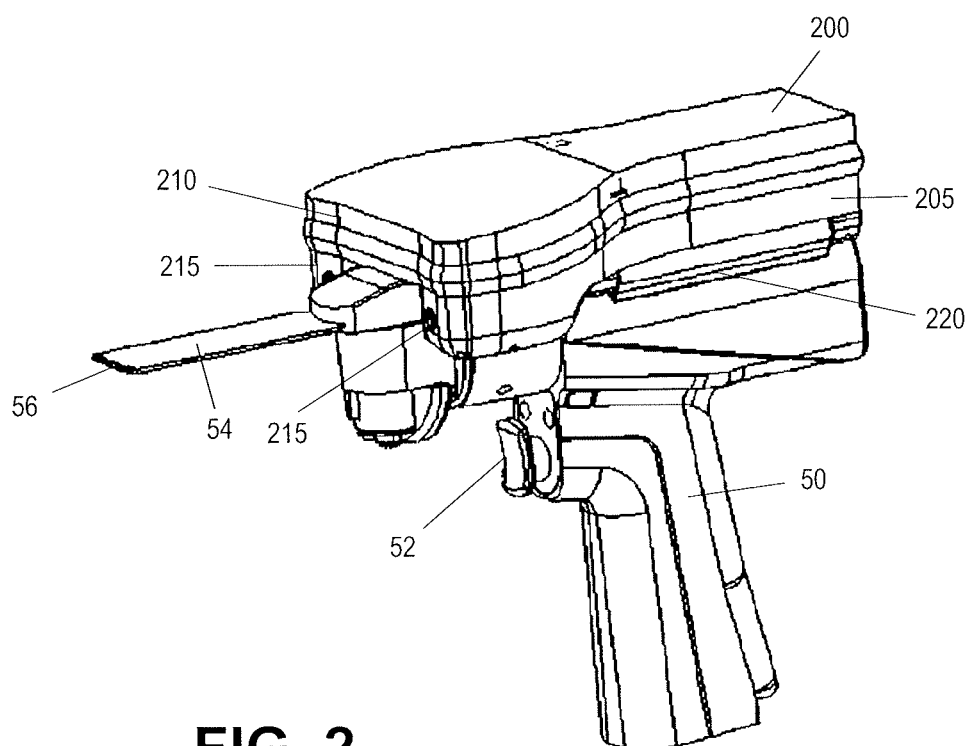
FIG. 2 illustrates an isometric view of an on tool tracking device attached to a surgical instrument.

FIG. 2 is an isometric view of an on tool tracking device (OTT) 200 and arranged for tracking and providing guidance during computer aided surgery using the surgical instrument 50. The OTT 200 has a housing 205 that includes a pair of cameras 215, in an opening for projector output 210. The OTT 200 and also as a housing 205 with a surface 220 adapted and configured to mate with the surgical instrument 50. The surgical instrument 50 includes a trigger 52 for operating a tool 54 having an active element 56. An illustrative embodiment of FIG. 2 the tool 54 is a saw and the active element 56 is the serrated edge of the distal end thereof.

Figure 3:
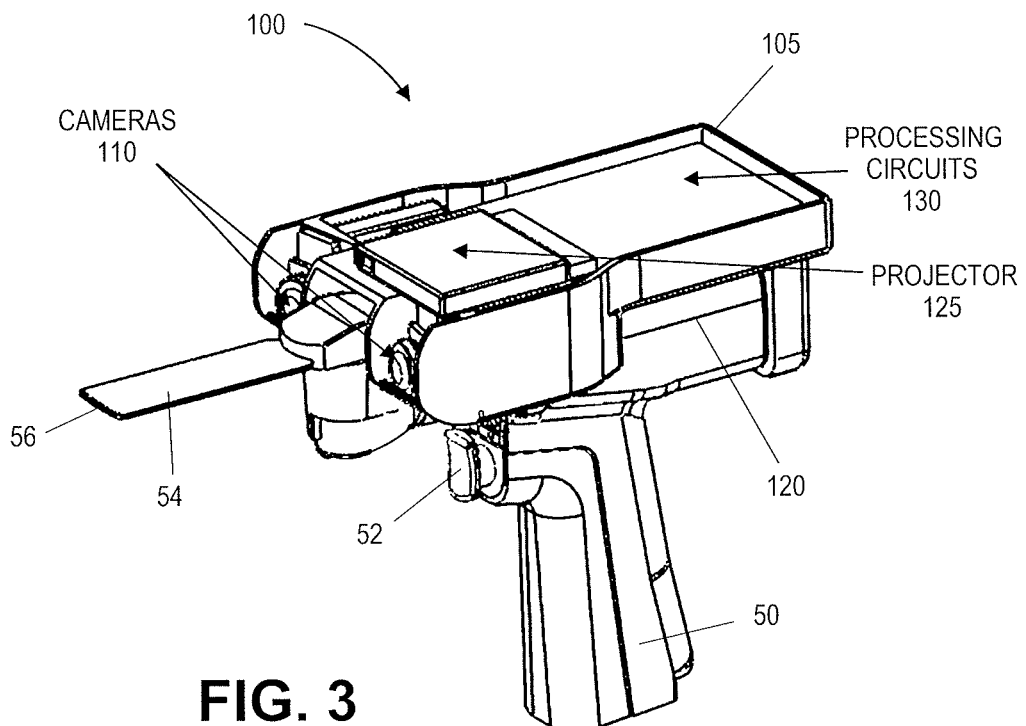
FIG. 3 illustrates an isometric view of the on tool tracking device of FIG. 1 with a cover removed to show internal components.
Figure 4:
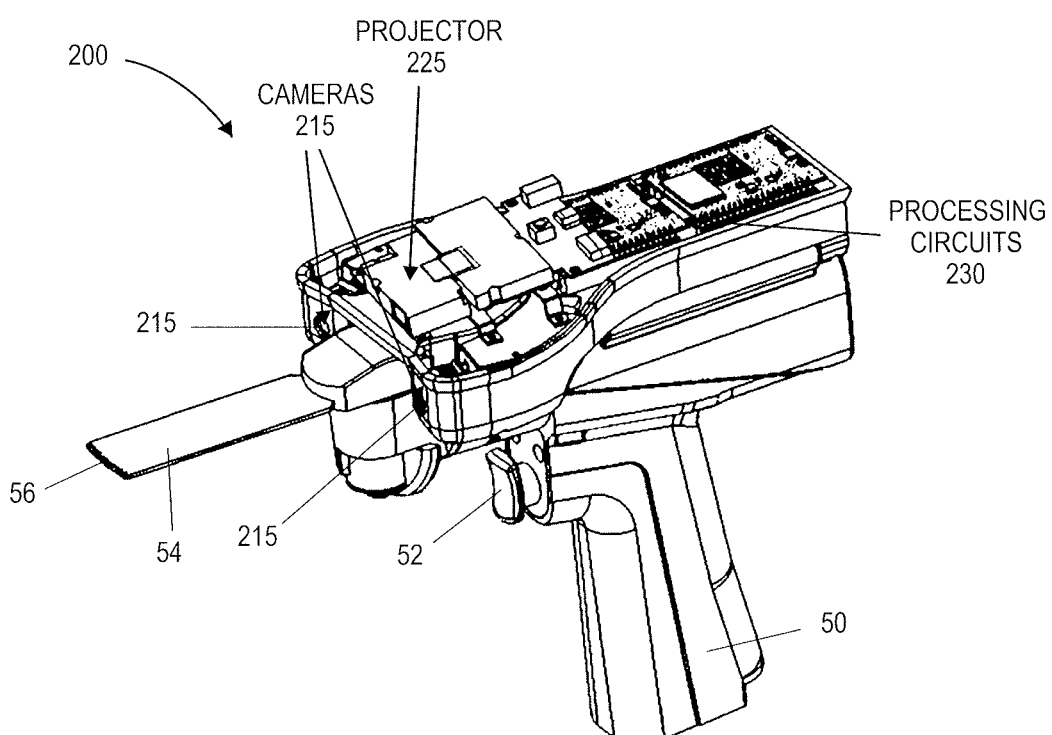
FIG. 4 illustrates an isometric view of the on tool tracking device of FIG. 2 with a cover removed to show internal components.

FIGS. 3 and 4 are isometric views of the on tool tracking devices of FIGS. 1 and 2 with the top cover of the housings removed. In the view of FIG. 3, the interior of the housing 105 exposed in shows the placement of the processing circuits 130, projector 125 and cameras 115. The projector 125 is illustrated in this embodiment in the position above a plane containing the cameras 115, but tilted to make the output of the projector 125 more symmetrically above and below the plane of the cameras 110. The projector can be tilted further or less vertically and some horizontally if needed in special situations, to optimize the image it projects with respects to various criteria such as occlusion (e.g., by the saw blade in FIGS. 3 and 4, or drill bits) or specifics of the nature, shape, reflection and other aspects of the anatomy or surface upon which the image is projected onto. In the view of FIG. 4, the exposed interior of the housing 205 shows the placement of the processing circuits 230, projector 225 and cameras 215. The output 210 of the projector 225 is illustrated in this embodiment in a position above that, and at an acute angle with a plane containing the cameras 215.

Figure 5:
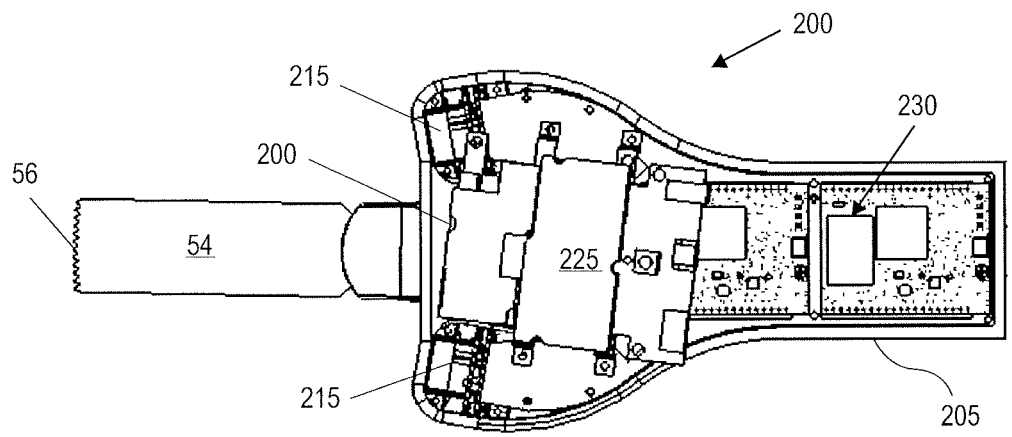
FIG. 5 illustrates a top down view of the on tool tracking device of FIG. 4
Figure 6:
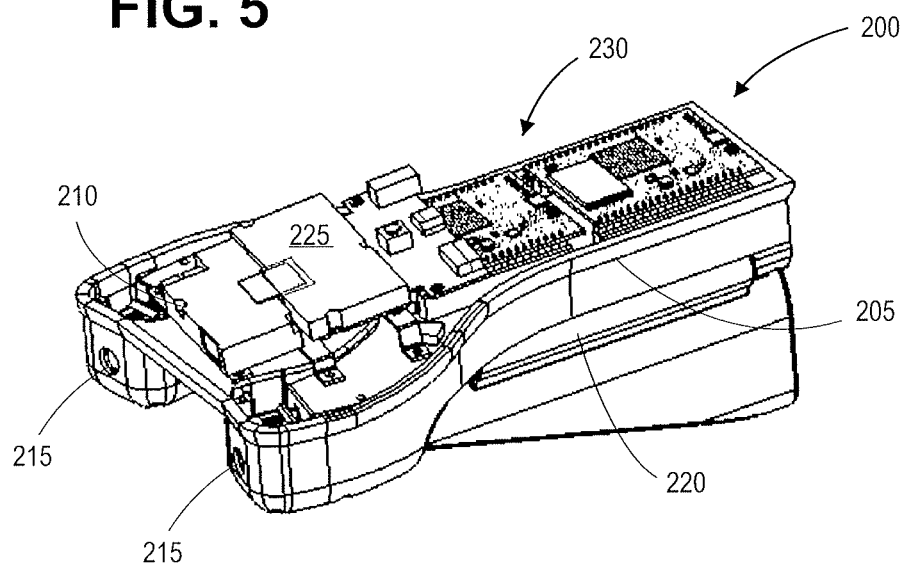
FIG. 6 illustrates an isometric view of the on tool tracking device of FIG. 5 separated from the surgical tool
Figure 7:
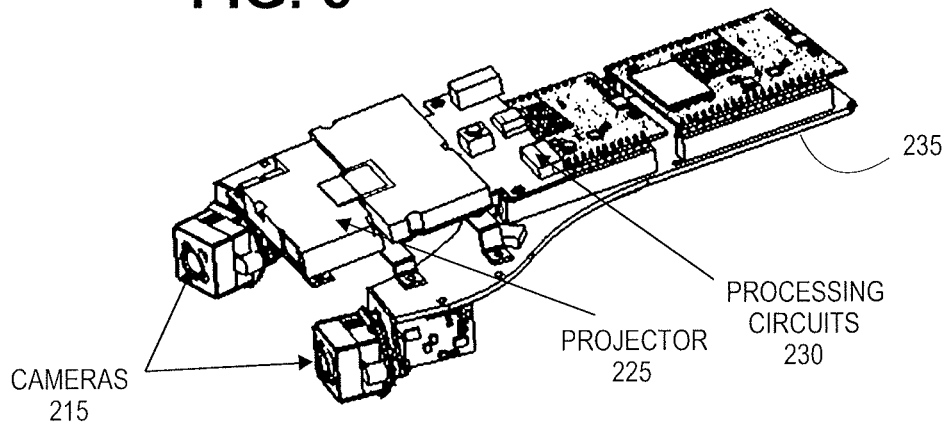
FIG. 7 illustrates electronics package and control circuitry visible in FIGS. 5 and 6 but in this view is removed from the OTT housing.

FIGS. 5, 6, and 7 represent one top down, and two isometric views of the on tool tracker 200. In the top down view of the on tool tracker shown in FIG. 4 the orientation and arrangement of the electronic components is clearly visible. As a result of the type of projector 225 used in this configuration, the projector has been positioned within the housing 205 at an angle and, as shown in FIG. 6 on a slightly inclined surface. In one embodiment, either or both of the cameras or the projector of an on tool tracking device may be positioned in any orientation and the result of that orientation to the operation of the respective device is then compensated for in other ways as described herein. In this way, various different OTT electronic circuits and component designs are possible since the slight physical misalignments may be adjusted for using software techniques as described herein. FIG. 7 illustrates an isometric view of the electronic components of the on tool tracker 200 separated from the housing 205. This figure illustrates one embodiment of a quote one piece" OTT electronics package having cameras 215, projector 225 and associated system and processing electronics 230 on a single board 235 for placement within the housing 205.

Figure 8A:
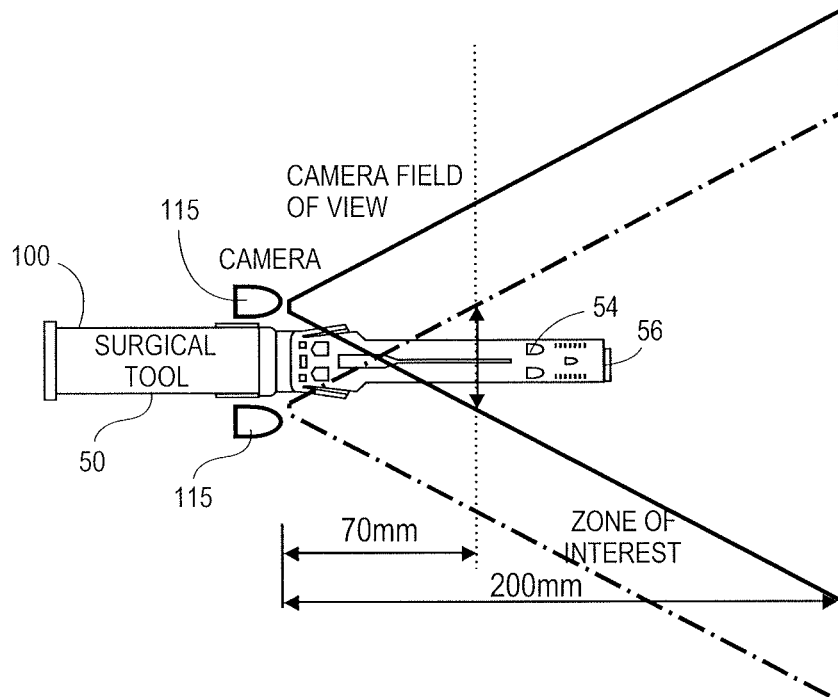
FIGS. 8A, 8B, 9, and 10 provide graphical information relating to the changes in camera field based on camera angle in some OTT device configurations.
Figure 8B:
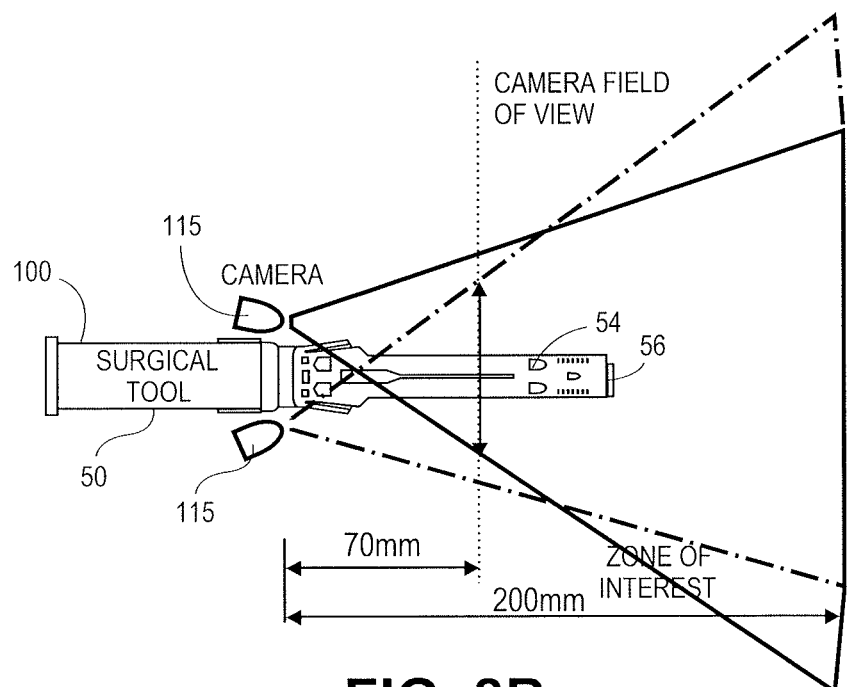
Figure 9:
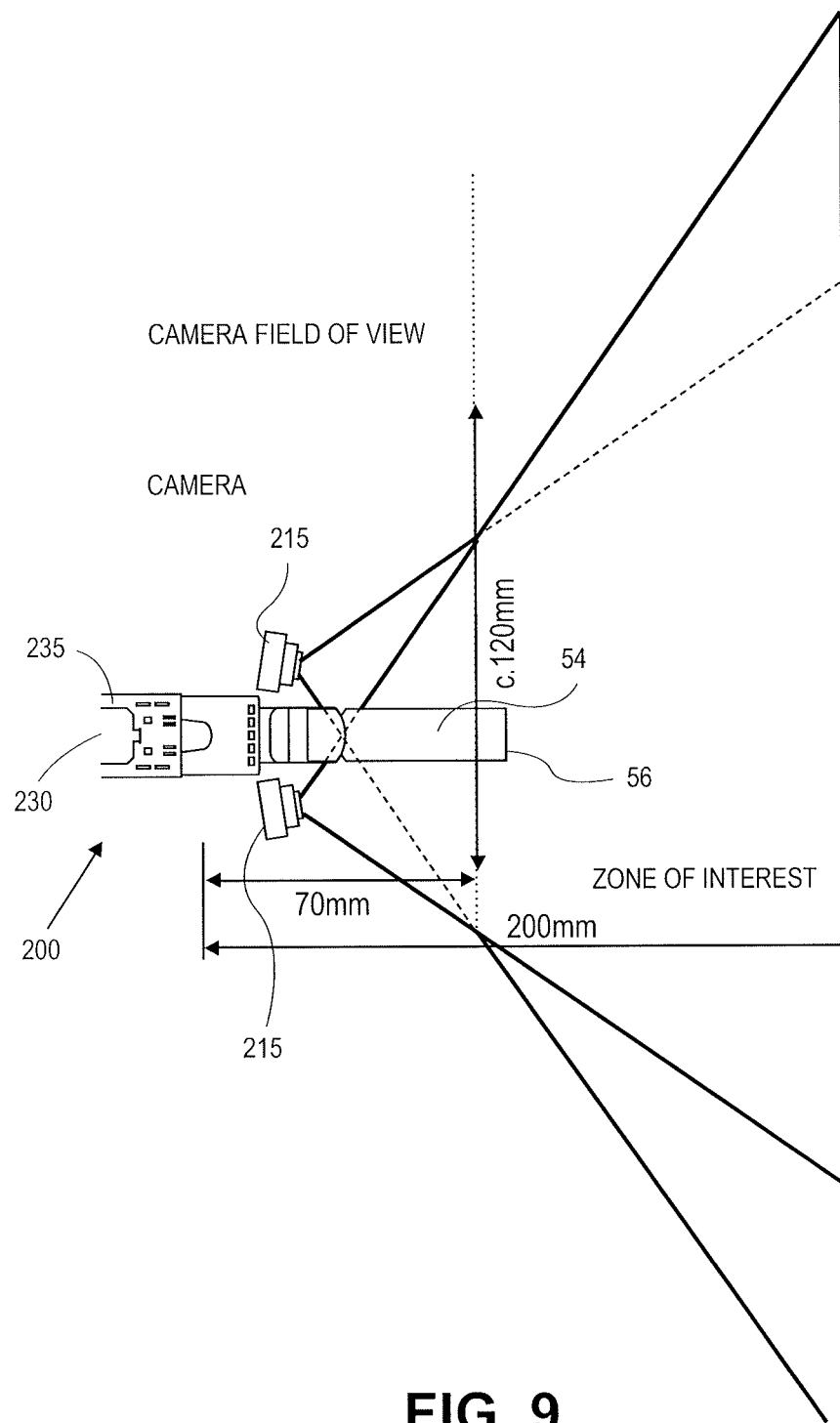
Figure 10:
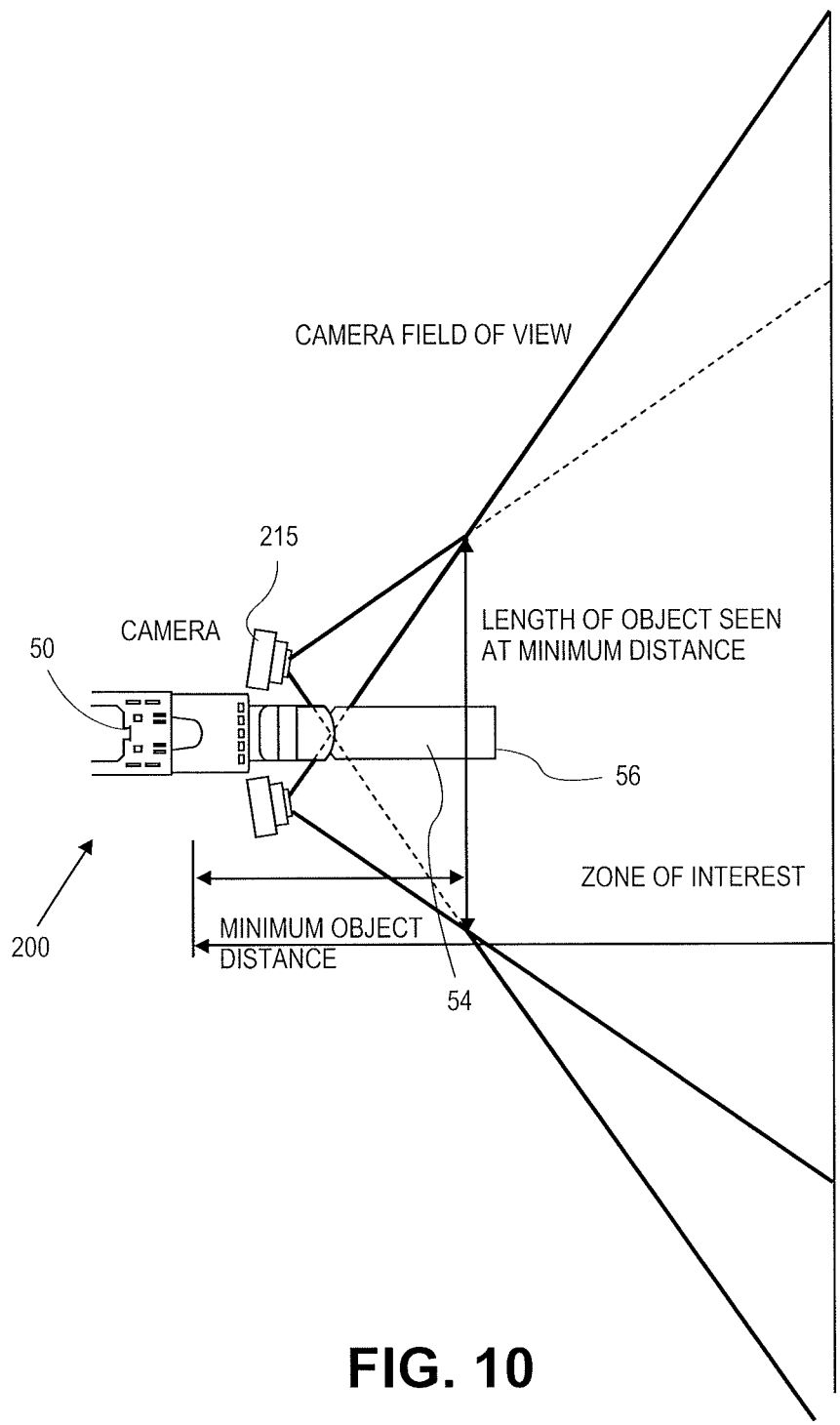

FIGS. 8A, 8B, 9 and 10 all illustrate the result on camera field of view for various angle orientations for the cameras included within an on tool tracking device. The cameras 115 in FIG. 8A are oriented in nearly parallel arrangement with regard to one another and the axis of the surgical tool 54. After accounting for blockage caused by other components, this configuration provides a camera field of view ranging from about 70 mm to about 200 mm. In other embodiments, the camera systems of an exemplary OTT device may operate in a camera field of view ranging from about 50 mm to about 250 mm. It is to be appreciated that the camera field of view may be physically or electronically altered depending upon the desired field of view needed for the particular computer aided surgery procedure that the OTT device will be used to perform.

Figure 11A:
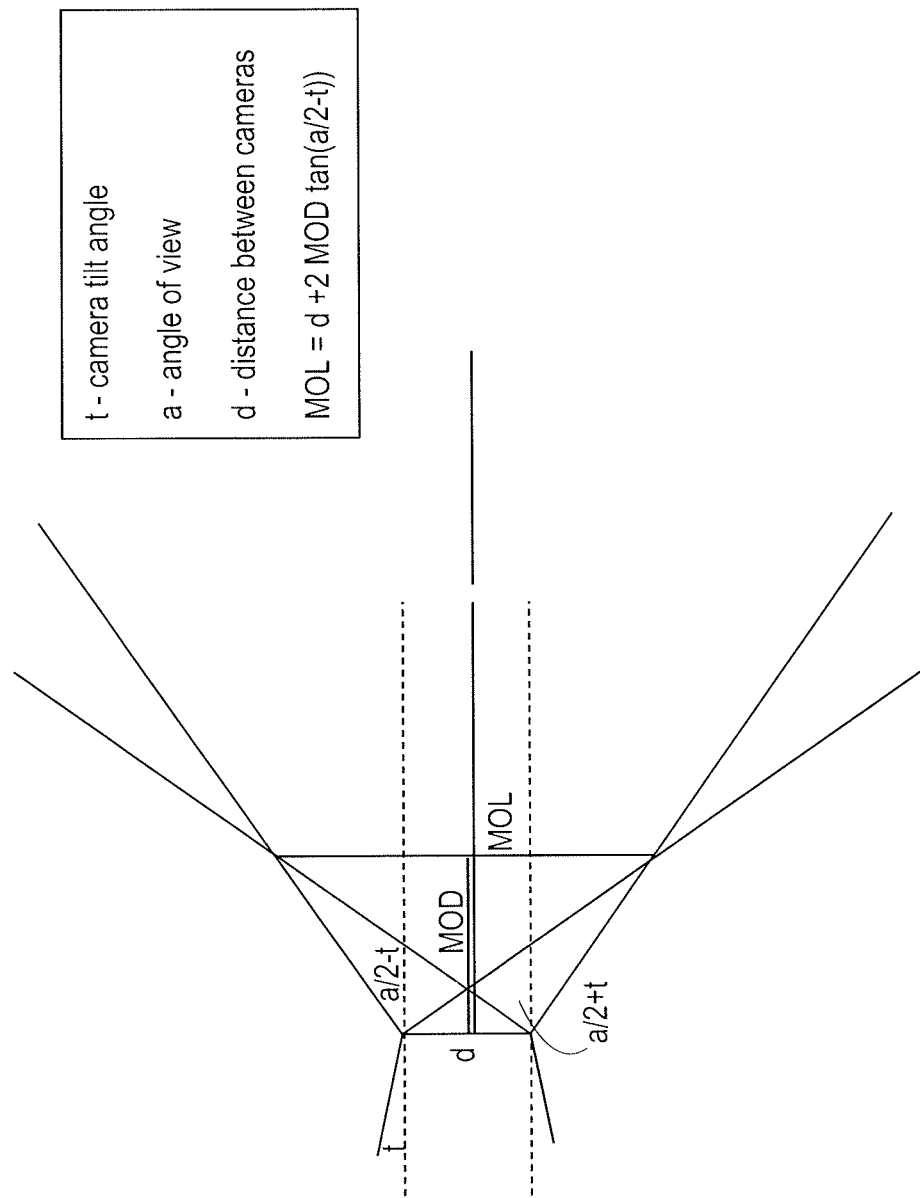
Figure 11C:
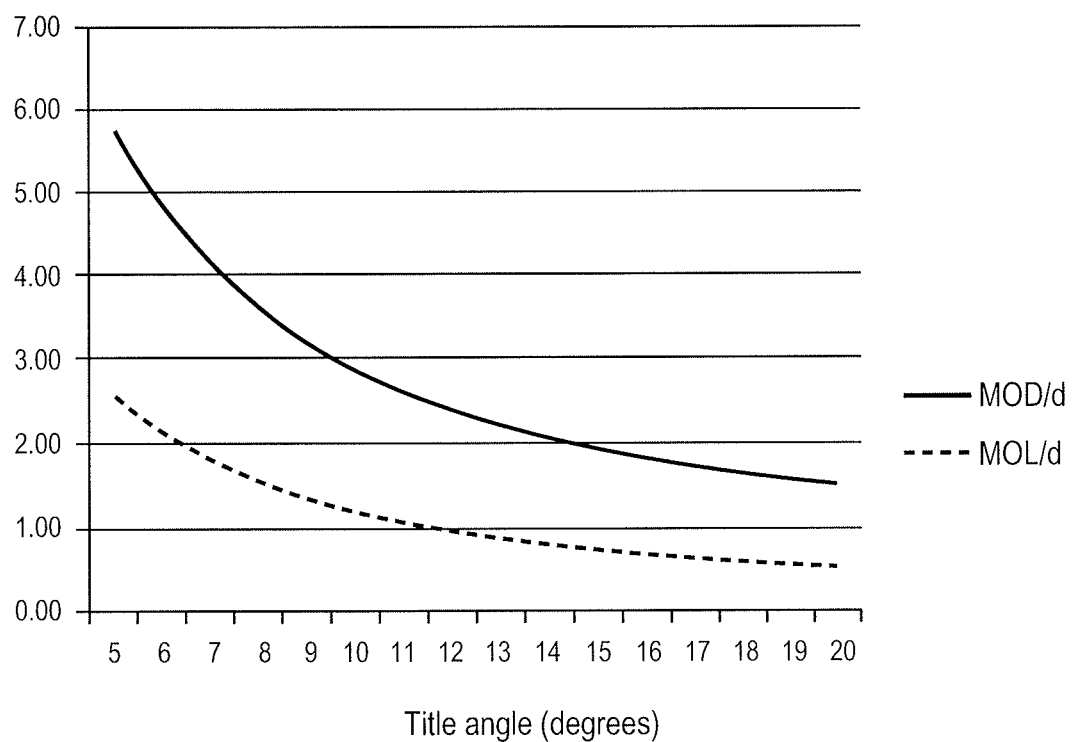
Figure 11D:
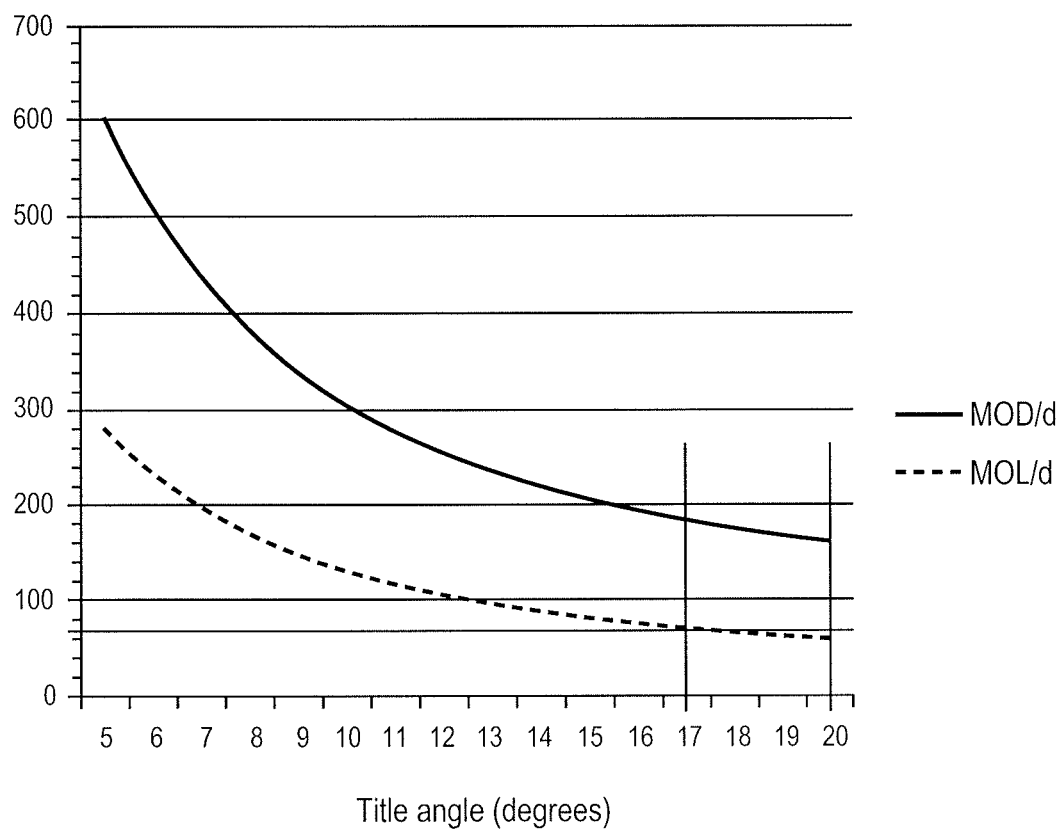

In contrast to the nearly parallel arrangement of the cameras in FIG. 8A, FIGS. 8B, 9 and 10 each demonstrate the result of different camera tilt angles and the resulting alteration of the camera field of view. The relationship of OTT camera positioning and tilt angle and their relationship to the angle of view, minimum object distance and maximum object length are better appreciated with reference to FIGS. 11A, 11B, 11C and 11D. FIG. 11A illustrates the geometric set up and formula for making the calculations used to produce the chart in FIG. 11B that relates tilt angle in degrees to a number of vision field factors. The data from this chart related to tilt angle is reproduced in the graphs shown in FIGS. 11C and 11D. The optical field information presented in these figures is useful in the design and optimization of camera positioning in some of the various embodiments of the OTT devices described herein.

Figure 12A:
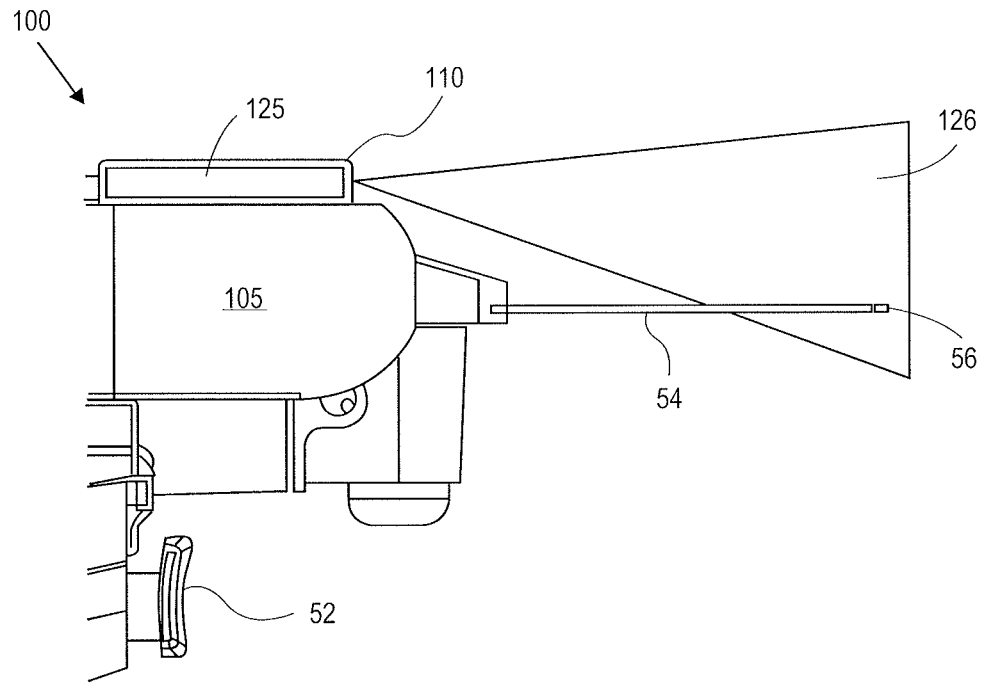
FIGS. 12A and 13A provide side and isometric views respectively of a projector used with an on tool tracking device.
Figure 12B:
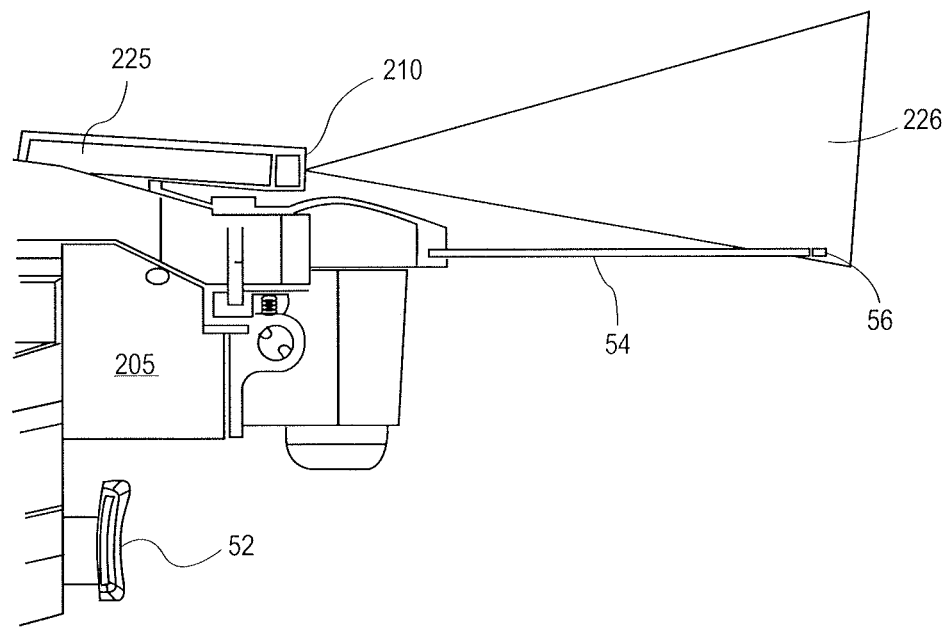
FIGS. 12B, 13B and 13C provide side, isometric and top views respectively of a projector in an angled orientation in use with an on tool tracking device.
Figure 13A:
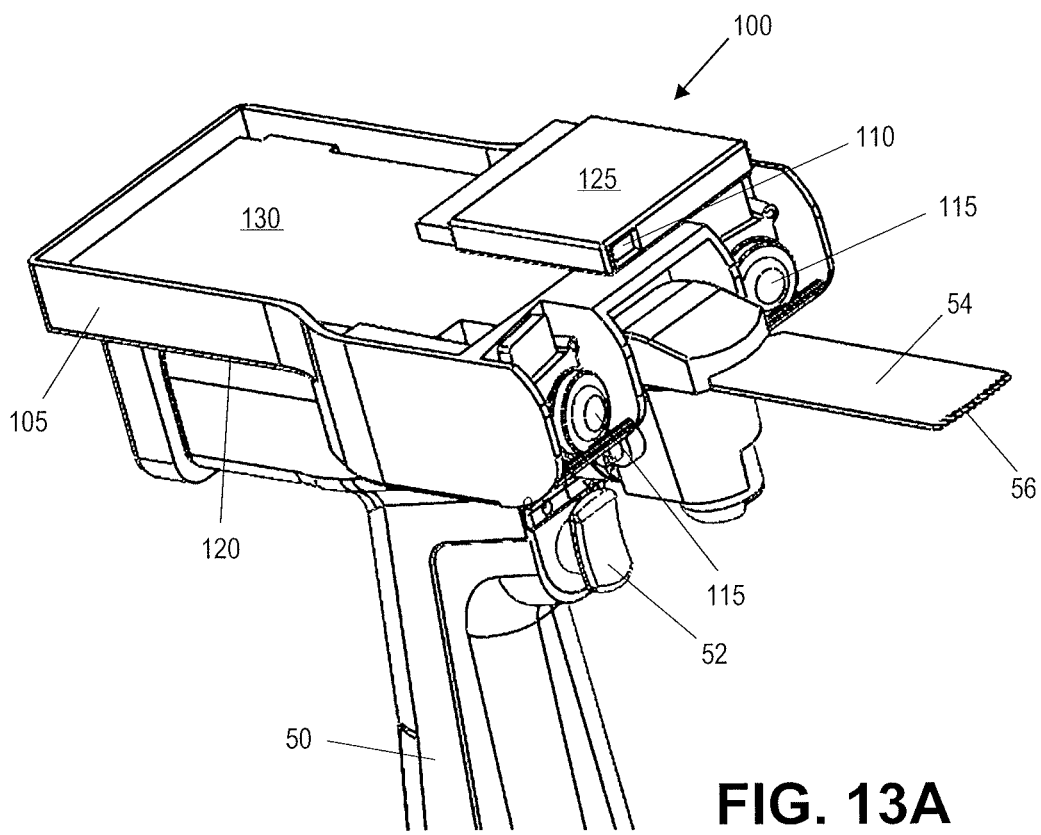
Figure 13B:
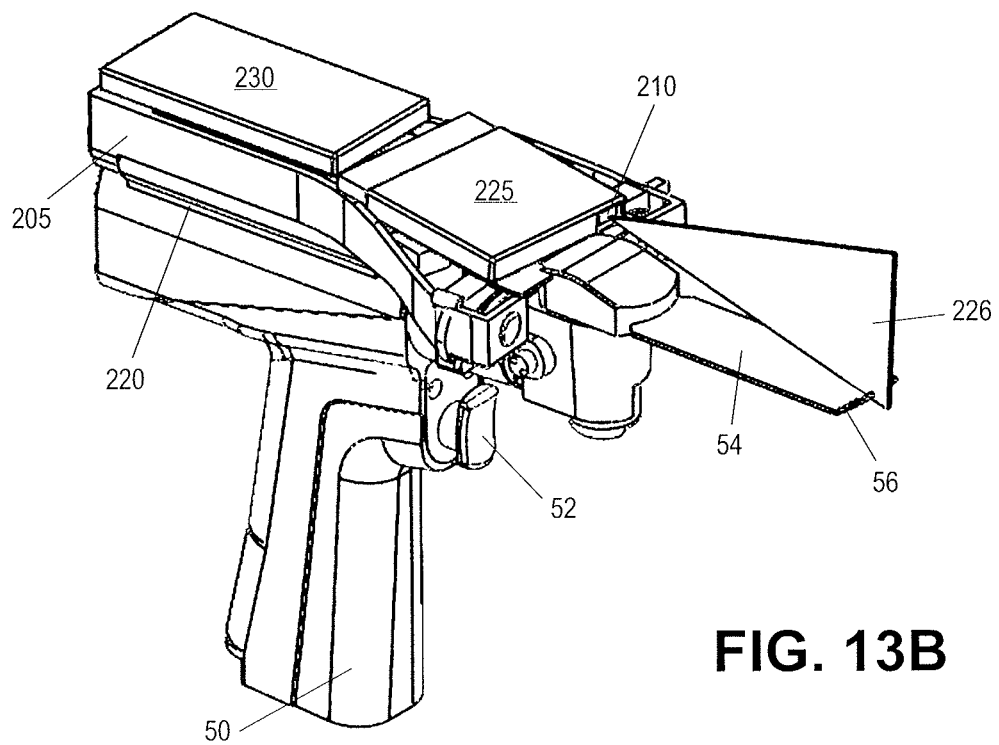
Figure 13C:
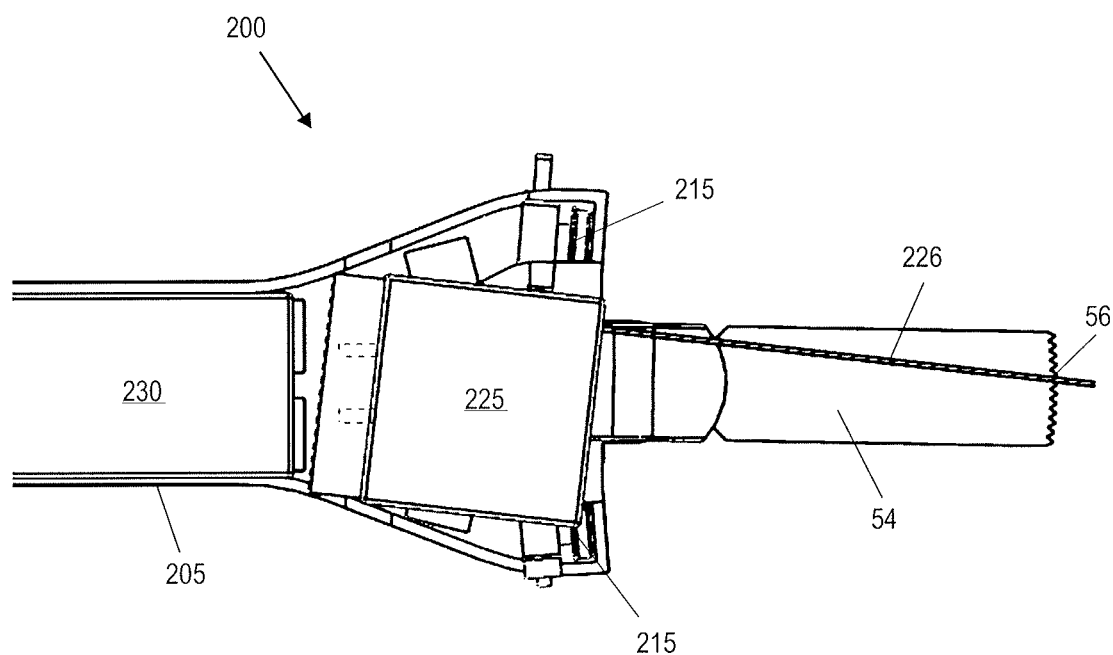

Additional aspects of the projector used with the various OTT embodiments may be appreciated for reference to FIGS. 12A, 12 B, 13A, 13B, and 13C. The impact on projector output based upon projector positioning within the OTT housing is demonstrated by a comparison between FIG. 12A and FIG. 12B. The projector 125 appears to be in a nearly planar relationship relative to the tool 54 as shown in both FIGS. 12A and 13A. However, notice how a portion of the projector output 126 extends beyond and below the tool (in this case saw blade) distal end 56. In contrast, the projector 225 is positioned at an acute angle in relation to the tool 54. Additionally, the projector 210 output is off to one side when compared to its relative position between the cameras 215. However, the projector output 226 is mostly above the blade 54 and crosses only at the distal end 56. Additional aspects of the projector output 226 are apparent upon review of the views in FIGS. 13A and 13B. It is to be appreciated that the projector outputs, projector size and orientations described in these embodiments is not limiting to all OTT device embodiments. A suitable OTT projector may be configured in a number of satisfactory ways and placement within the OTT housing, and may be adjusted based on package size of a desired projector. As is clearly illustrated by the sample outputs of the projector 225, many different projector sizes, orientations and angular relationships may be used and still be effectively operated to meet the projector requirements of the OTT CAS processing system. In other words, a wide variety of projector types, output locations and packaging may be used and still remain within the various embodiments of the OTT devices described herein.

Embodiments of the OTT device of the present invention are provided with a variety of imaging, projector and electronic components depending upon the specific operational characteristics desired for a particular OTT CAS system. The illustrative embodiments that follow are provided in order that the wide variety of characteristics and design factors may be appreciated for this part of the OTT CAS system.

Figure 14A:
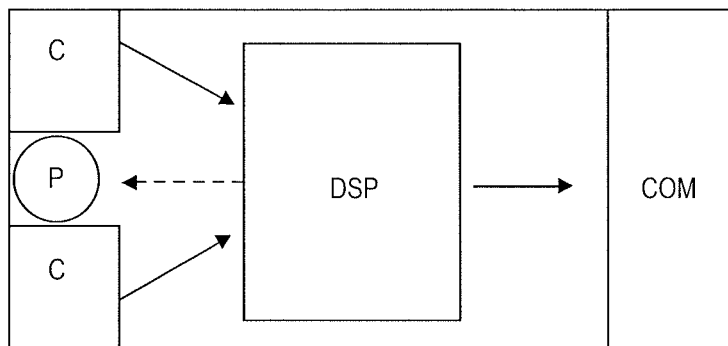
FIGS. 14A, 14B, 15A, and 15B each illustrate schematic views of several different electronic component configurations used by some on tool tracking device embodiments.

FIG. 14A illustrates a schematic of an embodiment of an OTT device. In this illustrated embodiment, there is provided

- Camera/dsp/processing (eg. NaturalPoint Optitrak SL-V120 range)
- Computer: PC—Windows 2000/XP/Vista/7; 1.5 GHz Processor; 256 MB of RAM; 5 MB of free hard disk space; USB 2.0 Hi-Speed port (minimum, faster is better)
- COM: Wireless Communication (eg. USB Port Replicator with Wireless USB support)
- Projector: (Laser Pico Projector type)

that are arranged within the OTT housing as shown in the view. This embodiment makes use of what is known as 'smart cameras'—cameras that have the capability of performing localized image processing. This processing can be programmable usually through Field Programmable Gate Arrays (FPGAs). The configuration of the components in this specific embodiment are utilized to provide image processing that occurs both on the OTT devices and on a OTT CAS computer. For example, DSP on the OTT device detects and processes marker data before transferring it to the OTT CAS computer. The configuration greatly reduces processing power required on the host computer while also minimizing the data needed to transmit. It is to be appreciated that the schematic view, while useful primarily to show the type of imaging, data processing and general computer processing capabilities of a particular OTT device or as between an OTT device and a OTT CAS computer, or as between an OTT device and one or more intermediary device driver computers, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an OTT CAS computer (if used) will vary depending upon the specific parameters and considerations of a particular OTT CAS procedure, mode or system utilized.

Figure 14B:
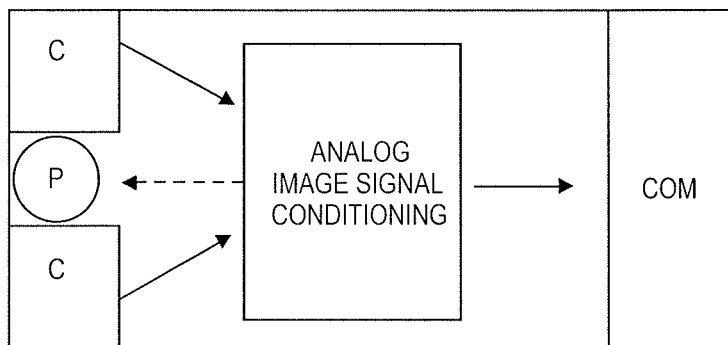

FIG. 14B illustrates a schematic of an embodiment of an OTT device. In this illustrated embodiment, there is provided Camera: Analog camera wired or wireless; eg FPV wireless camera DSP: uCFG Microcontroller Frame Grabber. This is connected to the PC PCI bus and becomes part of the PC.

Computer: Computer: PC—Windows 2000/XP/Vista/7; 1.5 GHz Processor; 256 MB of RAM; 5 MB of free hard disk space; USB 2.0 Hi-Speed port (minimum, faster is better)

COM: Hardwiring or Analog wireless transmitter

Projector: Microvision's SHOWWX Laser Pico Projector
that are arranged within the OTT housing as shown in the view. The configuration of the components in this specific embodiment are utilized to provide use of low cost commodity cameras where no image processing for tracking is performed onboard the OTT and the image signal is captured by a dedicated frame grabber that is part of the PC. The frame grabber accepts the captured image and deposits it into PC memory without any overhead processing by the PC. This embodiment results in a smaller, lighter and lower cost OTT device.

It is to be appreciated that the schematic view, while useful primarily to show the type of imaging, data processing and general computer processing capabilities of a particular OTT device or as between an OTT device and a OTT CAS computer or via one or more intermediary device driver computers, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an OTT CAS computer (if used) will vary depending upon the specific parameters and considerations of a particular OTT CAS procedure, mode or system utilized.

Figure 15A:
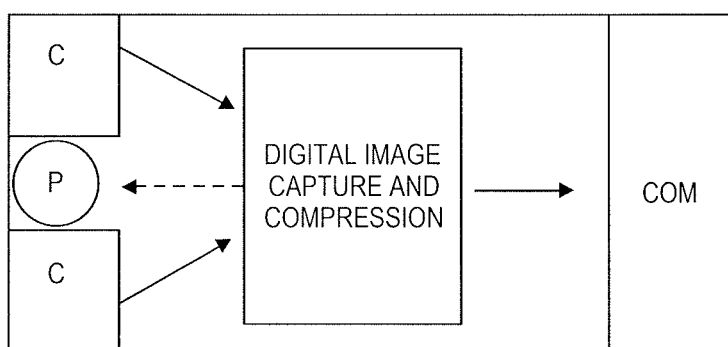

FIG. 15A illustrates a schematic of an embodiment of an OTT device. This embodiment utilizes commodity USB cameras with incorporated electronic circuitry that captures the image from the camera and conditions it to be USB compatible. This output is compressed and then transmitted through wires or wirelessly without further tracking related processing.

In this illustrated embodiment, there is provided

Camera: (e.g., miniature webcam)

Computer: (e.g., Dell Precision R5500 Rack Workstation)

COM: [e.g., Carambola 8 devices Core, or DTW-200D (CDMA2000 1x) and DTW-500D (EVDO Rev A)]

Miniature Projector: (e.g., Microvision's SHOWWX Laser Pico Projector)

that are arranged as shown in the view. The configuration of the components in this specific embodiment are utilized to provide a modular solution for providing the electronic OTT components. This embodiment uses commodity low cost cameras and allows the cameras to be used in a modular form where they can be changed or upgraded to reflect advances in technology without disrupting the OTT or the ground based systems.

There is no need to use an on-tool DSP if the OTT CAS or intermediary driver computer is optimized for DSP. This embodiment makes it possible to use any of the commercially available image processing libraries. For example, modern image processing software routines from open source or commercial libraries take only about 1 ms to process blobs (bone reference frame LEDs) and compute their centroids. Images can therefore be sent directly from the OTT tool to the OTT CAS Computer to be processed. It is important that the COM will need to be selected to handle higher bandwidth when compared to other embodiments. Similarly, the intermediary driver or OTT CAS Computer will need to be selected to handle more burdensome computation.

It is to be appreciated that the schematic view, while useful primarily to show the type of imaging, data processing and general computer processing capabilities of a particular OTT device or as between an OTT device and an intermediary driver or an OTT CAS computer, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and an intermediary driver (if used) or OTT CAS computer (if used) will vary depending upon the specific parameters and considerations of a particular OTT CAS procedure, mode or system utilized.

Figure 15B:
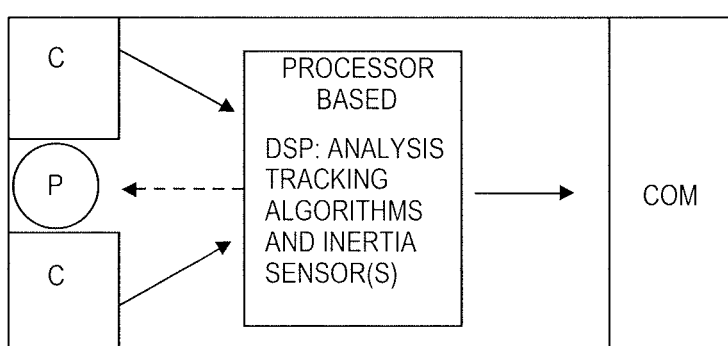

FIG. 15B illustrates a schematic of an embodiment of an OTT device. In this illustrated embodiment, there is provided Camera: Smart camera as in FIG. 15A or USB camera as in FIG. 15C

Inertia Sensors: (e.g., Bosch SMB380, Freescale PMMA7660, Kionix KXSD9)

Onboard processor: (e.g., ARM processor)

Computer: [e.g., PC—Windows 2000/XP/Vista/7; 1.5 GHz Processor; 256 MB of RAM; 5 MB of free hard disk space; USB 2.0 or USB 3.0 Hi-Speed port (minimum, faster is better)]

COM: (Standard IEEE 802.11 communications protocol or similar protocol for communication between the OTT borne processor and the ground station intermediary driver PC or OTT CAS PC.

Projector: (e.g., Microvision's SHOWWX Laser Pico Projector)

that are arranged as shown in the view. The configuration of the components in this specific embodiment are utilized to provide an embodiment that performs complex processing onboard the OTT device to accomplish most of the body tracking as needed for purposes of OTT CAS procedures. The device is a complete stand-alone tracking device. The OTT device further contains one or more inertia sensors. DSP involves the use of Inertia sensors to predict the location of the fiducials in the 'next frame'. As a result, the computational burden on the DSP on the OTT device is minimized.

It is to be appreciated that the schematic view, while useful primarily to show the type of imaging, data processing and general computer processing capabilities of a particular OTT device or as between an OTT device and an intermediary driver or OTT CAS computer, this view may not reflect the actual orientation, spacing and/or alignment between specific components. Electronic communications capabilities (COM) are provided via wired connection or any suitable wireless data transfer mode from and to a computer that is adapted and configured for use with OTT CAS processes, algorithms and modes described herein. The type, variety, amount, and quality of the processing data exchange between the OTT device and directly to an OTT CAS computer (if used) or via an intermediary driver computer will vary depending upon the specific parameters and considerations of a particular OTT CAS procedure, mode or system utilized.

In addition to the above described details and specific embodiments, it is to be appreciated that alternative embodiments of an OTT device may have electronic components including components with processing capabilities as well as software and firmware and electronic instructions to provide one or more of the following exemplary types of OTT CAS data in accordance with the OTT CAS processing methods, modes and algorithms described herein:

Receive and process visual and IR spectrum image data

Determining coordinates of the centroid of each of the markers within image frame Determining the sizes of all markers within an image frame Reporting the size and the coordinates of one or more fiducials Sub-pixel analysis to determine the location of the centroid within an image frame, a marker placement or selected marker placements Variable and controllable frame rate from 10 to 60 frames per second based on input from central computer or internal instructions or in response to an OTT CAS processing mode adaptation The inventive on tool tracking devices 100/200 illustrated and described in FIGS. 1-15B and FIGS. 47-52B may also include, for examples, one or more additional cameras, different types of camera functionality, as well as sensors that may be employed by an OTT CAS system as described herein and in FIGS. 31A-36, 63, 64 and 65. Various different OTT configurations will be described with reference to FIGS. 53-63A and 63B.

Figure 53:
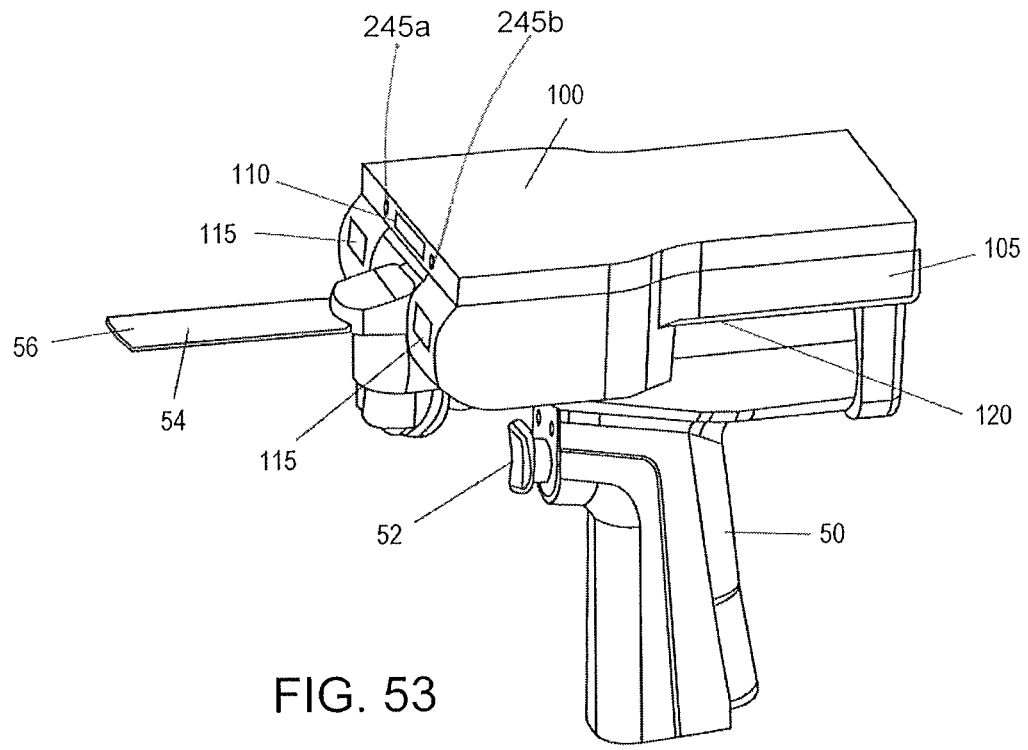
FIGS. 53, 54, 55, 56, 57A, 57B, 58, 59A and 59B illustrate various OTT module and multiple camera embodiments.

FIG. 53 is an isometric view of the on tool tracking device 100 mounted on the surgical tool 50. The embodiment of the on tool tracking device 100 illustrated in FIG. 53 a modified housing 105 and on-board electronics to include a pair of near field stereoscopic cameras 245a, 245b. In this embodiment the cameras 245a, 245b are mounted adjacent to the projector output or opening 110 near the top of the OTT housing 105. As described herein, the cameras 115 may be used to provide a wide field of view. The cameras 115 are mounted at the midpoint of the housing 105. The wide view stereoscopic cameras 115 are just above the plane that contains the surgical tool 54 that is being tracked by the OTT CAS system. In one aspect, the cameras or wide view cameras 115 are on opposite sides of the tool 54 under OTT CAS guidance. The OTT CAS system operation is similar to that described below in FIGS. 31A to 36 and FIGS. 63, 65 and 65 with the use of the additional camera inputs and data available for OTT CAS methods and techniques. The OTT CAS system and methods of performing freehand OTT CAS may be adapted to receive inputs from one or sets of cameras 115, 245a, 245b or from one or more of cameras 115, 245a, 245b in any combination. Furthermore, any camera of those illustrated may be used for tracking, display, measurement or guidance alone or in combination with the projector 225 in one or modes of operation under control of the OTT CAS system described herein.

Figure 54:
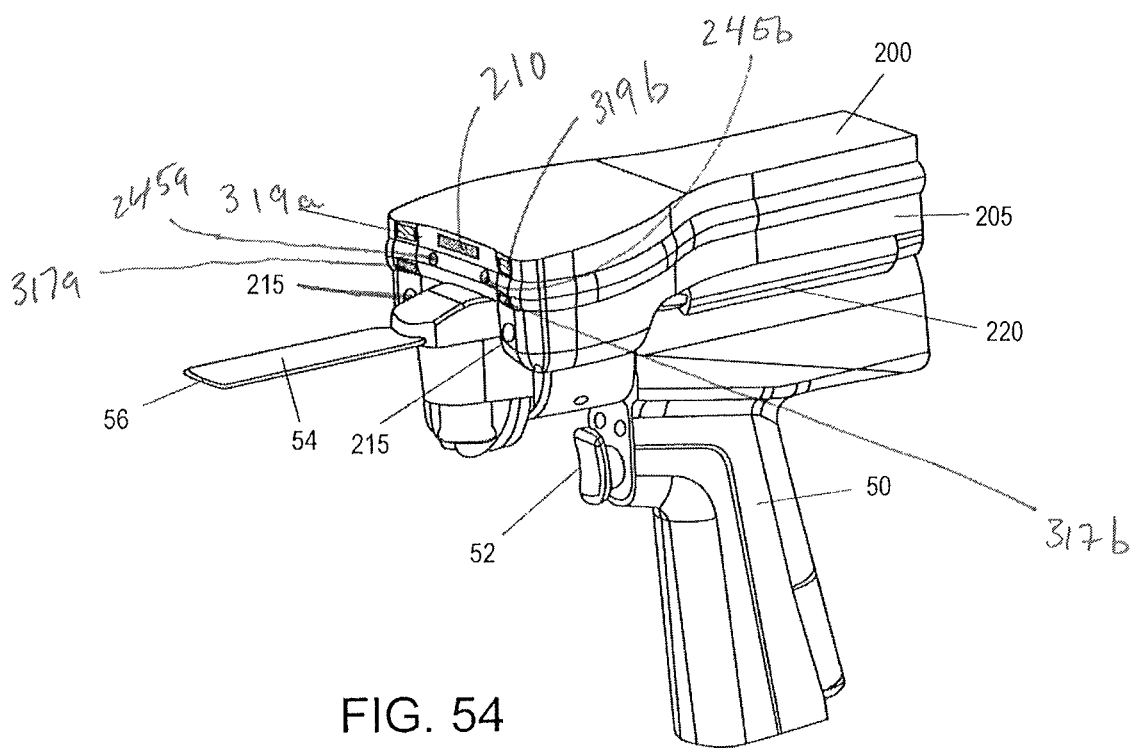

FIG. 54 is an isometric view of the on tool tracking device 200 mounted on the surgical tool 50. As described herein, the cameras 215 are mounted at the midpoint of the housing 205 used to provide a wide field of view. In this alternative embodiment of the on tool tracking device illustrated in FIG. 54, the housing 205 and on-board electronics are modified to include a pair of near field stereoscopic cameras 245a, 245b as in FIG. 53 along with additional cameras 317a, 317b, 319a, and 319b. The additional cameras may provide, for example, an additional wide field view (i.e., wider than that provide by cameras 215) or be configured as IR cameras. As with FIG. 53 the cameras 245a, 245b are mounted adjacent to the projector output or opening 110 near the top of the OTT housing 205. Cameras 319a and 319b are shown mounted adjacent to the projector output or opening 210 near the top of the OTT housing 205. The wide view stereoscopic cameras 215 are just above the plane that contains the surgical tool 54 that is being tracked by the OTT CAS system. Additional cameras 317a, 317b are provided between the cameras 245a, 245b and the cameras 215. In one aspect, the cameras or wide view cameras 215 are on opposite sides of the tool 54 under OTT CAS guidance. The OTT CAS system operation is similar to that described below in FIGS. 31A to 36 and FIGS. 63, 65 and 65 with the use of the additional camera inputs and data available for OTT CAS methods and techniques. The OTT CAS system and methods of performing freehand OTT CAS may be adapted to receive inputs from one or sets of cameras 215, 245a, 245b, 317a, 317b, 319a or 319b or from one or more of cameras 215, 245a, 245b, 317a, 317b, 319a or 319b in any combination. Furthermore, any camera of those illustrated may be used for tracking, display, measurement or guidance alone or in combination with the projector 225 in one or modes of operation under direct or indirect (via intermediary driver computer) control of the OTT CAS system described herein.

Figure 55:
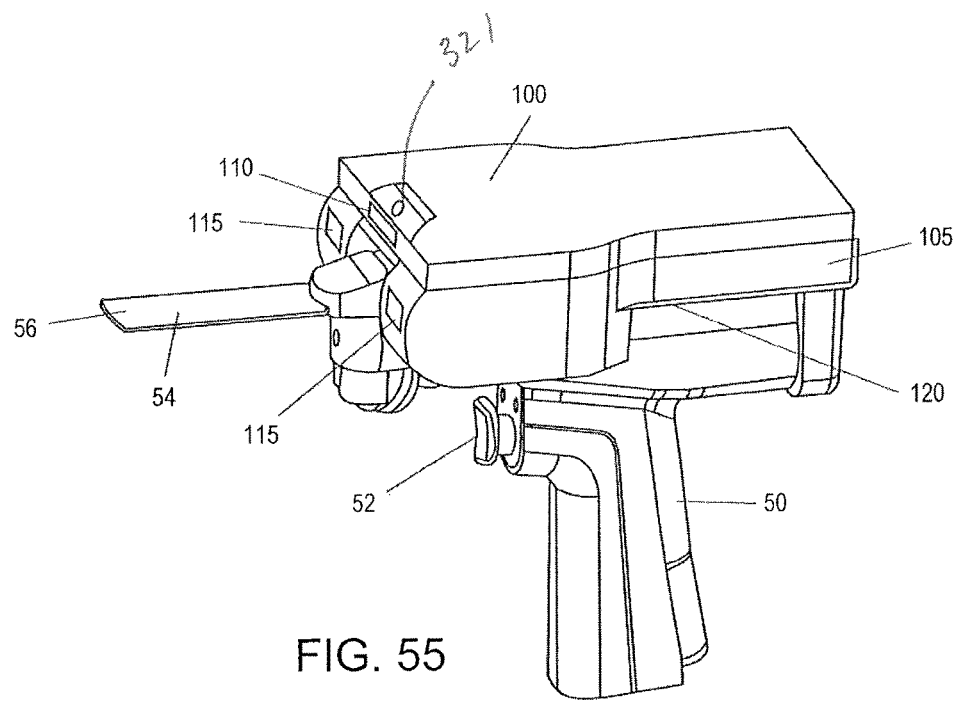

FIG. 55 is an isometric view of the on tool tracking device 100 mounted on the surgical tool 50. The embodiment of the on tool tracking device 100 illustrated in FIG. 55 has a modified housing 105 and on-board electronics to include a single, centrally located camera 321 located above the projector output 110. In this embodiment the camera 321 is mounted adjacent to the projector output or opening 110 build into the top of the OTT housing 105. As described herein, the camera 321 may be used to provide a variety of different fields of view either through mechanical or electronic lens control alone or in combination with software based imaging processing. As illustrated, the camera 321 is mounted at or near the central axis of the tool 54 with a clear view of the active element 56 or other tracking point on the tool 50. The stereoscopic cameras 115 are also shown just above the plane that contains the surgical tool 54 that is being tracked by the OTT CAS system. In one aspect, the cameras 115 are on opposite sides of the tool 54 under OTT CAS guidance. The OTT CAS system operation is similar to that described below in FIGS. 31A to 36 and FIGS. 63, 65 and 65 with the use of the additional camera input and data available for OTT CAS methods and techniques. The OTT CAS system and methods of performing freehand OTT CAS may be adapted to receive inputs from one or sets of cameras 115 or 321 or from one or more of cameras 115 or 321 in any combination. Furthermore, any camera of those illustrated may be used for tracking, display, measurement or guidance alone or in combination with the projector 225 in one or more modes of operation under direct or indirect control of the OTT CAS system described herein.

Figure 56:
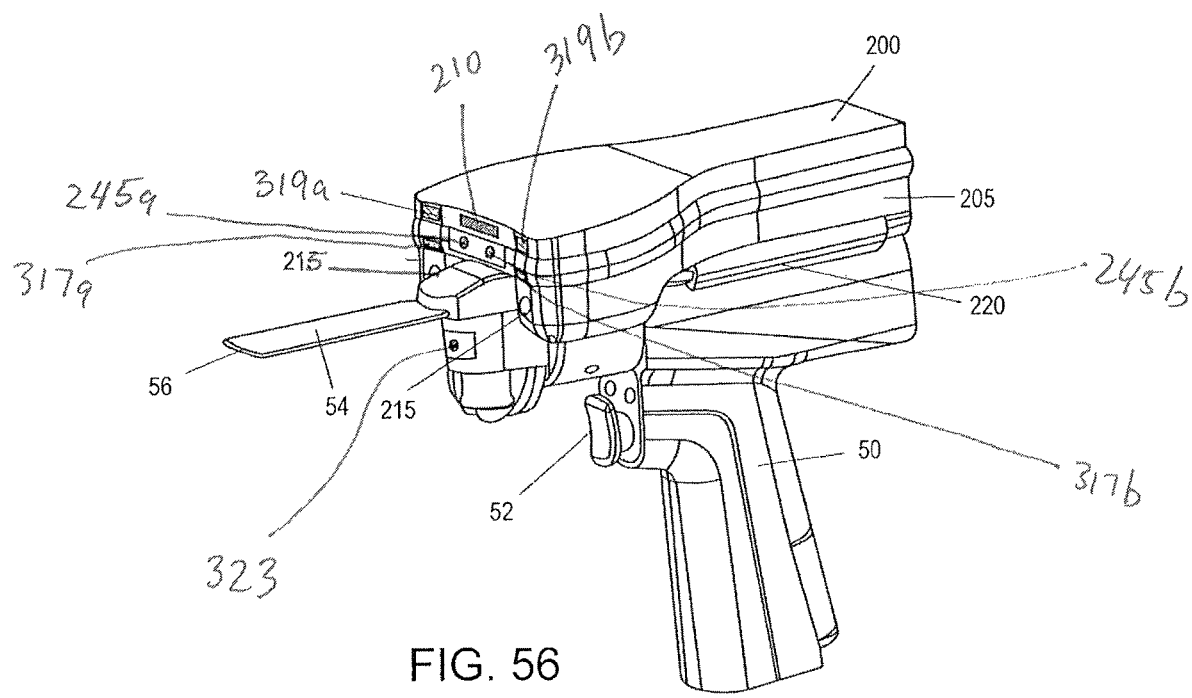

FIG. 56 is an isometric view of the on tool tracking device 200 mounted on the surgical tool 50. This OTT device embodiment is similar to that of FIG. 54 with an addition single camera provided as in FIG. 55. In contrast to FIG. 55, the single camera 323 in FIG. 56 is provided below the tool 53 and active element 56 being tracked under an OTT CAS system. One advantage of the location of camera 323 is that some tools 54—such as the illustrated saw—may block portions of the views available to other camera. In those instances, the input from camera 323 may be used to augment other imaging inputs provided to the OTT CAS system. Additionally, the camera 323 may be particularly useful in monitoring one or more reference frames or markers used as part of the OTT CAS guidance of the attached surgical tool 50. As described herein, the cameras 215 are mounted at the midpoint of the housing 205 used to provide a wide field of view. In this embodiment the camera 323 is mounted in a forward projection of the housing 205 below the tool 54. As described herein, the camera 323 may be used to provide a variety of different fields of view either through mechanical or electronic lens control alone or in combination with software based imaging processing. As illustrated, the camera 323 is mounted at or near the central axis of the tool 54 with a clear view of the underside of the active element 56 or other tracking point on the tool 50. In this alternative embodiment of the on tool tracking device illustrated in FIG. 54, the housing 205 and on-board electronics are modified to include the various cameras of FIG. 54 along with the single camera 323. The OTT CAS system operation is similar to that described above with reference to FIG. 54 as well as below in FIGS. 31A to 36 and FIGS. 63, 65 and 65 with the use of the additional camera inputs and data available for OTT CAS methods and techniques. The OTT CAS system and methods of performing freehand OTT CAS may be adapted to receive inputs from one or sets of cameras 215, 245a, 245b, 317a, 317b, 319a, 319b or 323 or, from one or more of cameras 215, 245a, 245b, 317a, 317b, 319a, 319b or 323 in any combination. Furthermore, any camera of those illustrated may be used for tracking, display, measurement or guidance alone or in combination with the projector 225 in one or modes of operation under control of the OTT CAS system described herein. It is to be appreciated that the single cameras as shown in FIGS. 55 and 56 may be combined into an OTT device as illustrated in FIG. 55 or in combination with other OTT device embodiments.

Figure 57A:
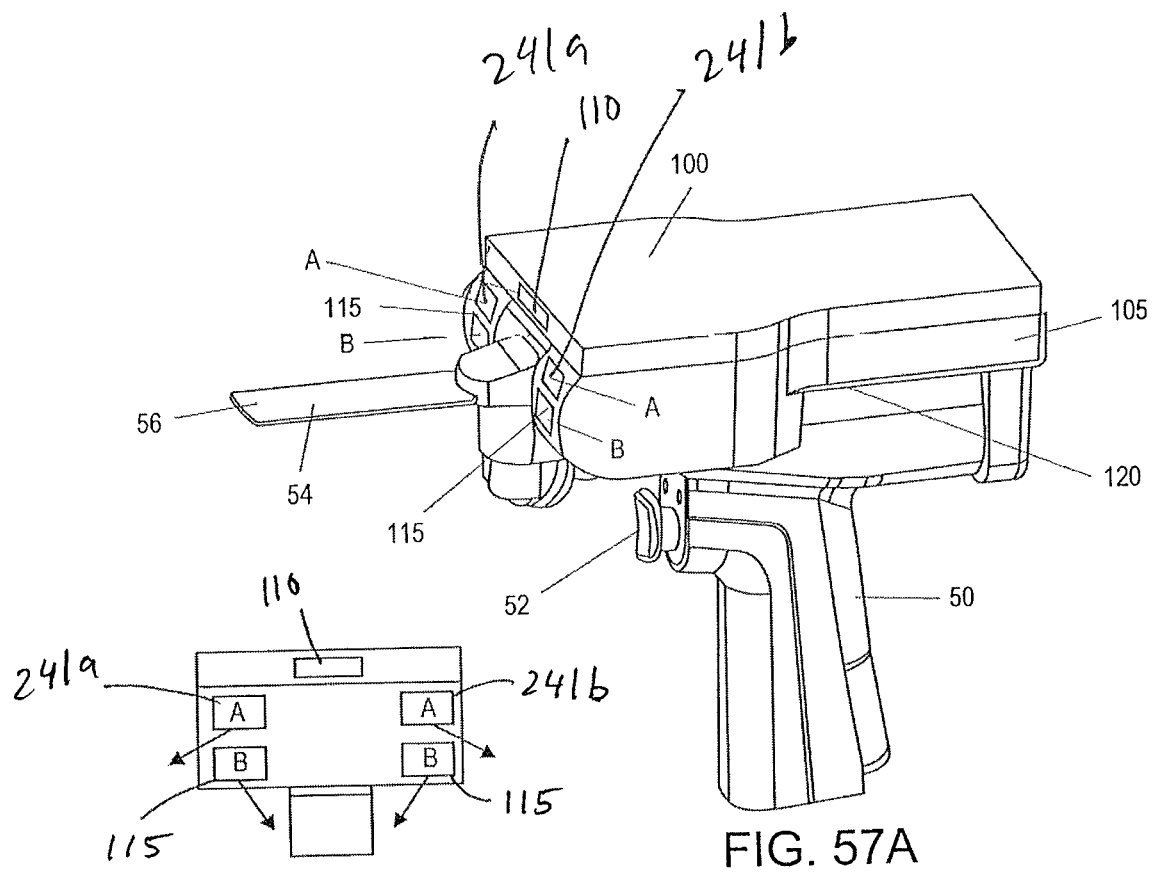
Figure 57B:
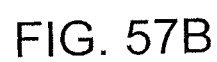

FIG. 57A is an isometric view of the on tool tracking device 100 mounted on the surgical tool 50. The embodiment of the on tool tracking device 100 illustrated in FIG. 57 has a modified housing 105 and on-board electronics to include an additional pair of cameras 241a, 241b located about the same aspect as cameras 115 and below the projector output 110. In this embodiment the cameras 241a, b are mounted in the OTT housing 105 as with cameras 115. As described herein, the cameras 115, 241a, 241b may be used to provide a variety of different fields of view either through mechanical or electronic lens control alone or in combination with software based imaging processing. As illustrated in FIG. 57B the cameras may by be used to provide different fields of view either by angling the cameras or by having the cameras 115 241a, 241b mounted on a movable stage that provides for altering the direction of camera orientation. FIG. 57B illustrates the embodiment where the cameras 115 are directed inwardly towards the central axis of the tool while the cameras 241a, 241b are directed outward of the central axis. The cameras may obtain the orientations of FIG. 57B by fixed or movable stages. The cameras in FIG. 57A, 57B are also shown just above the plane that contains the surgical tool 54 that is being tracked by the OTT CAS system. In one aspect, one camera of each pair of cameras is provided on opposite sides of the tool 54 under OTT CAS guidance. The OTT CAS system operation is similar to that described below in FIGS. 31A to 36 and FIGS. 63, 65 and 65 with the use of the additional camera input and data available for OTT CAS methods and techniques. The OTT CAS system and methods of performing freehand OTT CAS may be adapted to receive inputs from one or sets of cameras 115 or 241a, 241b or from one or more of cameras 115 or 241a, 241b in any combination. Furthermore, any camera of those illustrated may be used for tracking, display, measurement or guidance alone or in combination with the projector 225 in one or modes of operation under control of the OTT CAS system described herein.

Figure 58:
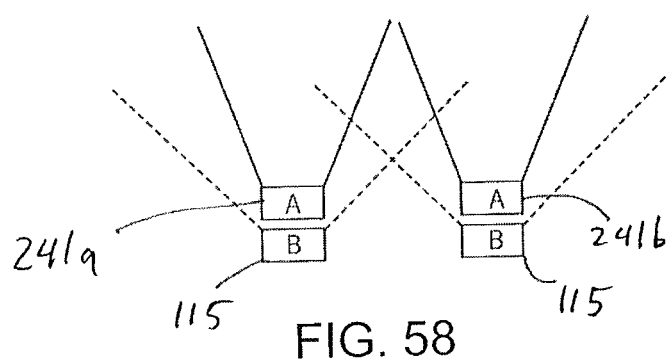

FIG. 58 illustrates another alternative embodiment of camera variation for the configuration illustrated in FIGS. 57A and 57B. In one alternative aspect, the cameras of FIG. 57A may be adjusted—via software or other suitable imaging processes—to provide the view of view illustrated in FIG. 58. In this embodiment, two pairs of cameras are provided as with the embodiment of FIG. 57A. In this embodiment of the camera of the OTT system, the camera angles A do not overlap as shown. The A angles are used to enhance the sides of the tool 54. In the image processing system the various views are synthesized into a unified view by the image processing system of the CAS tracking and guidance system. FIG. 58 illustrates the upper cameras (241a, 241b or A cameras) with a narrow and non-overlapping field of view within the surgical field. The lower cameras (115 or B cameras) have a wider and overlapping field of view. In this embodiment, the image tracking system is able to use the wider overlapping field of view and the narrow focused fields of view in order to provide a variety of different tracking schemes by synthesizing and obtaining information from the various camera views that are provided. The OTT CAS system operation is similar to that described below in FIGS. 31A to 36 and FIGS. 63, 65 and 65 with the use of the additional camera input and data available for OTT CAS methods and techniques. The OTT CAS system and methods of performing freehand OTT CAS may be adapted to receive inputs from one or sets of cameras 115 or 241a, 241b or from one or more of cameras 115 or 241a, 241b in any combination. Furthermore, any camera of those illustrated may be used for tracking, display, measurement or guidance alone or in combination with the projector 225 in one or modes of operation under control of the OTT CAS system described herein.

Figure 59A:
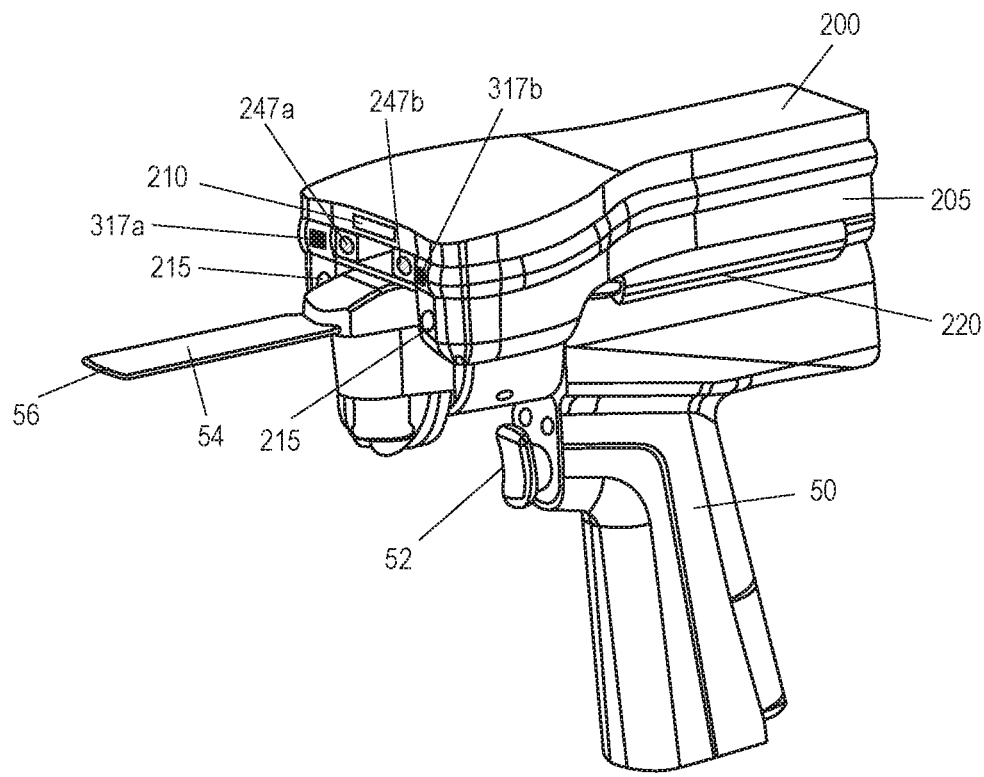
Figure 59B:
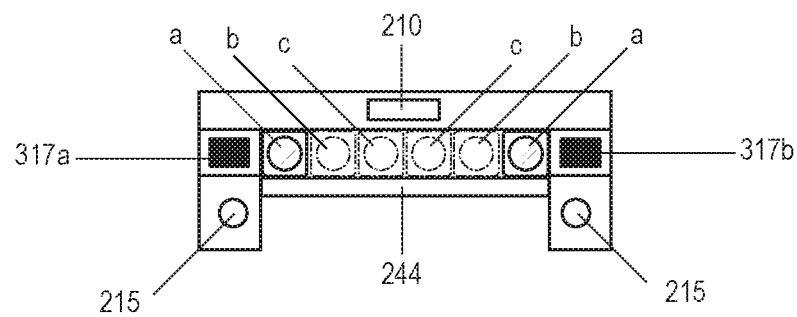

FIG. 59A is an isometric view of the on tool tracking device 200 mounted on the surgical tool 50. This OTT device embodiment is similar to that of FIG. 54 with a moveable camera stage 244 in place of camera pair 315a, 315b and without camera pair 319a, 319b. In this alternative embodiment of the on tool tracking device illustrated in FIG. 59A, the housing 205 and on-board electronics are modified to include a moveable camera stage 244 and included camera pair 247a, 247b. As in FIG. 54, the embodiment of FIG. 59A also includes cameras 215, 317a, and 317b. The additional cameras may provide, for example, an additional field or variable fields of view through OTT CAS system controlled operation of the stage 244. The stage 244 is shown mounted adjacent to the projector output or opening 210 near the top of the OTT housing 205. The stage 244 is provided with motors, a stage or other controlled movement device permitting the spacing between and/or angulation and/or focus of the cameras 247a, 247b to change. As best seen in FIG. 59B the cameras 247a, 247b may move from a wide angle position ("a" positions) a mid-range position ("b" positions) or a narrow range position ("c" position).

In addition or alternatively, the camera motion and selection of view along with the control of the camera motors, stage or other movement device are, in some embodiments, controlled based on user selected inputs such as a pre-set camera view in a smart views system. In still another alternative, the position or orientation of a camera or camera stage or motion device may vary automatically based upon the operations of an embodiment of the CAS hover control system described herein. By utilizing the camera movement capabilities of this embodiment, the image tracking system is also able to use a camera motor controller to obtain wider, mid-range or narrow field imaging as desired based on other CAS hover system parameters and instructions. As such, the moving camera capabilities of this embodiment of an OTT system provides a variety of different tracking schemes by synthesizing and obtaining information from the various camera views that are provided by the camera motion. The OTT CAS system operation is similar to that described below in FIGS. 31A to 36 and FIGS. 63, 65 and 65 with the use of the additional camera inputs and data available for OTT CAS methods and techniques as well as the ability for the OTT CAs system to control the movement of cameras 247a, 247b depending upon OTT CAS techniques and methods described below. The OTT CAS system and methods of performing freehand OTT CAS may be adapted to receive inputs from one or sets of cameras 215, 247a, 247b, 317a, or 317b or from one or more of cameras 215, 247a, 247b, 317a, or 317b in any combination. Furthermore, any camera of those illustrated may be used for tracking, display, measurement or guidance alone or in combination with the projector 225 in one or modes of operation under control of the OTT CAS system described herein.

In still further alternative aspects, it is to be appreciated that any of the OTT device embodiments described herein may, in addition to having multiple cameras or sets of cameras, may provide each camera with filters via hardware and/or software so that each camera may be used in either or both of the visible spectrum and the infrared spectrum. In such case, the two pairs of cameras can be thought as four set of cameras since in one sense the camera operates in the visible field and then those same cameras are operated via filters in the infrared field.

In still further alternative aspects, the OTT device embodiments described herein may, in addition to having multiple cameras or sets of cameras, may utilize any one or more of the onboard cameras to capture images for the purpose of recording and zooming while recording a certain aspect of the procedure for documentation, training or assessment purposes. In still another aspect, there is provided on an OTT module in software or firmware instructions a rolling recording loop of a preset time duration. The time duration could be any length of time as related to a complete OTT CAS procedure, step or portion of a step or planning or registration as related to a OTT CAS procedure or use of an OTT CAS device. There may be storage provided directly on the OTT CAS or on a related computer system. In one aspect, an OTT CAS module or electronics device includes a memory card slot or access to permit recording/storing the camera and/or projector outputs along with all or a portion of a OTT CAS surgical plan or images used in an OTT CAS plan. Still further, the video data and image storage may be on the OTT either a USB or other port or there is just a memory card as is common with handheld video cameras. The feed from the OTT camera(s) is recorded either on command, always on or done in response to a user or system input such as a mouse click, touch screen input, voice command and the like. Imaging data may be stored on the OTT itself or a device or another computer. In one example, the OTT CAS image data referenced here is stored, for example, on an intermediary driver computer. In still another aspect, the recording mentioned herein is started manually from a remotely sent command to the OTT from the master CAS computer, or, optionally from a touch screen command of the LCD screen onboard the OTT device. The commands can be "start video recording", stop video recording", "capture single image" etc. The recorded data or stored images can be stored locally on the OTT, and/or immediately or later relayed to the intermediary driver computer or to the master CAS computer to be associated with the surgical case file.

FIGS. 60, 61, 62A and 62B provide various alternative views of the OTT device electronics package illustrated and described with reference to FIGS. 5, 6 and 7. The various views of FIGS. 60, 61, 62A and 62B illustrate the wide variety of locations and sensor types that optionally may be incorporated into the various embodiments of the OTT device as well as providing further inputs, processing data or enhancements to the various alternative OTT CAS system embodiments and the alternative methods of using the same. In the exemplary representations of FIGS. 60-62B, a number of different sensor locations are provided. More or different locations are possible as well as the placement of sensors in each of the illustrative locations in different orientations or having multiple types of sensors or of the same type of sensor in one location.

Moreover, for each embodiment of a sensor enabled OTT device, each sensor location utilized has a corresponding modification to the housing 110/210, electronics 130, 230 along with the related specifications and details of FIGS. 5-15B as needed based on the number and type, or numbers and types of sensors employed in that embodiment. In addition, the OTT device is also modified and configured to provide as needed the appropriate number and type of electronic mounts, mechanical or structural supports, electronic or vibration insulation, electrical/data connections, hardware, software, firmware and all related configurations to provide for operation and utilization of each sensor type. The type, number and location of sensors on an OTT device are employed in order to provide enhanced information about the OTT device and/or CAS operating environment in conjunction with other tracking and operating parameters already employed by the OTT CAS system and described herein.

In various alternative operating schemes of utilizing a sensor enhanced OTT device, the OTT CAS system operations, decision making, mode selection and execution of instructions is adapted based upon the addition of data from one or more OTT device sensors to provide one or more of: position, movement, vibration, orientation, acceleration, roll, pitch, and/or yaw, each alone or in any combination as related to the OTT device itself or the surgical tool under OTT tracking and guidance. Still further, multiple sensors or detection or measurement devices of the same type may be placed on the OTT device in different positions and then those same input types from each of the different locations may also be used to provide additional OTT CAS operational inputs, determinations or control factors. Each of the separate sensor outputs or readings may be used individually or the data from the same types of sensors may be collected together and averaged according to the type of sensor and data use. Still further, the collection and use of sensor data (i.e., sampling rate, weighting factors, or other variables applied based upon hover mode state, and/or adjustment of one or more CAS system parameter) may be adjusted according to the various operational schemes described in FIGS. 31A-36 and in particular with regard to adjustments to operating parameters such as slew rate and data collection rates as described in FIG. 63.

Figure 60:
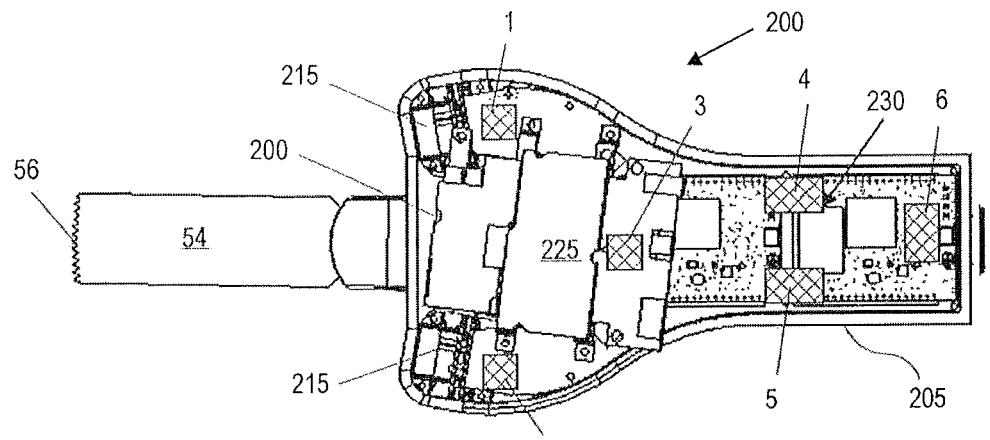
FIGS. 60, 61, 62A and 62B illustrate various OTT enabled sensor locations.

Turning now to FIG. 60, there is shown a top view of an embodiment of the OTT device 200 with the top of housing 205 removed. Sensor locations 1, 2, 3, 4, 5 and 6 are seen in this view. Sensor locations 1 and 2 are outboard on either side of the OTT device centerline. In this embodiment, the sensor locations 1, 2 are adjacent to the cameras 215. An additional sensor location 3 is illustrated in the central portion of the OTT device. The sensor location 3 may be positioned in, for example, the geometric center of the OTT device, at the center of mass or gravity of the OTT device, or at the center of mass or gravity for the combined OTT device/tool. The location of sensor position 3 may therefore be changed based on the type of tool 50 attached to the OTT device. In addition or alternatively, for OTT device embodiments configured to operate with a variety of different tool types, a corresponding number of appropriately positioned sensors may be placed depending upon the specific type of tool used. In these embodiments, the OTT CAS system is also configured to recognize or receive input as to the type of tool attached to the OTT device and then select or utilize the output from the sensor or sensors in the sensor locations and sensor types associated with that particular tool configuration.

Sensor locations 4 and 5 are positioned towards the rear on the left and right outer edges of the OTT housing 205. Sensor position 6 is on the central portion near the rear of the housing 205. The use of sensor locations 1, 2, 4, 5 and 6 alone or in any combination may be used in obtaining one or more or roll, pitch, or yaw angle data as well as inclination and/or multiple axis movement rates or vibration reading in each of these locations.

Figure 61:
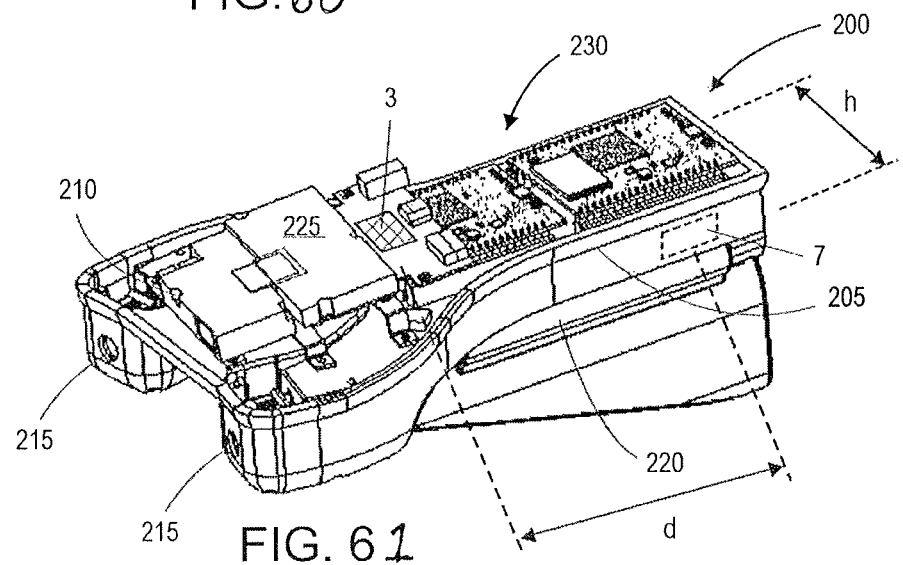

FIG. 61 is a perspective view of the OTT housing 205 of the view of FIG. 60. From this view, the sensor location 3 can be seen in its point near the center of the system. Sensor position 7 that is internal to the housing 205 is shown in phantom along the housing left side. The sensor position 7 is on or within the left wall portion towards the rear of the OTT housing 205. FIG. 61, illustrates the coordinate position of sensor location 7. In this illustrative example, the sensor location 7 is shown relative to a central OTT location, here sensor location 3. Any reference point may be used by the OTT CAS system directly or through a sensor driver intermediary computer for coordination and cross reference of the various sensor inputs. In this example, the sensor location 7 is—relative to the central location 3—spaced rearward by a distance of d. In addition, the sensor location number 7 is spaced by a height h from the elevation of the sensor location 3. The specific location of each one of the sensors may be used to advantage when determining the various parameters of the OTT in use. It is to be appreciated that the OTT CAS system may use absolute x, y, z coordinates, or relative coordinates for the sensor locations employed by an OTT device embodiment.

Figure 62A:
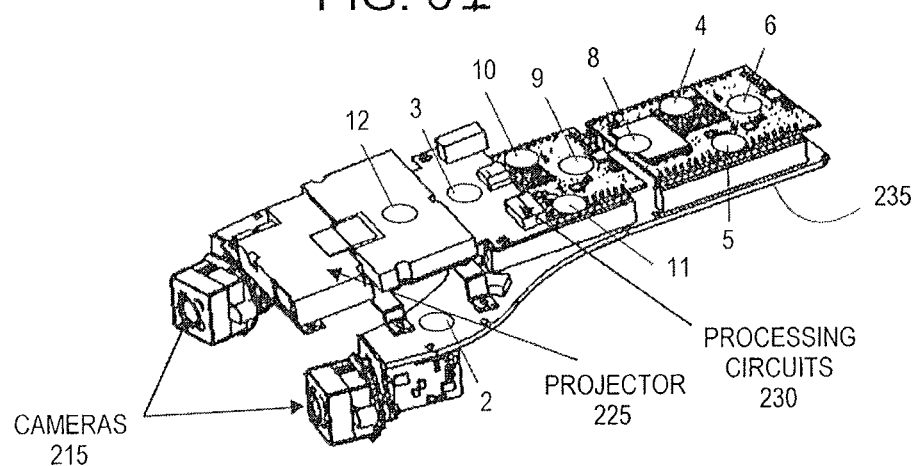
Figure 62:
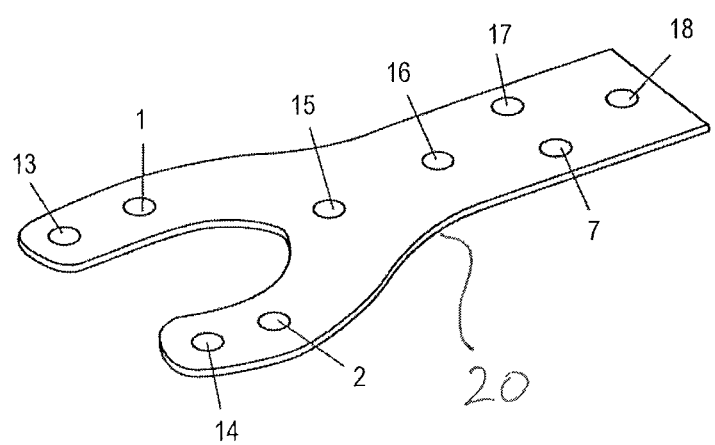

FIG. 62A is a similar isometric view to that of FIG. 61 with the lower OTT housing portion removed. The view of FIG. 62A is used to illustrate several additional optional sensor locations. Sensor locations 8, 9, 10, 11 and 12 are shown in this embodiment. Sensor locations 12, 9 and 8 are shown along the central longitudinal axis of the OTT device fore and aft of the central sensor location 3. Sensor locations 10, 11 provide additional outboard locations similar to positions 4 and 5 but longitudinally separated therefrom. While many of these exemplary locations are shown along or near the longitudinal center line of the OTT device, other sensor locations are possible. For example, sensors may also be located on the underside of the board 235 or other structure within, part of or attached to the OTT device housing. The sensor locations may be placed in, along, above or below the board 235 or in other locations based on design and space requirements for other components and the OTT device electronics package.

In addition to the sensor locations described in FIGS. 60, 61, and 62A, a sensor platform 20 may also be provided within OTT housing 205. A perspective view of an exemplary sensor base 20 is illustrated in FIG. 62B. The sensor base 20 is shown with representative sensor locations 1, 2, 13, 14, 15, 16, 17, 18 and 7. The sensor base 20 illustrates the alternative placement of sensor 7 on the base 20 instead of within or on the wall in FIG. 61. Similarly, sensor positions 1 and 2 are moved from the positions illustrated in FIG. 60 to the base 20. In addition, the location of sensor position 15 is selected to provide the functions of sensor location 3 described above. The various alternative sensor types, numbers and locations may be integrated as described above into an appropriately configured sensor base 20. In various implementations, one sensor base or more than one sensor base may be sized as shown in FIG. 62B where the sensor base mimics the size and shape of the OTT device housing 205. A sensor base may include all the sensors of a particular type, particular orientation, for a particular location or position or function related to the particular OTT device configuration. Given the rate of miniaturization of electronics and sensors, particularly in the field of micro electrical mechanical systems (MEMS), it is to be appreciated that all or substantially all of the sensors employed in an OTT device may be in the form of suitably miniaturized commercially available components.

FIG. 62B shows the sensor locations 13 and 14 corresponding to camera locations and forward of sensor locations 1, 2. Sensor positions 13, 14, 1 and 2 are provided in proximity to the camera locations. Sensor locations 15, 16 and 18 are near the center line of the OTT device module when the sensor board 20 is in place. Sensor locations 15 or 16 may be positioned above a specific location of interest in the OTT guided tool such as a vertical central axis of the tool, trigger location or other feature of interest to facilitate tracking of that tool. In one aspect, a sensor location is positioned to indicate the trigger of the surgical tool being used in the CAS system. In one embodiment, sensor locations 17 and 7 are positioned to the left and right outboard positions behind the center of mass for the tool. Sensor location 18 is the rearward sensor location furthest to the rear of the OTT module when the sensor board 20 is installed into the OTT housing 205.

Each one of the sensor locations illustrated and described with reference to FIGS. 60-62B and elsewhere in this specification, may be used to provide a variety of different sensor or instrumentation types to be used by the position and tracking systems described herein. By way of example and not limitation, the various instruments or sensors used in conjunction with an OTT device include: an inclinometer, a gyroscope, a two axis gyroscope, a three axis gyroscope or other multiple axis gyroscope, an one-two-three or multiple axis accelerometer, a potentiometer, a MEMS sensor or micro-sensor or MEMS instrument configured to provide one or more of roll, pitch, yaw, orientation, or vibration information related to the OTT device, or the operation of an OTT device/surgical tool combination or the operation, use or status of a tool attached to an OTT device and being used under an OTT CAS system as provided herein or as otherwise used in an operating environment of the OTT system for tool or prosthetic registration, fit assessment or surgical planning, surgical plan revision and the like.

FIGS. 16A, 16B and 16C provide various views of a reference frame 300 for use in a computer assisted surgery procedure. There is a 305 frame having a planar or general 3D surface 310 bounded by perimeter 315. One or more active or passive fiducial marker 70 are arranged in a pattern 72 across the surface 310 or carried individually through some frame structure. There is a stem 320 extending from the frame 305 and a coupling 325 on the stem. The coupling 325 is used to join the frame 305 to a base 330. The base 330 has a first surface 335 configured to engage a portion of the anatomy within a surgical field related to the procedure. The base 330 has a second surface 340 to engage with the coupling 325. The coupling 325 and the second surface 340 are engaged in FIG. 16A but are separated in FIGS. 16B and 16C. In the views of FIGS. 16C and 16C at least one registration element is visible on the coupling and at least one registration element is visible on the second surface. In the illustrated embodiment, the registration element 342b is a female feature on the coupling 325 while the coupling element 325a on the second surface 340 is a male feature. The registration elements are sized and positioned to mating cooperation when the coupling 325 and the second surface 340 are engaged. It is to be appreciated that a variety of different registration element types and positions may be adapted and configured for providing mating cooperation when the coupling is engaged to the second surface.

The base 330 includes a second surface 335 used to engage the anatomy. All or a portion of the surface may include a serrated edge to assist in engaging with anatomy, particularly bony anatomy about the joint. The base first surface 335 comprises a curvature that is complementary to the anatomical site upon which the base first surface is to be affixed during the surgical procedure. In one aspect, the curvature is complementary to an anatomical site comprising a skin portion of the anatomy, where the bone may not be exposed but the reference frame is attached to it through the skin with screws or other fastening device mentioned below. In one additional embodiment, the bony portion of the anatomy is adjacent to a joint that is the subject of the surgical procedure. The joint may be selected from a knee, a shoulder, a wrist, an ankle, a hip, a vertebrae or any other surgical site where a bone osteotomy is to be performed. The base 330 includes at least one aperture 337 adapted and configured for a fixation element used to affix the base to a site on the body. The fixation element may be selected from one or more of a pin, a screw, a nail, surgical staple or any form of glue or cement to be applied to the element or to be exposed (e.g., peeling of a double sided tape).

Figure 17:
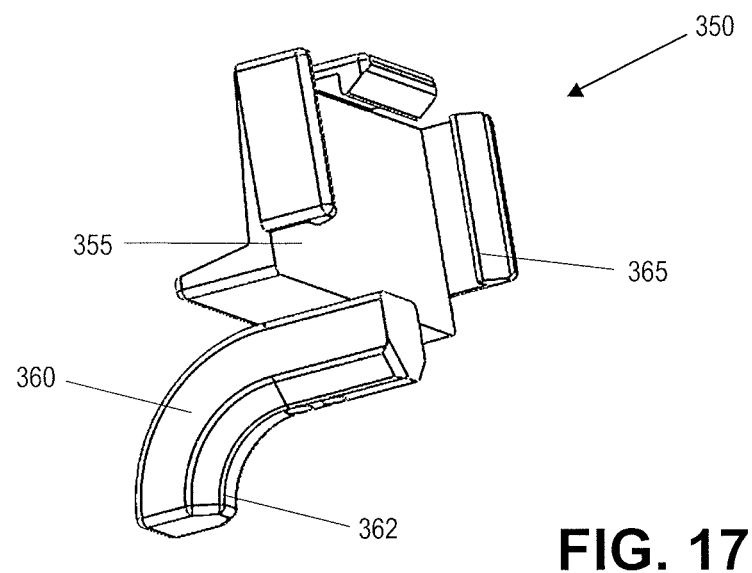
FIG. 17 illustrates an isometric view of a reference frame guide.
Figure 18:
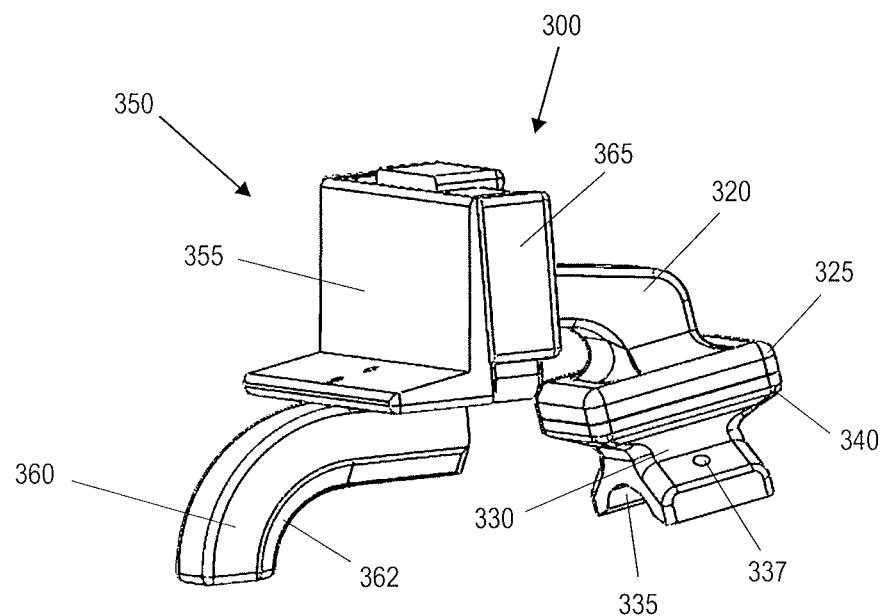
FIG. 18 illustrates the guide of FIG. 17 attached to the reference frame of FIG. 16A.
Figure 24A:
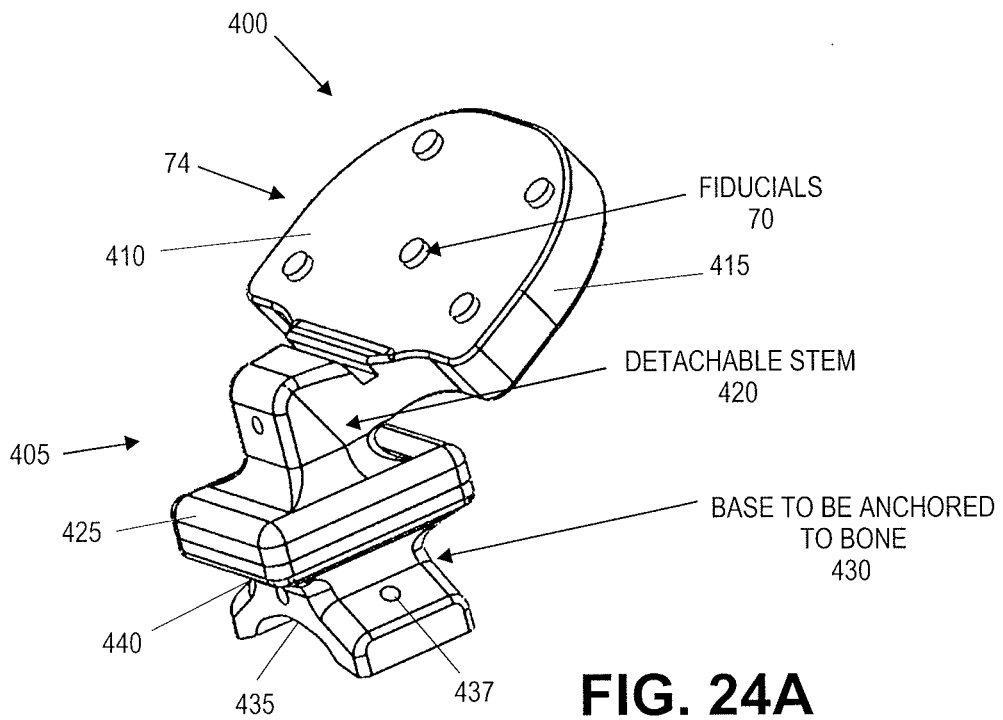
FIGS. 24A, 24B and 24C illustrate a reference frame and its components.
Figure 24B:
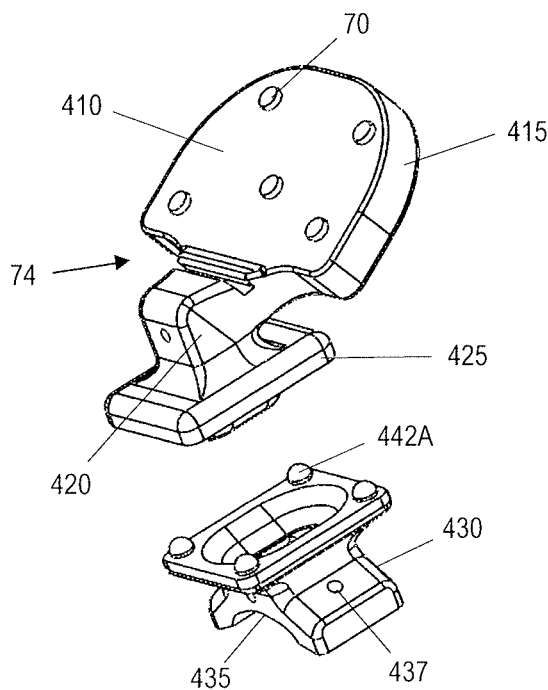

FIG. 17 illustrates an isometric view of the reference frame guide 350. The reference frame guide 350 has a frame 355 and a stem 360 extending from the frame 355. The stem 360 has a curvature or shape configured to engage with an anatomical feature to assist, when the frame guide is attached to the frame 305, the reference frame 300 is placed in a desired position and orientation within the surgical field. The reference frame guide 350 also includes one or more engagement elements 365 along the frame 355 for temporary engagement with the perimeter 315 or a portion of the reference frame 305 to permit proper positioning and adjustment of a base 330 associated with a reference frame 300 attached using the elements 365. FIG. 18 illustrates a reference frame guide attached to the frame 305 of a reference frame 300. In use, the engagement elements 365 may be broken off in order to remove the reference frame from the guide frame during surgical procedure. While illustrated in mating cooperation with reference frame 300, reference frame guide 350 may be adapted and configured to form a mating engagement with reference frames of different shapes and sizes, such as the reference frame 400 in FIG. 24.

Figure 19:
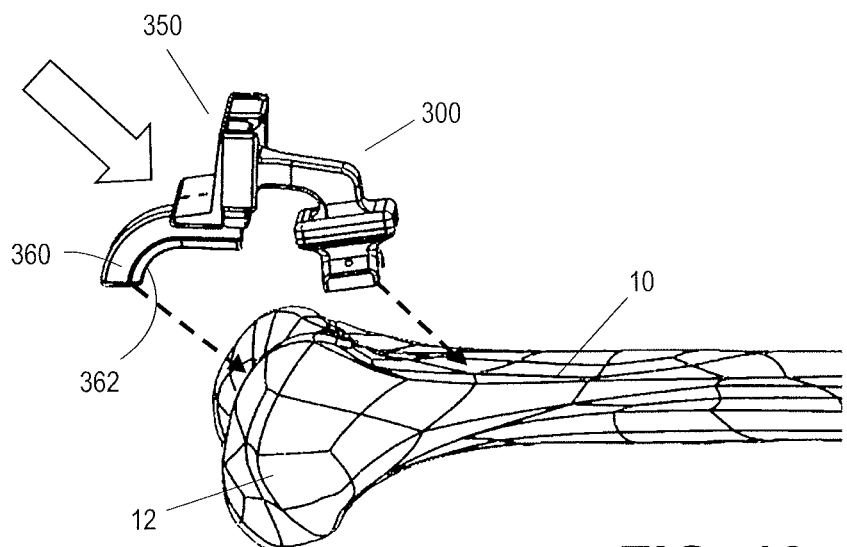
FIG. 19 illustrates the components of FIG. 18 being moved and position for attachment to the anatomy.
Figure 20:
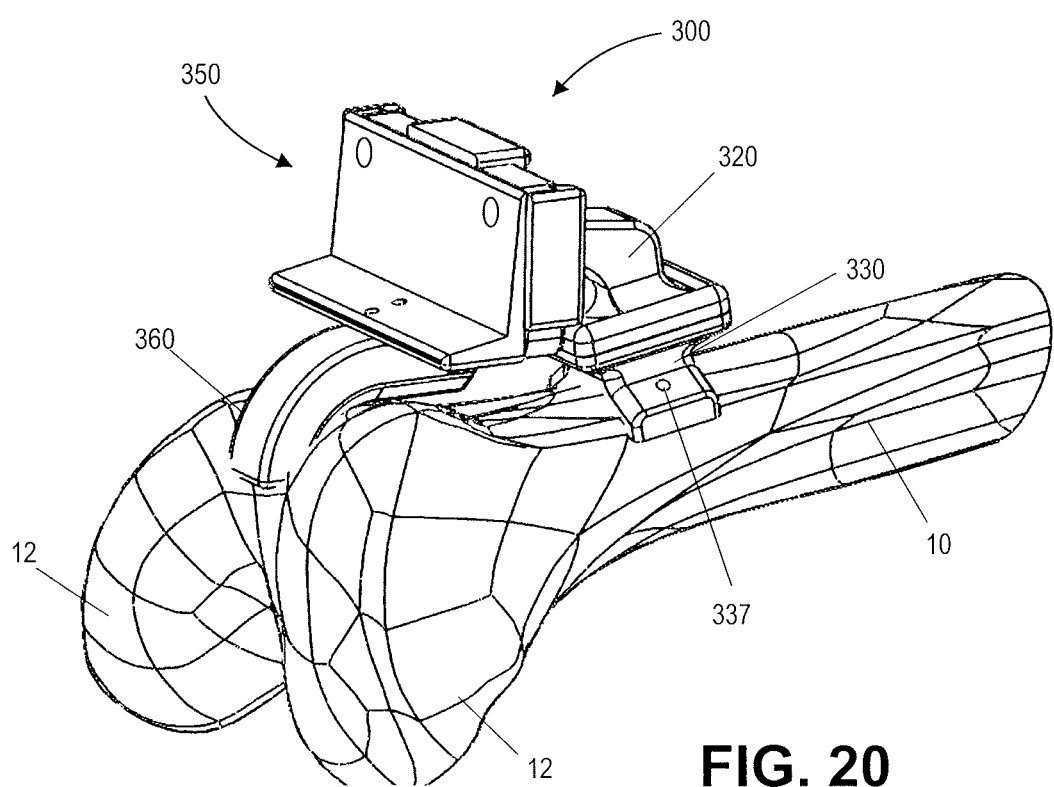
FIG. 20 is an isometric view illustrating said attachment.
Figure 21:
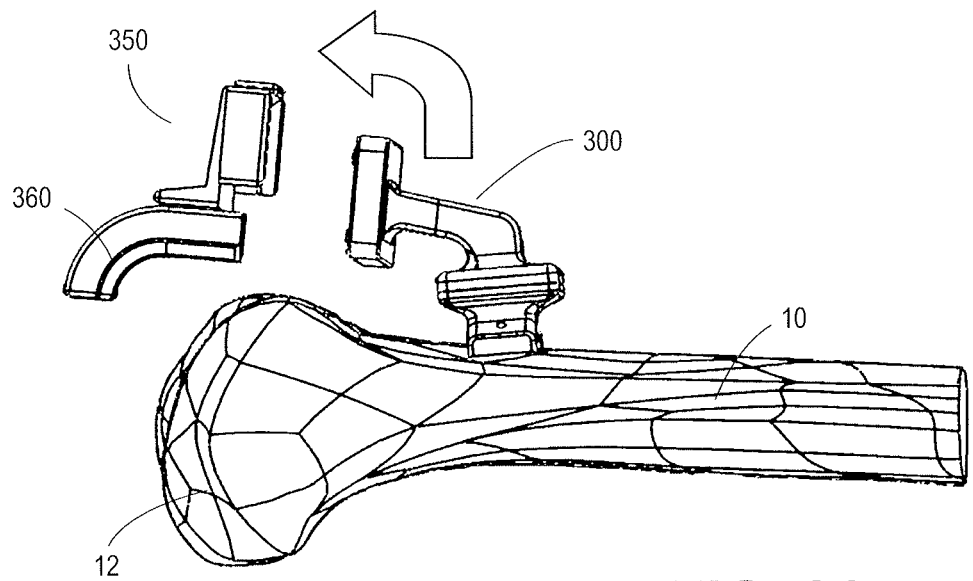
FIG. 21 illustrates the removal of the guide frame and FIG. 22 illustrates the remaining frame in position on the anatomy.
Figure 22:
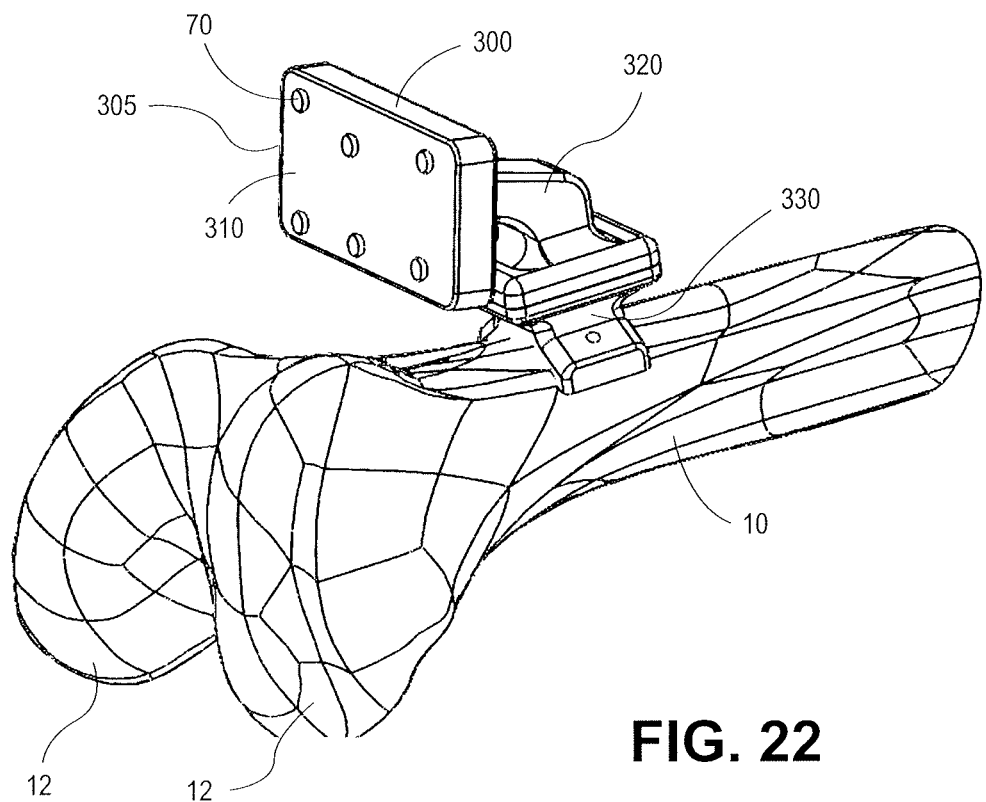

In one particular embodiment, the curvature or shape 362 of the stem 360 is configured for placement of the stem in relation to the condyles in order to provide alignment within the surgical field for the reference frame 300 along the femur. Positioning of the base 330 along the femur 10 is shown in FIGS. 19 and 20. The joint reference frame guide and reference frame structure (see FIG. 18) are positioned (following the arrow in FIG. 19) so as to align the curvature 362 of the stem 360 between the condyles 12 of the femur 10 in order to place the base 330 in proper orientation on the femur as shown in FIG. 20. Thereafter the reference frame 300 is attached to the femur 10 by joining the base first surface 335 using one or more methods such as and screws or nails applied the aperture 337 or the use of a biocompatible bone cement. Once the reference frame 300 is confirmed in the proper position, the reference frame guide 350 is removed (FIG. 21) leaving only the reference frame in the desired location along the femur 10 in the desired relation to the condyles 12 according to a surgical plan to be implemented (FIG. 22).

Figure 23:
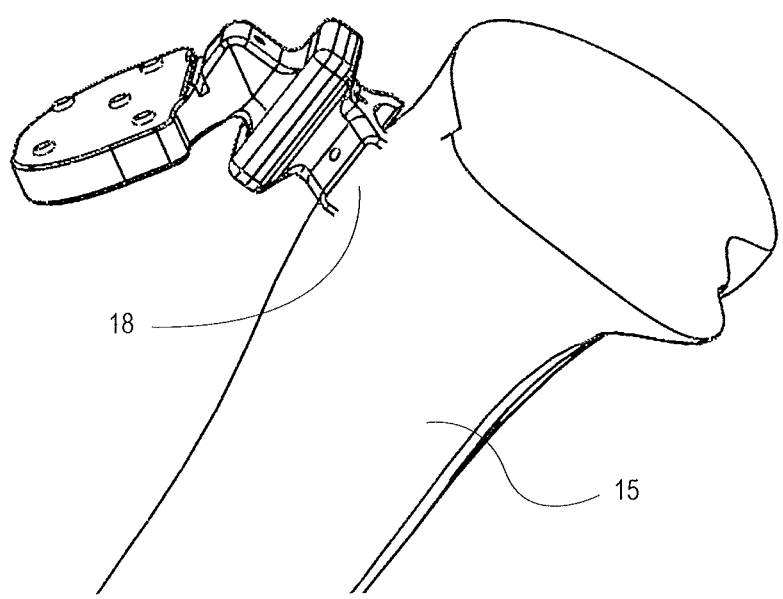
FIG. 23 illustrates another reference frame in position on the tibia.
Figure 24C:
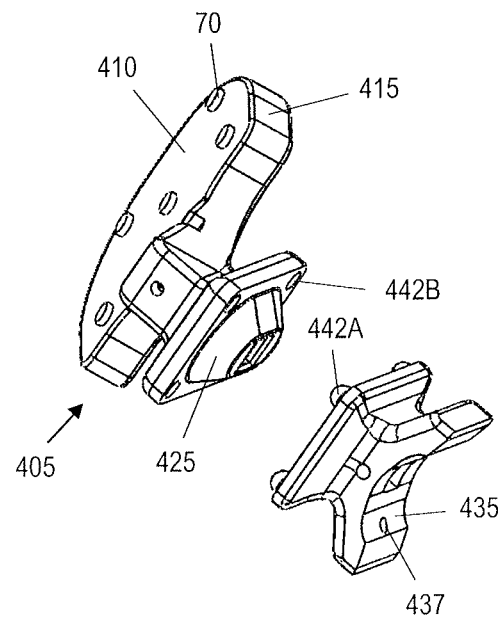
Figure 25:
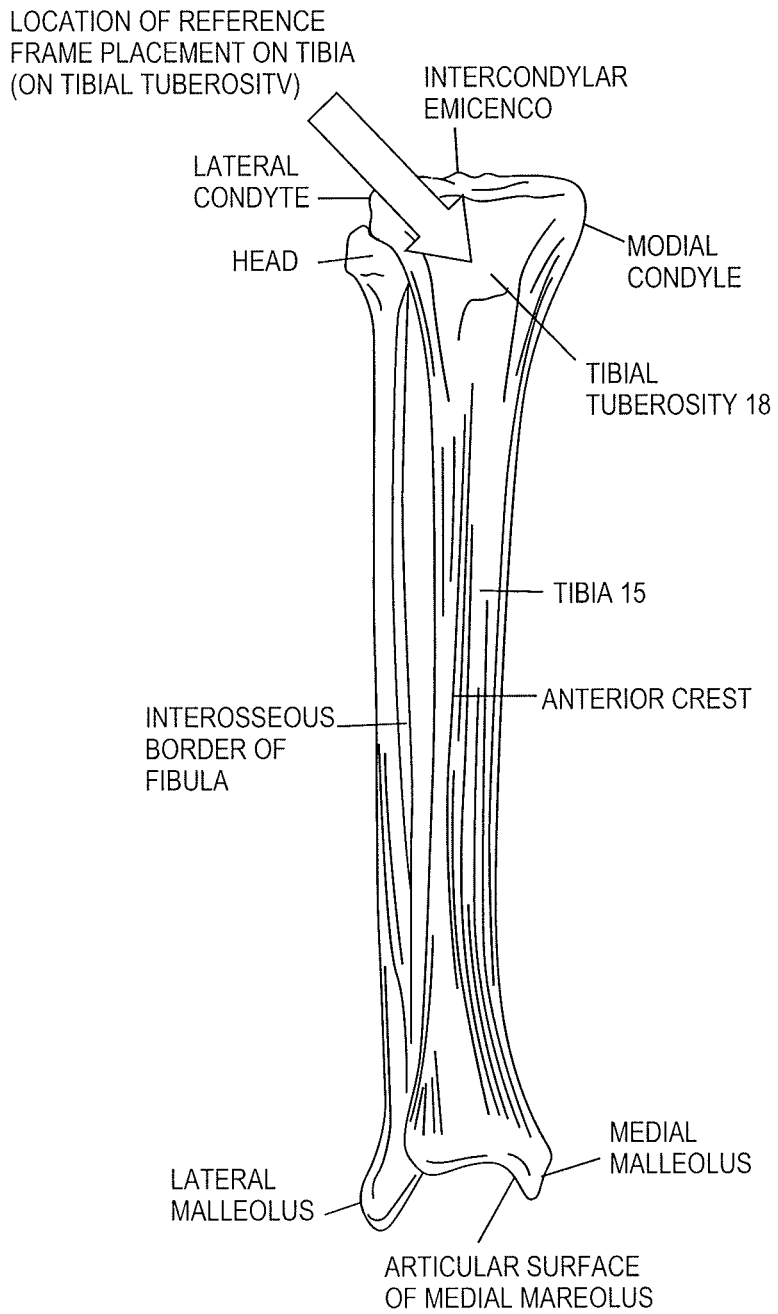
FIG. 25 illustrates an implantation site on the tibia.

FIG. 23 illustrates an embodiment of the reference frame 400 and position along the tibia 15. In this illustrated embodiment the reference frame 400 is attached on or about the tibial tuberosity (shown more clearly in FIG. 25) and secured to the bone using any one of the several fixing methods described above with regard to the reference frame 300. Additional details of the reference frame 400 may be provided upon review of FIGS. 24A, 24B and 24C. These figures provide various views of a reference frame 400 for use in a computer assisted surgery procedure. There is a 405 frame having a surface 410 bounded by perimeter 415. One or more active or passive fiducial markers 70 are arranged in a pattern 74 across the surface 410. There is a stem 420 extending from the frame 405 and a coupling 425 on the stem. The coupling 425 is used to join the frame 405 to a base 430. The base 430 has a first surface 435 configured to engage a portion of the anatomy within a surgical field related to the procedure. The base 430 has a second surface 440 to engage with the coupling 425. The coupling 425 and the second surface 440 are engaged in FIG. 24A but are separated in FIGS. 24B and 24C. In the views of FIGS. 24C and 24C at least one registration element is visible on the coupling and at least one registration element is visible on the second surface. In the illustrated embodiment, the registration element 442b is a female feature on the coupling 425 while the coupling element 425a on the second surface 440 is a male feature. The registration elements are sized and positioned to mating cooperation when the coupling 425 and the second surface 440 are engages. It is to be appreciated that a variety of different registration element types and positions may be adapted and configured for providing mating cooperation when the coupling is engaged to the second surface.

The base 430 includes a second surface 435 used to engage the anatomy. All or a portion of the surface may include a serrated edge to assist in engaging with anatomy, particularly bony anatomy about the joint. The base first surface 435 comprises a curvature that is complementary to the anatomical site upon which the base first surface is to be affixed during the surgical procedure. In one embodiment, the bony portion of the anatomy is adjacent to a joint that is the subject of the surgical procedure. The joint may be selected from a knee, a shoulder, a wrist, an ankle, a hip, or a vertebrae. The base 430 includes at least one aperture 437 adapted and configured for a fixation element used to affix the base to a site on the body. The fixation element may be selected from one or more of a pin, a screw, a nail, a surgical staple or a glue or adhesive based fixation.

Figure 26A:
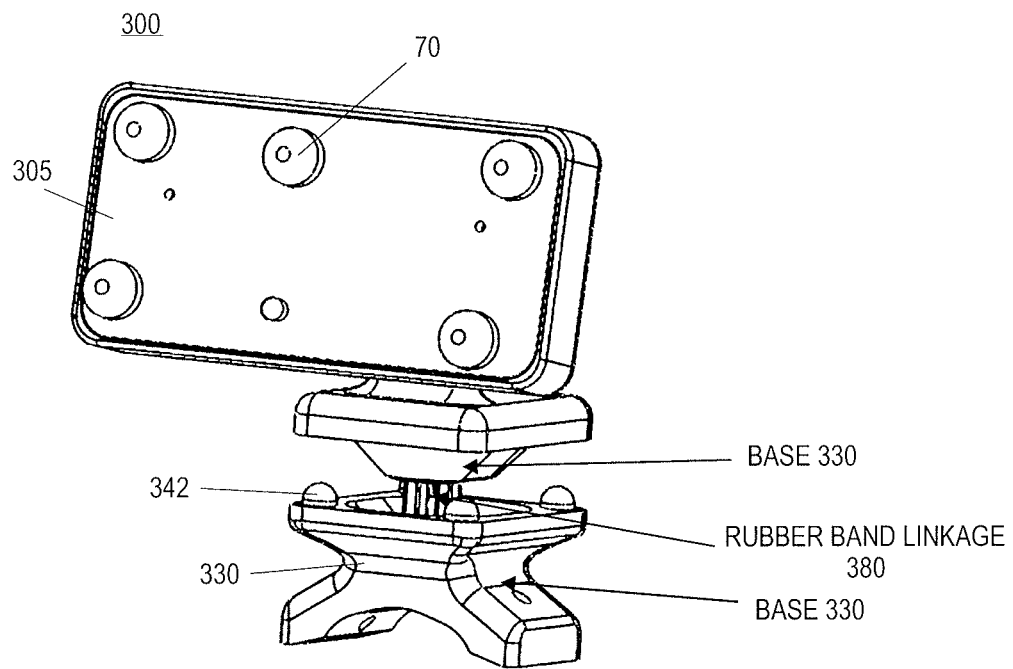
FIGS. 26A, 26B, and 26C illustrate another reference frame embodiment having a flexible linkage joining the components of the frame.
Figures 26B, 26C:
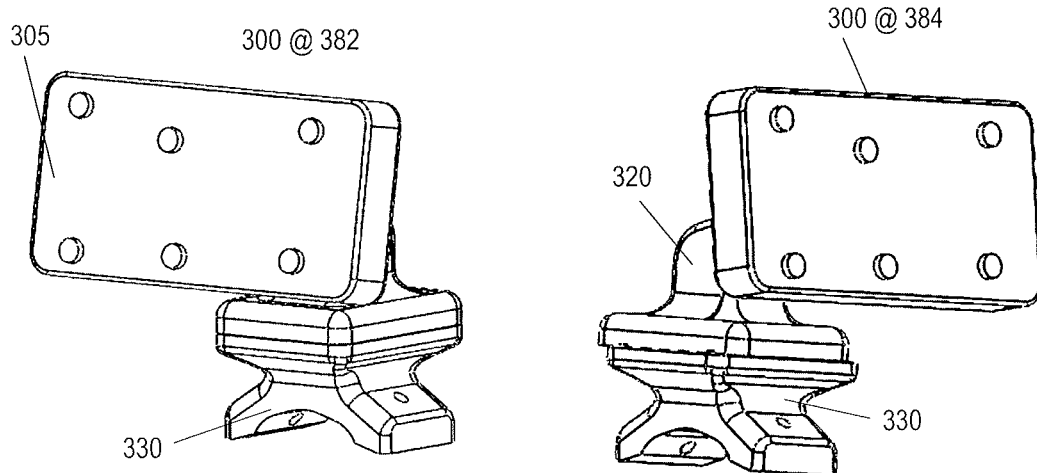

Turning now to FIGS. 26A, 26B and 26C, additional aspects of the reference frame designed to be described. With reference to FIG. 26A, the orientation between the frame 305 and the base 300 may be adjusted between a number of preset orientations. Altering the relationship between these two components is accomplished by altering which of a plurality of registration elements available to the joint as components are engaged. In one aspect, there are a plurality of registration elements on the coupling and a plurality of registration elements on the second surface. The orientation of the reference frame may be adjusted between a first orientation 382 and a second different orientation 384 based on which grouping of registration elements is used for joining the base 330 to the frame 305. In one embodiment, wherein a portion of the registration elements on the coupling are engaged with a portion of the registration elements on the second surface the result will orient the frame in a first orientation within the surgical field. In another aspect, the mating different registration elements on the coupling with different registration elements on the second surface, the result is that the frame 305 will present in a second, different orientation within the surgical field. In one aspect, the first orientation is a known position used in surgical preplanning. In still another aspect, the second orientation is another known position used in surgical preplanning. Either or both of the first orientation and the second orientation may be used in furtherance of the OTT CAS techniques described herein. Both can be used in sequence without new software registration each time. The registration for each configuration or only one is done first and once, and the software registration for the other is computed from the geometry or measured separately and its data stored and accessible whenever needed.

FIG. 26A also illustrates one embodiment of a mount coupling adapted and configured to maintain the relative position and orientation of the coupling and the second surface. In this embodiment a flexible linkage 380 is shown between the two components and is sized shaped and oriented within the reference frame to maintain the orientation of the frame 305 within the surgical field. In other words, the mount coupling is sufficiently rigid that if the frame 305 is bumped during a procedure, its components can be temporarily displaced relative to each other through deformation of the elastic element in the coupling, but then can return back or be returned back by the user to the original alignment, and so it will not lose its alignment due to the registration elements within it. If the bump of the reference frame was sufficiently strong, the registration elements would disengage and not return automatically, but the use can return them and the original software registered alignment is still not lost. In the illustrative embodiment, the flexible linkage 380 is disposed completely within the structure in use, here the base 330. As best seen in FIG. 26A, one portion of the linkage 380 attaches to the upper base 330 and another portion to the lower base 330. In another alternative aspect, a mount coupling is provided in so that when the mount coupling is attached to the reference frame the mount coupling substantially or completely surrounds the area of mating contact between the coupling and the second surface. FIG. 26B 1a illustrates a perspective view of a flexible mount coupling 383 that completely surrounds the interface between the upper and lower base 330. FIG. 26B1b illustrates a perspective view of the flexible mount coupling 383. FIG. 26B2a illustrates a perspective view of a flexible mount coupling 384 that substantially surrounds the interface between the upper and lower base 330. The coupling 384 includes four corner mounts connected by linkages. The corner mounts and linkages are—like coupling 383—designed for a snug fit around the interface between the upper and lower mounts. FIG. 26B2b illustrates a perspective view of the flexible mount coupling 383.

Figure 27A:
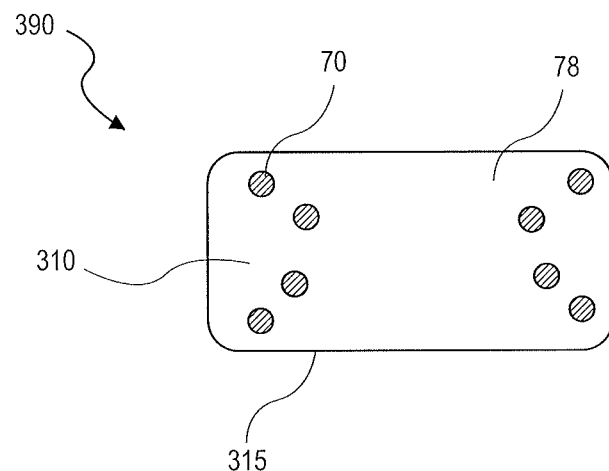
FIGS. 27A and 27B illustrate two alternative reference frame surfaces.
Figure 27B:
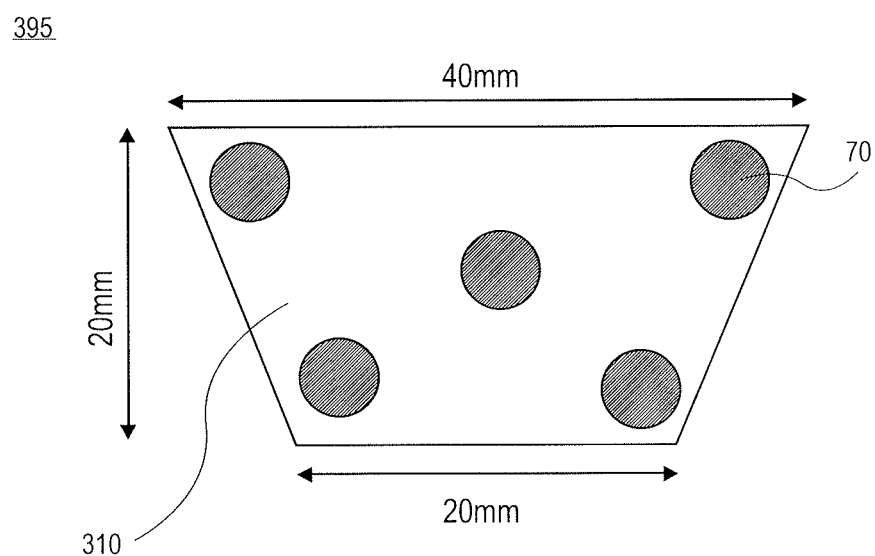

FIGS. 27A and 27B provide alternative reference frame surface shapes as well as alternative height to show marker patterns. FIG. 27A illustrates a generally rectangular frame 390 of a reference frame having a plurality of fiducial markers 70 arranged in a pattern 78. FIG. 27B illustrates a generally trapezoidal surface shape 310 on the frame 395. A plurality of fiducial markers 70 arranged in a pattern on the surface 305.

Figure 28:
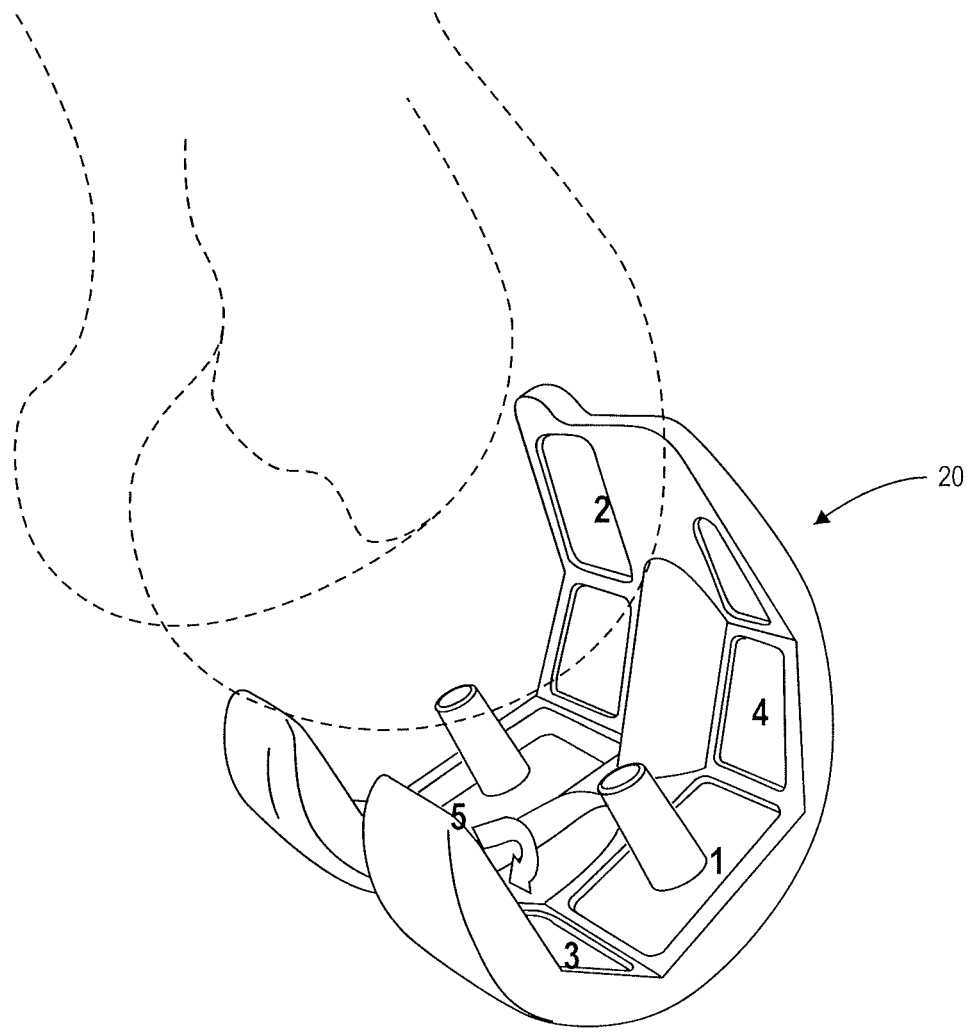
FIG. 28 is an isometric view of an exemplary knee prosthesis near a schematically outlined distal femoral bone.

FIG. 28 illustrates an isometric view of a representative of prosthesis 20 for use in a total knee replacement procedure. The numbers indicated on the prosthesis 20 are representative of the types of cuts undertaken during knee surgery. FIGS. 29A-29I and 30 illustrate one of the unique combinations of the OTT CAS system described herein. While each of the reference frames described above may be used independently or in conjunction with other anatomical sites or surgical equipment, the reference frames 300 and 400 have particular advantage for the on tool tracking devices and OTT CAS procedures described herein. One challenge of using on tool tracking devices for handheld precut surgery is obtaining relevant tracking information and maintaining a tracking frame of reference during the procedure. By the unique design and placement the reference frames 300 and 400 may be used to provide just this type of dynamic reference frame tracking using the OTT tracking techniques described herein. As shown in the figures that follow in each one of the representative cuts used for implanting the prosthetic 20, the vision system carried onboard the OTT 100 is able to visually identify and register with all or a portion of the reference frame 300 and the reference frame 400. While these particular configurations are illustrative of the capabilities of the OTT CAS system and tools for knee surgery, it is to be appreciated that the reference frames and vision guidance techniques described herein may be adapted to other joints in the body and to other procedures.

FIGS. 29A-29I and 30 each illustrate a representative surgical set up for the placement of a reference frame 300 on the femur 10 and the reference frame 400 along the tibia 15, in particular on or about the tibial tuberosity 18. Is to be appreciated that the illustrated OTT CAS procedure that follows utilizes the reference frames 300, 400—they are not moved but remain in the same position during all of the following OTT CAS process steps. An on tool tracking device 100 is coupled to a surgical tool 50 for the positioning and use of a tool 54 having an active element 56.

Figure 29A:
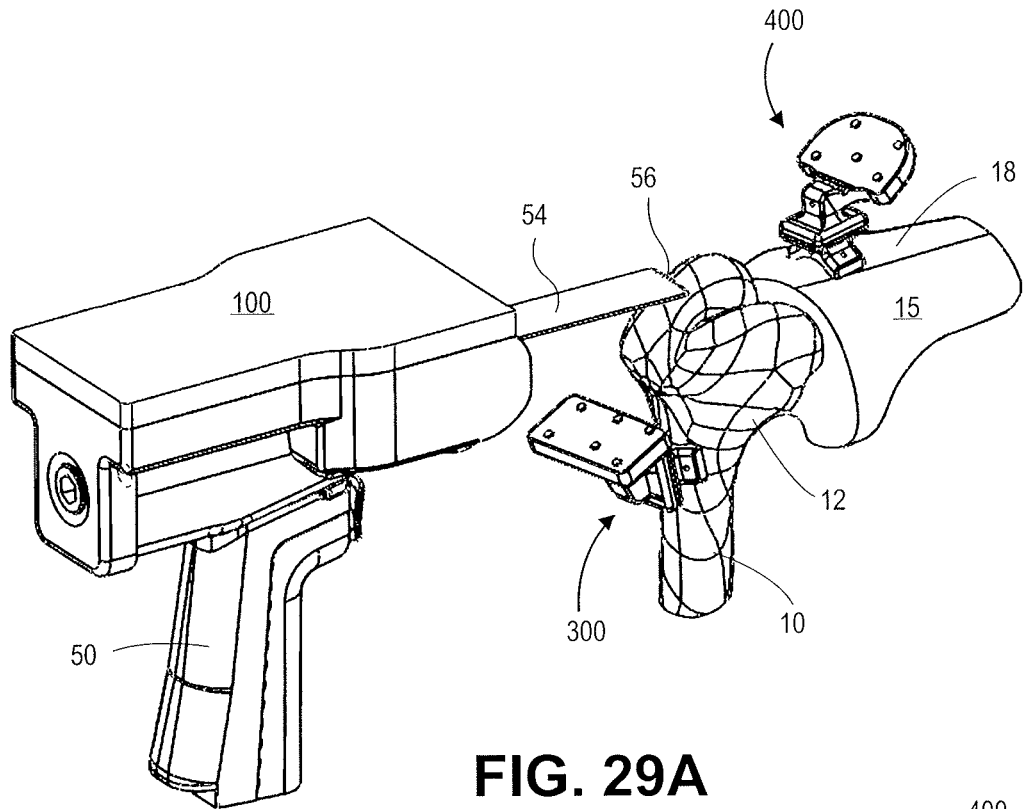
FIGS. 29A-29I and 30 illustrate the various views of an on tool tracking system and associated surgical tool in position for performance of a total knee replacement OTT CAS procedure.

In the illustrative embodiment of FIG. 29A, the OTT 100 is providing guidance for the use an active element 56 for making a distal lateral condyle cut. During this cut, the cameras carried onboard OTT 100 are capturing, imaging, and providing relative navigation and positioning information based on information received from both reference frames 300 and 400 during all or a substantial portion of the illustrated cut.

Figure 29B:
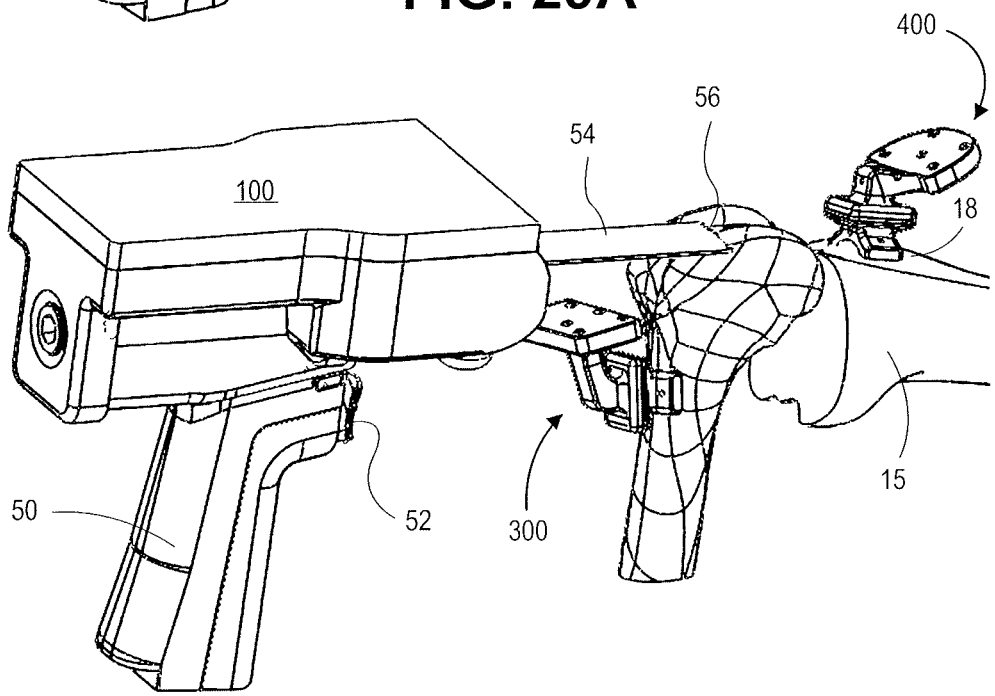

In the illustrative embodiment of FIG. 29B, the OTT 100 is providing guidance for the use an active element 56 for making a distal medial condyle cut. During this cut, the cameras carried onboard OTT 100 are capturing, imaging, and providing relative navigation and positioning information based on information received from both reference frames 300 and 400 during all or a substantial portion of the illustrated cut.

Figure 29C:
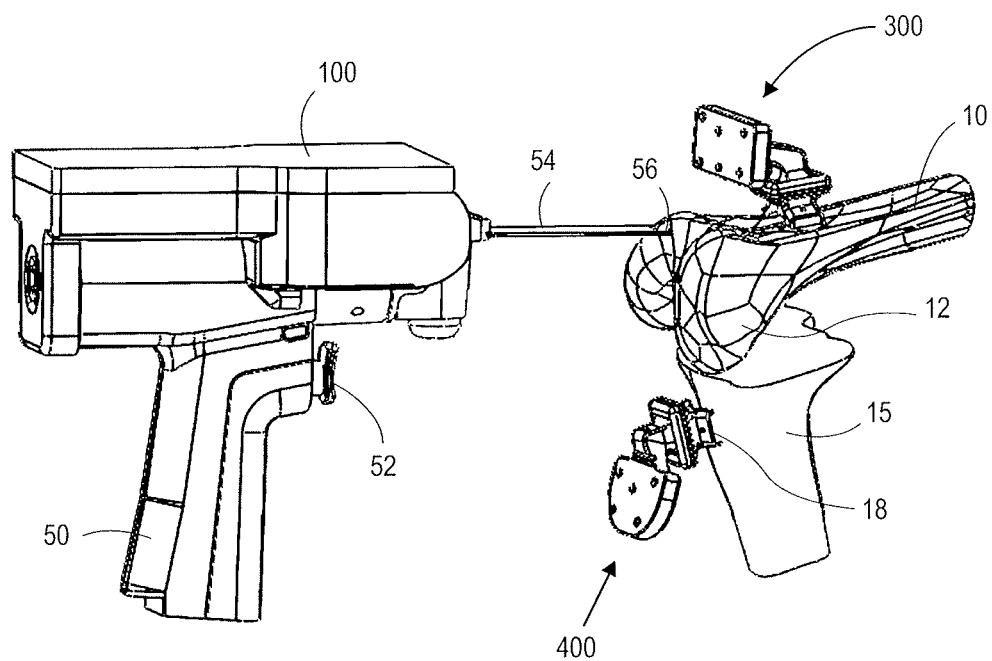

In the illustrative embodiment of FIG. 29C, the OTT 100 is providing guidance for the use an active element 56 for making an anterior cut. During this cut, the cameras carried onboard OTT 100 are capturing, imaging, and providing relative navigation and positioning information based on information received from both reference frames 300 and 400 during all or a substantial portion of the illustrated cut.

Figure 29D:
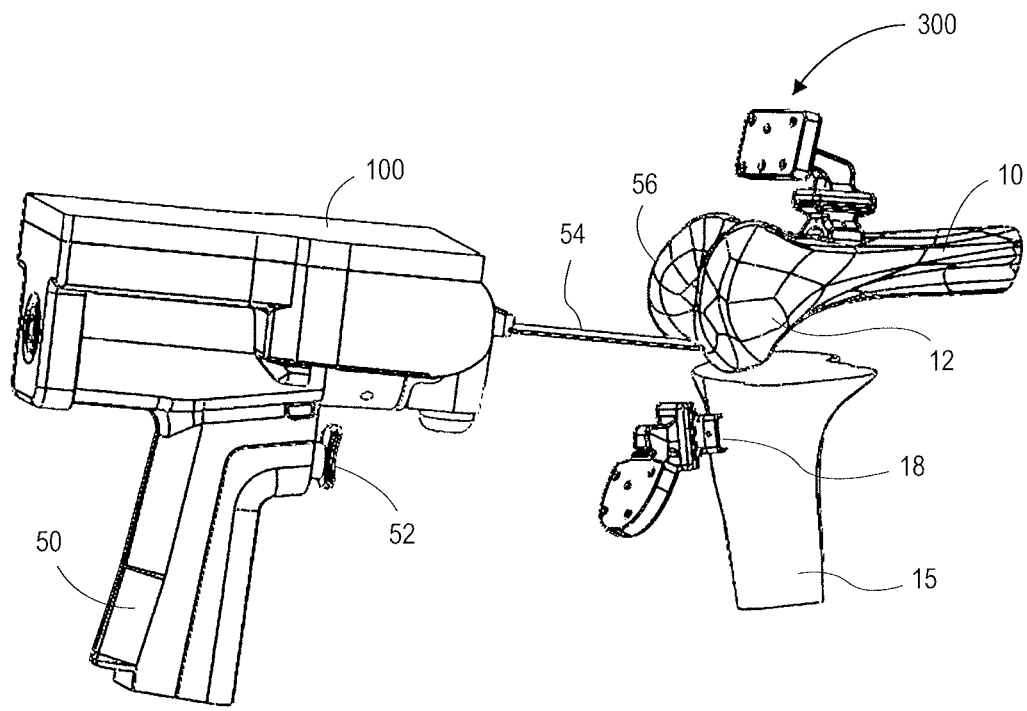

In the illustrative embodiment of FIG. 29D, the OTT 100 is providing guidance for the use an active element 56 for making a posterior lateral condyle cut. During this cut, the cameras carried onboard OTT 100 are capturing, imaging, and providing relative navigation and positioning information based on information received from both reference frames 300 and 400 during all or a substantial portion of the illustrated cut.

Figure 29E:
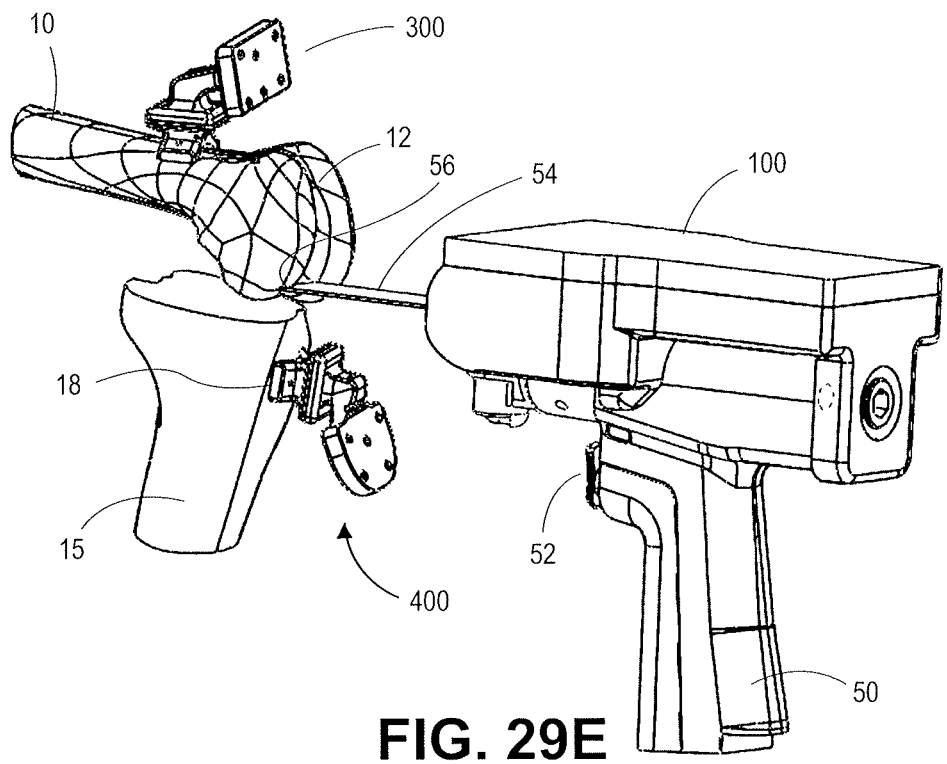

In the illustrative embodiment of FIG. 29E, the OTT 100 is providing guidance for the use an active element 56 for making a posterior medial condyle cut. During this cut, the cameras carried onboard OTT 100 are capturing, imaging, and providing relative navigation and positioning information based on information received from both reference frames 300 and 400 during all or a substantial portion of the illustrated cut.

Figure 29F:
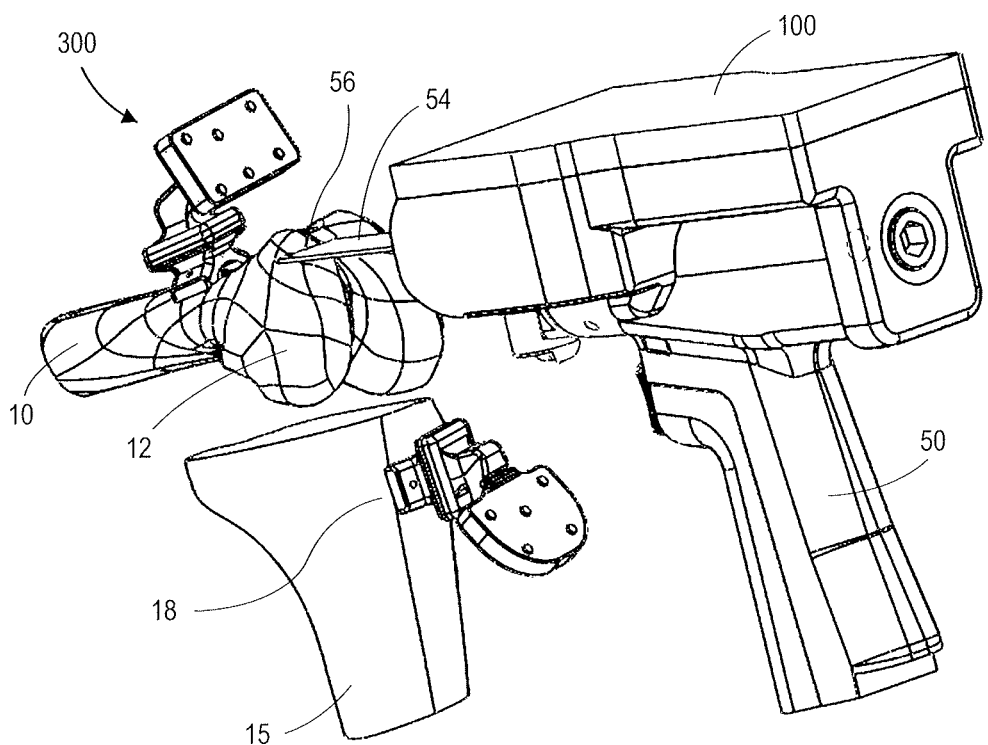

In the illustrative embodiment of FIG. 29F, the OTT 100 is providing guidance for the use an active element 56 for making an anterior chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29G:
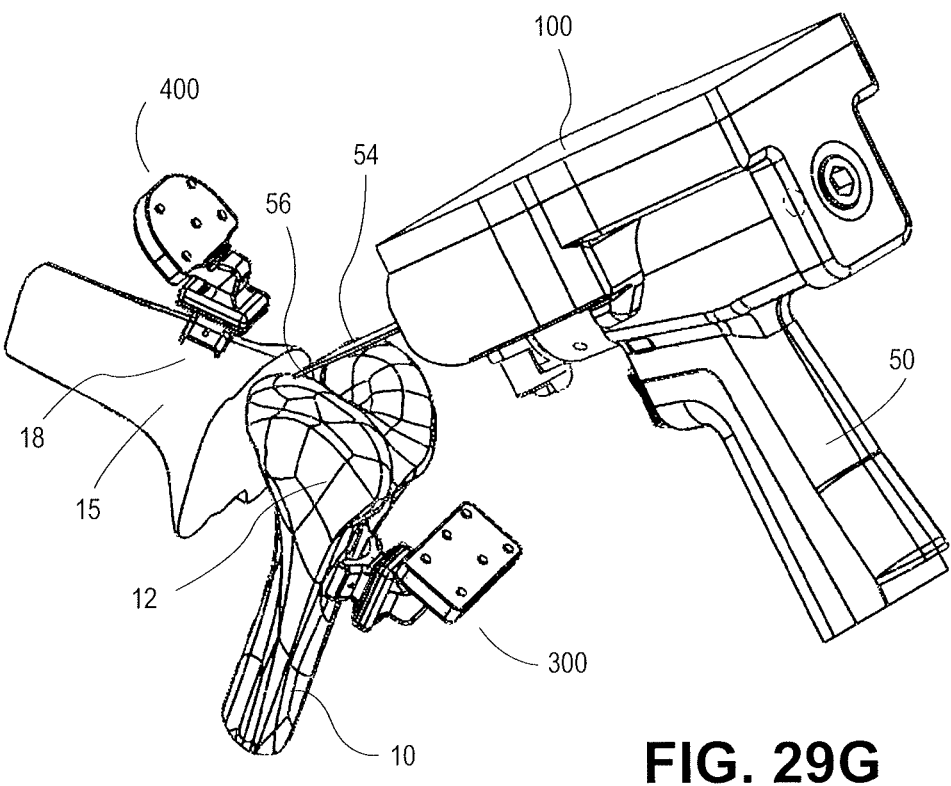

In the illustrative embodiment of FIG. 29G, the OTT 100 is providing guidance for the use an active element 56 making a posterior lateral condyle chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29H:
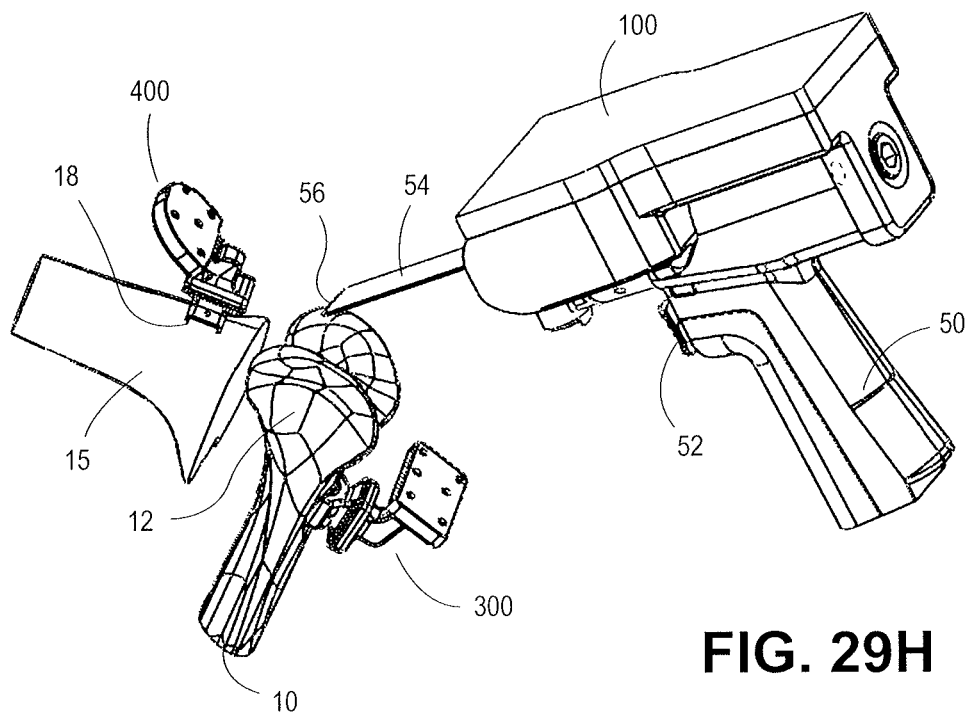

In the illustrative embodiment of FIG. 29H, the OTT 100 is providing guidance for the use an active element 56 making a posterior medial condyle chamfer cut. During this cut, the cameras carried onboard OTT 100 are capturing, imaging, and providing relative navigation and positioning information based on information received from both reference frames 300 and 400 during all or a substantial portion of the illustrated cut.

Figure 29I:
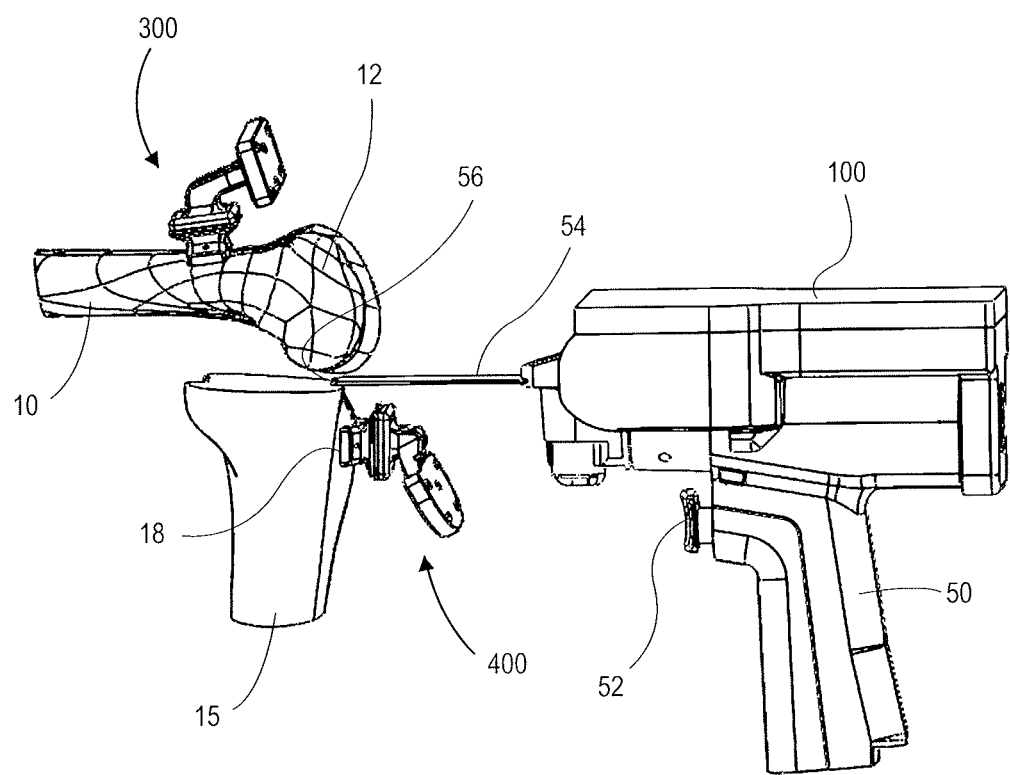

In the illustrative embodiment of FIG. 29I, the OTT 100 is providing guidance for the use an active element 56 making a tibial cut. During this cut, the cameras carried onboard OTT 100 are capturing, imaging, and providing relative navigation and positioning information based on information received from both reference frames 300 and 400 during all or a substantial portion of the illustrated cut.

Figure 30:
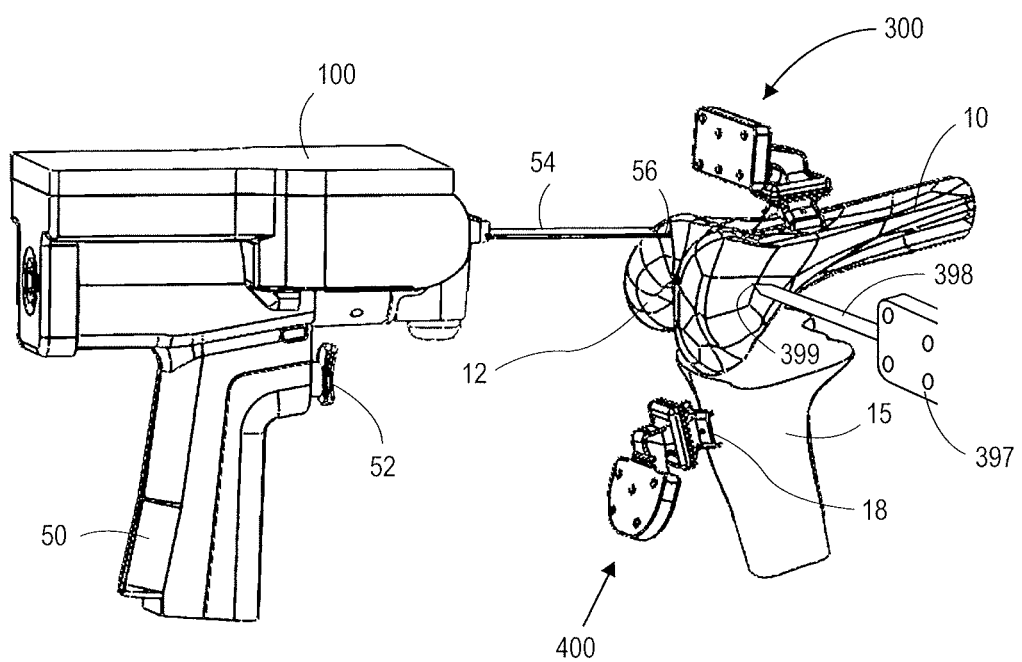

FIG. 30 illustrates an OTT 100 coupled to a surgical instrument 50 having a tool 54 and an active element 56. Reference frames 300, 400 are also shown in relation to a OTT CAS surgical site about the knee. An additional reference frame 397 having a stem 398 and tip 399 is being used for further registration or notation of the surgical field. The registration of the reference frame 397 is being provided by the imaging system of the OTT 100m with a tool. The registration frame 397 is being registered along with one or both of the registration frames 300, 400. While embodiments of the OTT CAS methods described herein by utilize both the reference frames 300, 400, it is to be appreciated that the, because of the improved image based tracking capabilities of the OTT and OTT CAS processing the OTT CAS system have both reference frames available but elect during processing to only use tracking information from one reference frame.

When considering the use of the unique reference frame embodiments described herein, consider the manner by which a view may be preferred by an OTT CAS system user. The OTT CAS system is pre-programmed so that certain views are shown by default for certain cuts. For instance, in the example of resecting a femur in preparation for a femoral prosthetic for a TKR procedure, several surfaces are to be cut, as shown in FIGS. 29 and 30. Each surface may be best viewed from a different perspective during the procedure. When cutting the anterior surface of the medial condyle a first view may be desirable, whereas when cutting the anterior surface of the lateral condyle a second view may be desirable. Accordingly, the system sets a pre-defined first view for viewing the virtual model when the anterior surface of a medial condyle is resected. Similarly, default visual views can be defined for a number of common resection procedures. When the OTT CAS system determines the cut to be performed, the system determines the best match for the cut and displays the default automatically without the intervention of the surgeon. In much the same way the vision based processes performed by the OTT CAS computer may be preselected to use all or a portion of the available tracking information from one or both reference frames, automatically, depending upon the circumstances. In addition, the OTT CAS may guide a user in adjusting orientation of a reference frame within a surgical field to improve guidance information from that frame. The adjustable orientation of the frame while maintaining the registration position of the base is described herein.

In another alternative aspect, there is a divot or other feature present on one or more of the reference frames described with reference to FIGS. 16A-30. In one aspect, contact is made with the divot using the surgical tool, touch screen, or navigated pointer and produces a result in the system indicating the initiation or completion of a step. In one example, contact with the reference frame (e.g., touching with a navigated pointer) the OTT CAS system registers the initiation of an operation or alternatively the completion of an operation. In one specific embodiment, the act of touching the reference frame indicates the start of an operation involving that particular reference frame. One exemplary operation conducted with a reference frame is bone registration. In an additional aspect, this input and/or interaction with a particular reference frame is also an input to or part of a selection criteria for a CAS Hover mode, smart view, display or other function.

It is to be appreciated that any of a number and variety of powered or non-powered tools can be utilized with the OTT CAS systems described herein. For example, in the orthopedic surgery field, the system can be built upon a single orthopedic power saw such as a Stryker System 6 Precision Oscillating saw. Similarly the system can be used with other power tools commonly used in orthopedic surgery, such as a burr or a drill. In such application, the system could be integrated within the design of the surgical tool, or added as a retrofit. In addition, the system could utilize a tool that does not require any external power source—such as a pointer, a marker or a scalpel. Ideally, the system could accommodate multiple smart tools to be used at different phases of a surgical procedure and make the system robust enough to perform a wide variety of surgical procedures. It is to be appreciated that the OTT 100 may be adapted to fit the housing of a wide variety of surgical tools, free hand tools as discussed above and elsewhere in this application. Alternatively, the OTT may be built (fully integrated) into the design of freehand tools or hand-held power instruments and its housing manufactured together with such tools.

The system could be used in other applications outside of orthopedic surgery. For example, it could be used in simulations and simulators for teaching and training surgeons for orthopedic surgery. Alternatively the system could be used for other medical procedures that require precise orientation and manipulation of rigid tissue. The present techniques computer assisted surgery could readily facilitate such dental procedures. The system can also be used in non-medical applications, for example in carpentry, sheet metal work and all other engineering marking and machining processes to guide the user to make a certain pattern of cutting or drilling of materials.

Embodiments of the OTT CAS system described herein eliminates the need for external tracking devices by placing one or more trackers on board the tool. The present invention can completely eliminate the need for an external tracking system or utilize the tracking sub-system to add new tracking data. In either configuration, the tool itself tracks the patient's anatomy, or tracks itself relative to a patient anatomy, as opposed to an external tracker that tracks both to determine the relative position of one to the other. Furthermore, because the components providing input to the tracking system are located on the tool itself, all tracked elements of the system are tracked relative to the tool. As a result, the tracking data produced by the on-tool trackers is very different. The position of the tool, for example, need not be independently tracked because all other tracked objects are tracked from the tool's vantage. The on board tracking system alleviates concerns faced by externally tracked systems, where all components of the system including the surgical instrument are tracked by an external device. Logistically, the present invention allows the operating room to eliminate or at least minimize the need for a separate piece of equipment in the operating room by placing the tracking or the components providing input to the processing part of the tracking system on the tool itself. With the sensors for the tracking on board the tool, this brings another advantage of being closer to the tracked target, and thus higher resolution and accuracy may result as well as less stringent requirements for "line of sight" access between the tracker and the tracked element of other systems.

The tracker-tracking subsystem further comprises one or more tracking elements that are detectable to the trackers on board the surgical instrument. There are a wide variety of tracking elements that can be utilized in the system. For example, reference frames that contain one or more reflective surfaces can reflect infrared or visible light back to the surgical tool. Light emitting diodes can similarly indicate the position of tracked objects back to the surgical tool. Other approaches, such as fiducial points or image recognition, could eliminate the need for external reference frames to be placed on the objects, such as the patient's tissue, that needs to be tracked. In further embodiments, the specific image of the patient's anatomy can serve as the tracking element without the aid of any other reference points.

The surgical instrument tracks the position of the tracked element by means of one or more trackers. In one embodiment, the system utilizes stereoscopic placement of two cameras as the tracker. The cameras are side by side, tilted at a range of angles suitable for stereo-vision, on either side of the saw's blade/drill-bit/burr, etc. For other tools, such as a drill, the cameras can similarly be placed stereoscopically, side by side, on either side of the drill bit or any other tool's end effector.

The placement of the cameras, relative to the end effector of the tool, impacts the operation of the tracker-tracking element subsystem. For example, placement of the camera or cameras far back from the end effector expands the field of view. For applications like joint replacement, or when the tool is in close proximity to the patient's anatomy, a wide field of view is helpful. With an expanded field of view, the tool can find the tracking element more easily. Placing the camera or cameras closer to the tool's end effector constricts the field of view, but adds magnification and resolution useful for applications such as dental surgery. In addition, placement of the camera must take into account the relative position of the other elements of the subsystem. Placing the cameras so their axes are in the plane of the end effector of the tool would minimize the extent to which the end effector blocks the view of the cameras. It is contemplated, however, that the cameras may be placed in any configuration that is deemed appropriate for tracking one or more tracking elements in a surgical procedure. As technology advances, configurations beyond those currently described may be more favorable in regards to particular tools and surgical environments.

The sub system can utilize a wide variety of cameras or systems of cameras. Generally, the system utilizes digital cameras. In addition, the system utilizes at least two cameras to provide stereoscopic vision. It is possible to use analog cameras, provided there was effective means of digital conversion such as the established technology of image format conversion which are sometimes known as 'frame grabbers' or 'capture cards'. Stereoscopic vision, and the ability to gain further information based on the differences in the images from the two cameras, helps the system to better locate the tracking element in three dimensions in terms of position and orientation or pose. Systems could utilize more than two cameras utilizing what is known as "redundancy" to improve the ability to navigate, such as in the cases when some of the tracked elements are not visible to one or more of the cameras and thus two cameras would not suffice in those instances. Additionally, a system could utilize a single camera but would need additional image processing to navigate as accurately as a stereoscopic system.

Alternatively, the subsystem could utilize a different system of trackers and tracking elements. In one alternative, the tracker is a high-resolution camera optimized for image recognition under the visible light spectrum present in standard Operating Room conditions. The tracking element is the patient's anatomy, based on the medical image stored in the surgical plan. In addition, a narrower field of view may also benefit the efficient recognition of the patient's anatomy. Finally, the surgical plan itself may need to incorporate or identify particular anatomical landmarks of the patient to establish functional tracking elements.

Regardless of configuration, the cameras need to have sufficient resolution to accurately track the tracking element to a certain predetermined level of accuracy. For example, a system with a tracking element that is a reference frame with infrared LED's, cameras with 640×480 resolution have sufficient resolution to track the tracking element with surgical accuracy. Systems can utilize additional elements, such as infrared filters, and isolate the tracking element for the cameras. A lower resolution camera, in such a system, can be sufficient to produce highly accurate tracking.

Resolution is not the only characteristic of the cameras that influences the operation of the system. The frame rate is an important consideration, depending upon the particular configuration of the system. For example, a very high frame rate of around 100 Hz (frames per second) would produce minimal latency but would be very burdensome on the image processor. The system would require a powerful processor in order to extract the tracking element from so many captured images in a given unit of time. Alternatively, if frame rate is too low then the system will produce too much latency. If the operator were to move the tool too quickly then the system would not be able to continuously track the tool. The minimally acceptable frame rate should be utilized in the system. For a system that utilizes infrared LED's in the reference frame along with an array of VGA cameras, a frame rate of 30 Hz would produce a system suited to freehand orthopedic surgery.

Together, these examples illustrate a variety of configurations for the tracking element and the cameras that comprise the exemplary camera-tracking embodiments of the tracker-tracking element subsystem. In addition to the accurate placement of the tracking element, the tracking element's location must be extracted from the images captured by the camera. An image signal received from the cameras must undergo digital signal processing (DSP) to convert the image of the tracking element to mathematical coordinates, relative to the tool. The mathematical coordinates are then sent to a computer system and compared against the surgical plan, allowing the computer system to determine if the surgical path is following the intended resection.

Consider that there are several steps to process the raw data from the cameras into the mathematical coordinates. Initially, the system must acquire the image. For the camera detecting the markers (e.g. infrared LED's, reflecting bodies, fiducials, etc.), the system must: determine the coordinates of the centroid of each of each individual marker used in the overall tracking element, determine the sizes of each element, and report the size and shape and the coordinates of each LED to the computer system. Additional operations to process the captured image, such as sub-pixel analysis to determine the location of the centroid can improve accuracy.

For systems that operate at 30 Hz, steps must be completed in approximately 33 ms, and the computer will need to determine the relationship between the individual LED's and calculate the position and orientation of the tracking element. From that data, the computer will have to determine the orientation of the model and the relative positions between the bone and the surgical tool. The signal processing only has the amount of time between two successive frames to perform any needed operations. (For example, for a frame rate of 30 Hz, the processing system has the above mentioned 33 ms period to perform these operations) In one embodiment, the majority of the forgoing steps can be accomplished on the tool itself often by integrated CPU's on the cameras (or other trackers) themselves.

For example, additional processing of images captured by the cameras can be accomplished via a CPU that is integrated into the camera, or on the computer system or some combination of the two. For example, many small cameras have integrated CPU's capable of running digital signal processing algorithms prior to exporting the data signal. The DSP can comprise a simple step, like converting color images to grayscale or complex operations, like cropping the video image to a small box that surrounds the identified LED's. The initial processing makes the final extraction of the tracking element from the images captured on the camera less computationally burdensome and the overall tracking process more efficient.

The camera-tracking element subsystem can either utilize digital cameras with digital image transmission, or with wireless transmission. There is a wide variety of cameras with digital image transmission which are generally termed "IP" or "Wifi" cameras. Many small, low cost solutions can be used, streaming images (which can be synchronized between two cameras) in any format (e.g. Mpeg) and fed to the processing electronics through one of many known digital streaming protocols. Alternatively, analogue Image transmission can used as has been in model airplanes with what is known as First Person View (FPV) technology. This facilitates readily available commodity cameras, with minimal weight and size, small wireless transmission and low cost. After image processing and extraction of the coordinates for the tracked elements, additional processing is necessary to create tracking data sufficient to inform the computer system. The coordinates of the tracked elements are combined with information about the cameras (such as the specifications and calibration data) to further refine the location space of each tracked element. Based on the refined location of each tracked element, the sub system utilizes user-defined definition of clusters for the particular tracking element (sometimes called a reference frame) to detect valid clusters for the tracking element and their position and orientation in space. The data determining position and orientation in space is the formatted for use. For example, the system can place the special coordinates into a matrix that is compatible with the overall definition of the space used in a surgical plan.

The forgoing processing is different from the processing that can occur on the tool and is not image conditioning and spatial extraction. It can be processed through dedicated software that could be in the same computer system where the surgical plan and planned resection is computed or it could happen on an intermediary computer that could be on the tool or separate from both the tool and the computer system.

Additional navigation data can augment the camera-tracking element system. The tool can further contain one or more accelerometers or inertia sensors to determine the orientation and movement of the tool along the surgical path. The accelerometers can provide additional data to the computer system, in addition to the tracking data from the camera or cameras. Alternatively, an external tracking system can augment the on-board tracking of the tool. No such application is required but can serve to augment the tracking capability of the system mainly by 'anticipating' the movement of the user. Systems could further include multiple tracker-tracking element modalities. For example, the system could include an infrared camera and a tracking element with an infrared LED as well as a visible light camera for optical resolution. Tracking information from both could be processed to establish the coordinates of the tool in three dimensions.

As is typical in computer aided surgery, a surgical plan is determined before commencing the desired surgical procedure or prior to performing a step in the desired surgical procedure. The surgical plan is based on intended resections designated by the surgeon on a computer rendition of a patient's anatomy. A computer rendition of a patient's anatomy may be procured through a variety of medical imaging techniques, such as CT or MRI scanning. In addition, a computer rendition of a saw, drill, burr, implant, or any surgical instrument or part thereof may be procured by design specifications (or models) programmed into the computer system. Once a computer rendition of patient's anatomy is accessible through a computer interface such as a display, mouse, keyboard, touch display, or any other device for interfacing with a computer system, the surgeon may manually designate resections for the surgical plan by entering one or more cuts to be performed, a region to be drilled, or a volume of tissue to be removed into the computer system. Alternatively the computer system may be configured to generate the surgical plan based on a set of specified parameters selected by the surgeon. The specified parameters may correspond, for instance, to the shape, size, and/or location of an implant that the surgeon wishes to attach to the patient's anatomy. The computer may accordingly generate a surgical plan comprising the resections necessary to fit the implant to the patient's anatomy. Once the surgical plan is designated by the surgeon, the computer system translates the surgical plan into one or more mathematically defined surfaces defining the boundaries of the intended resections that comprise the surgical plan. Data acquired by the previously described tracker-tracking element subsystem can then be used to compare the instrument's surgical path with the surgical plan in order to determine the deviation of the surgical path.

Next, the surgical plan is delineated as one or more surfaces mathematically defined in an acceptable three dimensional coordinate system such as Cartesian, spherical, or cylindrical coordinates, or other anatomically based coordinate systems. For example, in a surgical plan that uses Cartesian coordinates, a cut may be defined as a specified distance along each of the X, Y, and Z axes from an XYZ coordinate defining the origin. The specified distances along each axis need not be linear. For example, a cylinder representing a region to be drilled in the patient's anatomy may be defined in Cartesian coordinates as a circular surface having a specified diameter located around an origin and protruding for a specified distance from the origin in a direction that is perpendicular to the circular surface. Any cut, series of cuts, or volume of tissue to be removed may be mathematically defined through a similar approach of defining surfaces that delineate the boundaries of the surgical plan that the surgical instrument must follow to complete the designated resections.

As previously noted, the surgeon may manually designate the resections of the surgical plan on a computer rendition of the patient's anatomy. In one embodiment the surgeon can use the computer interface to view and manipulate a three dimensional rendition of the patient's anatomy and make marks representing cuts. The marks made on the three dimensional rendition are then translated into the mathematical surfaces delineating the surgical plan that the surgeon must follow with the surgical instrument.

In surgical procedures utilizing implants such as a total knee replacement surgery, it is advantageous to use the physical specifications of the implant when delineating the surgical plan for better assurance that the implant will fit onto the patient's anatomy correctly. In such an embodiment, the surgeon can use the computer interface to view and manipulate a three dimensional rendition of the patient's anatomy as well as one or more specified implants. For example, the surgeon may be able to choose from a catalog of implants having different physical characteristics such as size, shape, etc. The surgeon may choose the appropriate implant and manipulate the three dimensional rendition of the implant to fit over the three dimensional rendition of the patient's anatomy in the desired alignment. The surgeon can then select an option for the computer system to generate the surgical plan comprising the planned resections required to prepare the patient's anatomy to receive the implant. Accordingly, the computer system may be configured to generate the appropriate mathematical surfaces to delineate the surgical plan by calculating the surfaces at each intersection between the computer renditions of the implant and the patient's anatomy as they have been aligned by the surgeon.

In order to guide the surgeon to follow the surgical plan with the surgical instrument there must be a means for comparing the path of the surgical instrument with the planned resection. The tracker-tracking element subsystem may accordingly track the three dimensional location and orientation of the mathematically defined surfaces of the surgical plan relative to the tool. In one embodiment, the mathematical surfaces are referenced by the tracking element located at a fixed position on the patient's anatomy. For better accuracy the tracking element may be fixed to rigid tissue at an easily identifiable location. Doing so will simplify registration of the patient's anatomy with the tracking system and will avoid unwanted error that may be caused by unpredictable movement of soft tissue. Once the patient's anatomy is registered with the tracking system, the mathematical surfaces defined in the computer system can be tracked based on their coordinates relative to coordinates of the tracking element's fixed position. Since the tracking system is located on the surgical instrument, tracking data collected by the tracking system regarding the location and orientation of the patient's anatomy and the corresponding mathematical surfaces of the surgical plan are relative to a defined reference point on the surgical instrument. Accordingly, during the surgery, the computer system may use the tracking data to make iterative calculations of the deviation between the surgical path followed by the surgical instrument and the surfaces of the surgical plan. Errors in alignment between the surgical path and the surgical plan as well as corrective actions may be communicated to the surgeon by an indicator such as a graphical notification on a computer screen, LCD, or projected display, a flashing light, an audible alarm, a tactile feedback mechanism, or any other means for indicating deviation error.

In one aspect, an indicator is a system to provide guidance to the surgeon on how to align the surgical path to achieve the intended resection of the surgical plan. In one embodiment, the indicator is an element of the computer system used to provide information to the surgeon in the operating room. U.S. patent application Ser. No. 11/927,429, at paragraph [0212] teaches the use of an operating room computer to guide the surgeons operation of a surgical tool. One means of indication taught in the '429 patent is the actuation of the surgical instrument. As the surgeon's surgical path deviates from the intended resection, as detected by the on-board camera-tracking element subsystem, the computer system will communicate with the surgical tool to slow or even stop the tool from operating. In such a system, the actuation of the surgical tool is the means by which the surgeon receives indication from the computer assisted surgery system as further taught in the '429 application at paragraph [0123].

In another embodiment, the computer system could indicate when the surgical path deviates from the intended resection via an external display. The computer system can display a three dimensional rendition of the surgical tool and the patient's anatomy. Overlaid onto that image is a three dimensional rendition of the surgical plan. The computer system updates the relative position of the surgical tool and the patient's anatomy, as determined by the camera-tracking element sub system, and overlays the intended resections. The surgeon can then utilize the display to align the surgical path with the intended resection. Similarly, the relative position of the surgical tool and the patient's anatomy can be displayed on other screens, such as a personal eyeware display, a large projected display in the operating room, a smartphone or a screen attached to the tool. The combination of an external screen, such as the one on the computer system, and other screens, such as a screen on the tool itself, may provide the surgeon with an optimal amount of information. For example, the screen on the computer system can provide the surgeon with a global overview of the procedure whereas the screen on the tool can provide particular guidance for a specific resection or step in the procedure.

A screen on board the surgical tool is taught in the '429 application at paragraph [0215]. The on board screen could display the same kind of image as described above on external display. An exemplary implantation in the context of an OTT device is shown and described in FIGS. 52A and 52B. The on board screen could display a simplified depiction of the alignment of the surgical path and the intended resection. In one embodiment, the simplified display is comprised of three lines. The surgical path is depicted by two lines, one small and one large. The small line depicts the distal end of the surgical path while the wider line depicts the proximal end of the surgical path. The third line depicts the intended resection. The first two lines are calculated from the navigated position (location and orientation) of the surgical tool. The computer system compiles all three to display on the screen on the surgical tool. The display shows both the proximal and distal parts of the surgical path, indicating to the surgeon its relative position in three dimensions. When the surgical path is aligned with the intended resection, all three lines are aligned. The indicator shows the surgeon how to correct the position of the tool in three dimensions.

In one embodiment, the display is optimized to provide guidance for navigating a saw. The surgical path is depicted by lines, which roughly correspond to the shape of the cut that a saw makes. In another embodiment, the simplified depiction could be depicted by two circles: a small circle depicting the distal end of the surgical path and the larger depicting the proximal end. A second shape that is roughly equivalent in size, such as a cross or diamond, depicts the intended resection. As previously described, the surgeon can align the surgical path to the intended resection by lining up the shapes. The circles depict the surgical path of a different tool, like a drill. In this manner, the system can provide guidance for a wide variety of surgical tools. In one embodiment, the position of all of the elements described in the indicator should be updated, by the computer and tracking sub systems, at a rate that is faster than human reaction time.

One limitation of surgical displays is that they divert the surgeon's attention away from the patient. One solution is to project the indication information directly onto the part of the patient's body where the procedure is taking place. Any variety of projectors could be placed onto the tool and display any of the indication methods onto the patient. In one embodiment, an on board Pico projector could display the three line simplified approach described above. In many respects, the third line would be enormously helpful as it would depict, precisely onto the patient, where the intended resection would start relative to the rest of the patient's anatomy. In addition, the indicator can provide more direct guidance as to how to correct the surgical path for alignment with the intended resection and project the guidance information directly onto the patient. For example, the projector can depict an arrow that points in the direction the surgeon needs to move to correct the surgical path.

There are several challenges to accurately project the indication information onto the patient anatomy. Foremost, for an onboard, on-the-tool approach, the projection platform would be constantly in motion. In addition, the surface that the projector is projecting on is not flat. To resolve the second question the system utilizes information obtained during the surgical planning. First, the system knows the geometry of the surface of the patient's anatomy. The surgical plan contains a medical image of the patient, such as a CT scan, from which it can extract the geometry of the surface that the indicator will project on. The system accordingly projects guidance information so that it is properly seen by the surgeon viewing the projected information on the surface of the patient's anatomy. For example, if the system is to indicate where the surgeon should cut with a saw, by utilizing a straight line, then the system can bend and curve the line so that, when projected onto the patient's anatomy, it will appear to be straight. Utilizing that approach, the indicator can project the three line simplified depiction of alignment taught above.

Similarly, the system also calculates the relative position of the tool by means of the tracking system. With that information, the system can continuously modify the angle of projection to ensure that the indicator projects to the proper position of the intended resection on the patient's anatomy. The indicator can use a wide variety of projectors such as a mini standard-LED projector or a laser-scanning pico projector system. Notwithstanding, nothing in the forgoing prevents the utilization of a projector that is not on board the tool or used in any other form of computer-assisted surgery. For example, an externally tracked system could include a separate projection system that would similarly project indication information onto the patient's anatomy.

In addition to a screen or a projector on board the saw, the system can utilize a smartphone or tablet computer, such as an Apple IPhone 4G, to provide indication to the surgeon. An indicator that uses a smartphone or tablet computer has the further advantage of a removable screen. Additionally, just as the on board screen, the smartphone can display renditions of both the tool and the patient or a simplified image, such as the two line embodiment. A different simplified display could provide indication when the surgical path and the intended resection are aligned and direction when they are misaligned. For example, if the surgeon is approaching the resection too low, then the screen can depict an arrow pointing up. The arrow can be rendered in three dimensions, providing further indication to the surgeon.

For simplified indicators, the display need not be as robust as a smartphone or other high-resolution screen. A bank of LED's, for example, could display either the three line or arrow indication previously described. The Indication method need not be visual. The system could audibly indicate to the user when the surgical path deviates from the intended resection, as further described in the '429 application at paragraph [0122].

As detailed above, computer assisted surgery proceeds from a computer-based anatomical model such as those based on images and reconstruction obtained using any known medical imaging modality, or from anatomical models generated through morphing or other known processes for rendering anatomical or bone models for use in computer aided surgery with the aid of computer-based anatomical models, a surgical plan is developed to be implemented for a specific patient and procedure. Surgical preplanning includes a number of steps such as obtaining pre-surgery image data, surgical planning for the specific procedure to be undertaken, adaptations of the plan for patient specific anatomy or condition and, if appropriate, to any specific prosthesis, devices, implants, or other structures to be placed in, joined to or used at a chosen 3D alignment during the CAS procedure. With this general pre-surgical planning information in hand the surgeon moves to the patient specific intraoperative planning to be implemented at the surgical site. The patient specific intraoperative surgical plan will be adapted to address the specific site or specific procedure such as any orthopedic procedure or minimally invasive procedure that may be enhanced through the use of computer assisted surgery. For example a specific joint may be aligned for some form of repair, for partial replacement or for full replacement. It is to be appreciated that the techniques described herein may be applied to other joints such as the ankle, hip, elbow, shoulder or for other portions of the skeletal anatomy (e.g. osteotomies or spine surgery procedures) that would benefit from the improvements to computer aided surgery described herein. Examples of skeletal anatomy that may benefit from these techniques include, without limitation, vertebrae of the spine, the shoulder girdle, bones in the arm, bones in the leg, and bones in the feet or hands.

By way of a non-limiting example a total knee arthroplasty will be used as a specific example. For purposes of discussion the total knee arthroplasty will normally include five surgical cuts for the femur (on a CR or PCL retaining and eight cuts on a PS or PCL sacrificing) and one or more cuts for the tibia each of them described below in greater detail. It is to be appreciated that these cuts may be modified to emphasize a particular aspect or aspects of a portion of a surgical procedure or step. For example, the specific geometry, orientation, or feature of a prosthetic device for a particular procedure may lead to modifications in certain aspects of the surgical plan. In another example, a particular procedure or prosthesis may benefit from a specific type of cut, tool, or surgical approach. Any of these factors may also be used to adjust the way that the computer aided surgery proceeds according to the embodiments described herein. By way of a non-limiting example, the computer aided surgery system may select the surface (e.g. plane) of cut as the most important information to be presented to the surgeon immediately prior to or during a computer aided surgery step. In still further aspect, and OTT CAS will permit the user to select or base surgical step decisions using 2-D, 3-D or other output information related to a representation of either the surgical tool being used or the resulting use of that tool on the anatomy. For example, if the surgical tool is a saw then the user may select from rectangular shapes generally sized to correspond to the profile of the saw, or to one or more surfaces (in this specific example a plane) that correspond to the resulting cuts formed in the anatomy by the saw. In an additional example, the surgical tool includes a drill and the user is provided with or the system basis processing decisions using circles corresponding to the size of the drill, cylinders related to the anatomical impact of the use of the drill, as well as other factors that might represent the engagement of the drill cutting tip to the anatomy. In still another example, the surgical tool includes a reamer or other spherically shaped tool. In this example, the system or the user is provided with circular, cylindrical, hemispherical, or spherical representations that are likewise used for display and feedback to the user or as part of processing decisions used within the OTT CAS system. In a final example, the surgical tool includes a flat filing blade, whereby the representation will again be a flat surface (or thin rectangular block) depicting a certain thickness of filing action which would result upon contact to the anatomical surface.

In the embodiments that follow, an on-tool tracking system (OTT) embodiment is used to acquire, perform some data-processing on board, and provide real-time data regarding the surgical procedure to the computer-aided surgery computer, and to receive commands from the latter to set its own motor speed, attenuate speed or even stop to prevent unintended cutting. The on tool tracking system is used to provide a variety of data for use by the computer aided surgery system. One form of data is imaging data from imaging sensors provided by the on-tool tracker. The data provided by these imaging sensors include for example stereoscopic images, which once processed, can be used for tracking and information to be projected onto the surgical field by a standalone or an embodied projector or any type of projector provided for use with the on tool tracking system. Other data provided by the imaging sensors includes, reference frame location, orientation, alignment or other physical attribute of a reference frame used for defining the surgical field. One or more reference frames that may be positioned around the field, around the joint, around the knee, or sized and shaped in relation to a surgical field where the reference frame is visible during at least a portion of all or substantially steps of a surgical procedure. (See, for example, reference frame embodiments described with regard to FIGS. 16-30. Still further, data may be selected only from a relevant reference frame or portion thereof based upon the dynamic, real time assessment of a CAS procedure or CAS step.

For example, in a CAS procedure where two frames are present, both may be used at the beginning of a cut and then the system shifts to using only one reference frame used during the cut. In a similar way, the system may use less than all the fiducial markers available on a specific reference frame during a procedure in furtherance of the mode adjustments described below. Fewer fiducials to process may permit faster updates or reduced image processing computer cycle time. As shown and described herein, the reference frames may have the same shape or different shapes and may contain any of a variety of fiducial markers in any of a variety of suitable arrangement for detection by a visual or an infrared tracking system in the OTT. Still further data available from the imaging sensors includes scene information such as anatomical configurations of real or artificial anatomy or structures, markers positioned on the patient, additional targets positioned around the surgical field such as pointers, markers or the instrument being used in the field such as a saw, drill, burr, file, scene information refers to image capture, image processing or camera adjustments to select and process a portion of a frame, adjust a camera to zero in on or focus or zoom to a portion of interest in the surgical field based on real-time dynamic CAS procedures and consideration of a CAS surgical plan, reamer or any other surgical tool to which the on tool tracking system is mounted.

When resecting the various portions it may be desirable to modify the view of the virtual model displayed on the OTT monitor. For instance, when cutting along a first plane it may be desirable to view the virtual model from a first perspective, and when cutting along a second plane it may be desirable to view the virtual model from a second perspective. Accordingly, the OTT CAS system tracks various data regarding the status of a procedure, including, but not limited to the following: the position of the surgical tool relative to the tissue to be resected and the orientation of the surgical tool relative to the tissue to be resected. Based on the position and orientation of both the tissue and the surgical tool, the system calculates which surface is about to be cut during the procedure and update the OTT monitor accordingly.

Further, the OTT CAS system can be configured to account for the preference of each user as well as the characteristics of the instrument using the OTT device. Specifically, a surgeon may desire a different view than the default view for a particular resection step or cutting plane. The system allows the surgeon to override the default selection and specify the view for a particular cut. The system stores the information regarding the desired view for the particular cut for the particular surgeon and uses the view as the default view in the future when the system determines that a similar cut is to be made. The system tracks the user preference based on the user logged into the OTT CAS system.

In addition to the types of data described above, the on tool tracking system may also provide other kinds of data such as output from one or more sensors on the on tool tracker. Exemplary sensors include position sensors, inclinometers, accelerometers, vibration sensors and other sensors that may be useful for monitoring, determining or compensating for movements of the tool that is carrying the on tool tracking system. For example, there may be sensors provided within the on tool tracking system to compensate for noises or vibrations generated by the tool so that the noise and vibration may be compensated for i.e. cancel out of the imaging data or other OTT data being transmitted to the computer aided surgery system computer. In still another example, an accelerometer or motion sensor may be provided to produce an output to the computer aided surgery system used in predicting the next frame or estimating where relevant information in an imaging frame may be located based on the movement of the tool and a tracking system. In still another aspect, sensors carried on board the on tool tracking system may be used to detect, measure and aid in canceling unwanted movement that may interfere with, impair the quality of or complicate CAS or OTT image processing. Specific examples of this type of feedback include sensors to detect and aid in the cancellation of hand shaking or movement by the user. In still another example sensors may be provided to detect and aid in the cancellation or compensation of unwanted movements or other interference generated during active surgical steps.

In other variations, image capture, processing and camera adjustment may also be used in or become the subject of compensation techniques, including to dynamically optimize the field-of-view and volume-of-interest. In one example, a camera provided on the OTT contains an auto focus capability that, under instructions from the CAS computer and the various factors described herein, will dynamically adjust the camera and view to zoom, track, pan or focus on a frame, a portion of a frame or a natural or artificial feature. In another aspect, the imaging portion of a camera on the OTT is provided with a suitable on board movement system to tilt or adjust the lens to direct the lens to one or more features under the direction of the CAS computer. This tilting lens may be used in conjunction with the dynamic lens above or with a lens having fixed (i.e., not adjustable characteristics). In one aspect, a micro mechanical base supporting the camera lens is adjusted according to the instructions from the CAS computer. It is to be appreciated that while the lens/camera adjustment may be done internally with a MEMS structure, it may be done external to as well. For example, a camera in a housing may be carried by a dynamic stage (x-y-z or x-y motion for example) where the state receiver instructions from the CAS computer to adjust the camera position in accord with the OTT CAS processes described herein. Still another form of compensation provides for image processing or other adjustments for OTT-tool orientation such as top mounted OTT, left side mounted OTT or right side mounted OTT. Still further, the various aspects described above for controlling the field of view (including either or both of the horizontal and vertical field of view alone or in any combination) along with adjustments to a volume of interest within the surgical field may be accomplished dynamically and optimized in real time utilizing the instructions contained within the OTT CAS system, the CAS mode select processing sequences and/or any of the specific CAS mode algorithms including vision based algorithms or specific mode algorithms.

Another example of settings and compensation techniques include the implementation and switching on/off of infrared filters placed in front of the camera lens so that the imaging can be of infrared only or emitted or reflected by the reference frame markers to cut-out white light noise and to ease image processing and marker detection.

It is to be appreciated that these aspects of compensation may be implemented mechanical components, electrical components or with software, each alone or in any combination.

For purposes of discussion and not limitation the data from the on tool tracking system will be categorized as imaging data and sensor data to capture the broad categories described above. Using system resources provided either on the on tool tracking system itself or provided by the computer-aided surgery computer, the data is processed to provide an output for use by the computer aided surgery system. The desired output of data processing comes in a number of different forms depending upon the specific processes being evaluated and as described in greater detail below. For purposes of this overview, one may consider that the data output obtained from the on tool tracking system may include such things as the orientation of the on tool trackers in the surgical field, the position of the tools or the on tool trackers in relation to the surgical field, information regarding the surgical field such as physical changes to the anatomy undergoing surgery, movement of the OTT tracked tool within the surgical field, displacement of the tool within the surgical field, apparent progress of the surgical step being tracked and other information related to the initiation, progress or completion of a surgical step or a computer aided surgical procedure.

The output of the on tool tracker, in whatever form suited to the particular computer aided surgical procedure undertaken, is next compared to the step, or procedure undertaken according to the surgical plan. The result of this comparison produces an output back to the on tool tracker that gives information related to the plan, step, or progress with in a step of the surgical plan. In general, this output is manifested for the user as the result of a projected image from a projector on board the on tool tracker, but it can also include audio feedback, changes/messages in a computer screen if available, actions on the cutting tools (e.g. changes of cutting speed, direction and stopping), etc. It is to be appreciated that the output from this projector (as example) may be adapted based on a number of considerations such as the available surgical field upon which an image may be projected, the likely position and orientation of the on tool tracker and its tool to the surgical field, and the likely challenges of making the projected image visible to the user. As a result, the onboard projector is capable of projecting images in a variety of configurations based upon the dynamic, real-time circumstances presented during the surgical procedure. Moreover, the on tool tracking system may be provided with additional illumination sources to enable the system or the user to obtain image data in the visible spectrum, infrared spectrum, or in any other spectrum suited to image processing using the on tool tracking system. In still further aspects, one or more of the CAS mode processing methods described herein may be modified to incorporate the use of any of a variety of pattern recognition, computer vision, or other computer-based tracking algorithms in order to track the location and orientation of the OTT instrument in space relative to the surgical site, or relative to other instruments near the surgical site, and progress of an OTT CAS surgical step, without or substantially without the use of reference frame-based tracking information. In other words, the embodiments of an OTT CAS method include the use of visual information obtained from the trackers or cameras on board the OTT for the purpose of identifying, assessing, tracking, and otherwise providing the CAS data sufficient for the purposes of providing appropriate CAS outputs for the user to complete one or more CAS processing steps. In one aspect, a portion of the anatomy within the surgical field is marked or painted for the purpose of enhancing vision based tracking and vision based algorithm processes. As a result of being provided information from the projector of the on board tracking system, the user may respond to that information by making no change to his actions or by adjusting, as warranted under the circumstances for the step or procedure, one or more of the operation, placement, orientation, speed, or position of the tool in the surgical field. The information from the projector may be provided alone or in combination with other OTT components or feedback or indications such as tactile or haptic feedback.

Next, the continued action or change of action by the user is detected by the on tool tracking system and the process of providing data processing data and providing it for comparison and evaluation by the computer aided surgical system continues.

Against this general overview is to be appreciated how, in use, embodiments of the on tool tracking enabled computer aided surgery system described in herein monitors and evaluates one or more of the position, movement, use, predicted movement of an instrument using the on tool tracker against the planned computer aided surgery procedure and produces appropriate computer aided surgery outputs to the user based at least in part on a real-time computer aided surgery assessment by the computer aided surgery system.

Figure 31A:
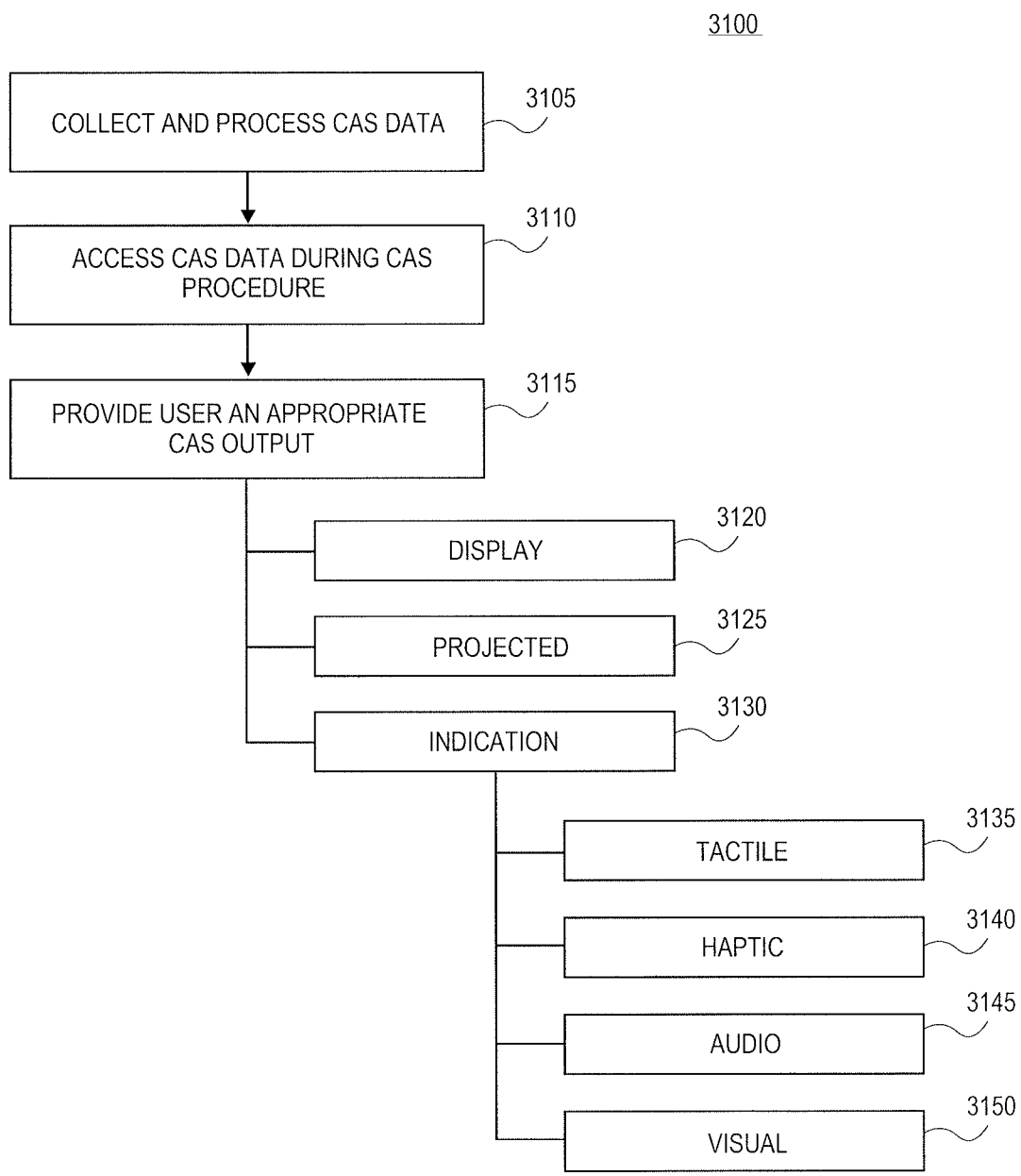
FIG. 31A is a flowchart representing an exemplary loop of a cyclic OTT CAS method (i.e looped or repeated in time).
Figure 31B:
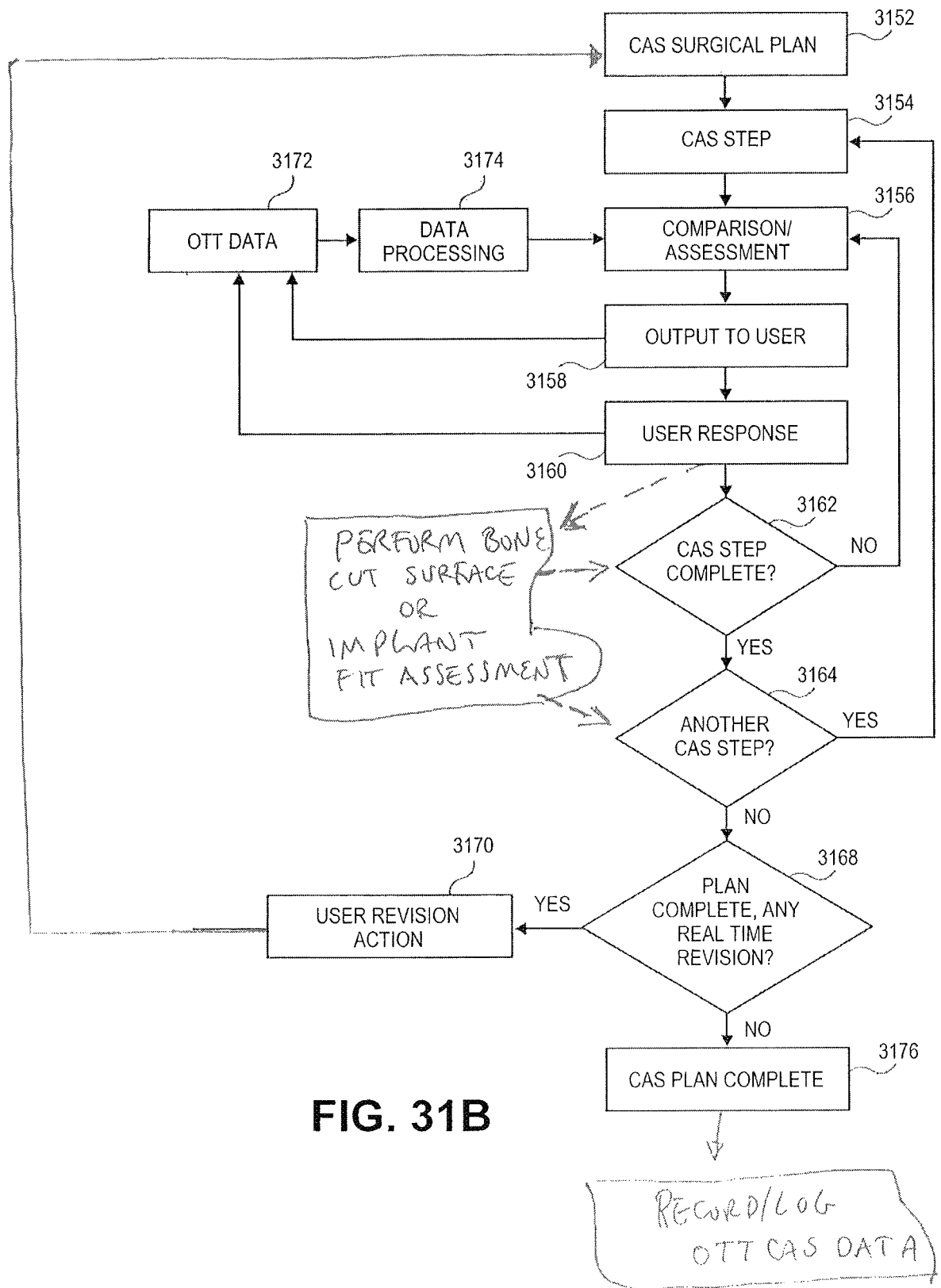
FIG. 31B be is a flowchart providing additional details of the exemplary processing steps performed using the method described in FIG. 31A.

Turning now from the general overview to more specific discussions of how computer aided surgery is modified by the use of the on tool tracking system described herein. FIG. 31A illustrates a general process flow of information for computer assisted surgery. FIG. 31B similarly represents the general step wise approach used during the actual delivery of the computer assisted surgical plan. These two flow charts will be used to provide a general frame work for the improvement to computer assisted surgery according to embodiments described herein.

With reference to FIG. 31A, information obtained by the system is processed. This can include information from a variety of sources located within the surgical field or from instruments used during surgical procedure in a continuously running feedback loop. Next, the information that has been obtained and processed is assessed using an appropriate computer assisted surgery algorithm. Finally, an output is produced from the assessment to aid the user in performance of the surgical procedure. The output produced may include one or more of the display, a projected image, or an indication. Indications may include, for example, a tactile feedback signal including for example temperature variations, a haptic feedback signal with forces or vibration of different frequency and/or amplitude, remote or onboard control of the instrument's motors or actuators with regards to their speed, direction, brake and stopping, an audio signal or visual signal provided to the user in a manner appropriate to the circumstances and use of the on tool tracking system and the instrument attached thereto.

While similar to the conventional computer aided surgery in some respects, the systems and techniques described herein are different and provide unique advantages over conventional computer assisted surgery systems and methods.

The on tool image and projection module is adapted and configured with a number of different characteristics based upon the type of computer assisted surgery being undertaken. OTT position in relation to surgical field during expected use for a CAS procedure, orientation of projector to the tool being guided, shape and surface condition (i.e., rough presence of blood or surgical debris) of the surface in the surgical field being projected on, horizontal field of view accommodation, vertical field of view accommodation are just a number of the considerations employed in the embodiments described herein.

Still other embodiments of the computer aided surgery system described herein compensate for variations and alternatives to the component selection and configurations resulting from the above described features. One exemplary compensation relates to camera adjustment or image adjustment (discussed above) for the surgical step or field adjustment based on a particular computer aided surgery technique. Another exemplary compensation relates to the actual projector position on a particular embodiment. The projector position of a particular embodiment may not be on the centerline of the device or in an optimum position based on horizontal or vertical field of view or may be tilted in order to address other design considerations such as making a device smaller or to accommodate other device components. One form of compensation for this aspect is for the projector output to be adjusted based on the actual projector location.

This type of compensation is similar to keystone adjustments for a projector output. The projector provided on board the on tool tracking system may have its output compensated for the expected or actual portion of the surgical field where the projector output will display. During the surgical procedure the surgical site is likely not to be flat and so would not faithfully reflect the intended image from the projector. However, since the geometry of the target anatomy (e.g. bone surface) is known, the image to be projected by the projector can be changed by software to compensate such that when projected on the non-flat surface, it would appear clearer as intended to the user. The target anatomy surface for projection may vary in shape, orientation, curvature or presence of debris, blood and still further, the output of the OTT projector may be adjusted based on real time factors such as these detected by the OTT vision system and object detection techniques. When the cutting has started, there would be a new source of 'unflatness', namely, the interface between the original native surface of the bone, and the new surface introduced by the cut. This can be calculated (and compensated for) during cutting by logging where the cut was made, or assumed to be the desired ideal/planned surface, or digitized (e.g. with the pointer) after each cut.

Still further differences between the OTT surgical technique and conventional computer assisted surgical techniques include the types and manner of providing outputs or receiving inputs from the on tool tracking system or the user. Sensors and systems to provide tactile, haptic or motion feedback may be used as well as a variety of indicators such as alarms, visual indicators or other user inputs specific to the capabilities of a specific OTT system.

FIG. 31B relates the general OTT enabled CAS process with added details to call of additional aspects of the OTT CAS system. When the procedure begins, the user has a selected surgical tool with the on tool tracking system mounted thereto in either top mount, right side mount, left side mount or bottom mount as determined by the user and the OTT CAS plan. The tool with attached OTT is identified to the system through a tool registration procedure such as the tool transmitting an identification signal or a self-registration process or other suitable registration process. The pre-surgical planning steps, as needed, are completed according to the procedure to be undertaken. Beginning with the computer aided surgery surgical plan, the user initiates a computer aided surgery step. As a result of the use of the on tool tracking system, on tool tracking data is generated. The on tool tracking data is processed and then provided to the computer system that compares and assesses the planned surgical step information to that received from the on tool tracking data. As a result of this comparison and assessment of the on tool tracking data, an appropriate output is provided to the user or to the OTT's on board motor control circuitry as a motor or actuator control signal to slow, stop or reverse the instrument or let it continue at the speed desired by the user through the manual onboard hand trigger. This output is detected and acted upon by the on tool tracking system which provides additional data that is again provided to the tracking computer. Next the user responds to the output provided and either continues the current action, or changes the use of the tool being tracked by the on tool tracking system. The users response, whether involving action or not, is detected by the on tool tracking and becomes additional data input to the surgical computer. These processes continue as the computer system processes the progress of the step against the surgical plan. If the answer to step completion is no, comparison of data and output to the user continues. If the answer to step completion if yes, then the user may initiate the next surgical step or the surgical planning computer may provide an output to the user to notify him that one step is completed and any one of other remaining other steps can be undertaken. The sequence of CAS steps to be performed are totally up to the user, except in situations where one step cannot be performed without a prerequisite other step(s) identified in the set surgical plan. The control is totally in the hands of the user, with the computer being only (optionally) suggestive of what steps can be done, or (optionally) prohibitive of what steps cannot be done. These processes continue in accordance with computer aided surgery procedures until the plan is delivered. If the plan is complete, the use may determine whether any real-time revision of the surgical area is to be undertaken. The revision process may also be tracked and monitored to provide information to the user. If no revision is required or the CAS plan is completed, then the CAS plan is completed.

Figure 32:
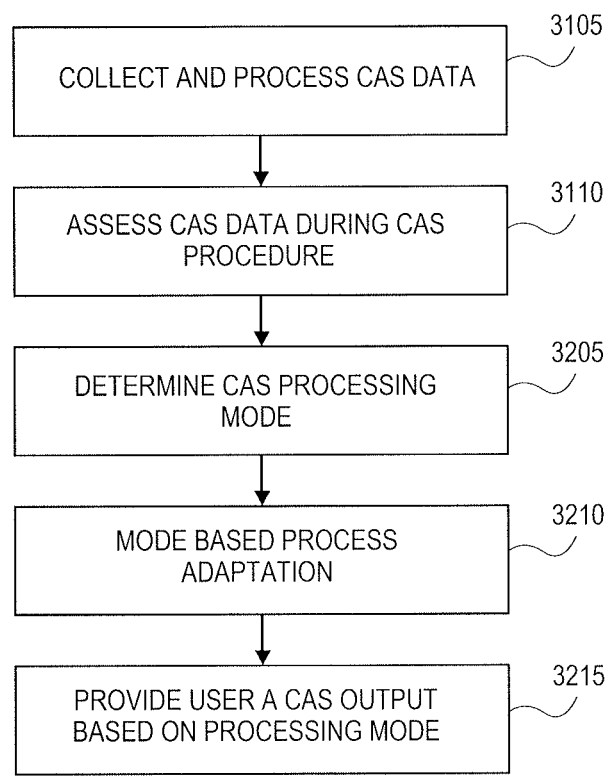
FIG. 32 is a flow chart providing exemplary additional details of the processing steps used for determining a CAS processing mode.

FIG. 32 provides a flowchart that will be used to describe still another improvement to computer aided surgery provided by embodiments of the on tool tracking system described herein. As before, the system will collect and process computer aided surgery data. Next, the computer aided surgery system will assess the CAS data during the CAS procedure. As a result of this assessment, the CAS computer will determine the CAS processing mode. Thereafter, mode based processed adaptation will be applied to the data used in the CAS process. Finally, the OTT CAS system provides a user or the instrument motor/actuator a CAS output (or speed and motor direction set-point) based on the processing mode.

Figure 33:
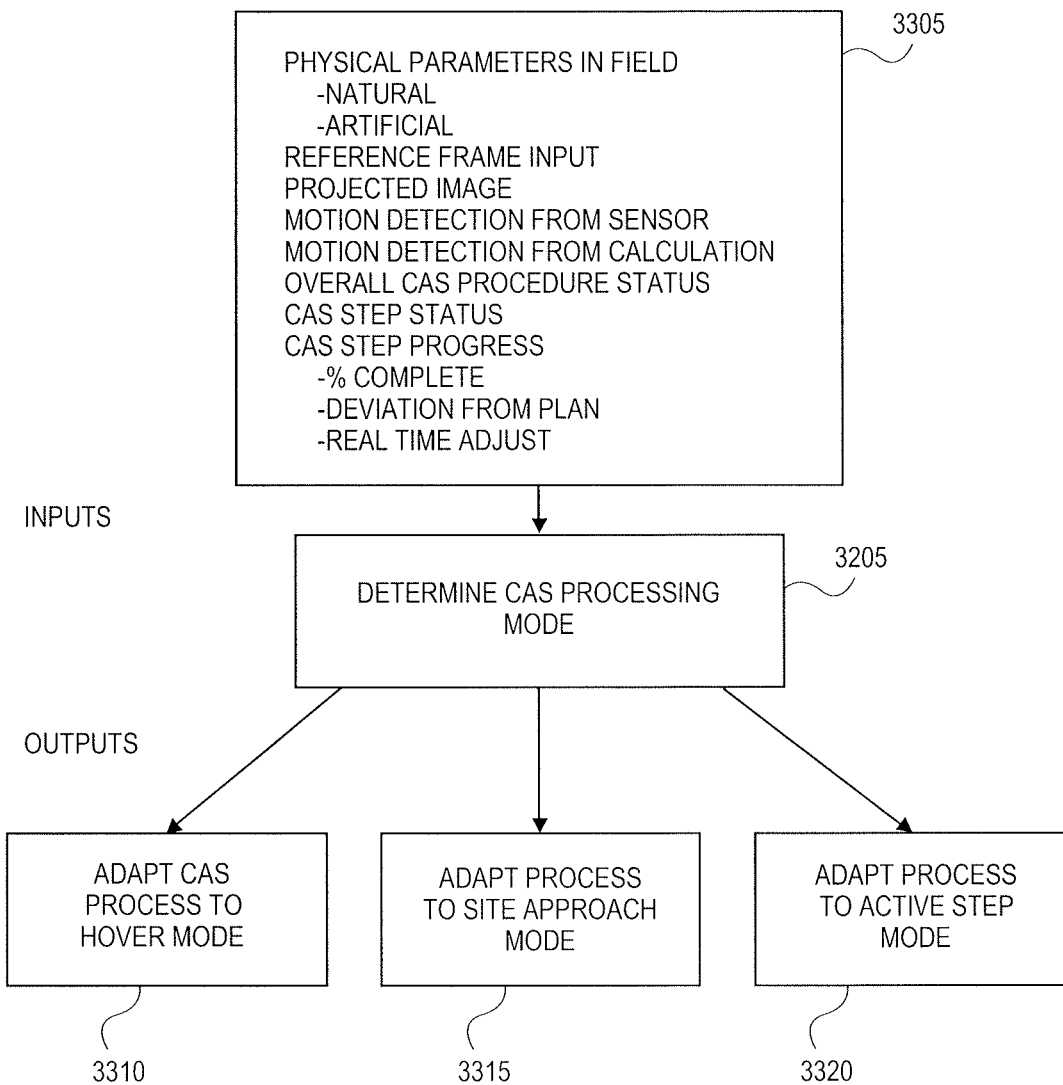
FIG. 33 is a flowchart diagramming a number of factors considered as inputs for determining a CAS processing mode as well as a representative outputs.

Mode selection relates to the OTT CAS system ability for a dynamic, real time assessment and trade off of a number of aspects of the CAS operation including the need to update the user, processing rates, cutting instrument motor control/actuation instantaneous speed and prospective response times and requirements to obtain improved or different data, relative importance of portions of data based upon CAS step progress or interaction with the patient or other factors relating to the overall responsiveness of the OTT CAS system. Additional aspects of the step of determining the CAS processing mode described above in FIG. 32 may be appreciated with reference to FIG. 33. FIG. 33 relates to the inputs considered by the system to determine the processing mode and the result of that determination. Exemplary inputs used by the OTT CAS system for determining processing mode include, by way of example and not limitation, one or more of the following: speed or motion of the tool or its motor/actuator speed, input or indication from a tool monitoring device, voice input or indication from user, physical parameters in the surgical field, including natural or artificial parameters; reference frame input; projected image; motion detection from sensors; motion detection from calculations; overall CAS procedure status; CAS step status; user input (e.g. CAS screen, OTT touch screen, touch screen, motions sensor, gesture recognition, GUI interface, etc.); CAS step progress including, for example, percentage complete, deviations from plan, real-time adjustments. As a result of the determination step performed by the OTT CAS computer a processing mode will be selected based on the real-time circumstances and evaluation of the surgical procedure as made by the algorithms of the CAS for OTT computer. Criteria used by the OTT CAS computer for determining mode include such factors as the physical proximity of the surgical tool to the patient anatomy, actions being undertaken by the user, sensor inputs of tool motion, predicted tool motion, speed of tool motion, speed of the tool's motor or cutting actuator and other factors related to the placement, orientation, or use of a surgical tool within the OTT image field. By way of non-limiting example, CAS processing modes may include a hover mode, a site approach mode, and an active step mode. In general terms, hover mode refers to those circumstances during an OTT CAS procedure when the on tool tracker and tool is near or within the surgical field without contact between the tool and the patient. In general terms, site approach mode refers to those circumstances during an OTT CAS procedure when the on tool tracker and tool is within the surgical field and in contact with patient, but without the tool actively engaging the patient anatomy to perform a surgical step such as sawing, cutting, reaming, drilling, burring, shaving, filing and the like. In general terms, active step mode refers to those circumstances during an OTT CAS procedure when the on tool tracker and tool is engaged with the patient anatomy to perform a surgical step such as sawing, cutting, reaming, drilling, burring, shaving, filing and the like. As a result of the determine CAS processing mode decision, the OTT CAS computer will adapt the CAS processing mode to or between: hover mode, site approach mode, or active step mode as is appropriate under the circumstances.

Figure 34:
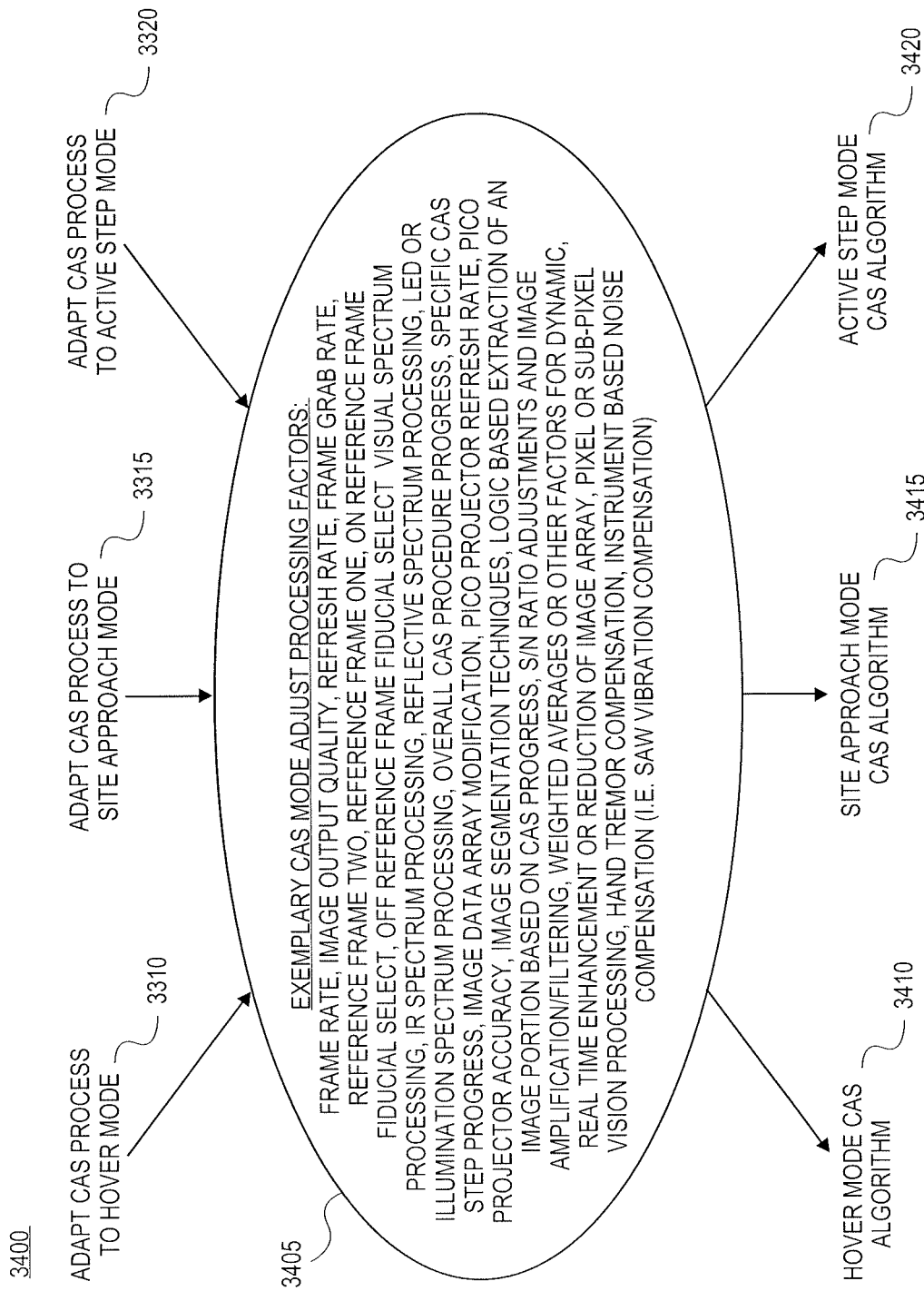
FIG. 34 is a flowchart representing the exemplary OTT CAS mode adjust processing factors used to determine the process loads for a hover mode, a site approach mode and an active step mode.

Step of adapting the CAS process to a particular mode as described above with regard to FIG. 33 is further described with reference to FIG. 34. In general terms, the OTT CAS computer is adapted and configured to adapt the CAS process mode based on adjustment factors to produce a particular mode processing algorithms. By way of example, the various mode adjust processing factors are shown in FIG. 34. Based on the processing inputs as detailed in the flowcharts above, the OTT CAS computer will adjust the processing steps undertaken for OTT CAS based on one or more of or combinations of or variations of the following CAS mode processing adjustment factors: camera frame size and/or camera orientation (if camera software or firmware provides for such adjustment); adjustments to camera image outputs to modify a size of a region of interest within a horizontal field of view, the vertical field of view or both the horizontal and the vertical field of view of the camera; drive signals for adjustable camera lens adjustment or positioning; image frame rate; image output quality; refresh rate; frame grabber rate; reference frame two; reference frame one; on reference frame fiducial select; off reference frame fiducial select; visual spectrum processing; IR spectrum processing; reflective spectrum processing; LED or illumination spectrum processing; surgical tool motor/actuator speed and direction, overall CAS procedure progress; specific CAS step progress; image data array modification; pico projector refresh rate; pico projector accuracy; set projector or other OTT electronics "OFF" or in sleep mode or power save mode; image segmentation techniques; logic-based extraction of an image portion based on a CAS progress; signal-to-noise ratio adjustment; image amplification and filtering; weighted averages or other factors for dynamic, real-time enhancement or reduction of imager rate, pixel or sub-pixel vision processing; hand tremor compensation; instrument-based noise compensation (i.e. saw vibration compensation). Put another way, the various factors listed above may be grouped into the various ways of providing adjustments of the camera based on those adjustments that can take place within the camera such as in the software or firmware or operating modalities provided by the camera electronics themselves on the one hand. And on the other hand, on a broader scale, the overall adjustment of the camera in its housing in relation to the OTT housing. In this way camera movement speaks of a more general shifting of the entire camera body or the camera lens itself rather than internal electronic modifications or adaptations of camera output based on electronic processing of camera image information. For within camera variations these are such things as focal point, zoom, exposure, aperture and other camera based modifications that will adjust the cameras output as part of an imaging adjustment. In one specific example, one or more of the above features are used to produce a hover mode CAS algorithm that is used during hover mode processing adaptation. In one specific example, one or more of the above features are used to produce an approach mode CAS algorithm that is used during approach mode processing adaptation. In one specific example, one or more of the above features are used to produce an active step mode CAS algorithm that is used during active step mode processing adaptation.

Figure 35:
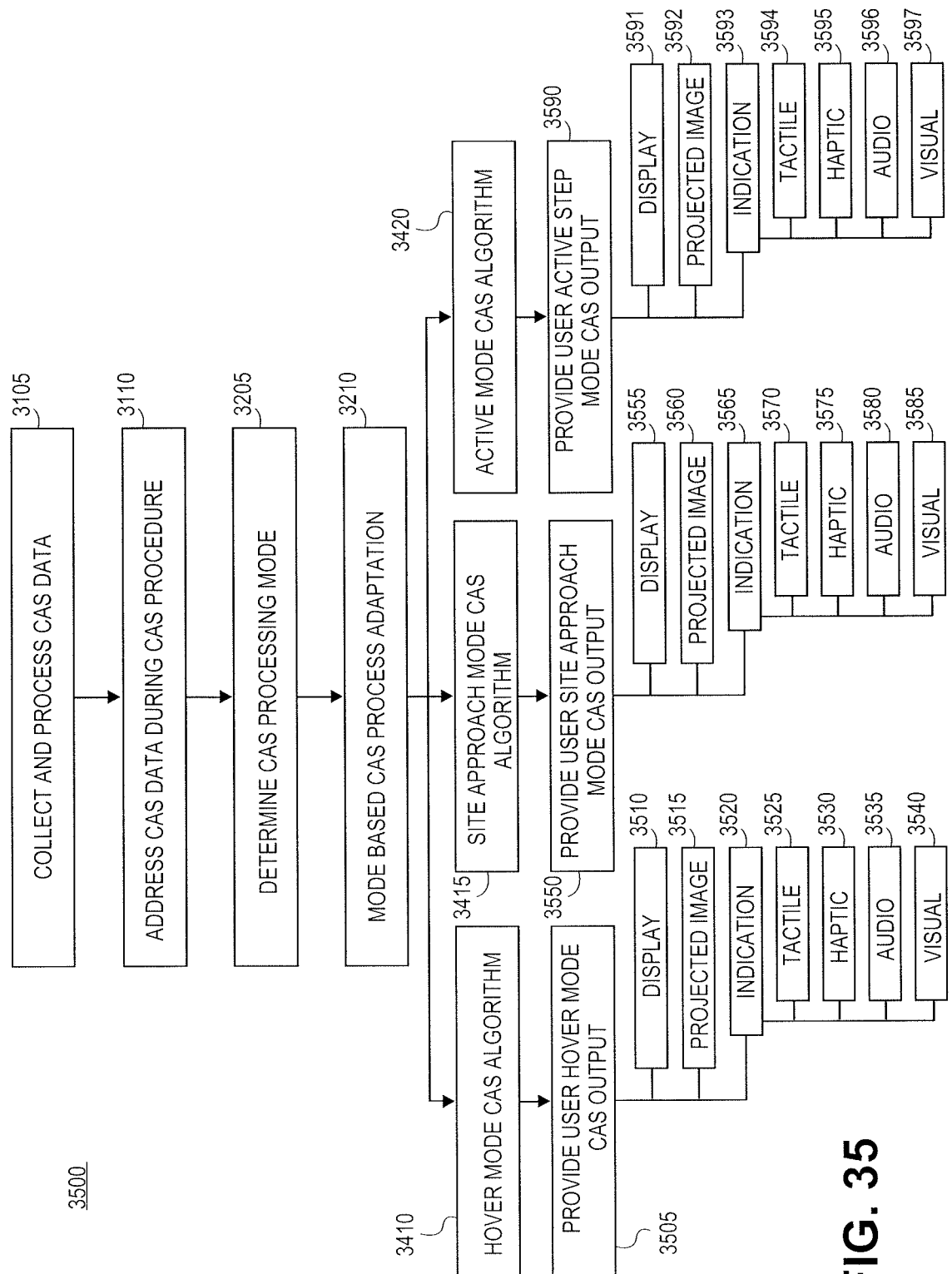
FIG. 35 is a flowchart representing an exemplary OTT CAS process including the result of an OTT CAS process adaptation and the resultant mode algorithm and modified outputs thereof.

FIG. 35 illustrates a flowchart of an exemplary OTT CAS process building upon the steps described above. Collect and process CAS data. Assess CAS data during a CAS procedure. Determine CAS processing mode. Undertake mode based CAS assess adaptation. Based on the result of the mode based determination, if hover mode, apply hover mode CAS algorithm to processing. Provide the user with hover mode CAS outputs, or provide the OTT motor control circuitry with speed control commands/signals. Exemplary user outputs include hover mode display outputs, hover mode projected image outputs, hover mode indications such as tactile, haptic, audio and visual indications adapted to the processing steps used in the hover mode. Based on the result of the mode based determination, if site approach mode, apply site approach mode CAS algorithm to processing. Provide the user with site approach mode CAS outputs. Exemplary outputs include approach mode display outputs, approach mode projected image outputs, approach mode indications such as tactile, haptic, audio and visual indications adapted to the processing steps used in the approach site mode.

Based on the result of the mode based determination, if active step mode, apply active step mode CAS algorithm to processing. Provide the user with active step mode CAS outputs. Exemplary outputs include active step mode display outputs, active step mode projected image outputs, active step mode indications such as tactile, haptic, audio and visual indications adapted to the processing steps used in the active step mode.

Figure 36:
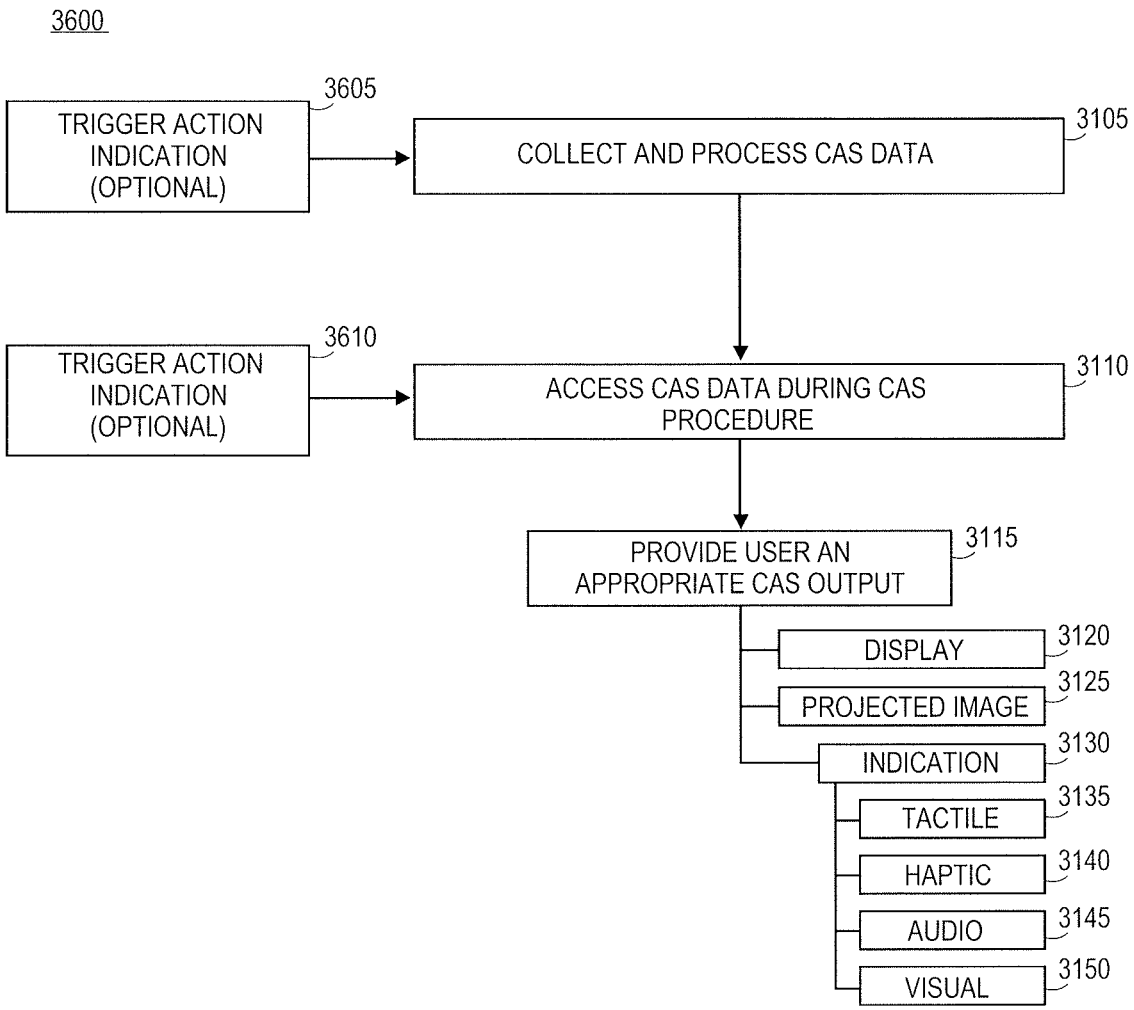
FIG. 36 is a flowchart representing an exemplary OTT CAS process including modification of any of the above described OTT CAS processes to include associated surgical tool operational characteristics, parameters or other data related to the use of an active element in any OTT CAS process or procedure.

FIG. 36 illustrates a flowchart amid exemplary OTT CAS process based upon those described above but using a unique trigger action indicator tool monitor or tactile or haptic feedback to further provide benefits to users of an OTT CAS system. Various alternative embodiments of the trigger action indicator are provided below with regard to FIGS. 37A-52B. As before, the OTT CAS process proceeds by collecting and processing CAS data. In one alternative aspect, the collection and processing may also include an indication from the trigger action. Next, following the processes described above, the OTT CAS system will assess CAS data during a CAS procedure. Here again, a trigger action indication may also be applied to this step and assessed along with other CAS data. Thereafter, the user will be provided with an appropriate CAS output based upon the use of one or more trigger action indicators as described above. The appropriate CAS outputs may include a display, a projected image, or any of a number of indications such as tactile indications, haptic indications, audio indications or visual indications as described above or as are typical in CAS procedures.

Against this backdrop of the various aspects of OTT CAS processes, the following examples are provided.

It is to be appreciated that OTT CAS mode may be detected and determined by many factors (e.g., reference frame(s), positions, relative motion, etc.). Additionally, in the context of a surgical procedure, there is also benefit in relating the defining attributes of an OTT CAS mode based on tool/target proximity or use. Consider the following examples of: A) Hover: both tool and target within surgical field, but no contact; B) Approach: Both tool and target within surgical field AND they are in contact; and C) Active step mode: Both tool and target within surgical field AND they are in contact AND there is active engagement of tool with tissue. In one aspect, the OTT device electronics incorporates this mode selection functionality in a 'smart views' module. This module is provided within the main CAS system computer or within the OTT device where electronics including software and firmware implement all or a substantial part of the modes detection algorithms, and triggers the different events of the OTT CAS mode selection functionality.

In some additional aspects of OTT CAS mode control, one or more of the following variations or alternatives may be incorporated:

1. Due to the temporal/special resolution on an OTT CAS system and CAS system generally, some embodiments of the Approach mode may be considered appropriate when tool and target are within a given user-pre-selected (settable) distance envelope. The distance envelope may be designated in a measurement range. One exemplary range may be between 10 mm to 0 mm as determined by the OTT CAS system. In other aspects, the Approach mode may be delineated by the OTT CAS system determining that there is likely contact between an active element of a surgical tool and the anatomy within the OTT CAS surgical field.

2. In some aspects, an OTT CAS mode is provided with a 'hysteresis' factor. This OTT CAS hysteresis factor is selected to include the types of circumstances or CAS conditions that, if satisfied such as continuously for a pre-determined time period, will result in that CAS mode being maintained. In other words, the parameters of the OTT CAS mode hysteresis must be met continuously during a period of time to 'lock into the mode' or maintain that OTT CAS mode. As used herein, continuously is meant to be within the context of the time domains of OTT processing times and sample rates and is not intended to denote the absolute non-interruption of the conditions monitored. By way of similar example, the hysteresis or some of the hysteresis conditions have to NOT be met continuously during a period of time to 'un-lock' or permit adjustment of the OTT CAS mode. The use of OTT CAS mode hysteresis factors improves the system response to transients, avoids or reduces the likelihood of the system to jump from one OTT CAS mode to another inappropriately and improves usability of the system since the user is likely to see more stable OTT CAS outputs as the system will be providing those outputs from a single OTT CAS mode.

3. During some OTT CAS steps, there are activities performed by the user that may not require use of the projector, may require different input-output (TO) devices (e.g. during implant location assessment it may not be possible to project information on the bone), and/or may not have a defined target-tool relationship (e.g. knee range of motion assessment only requires seeing tibial and femoral reference frames). It is to be appreciated that the OTT CAS system may also receive inputs from other sources and there are OTT CAS outputs where no projector output is provided or utilized.

4. In general, the processing algorithms and OTT CAS mode factors are selected based on the probability or likelihood that, as for such things as the relative motion for bones, instruments, implants, etc. will be decreasing as the OTT CAS mode progresses from Hover to Active. The one exception to this general process assumption is when the OTT CAS device or system is used for the process of an assessment of a range of motion for an involved joint within the surgical field or for that joint that is the objective of the OTT CAS procedure or step.

OTT CAS Mode Examples

Bone Registration:

Objective:

Finding out the geometrical relation between the origin of the reference frame and the origin of the bone model.

Procedure:

Digitization of points on the surface of the bone with a tool (e.g. navigated pointer), and processing of these points against pre-determined geometry data of the bone model How the OTT CAS system identifies this task:

Pointer's AND bone's (either tibia or femur) reference frames (RFs) are visible to OTT.

Initiation of the task:

The OTT CAS system recognizes both reference frames coexisting in the scene (for at least a minimum period of time suited for this registration)

An additional 'guess' factor is the stage of the procedure because for example, cutting cannot be done until the bones are registered.) In this case, the trigger for this event may be the OTT device is maintained in position to keep two reference frames within the field of view until a bone registration process is completed. This trigger can optionally be confirmed by the system computer prompting the user to confirm and they respond.

The information obtained during OTT device bone registration may be annotated or overwritten if needed by user's input (touch screen, voice command, touching with the pointer on a specific divot on the bone's reference frame, etc.)

The latter (divot) is a specified point (position) on the reference frame that when touched by a navigated pointer, would tell the system that the user is intending to perform a task (or one of the dedicated tasks) which involve that reference frame itself. For example, this could be a registration of the bone attached to that reference frame, and this may also invoke a change of mode from eg. from Hovering/smart-views to registration screen etc.

OTT CAS Modes

Hovering:

Range Condition: OTT device is too far away from the RFs, or the 2 RFs are too far apart. The range to trigger this condition is settable during the calibration/tuning of the system, or by user preferences, and is specified as a distance threshold between the cameras to the target anatomy reference frame beyond the optimum FOV (in our embodied case greater than 200 mm).

Tracker: Lower refreshing rate

Projector: May not project any image on the bone (as the bone location is not yet defined), but can project elementary helpful information such as confirming this mode/status etc. on any reflective surface which happens to be in the way. Low refreshing rate, limited by the trackers.

System: Monitors the pointer's tip and the bone's RF location in 'world' coordinates. Drives tracker, projector, and other IO devices.

Approach:

Range Condition: Medium OTT/RFs and RF/RF distances. The range to trigger this condition is settable during the calibration/tuning of the system, or by user preferences, and is specified as a distance range from the target anatomy reference frame such as 100-200 mm Tracker: High refreshing rate, optimizing pointer and bone RFs readings (e.g. ignoring or disregarding other RF's)

Projector: As above, may not project any defined image (as the bone location is not yet defined), but can project a solid screen that changes colors (e.g. red, yellow and green) based on 'readiness' to start collecting registration points.

System: Monitors the pointer's tip and the bone's RF location in 'world' coordinates. Drives tracker, projector, and other IO devices.

Active:

Smaller OTT/RFs and RF/RF distances. For example, less than 70-100 mm distance from the target reference frame, again settable by user preferences as above.

Tracker: High refreshing rate, optimizing pointer and bone RFs readings

Projector: As above.

System: Monitors the pointer's tip and the bone's RF location in 'world' coordinates. Records pointer's tip location for each digitized bone. Drives tracker, projector, and other IO devices. Monitors progress of the registration process, and when finished it calculates the final registration matrix.

May or may not require additional IO device (e.g. touch screen)

OTT CAS Considerations for Transitions Between Modes:

Mode shift is based on distance thresholds.

If there is no bone registration information then it is not possible to determine bone-pointer 'contact' or 'closeness'. The system alternatively looks at a nominal distance between the pointer (which IS registered) and the bone's reference frame (instead of the bone itself). The resulting nominal distance may then be used to estimate or assume approximate registration based on the nominal position in which that (bone) reference frame is usually recommended to be placed (see picture sheet 18-23). Another alternative is to (optionally) simply use any old registration information by the system (of another default bone or one from a previous patient or surgery) to make the approximate registration for the purposes of determining what "mode" the system should be in. The availability of this option is also settable/selectable by the user.

Or by user's input.

End of the Task:

All registration landmarks have been visited and pointed (registration process is fully completed).

OR the system ceases to see the pointer's RFs (for at least a minimum period of time)

Alternatively, the process could be complemented or overwritten by user's input (touch screen, voice command, touching with the pointer on a specific divot on the bone's reference frame, etc.)

Bone Cutting/Drilling:

Objective:

Re-shaping the bone with a tool (usually a powered, smart instrument such as a saw, drill, burr, file, etc.) to allocate and implant.

Procedure:

Following the system's direction, the user cuts/drills (usually) one surface at a time. This particular activity applies to different individual 'target surfaces' on each bone, one per cut/hole to be performed, so the system will maintain such reference when using or processing locational or orientational errors of the tool relative to the bone. Different tools have different active elements (e.g. cutting tips), and so the different active elements of each tool shapes result in different 2D and 3D modification of the anatomy when the tool or tool active element interacts with the anatomy in the surgical field. As such, the guidance for each tool will vary with the type of tool and active elements in use during an OTT CAS process step.

How the System OTT CAS System Identifies this Task:

OTT detects at least one bone's reference frame (RFs).

The named bone is registered.

The reference frame of the bone being cut is within a user selectable maximum distance (say, for example only, less than 200 mm).

Initiation of the Task:

The system recognizes both RFs coexisting in the scene (for at least a minimum period of time)

This could be complemented or overwritten by user's input (touch screen, voice command, touching with the pointer or the cutting instrument on a specific divot or mark on the bone's reference frame or the bone itself, etc.)

Modes

Hovering:

OTT is too far away from the bone. For example, more than 200 mm (values settable by the user).

Tracker: Lower refreshing rate

Projector: May not project any image (the bone could be out of the projector's sight) or may just display rough shapes (e.g. arrows to indicate in what direction to move the instrument—e.g. saw, drill, etc.—to align it with the bone). Optionally, the projector output is modified to simply show different colors as in the previous example. Low refreshing rate, limited by the tracker's refresh settings.

System: Monitors the tool location and orientation relative to the bone (i.e. in bone's coordinates). Drives tracker, projector, and other IO devices. Communicates bi-directionally and drives smart instruments.

Approach:

OTT is at medium distance to the bone. For example, between 100 mm and 200 mm

Tracker: High refreshing rate, optimizing pointer and bone RFs readings.

Projector: Shows alignment aids (colored text, lines, circles, arrows, etc.) corrected for bone geometry at medium refreshing rate.

System: Monitors the tool location relative to the bone (i.e. in bone's coordinates) and calculates roll, pitch, yaw, and distances deviations. Drives tracker, projector, and other IO devices. Communicates bi-directionally and drives smart instruments.

Active:
OTT is close to the bone. For example, between 70 mm and 100 mm

Tracker: High refreshing rate, optimizing pointer and bone RFs readings.

Projector: Shows alignment aids (colored text, lines, circles, arrows, etc.) corrected for bone geometry at high refreshing rate.

System: Monitors the tool location relative to the bone (i.e. in bone's coordinates) and calculates roll, pitch, yaw, and distances deviations. Drives tracker, projector, and other IO devices. Communicates bi-directionally and drives smart instruments at higher speed.

Transition Between Modes:
Transition may be based on distance thresholds.
Transition based on user input.

End of the Task:
User moves on to another task
All cuts and refinements are fully completed.
In one alternative, the OTT CAS system ceases to see the bone's RFs (for at least a minimum period of time)
This step could be amended, complemented or overwritten by user's input (touch screen, voice command, touching with the pointer on a specific divot on the bone's reference frame, etc.)

Assessment of Bone Cut:

Objective:
Evaluating a new surface (e.g. plane, cylindrical hole, etc.) orientation, surface roughness, depth, etc.

Procedure:
Total or partial digitization of the surface (e.g. touching/traversing it with a navigated pointer), assessing a cut location and orientation with a 'surface monitor' (a navigated tool with a flat surface that sits on the flat cut), gauging the depth of a hole with a navigated pointer, etc.

How the OTT CAS System Identifies this Task:
OTT sees at least one bone's reference frame (RFs) as well as the assessing instrument's (surface monitor or pointer) RF.
The named bone and the instrument have been registered.
At least a cut has been performed.
The bone being cut is within a maximum distance 'D'.

Initiation of the Task:
The system recognizes both RFs (bone and instrument) coexisting in the scene (for at least a minimum period of time), while the conditions above are fulfilled.
This could be complemented or overwritten by user's input (touch screen, voice command, touching with the pointer or the cutting instrument on a specific divot or mark on the bone's reference frame or the bone itself, etc.)

Modes

Hovering:
OTT is too far away from the RFs, or the 2 RFs are too far apart.

Tracker: Lower refreshing rate.

Projector: May not project any defined image (as the bone can be out of projector's sight), or it can project a solid screen that changes colors (e.g. red, yellow and green) based on 'readiness' to start the process. Low refreshing rate, limited by the tracker's.

System: Monitors the tool location relative to the bone (i.e. in bone's coordinates). Drives tracker, projector, and other TO devices.

Approach:
OTT is at medium distance to both RFs AND medium bone-tool distance.

Tracker: High refreshing rate, optimized for instrument and bone RFs readings.

Projector: May not project any defined image (as the bone can be out of projector's sight), or it can project a solid screen that changes based on 'readiness' to start the process. Medium refreshing rate.

System: Monitors the tool location relative to the bone (i.e. in bone's coordinates). Drives tracker, projector, and other TO devices.

Active:
OTT is at medium/close distance to both RFs AND small bone-tool distance.

Tracker: High refreshing rate, optimized for instrument and bone RFs readings.

Projector: May not project any defined image (as the bone can be out of projector's sight), or it can project a solid screen that changes based on process status (start to end of data collection). High refreshing rate.

System: Monitors the tool location relative to the bone (i.e. in bone's coordinates). Records pointer's tip location for each digitized point or surface monitor location and orientation. Drives tracker, projector, and other TO devices. Monitors progress of the assessment process, and when finished it calculates, records and displays the calculated parameters.

May or may not require additional IO device (e.g. touch screen)

Transition Between Modes:
Simply based on distance thresholds.
Or by user's input End of the Task:
Assessment process is fully completed.
Optionally, the OTT CAS system ceases to see the instrument's RFs (for at least a minimum period of time)
This could be complemented or overwritten by user's input (touch screen, voice command, touching with the pointer on a specific divot on the bone's reference frame, etc.)

Assessment of Implant Fit and Alignment

Objective:
Comparing the actual location of the implant (or trial) on a bone, relative to where it was expected to be according to plan. This can happen during trial, and before/during/after implant cementing or locking.

Procedure:
An implant (e.g. femoral component, tibial tray, etc.) gets a RF attached, and is tracked in 'bone' coordinate system. At any given time the system can display/record its position (relative to the bone), and instant errors (if any) compared to where it was supposed to be.

How the System Identify this Task:
OTT sees at least one bone's reference frame (RFs) as well as the corresponding implant's RF.

The named bone and the implant have been registered.
All cuts have been performed.
The bone being and implant are within a maximum distance 'D'.
Initiation of the Task:
The system recognizes both RFs (bone and implant) coexisting in the scene (for at least a minimum period of time), while the conditions above are fulfilled.
This could be complemented or overwritten by user's input (touch screen, voice command, touching with the pointer or the cutting instrument on a specific divot or mark on the bone's reference frame or the bone itself, etc.)
Modes
Hovering:
  OTT is too far away from the RFs, or the 2 RFs are too far apart.
  Tracker: Lower refreshing rate.
  Projector: May not project any defined image (as the bone can be out of projector's sight), or it can project a solid screen that changes colors (e.g. red, yellow and green) based on 'readiness' to start the process. Low refreshing rate, limited by the tracker's.
  System: Monitors the implant/trial location relative to the bone (i.e. in bone's coordinates). Drives tracker, projector, and other TO devices.
Approach:
  Medium OTT/RFs distance AND implant/trial relatively close to the bone.
  Tracker: High refreshing rate, optimized for implant/trial and bone RFs readings.
  Projector: May not project any defined image (as the bone can be out of projector's sight), or it can project a solid screen that changes based on 'readiness' to start the process. Medium refreshing rate.
  System: Monitors the implant location relative to the bone (i.e. in bone's coordinates). Drives tracker, projector, and other TO devices.
Active:
  Smaller OTT/RFs distance AND implant/trial is close/touching to the bone.
  Tracker: High refreshing rate, optimized for implant and bone RFs readings.
  Projector: May not project any defined image (as the bone can be out of projector's sight), or it can project a solid screen that changes based on process status (start to end of data collection). High refreshing rate.
  System: Monitors the implant/trial location relative to the bone (i.e. in bone's coordinates). Calculates and displays (and record when needed) the errors defined by the actual location/orientation of the navigated implant relative to where it is supposed to be according to plan. Drives tracker, projector, and other IO devices. Monitors progress of the assessment process, and when finished it calculates, records and displays the calculated parameters.
  May or may not require additional IO device (e.g. touch screen)
Transition Between Modes:
  Simply based on distance thresholds.
  Or by user's input
End of the Task:
Assessment process is fully completed.
(or)The system ceases to see the instrument's RFs (for at least a minimum period of time)
This could be complemented or overwritten by user's input (touch screen, voice command, touching with the pointer on a specific divot on the bone's reference frame, etc.)
Range of Motion:
Objective:
Assess the range of motion and biomechanics of the joint after implantation. It can be done with trials or final implants on.
Procedure:
After placing the trial (or actual implant) on, before removing the bones' RFs and closing the wound, the surgeon flexes the knee and performs handles the joint, reaching limit positions like maximum flexion and hyper extension). This maneuvering is performed while pointing OTT to the tibial and femoral RFs. Dynamic measurements (tibia relative to femur) are expressed in anatomical terms.
How the System Identify this Task:
OTT sees both tibia's and femur's reference frames (RFs).
Both bones have been cut. (Bone cutting and implant location could have or could have not been performed.)
Initiation of the Task:
The system recognizes both RFs coexisting in the scene (for at least a minimum period of time), while the conditions above are fulfilled.
This could be complemented or overwritten by user's input (touch screen, voice command, touching with the pointer or the cutting instrument on a specific divot or mark on the bone's reference frame or the bone itself, etc.)
Modes
Hovering:
  OTT is too far away from the RFs.
  Tracker: Lower refreshing rate.
  Projector: May not project any defined image (as the bone can be out of projector's sight), or it can project a solid screen that changes colors (e.g. red, yellow and green) based on 'readiness' to start the process. Low refreshing rate, limited by the tracker's.
  System: Monitors the tibia location relative to the femur. Drives tracker, projector, and other TO devices.
Approach:
  Medium OTT/RFs distance.
  Tracker: High refreshing rate, optimized for bones' RFs readings.
  Projector: May not project any defined image (as the bone can be out of projector's sight), or it can project a solid screen that changes based on 'readiness' to start the process. Medium refreshing rate.
  System: Monitors the implant location relative to the bone (i.e. in bone's coordinates). Drives tracker, projector, and other TO devices.
Active:
  Smaller OTT/RFs distance AND implant/trial is close/touching to the bone.
  Tracker: High refreshing rate, optimized for implant and bone RFs readings.
  Projector: May not project any defined image (as the bone can be out of projector's sight), or it can project a solid screen that changes based on process status (start to end of data collection). High refreshing rate.
  System: Monitors the tibia location relative to the femur. Calculates and displays (and record when needed) the dynamic motion (flexion/extension, varus/valgus, internal/external rotation, AP motion, etc.). Drives tracker, projector, and other IO devices. Monitors progress of the assessment process, and when finished it saves all parameter recorded and notifies the user.

May or may not require additional IO device (e.g. touch screen)

Transition Between Modes:
Simply based on distance thresholds.
Or by user's input End of the Task:
Assessment process is fully completed.
(or)The system ceases to see the bones' RFs (for at least a minimum period of time)
This could be complemented or overwritten by user's input (touch screen, voice command, touching with the pointer on a specific divot on the bone's reference frame, etc.)

Other activities (e.g. registration verification, bone cut refinement, etc.) can be considered sub-cases of the above.

In one aspect in any of the above described examples, lower refreshing rate refers to changes in refresh rate from about 30-100 Hz to as low as 1-10 Hz.

When resecting a portion of a bone a surgeon may cut more rapidly and aggressively when the cutting tool is relatively far from the boundary of the area to be resected. As the OTT CAS detects the surgeon approaching the boundary of the resection area, the surgeon may receive appropriate OTT CAS outputs to slow the pace of cutting to ensure that the resection remains within the desired boundaries. To help the surgeon readily assess the proximity to the resection boundary, the OTT CAS system may provide a number of appropriate OTT CAS outputs to the surgeon as the surgeon approaches the boundary. Further still, the OTT CAS system may be configured to provide feedback related to the control the operation of the OTT equipped surgical tool in response to the proximity of the tool to the resection boundary and the corresponding OTT CAS data processing response and resulting CAS outputs.

As described above, the OTT CAS system provides for the pre-operative analysis of a patient model and the identification of the tissue to be resected. After the portion of the tissue to be resected is determined, the OTT CAS system may analyze the data for the model and identify the boundary for the resection. The tissue to be resected may then be identified in the OTT projector output using a plurality of colors based on the relation to the resection boundary.

For instance, the OTT projector output may be adapted based on OTT CAS processing factors to project onto a portion of the tissue that is not to be removed in red. Optionally, the OTT projector output may indicate a portion of the tissue that is to be resected that is relatively close to the resection boundary in yellow. In still another alternative, the OTT CAS processes may produce an OTT projector output whereby the remainder of the tissue to be resected may be eliminated in green. In this way, as the surgeon views the surgical field during a procedure the surgeon may cut rapidly and aggressively while the OTT projector output indicates the tool is operating on tissue in the green zone. As the surgeon approaches the resection boundary, the OTT-based projector output indicates the tool is operating on tissue in the yellow zone. These OTT CAS determined projector outputs serve as indications to the surgeon to proceed more slowly as the tool approaches the resection boundary. In this way, the OTT CAS system provides a readily identifiable visual and graphical display directly onto the surgical field that informs the surgeon of the proximity of the current surgical action to a resection boundary.

Similarly, the OTT CAS system can be used to visually recognize and use an OTT-based projector output to identify the proximity of the surgical tool to sensitive anatomical structures, such as nerves, vessels, ligaments etc. OTT CAS output to the projector may include distinctive color schemes to identify the structures within the surgical field as part of OTT CAS output for the user.

FIGS. 37A-44 relate to various alternative tactile feedback mechanisms along with related kinematic responses and design criteria.

FIG. 37A illustrates a bent form that deflects to move an actuator in response to trigger force. FIG. 37B illustrates a sliding trapezoid form that will deform and restore its shape in response to trigger force. FIG. 37C illustrates a rotating reader or encoder used to provide a rotating response to the trigger force. FIG. 37D illustrates a frame moving in response to trigger force to depress a shaft into a base where the movement of the shaft may be registered as an indication of trigger force. FIG. 37E illustrates a pinned element that may deflect to indicate an amount of trigger force.

Figure 38A:
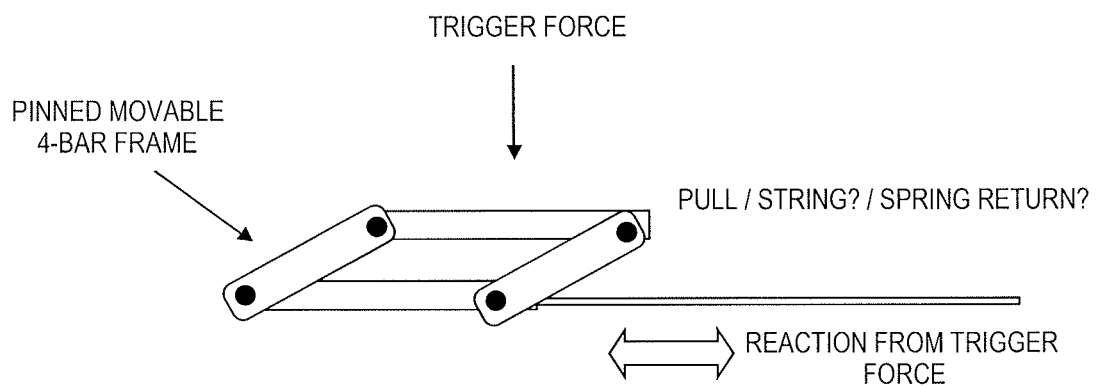
FIGS. 38A and 38B illustrate a simple four bar mechanism, in a raised and lowered, positions respectively that may be used to register trigger force and displace a shaft.
Figure 38B:
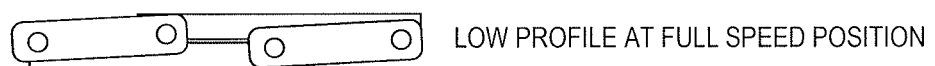

FIGS. 38A and 38B illustrate a simple four bar mechanism, in a raised and lowered, positions respectively that may be used to register trigger force and displace a shaft.

FIGS. 39A, 39B and 39C each illustrate a scissor mechanism 80 without a position restoration element (39A) and driving an actuator 80, with a tension spring as a position restoration element 84 (39B) and a compression spring as a position restoration element 84 (39C). The movement of the actuator shown determines the height of the upper end of the scissor arms therefore the elevation of the scissor mechanism. This height will press against, and will be felt by the user placing his or her finger on the tool trigger.

Figure 40A:
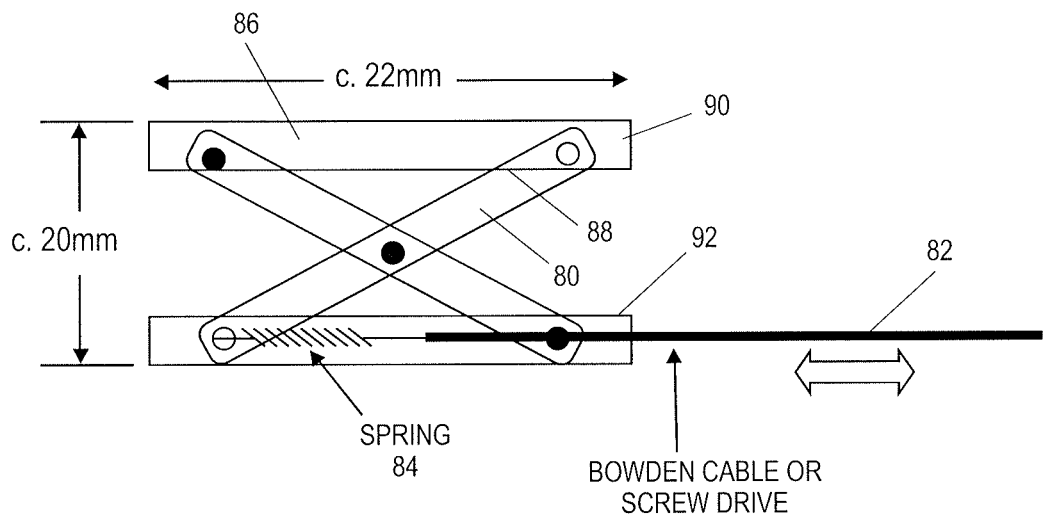
FIGS. 40A and 40B illustrate a side view of a scissor mechanism in a raised and lowered configuration, respectively.
Figure 40B:
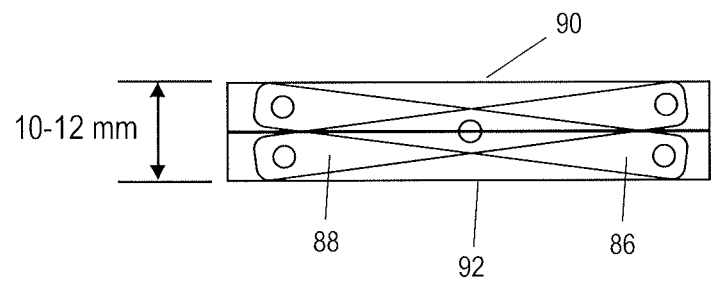

FIGS. 40A and 40B illustrate a side view of a scissor mechanism in a raised and lowered configuration, respectively. The scissor mechanism 80 includes a first link 86 and a second link 88 coupled at a pivot point whereby movement of the scissor raises and lowers the first and second platforms 90, 92. A position restoration element 84, here shown as a spring, is coupled to one end of the second link and to an actuator 82. The platforms have a length of about 22 mm and a maximum rise of about 20 mm in the elevated condition shown in FIG. 40.

Figure 40C:
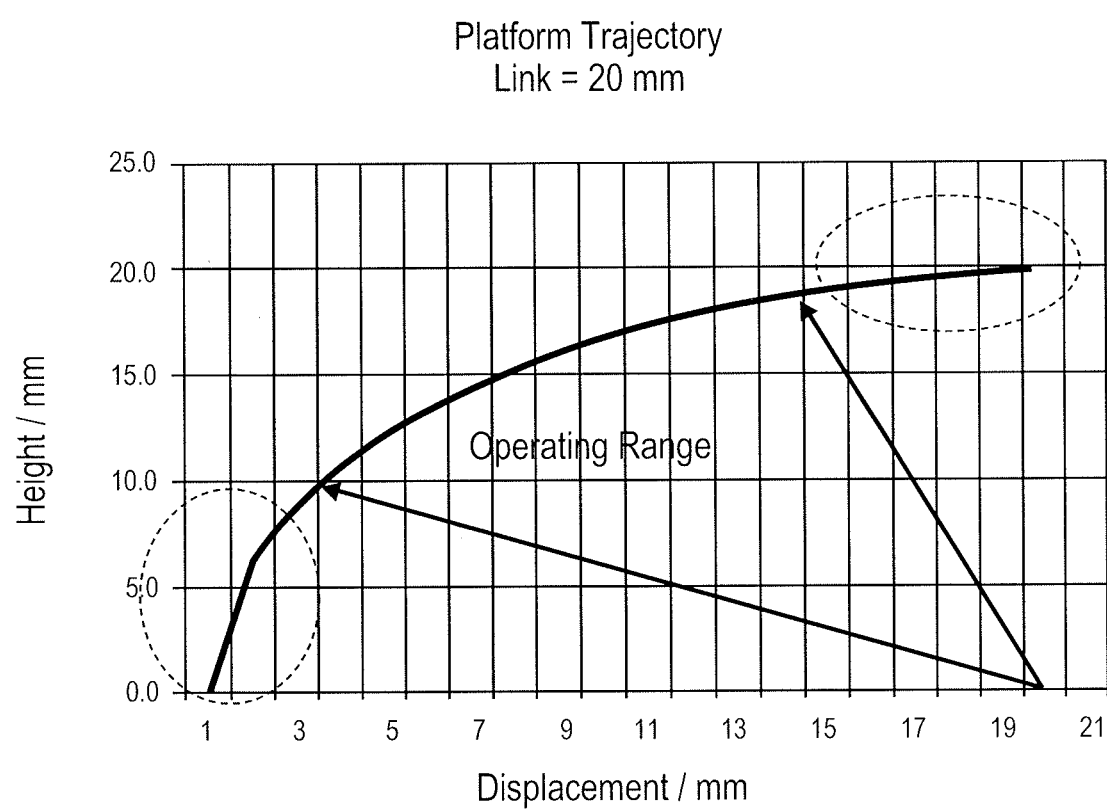
FIGS. 40C and 40D are charts relating to the displacement characteristics of the scissor mechanism 80 of FIGS. 40A and 40B.
Figure 40D:
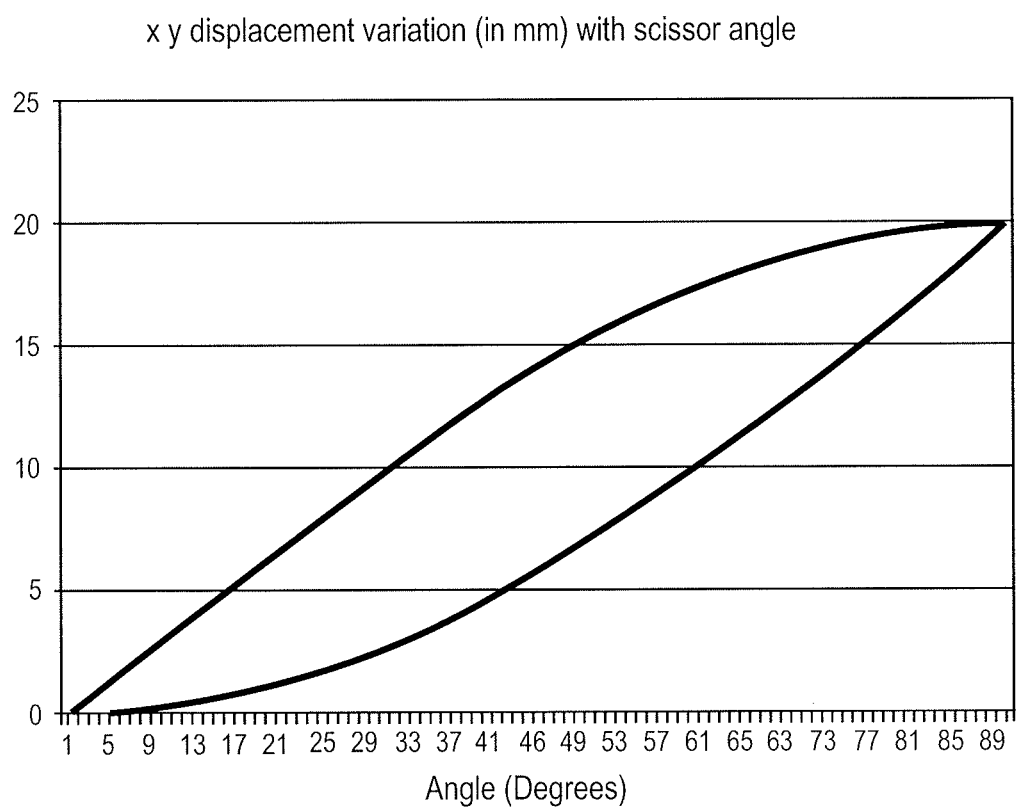

FIGS. 40C and 40D are charts relating to the displacement characteristics of the scissor mechanism 80 of FIGS. 40A and 40B. FIG. 40C relates a platform trajectory with a height of the device. FIG. 40D relates to the scissor angle with the displacement variation of the device.

Figure 41:
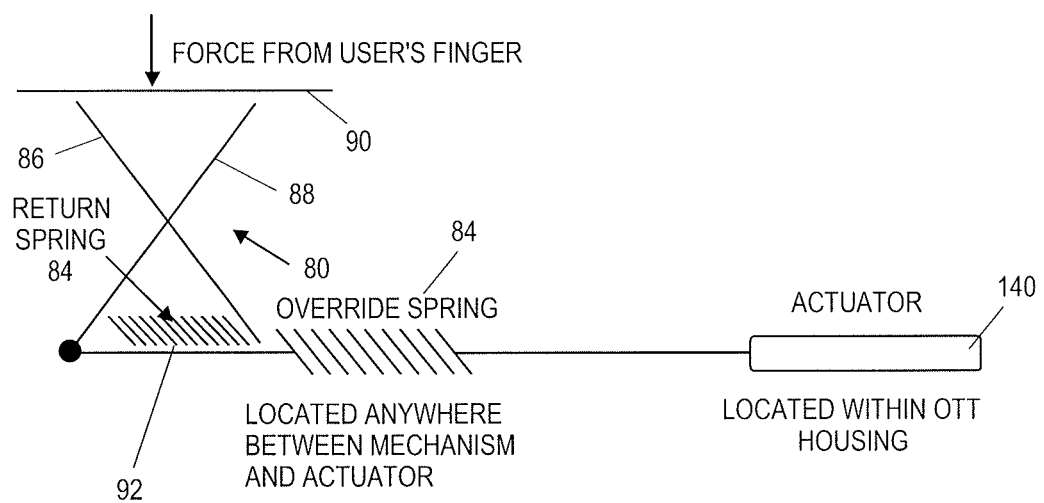

FIG. 41 illustrates another scissor mechanism 80 having a surgeon system override capability. The override capability is provided via the inclusion of a spring in line with the force application through the actuator. The actuator may be a component 140 is used for providing or receiving OTT CAS data during computer assisted surgery procedures. In this aspect, the on tool tracking device includes a component 140 adapted and configured to translate a movement received from a feedback mechanism, such as from the shaft 80 relative movement into a signal used in a computer assisted surgery procedure. The component 140 may be provided in a number of different configurations such as an encoder, an actuator or a motion transducer. In one aspect, the signal relates to the operation of the surgical tool operated by the trigger. In still a further embodiment, the component is or is adapted to include an actuator to impart movement to the shaft to influence the relative movement between the first platform and the second platform. In a further aspect, the actuator is configured to impart movement to the shaft in response to a signal related to controlling the operation of the surgical tool during a computer assisted surgery procedure.

The illustrated scissor mechanism embodiment shows the relationship of the first platform 90 and the second platform 92 borne by the links 86, 88 of the scissor mechanism 80. In addition, this embodiment shows a scissor mechanism having a pair of position restoration elements used in conjunction with the scissor mechanism 80. One position restoration element is the return spring positioned within the scissor mechanism 80. Another position restoration element is the override spring positioned between the scissor mechanism and the actuator or component 140.

Figure 42:
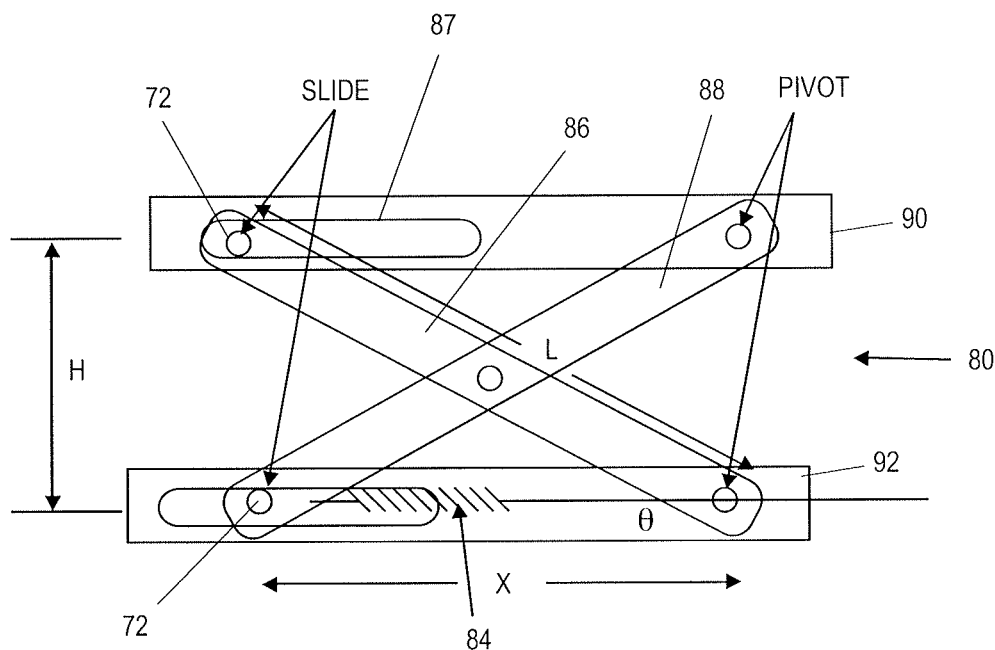
Figure 43:
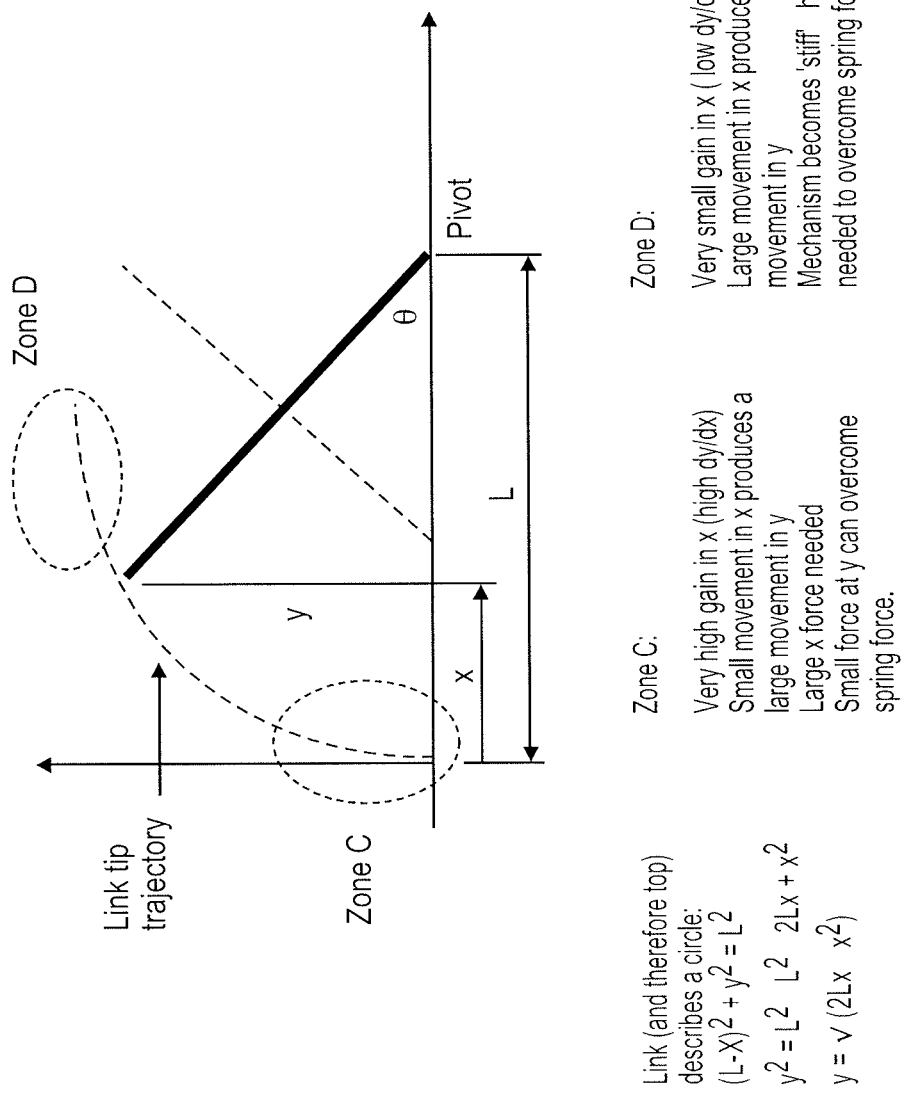
Figure 44:
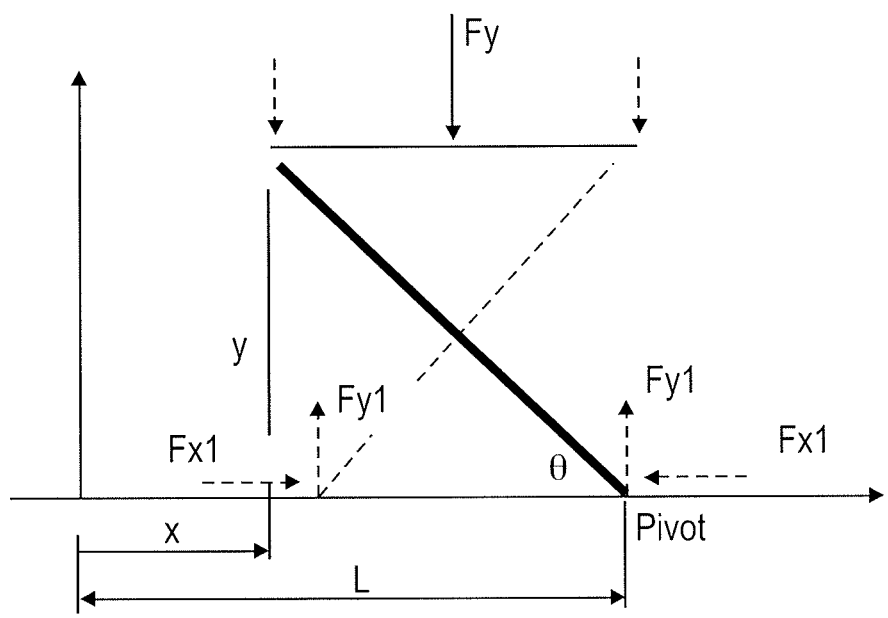

FIG. 42 illustrates a scissor mechanism similar to the schematic mechanism illustrated in FIG. 41. The scissor mechanism 80 includes a first platform 90 and the second platform 92 connected at one end of the links 80, and 86 in the pivoting relation to the first and second platform and sliding relation with the other end of the links 88, 86. A position restoration element, here a spring, is placed between the actuator or cable and a sliding and of a scissor link 88. This embodiment also includes the details of the elongate slots the first and of the platforms to permit sliding movement of the link first end relative to the first and second platform. The second end of the links 88, 86 are coupled in pivoting relation to the first platform and the second platform 90, 92. Here the motion of the first and second platforms is adjusted to the use of the spring or under the influence of the actuator. The operational characteristics of the mechanism of FIG. 42 are better appreciated with reference to the charts and FIGS. 43 and 44.

Figure 45:
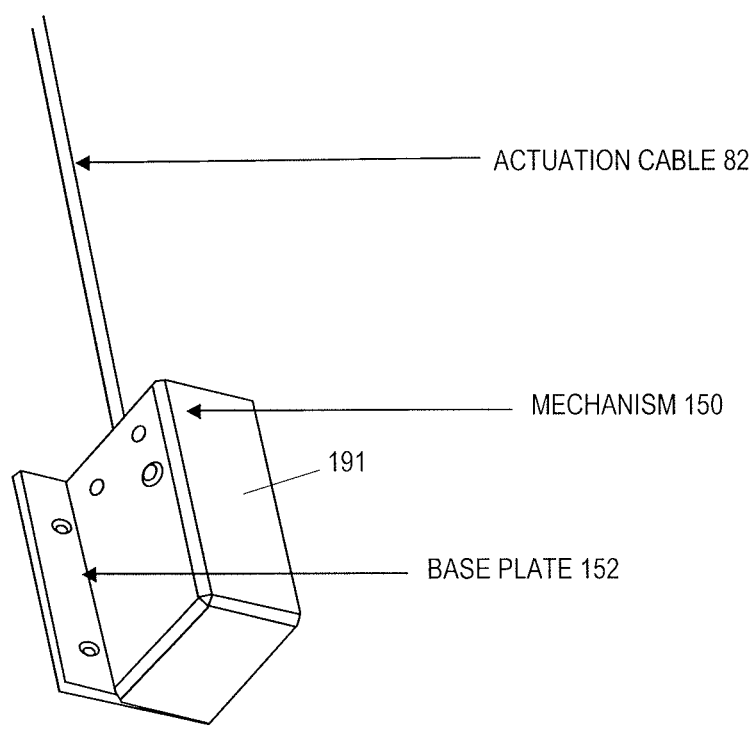
FIG. 45 is an isometric view of a tactile feedback mechanism.
Figure 46A:
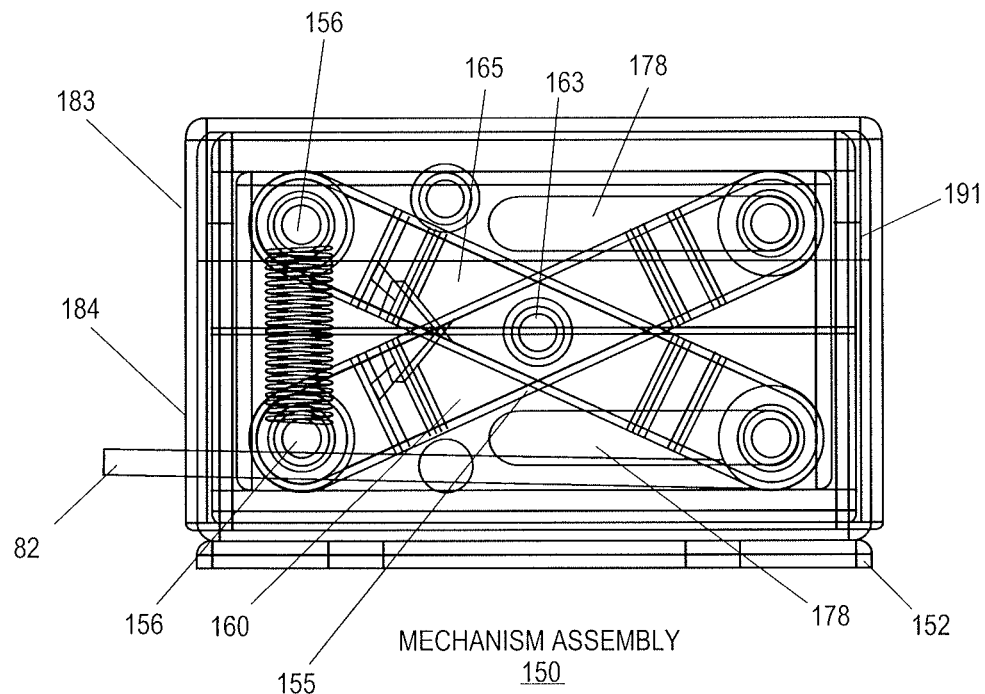
FIGS. 46A-46F illustrate various views of the components and operation of the mechanism of FIG. 45.

FIG. 45 is an isometric view of a tactile feedback mechanism. FIGS. 45 and 46A illustrate isometric and side views of a tactile feedback mechanism 150, respectively. The view of FIG. 45 shows the base plate 152 use for attachment to a surgical tool 50 adjacent a trigger 52. The scissor mechanism (best seen in FIG. 46A) is covered by a cover 191 that is borne by the first platform 183 and moves along with the platform. An actuation cable 82 is coupled to the scissor mechanism and moves in response to movement of the scissor mechanism.

Figure 46B:
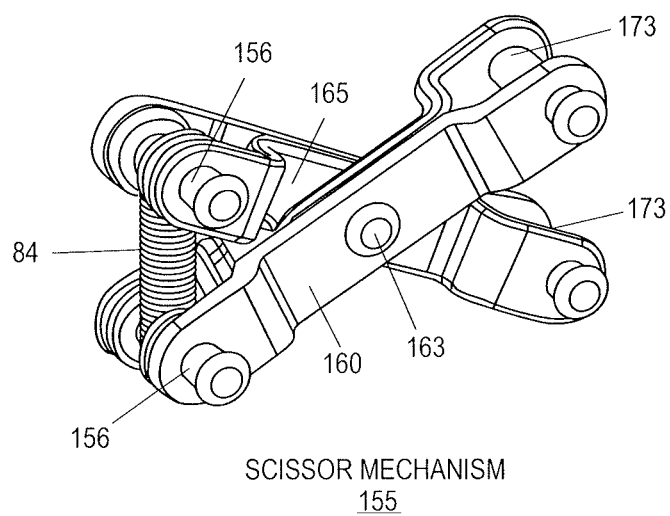

FIG. 46B illustrates an isometric view of the scissor mechanism 155 of FIG. 46A without the cover 191 or the platforms 183, 184. The Y-shaped linkage 160 and 165 are pinned 163 to form a scissor mechanism 155. A position restoration element 84 is positioned between the first ends of the first link and the second link. Also visible in this view are is the shaft 173 used to slide along the slots 178 in the platforms.

Figure 46C:
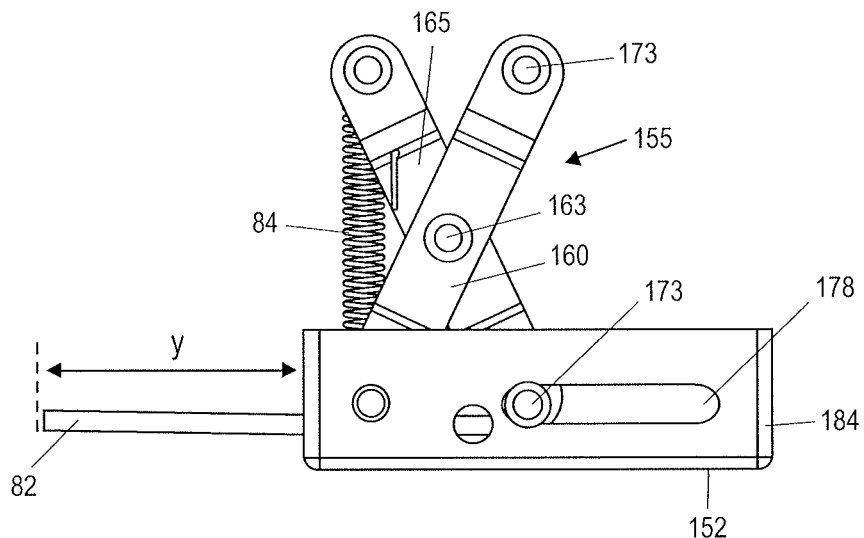
Figure 46D:
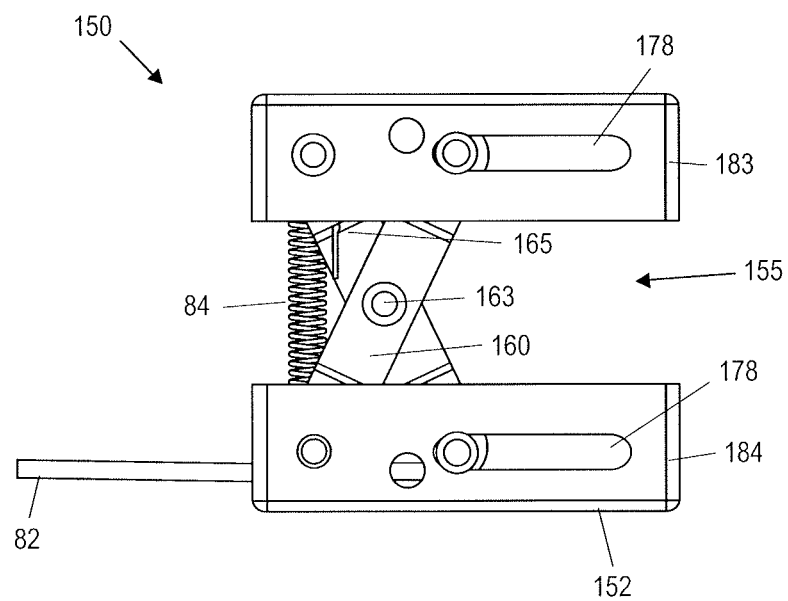

FIGS. 46A-46F illustrate various views of the components and operation of the mechanism of FIG. 45. FIGS. 46C and 46D show the TFM 150 of FIGS. 45 and 46A in an extended condition with (FIG. 46D) and without (FIG. 46C) the top platform 183. The cable 82 is moved a displacement +y from the lower platform 184 in relation to the length of movement of the links along the slots 178.

Figure 46E:
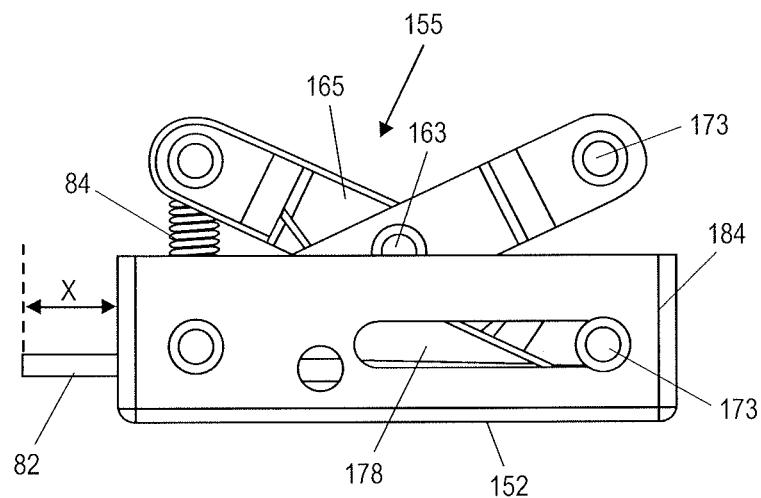
Figure 46F:
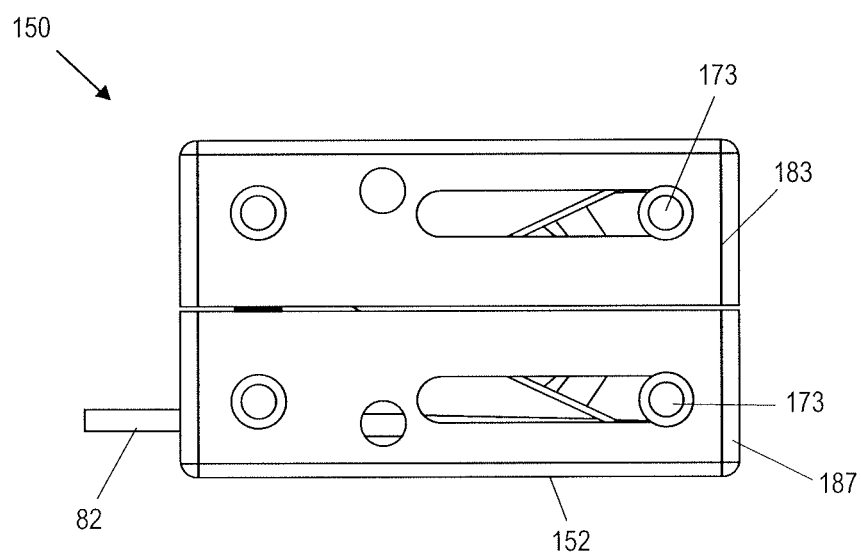

FIGS. 46E and 46F show the TFM 150 of FIGS. 45 and 46A in an closed or retracted condition with (FIG. 46F) and without (FIG. 46E) the top platform 183. The cable 82 is moved a displacement +x from the lower platform 184 in relation to the length of movement of the links along the slots 178.

Figure 47:
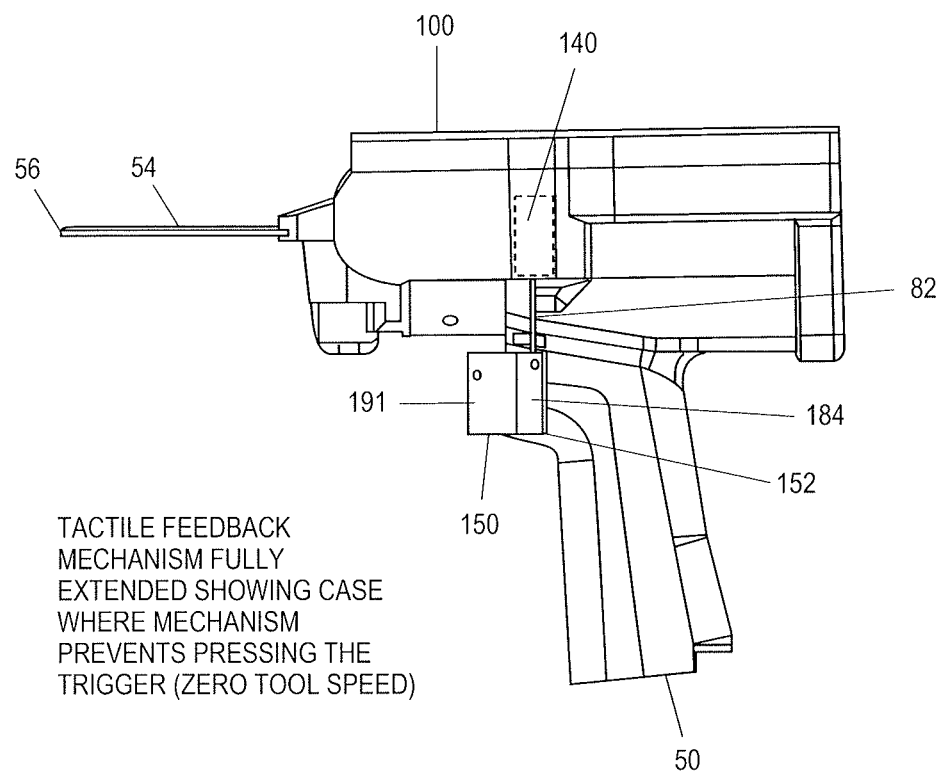
FIGS. 47 and 48 illustrate a side view of an on tool tracking device mounted on a surgical instrument having a tool (here a saw) with the tactile feedback mechanism of FIG. 45 in position to interact with the trigger of the surgical instrument.
Figure 48:
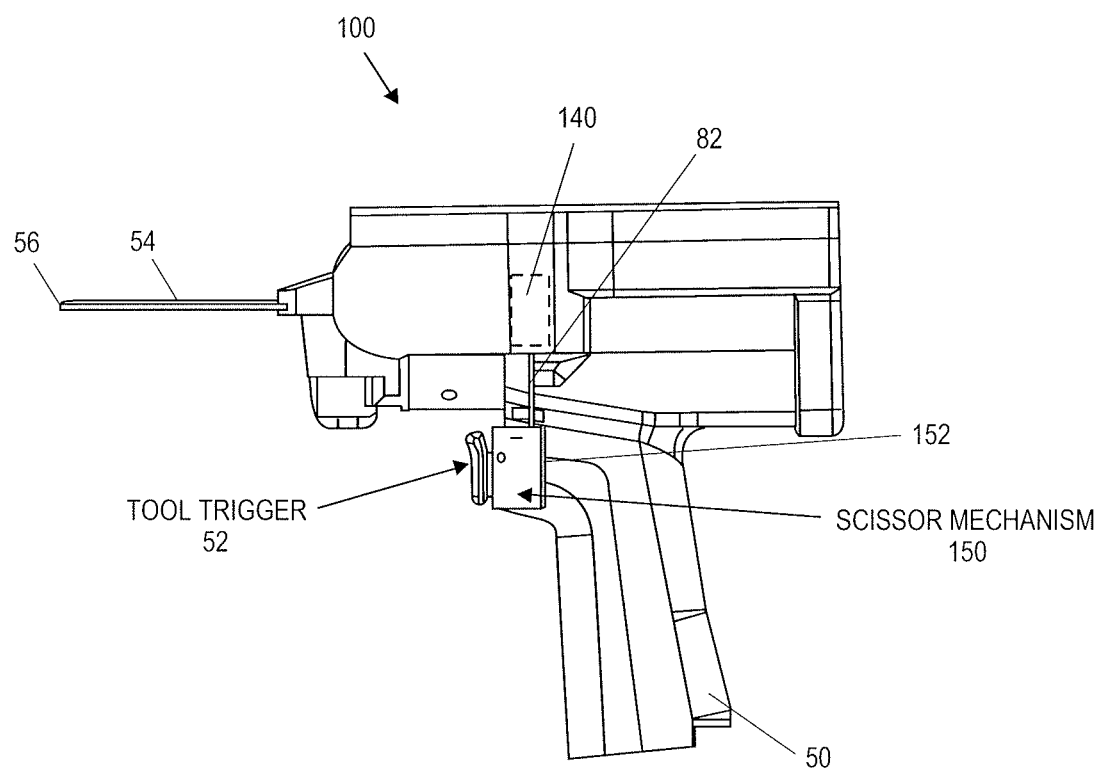

FIGS. 47 and 48 are side views of an OTT 100 on a surgical tool 50 having a TFM 150 positioned adjacent the trigger of the surgical tool. The actuator 82 extends from the TFM into the OTT 100. A component 140 within the OTT is configured to receive and provide output to or receive from the TFM. In this embodiment, the cover 191 is expended away from the base 152 exposing a portion of the base 184.

When the TFM moves the cover 191 into the position show, the trigger function on the surgical tool is impaired by the cover 191 that blocks access to the trigger 152. FIG. 48 illustrates the cover 191 in a losered configuration where the trigger 52 is accessible.

FIGS. 47 and 48 illustrate a side view of an on tool tracking device mounted on a surgical instrument having a tool (here a saw) with the tactile feedback mechanism of FIG. 45 in position to interact with the trigger of the surgical instrument. FIG. 47 illustrates the tactile feedback mechanism in an expanded configured that covers the trigger and FIG. 48 shows the tactile feedback mechanism collapsed to expose the trigger.

Figure 49A:
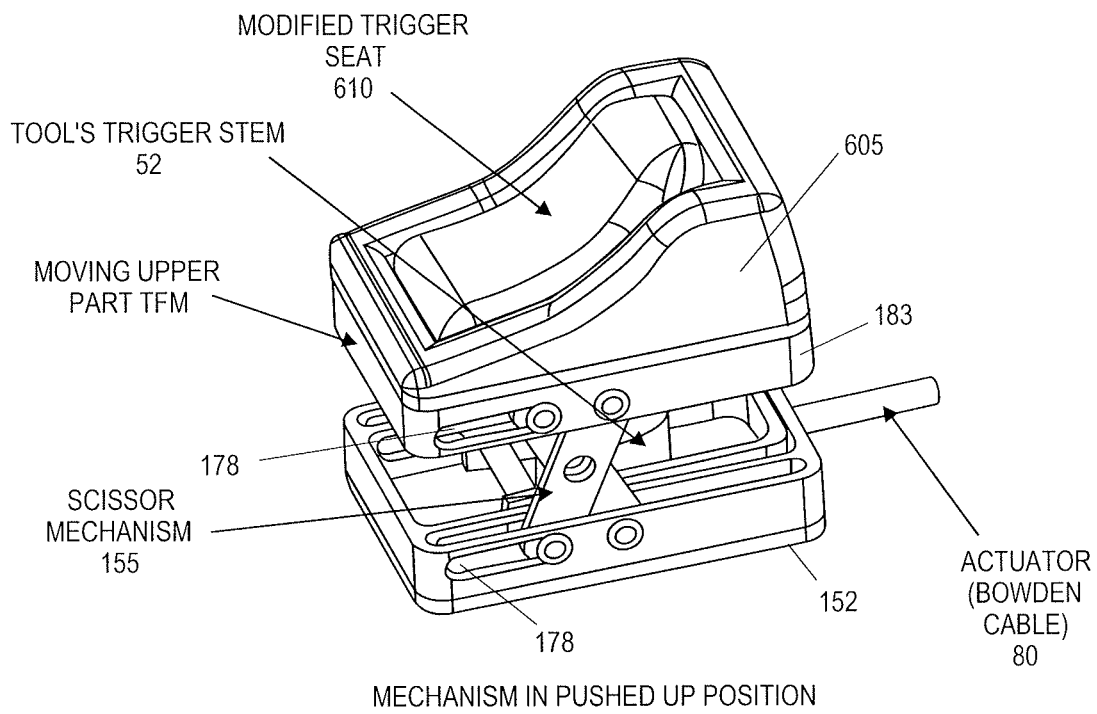
FIGS. 49A and 49B illustrate another alternative of a tactile feedback mechanism in an open or expanded state (FIG. 49A) and a closed state (FIG. 49B).
Figure 49B:
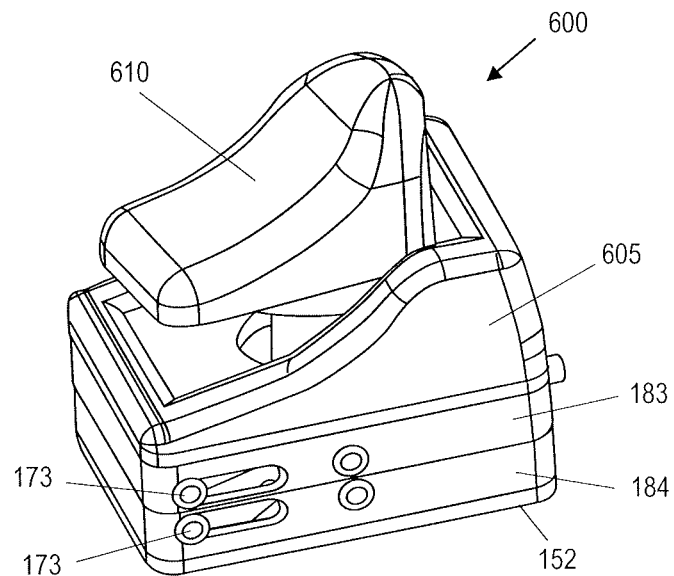
Figure 49C:
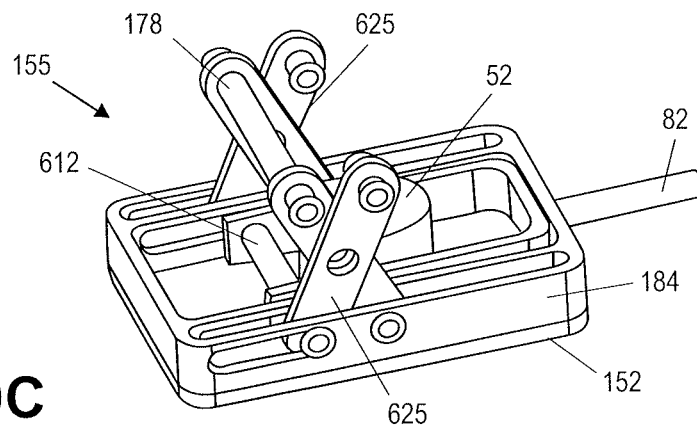
FIGS. 49C-49E illustrate the various views of the internal mechanisms of the devices in FIGS. 49A and 49B.
Figure 49D:
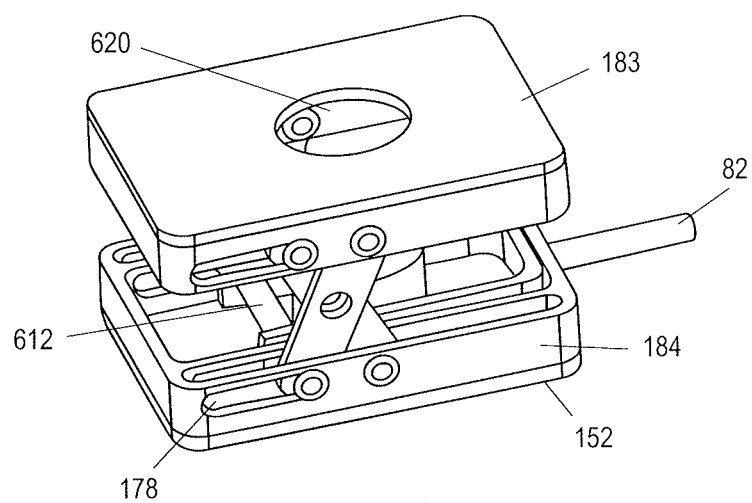
Figure 49E:
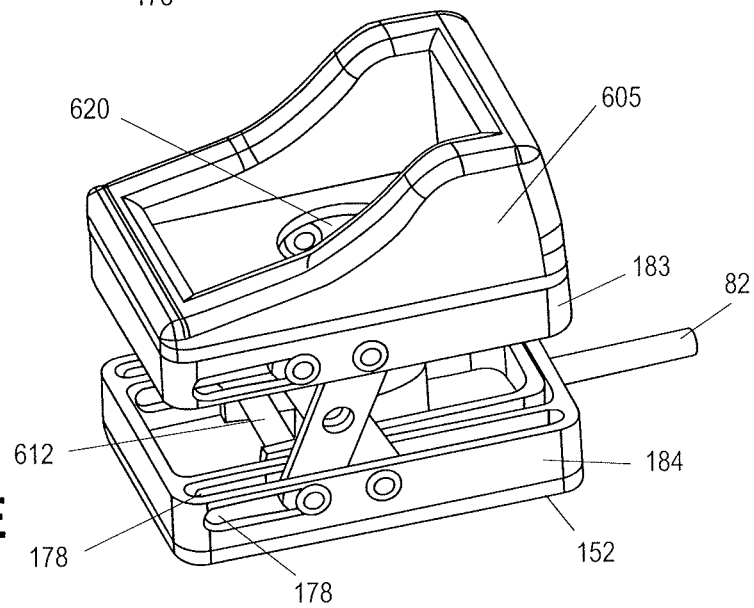

FIGS. 49A-49B illustrate another alternative of a tactile feedback mechanism in an open or expanded state (FIG. 49A) and a closed state (FIG. 49B). FIGS. 49C-49E illustrate the various views of the internal mechanisms of the devices in FIGS. 49A and 49B.

The FIGS. 49A and 49B illustrate isometric views of an over the trigger tactile feedback mechanism 600 in a raised and lowered condition, respectively. The over trigger tactile feedback mechanism 600 has a trigger adapter 605 attached to the first platform 183. A modified trigger seed text and is adapted to engage with the trigger 52. The modified trigger seed fits within and is movable relative to the trigger adapter 605. A scissor mechanism 155 is provided as before to move the first platform and the second platform.

The relative positions of the platforms in views illustrate how in the collapsed condition the modified trigger seat 610 is raised above the trigger adapter 605. In contrast, in the raised condition the modified trigger seat 610 is withdrawn within and below the upper surfaces of the trigger adapter 605.

FIG. 49C is an isometric view of the scissor mechanism 155 in a raised condition with the upper platform and the trigger adapter removed. FIG. 49D is similar to the view of FIG. 49C with the upper platform 183 attached to the scissor mechanism 155. An aperture 620 is provided in the upper platform 183. The aperture 620 used to provide coupling between the modified trigger seat 610 and the trigger 52.

Figure 50:
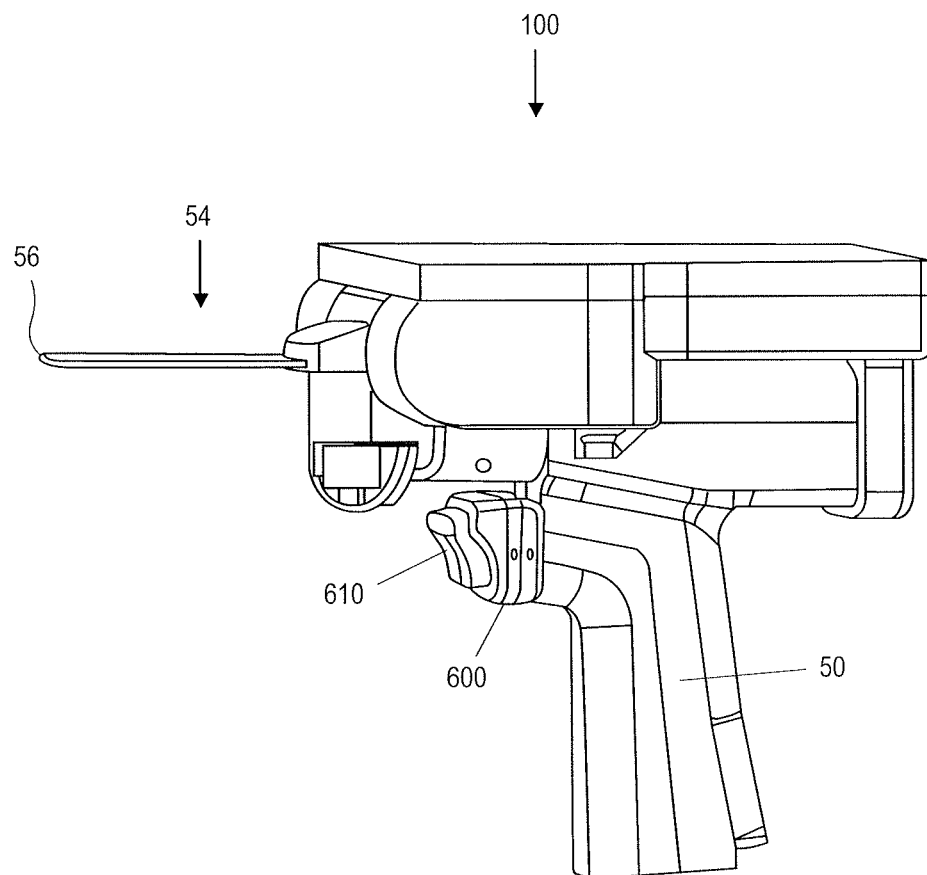
FIG. 50 illustrates an embodiment of an OTT coupled for use with a surgical tool having an embodiment of the mechanism of FIGS. 49A and 49B mounted for cooperation with the trigger of the surgical tool and configured to send and to receive trigger related signals with a component in the OTT.

FIG. 49E is similar to the other embodiments with the addition of the trigger adapter 605 in position on top of the first platform 183. FIG. 50 illustrates an embodiment of an OTT 100 coupled to a surgical tool 50 where the trigger 52 of the tool 50 is covered by the tactile feedback mechanism 600.

In the configuration of FIG. 50, a user's ability to manipulate the trigger 52 is covered by the operation of the tactile feedback mechanism 600.

FIG. 50 illustrates an embodiment of an OTT coupled for use with a surgical tool having an embodiment of the mechanism of FIGS. 49A and 49B mounted for cooperation with the trigger of the surgical tool and configured to send and to receive trigger related with a component in the OTT.

Figure 51:
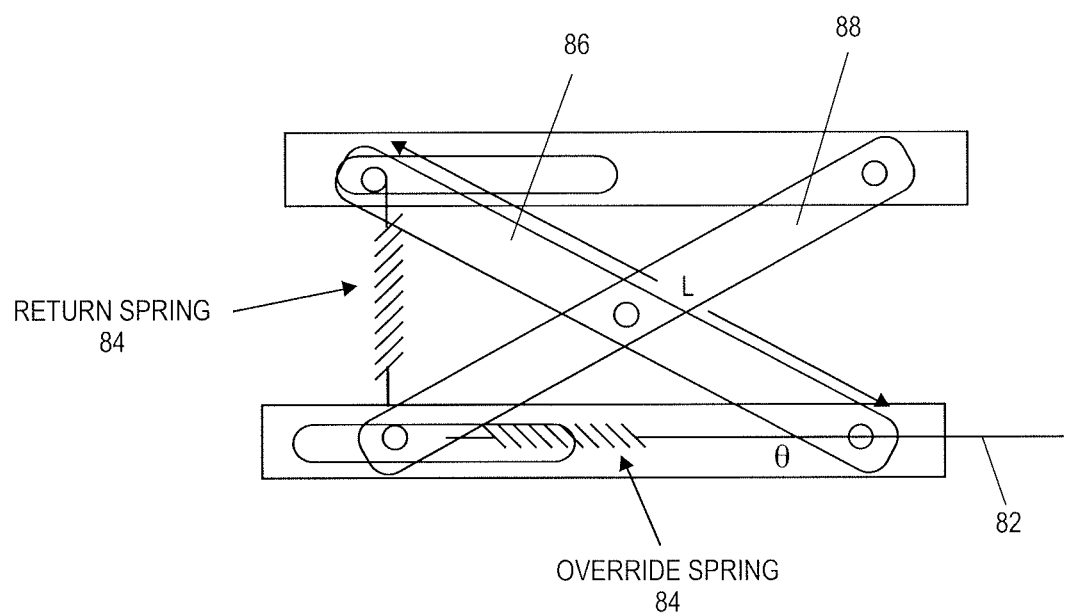
FIG. 51 is a cut away view of an alternative embodiment of a scissor mechanism utilizing two position restoration elements.

FIG. 51 is an alternative embodiment of a scissor mechanism utilizing two position restoration elements. FIG. 51 illustrates a scissor mechanism similar to FIG. 42. In contrast to the scissor mechanism of FIG. 42, the illustrated scissor mechanism in this embodiment includes a pair of position restoration elements. One position restoration element 84 is a return spring extended between the first and second platforms and coupled to the first ends of the links 86, 88. The return spring is used to modify the movement platforms and hence control trigger responsiveness. The other position restoration element is the override spring extending along the second platform. The override spring is coupled to a sliding and of the link 88 and the cable 82. The return spring in the override spring work in concert to provide a variety of different responsive features to the tactile feedback mechanism as schematically represented by FIG. 51. As a result the use of more than one in different types of position restoration element provides a wide variety of response characteristics for the tactile feedback mechanisms described herein.

Figure 52B:
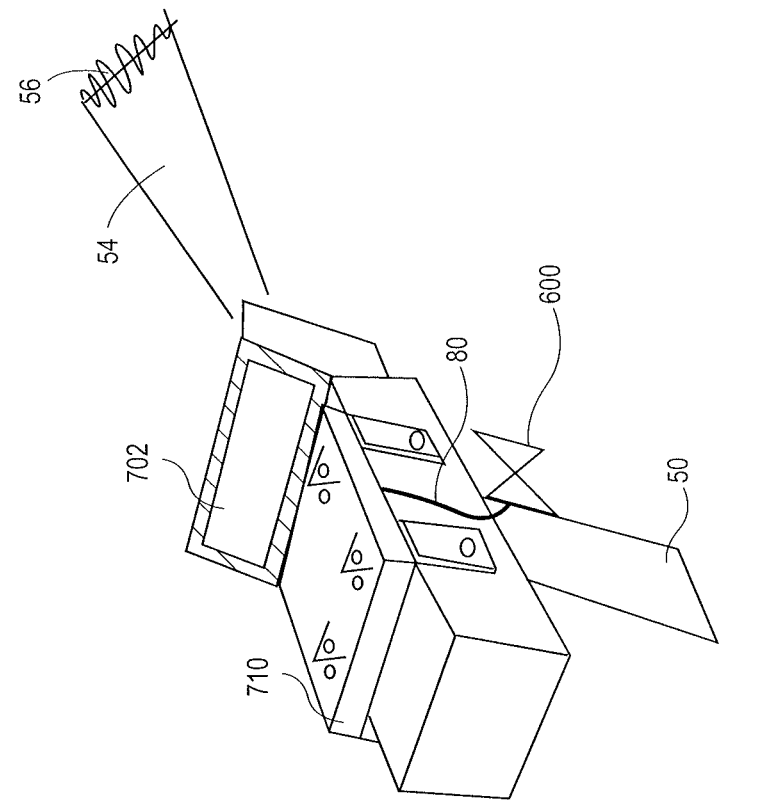
FIGS. 52A and 52B are front and rear isometric views respectively of an on tool tracking and navigation device (OTT) that includes a display with OTT housing coupled to a surgical tool having a trigger based feedback mechanism coupled to the OTT. The view also shows an exemplary computer system in communication with the OTT.
Figure 52A:
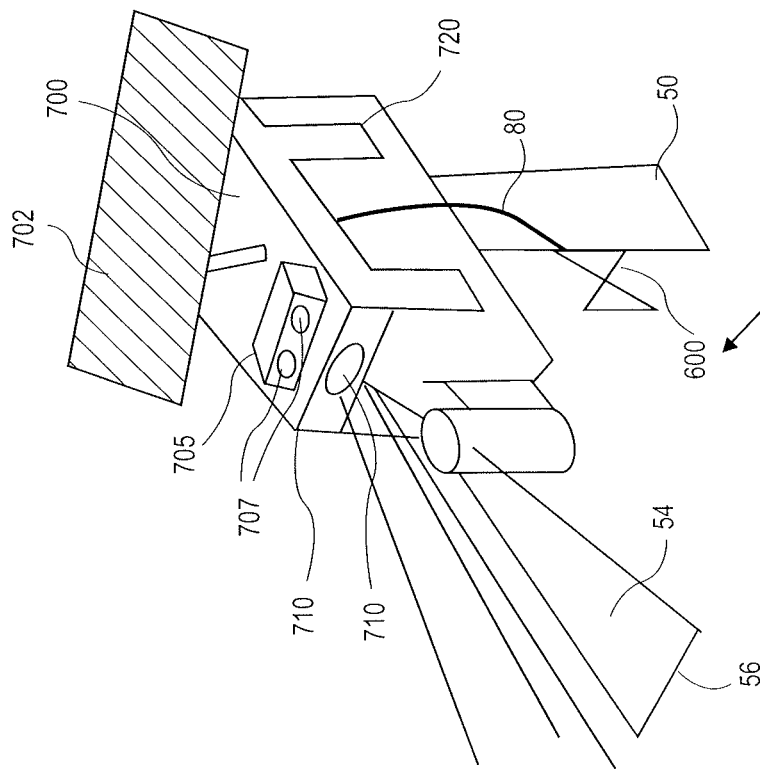
Figure 52A:
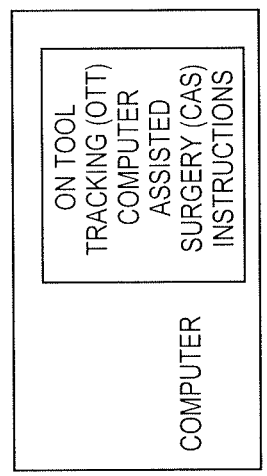

FIGS. 52A and 52B illustrate front isometric and rear isometric views, respectively, of another OTT embodiment coupled to a surgical tool 50. OTT 700 includes a housing 710 having a camera mount 705 and projector 710. In this embodiment, the camera mounts 705 is on the upper surface of the housing 710. The mount 705 contains a pair of cameras 707 directed towards the tool 74 for imaging the active element 56. In addition, this embodiment includes a TFM hundred over the trigger of the tool 50. The cable 80 provides an interface between the TFM 600 and the OTT 700 for the various purposes of tactile feedback as described herein. The OTT 700 also includes a display 702 on the upper surface of the housing 710. The display 702 may be used to provide OTT CAS output information for the user. Additionally or alternatively, display 702 is used as a user interface for user inputs. The display 702 may be configured as a graphical user interface (GUI) or other type of computer input device. Also shown is a computer in communication with the OTT 700 for the purpose of utilizing the information obtained from the use of the OTT during a CAS procedure in furtherance of the completion of a computer aided surgery. The computer includes within an electronic memory accessible to the processing unit instructions for on tool tracking computer assisted surgery. In one embodiment, computer is included within the OTT 700 as part of the electronics package within the housing. In another embodiment, the computer is an external component configured for receiving and transmitting data related to OTT CAS processes either wirelessly or via a wired connection to and from the OTT 700.

As the above examples in the illustrative embodiments make clear, embodiments of the TFM mechanisms of the present invention may be adapted or configured to provide outputs related to trigger movement or position or for further processing by the OTT CAS computer. The various TFM mechanisms provided herein may be used to provide in a minimally intrusive manner an indication of tool operation, characteristics or parameters (speed, position, rotation, setting, power level and the like) for use by the OTT CAS system. An output from a tactile feedback mechanism may be provided via an encoder/reader in the mechanism, in the OTT device, or mounted on the surgical tool itself. Still further, feedback mechanism embodiments may include wireless communications for transmitting tactile feedback mechanism information or trigger information for further processing in the OTT device or the OTT CAS computer. In a still further aspect, one or more components of the tactile feedback mechanism may be driven under instructions received based on OTT CAS processes, modes or algorithms. In some embodiments, tactile feedback mechanism indications and data are used to provide a dynamic real-time feedback loop from the OTT CAS system. Indications from the tactile feedback mechanism may also be used to provide the automatic control of one or more surgical tool control features such as: the tools motor, actuator attenuating its motor/cutting/drilling action speed or stopping it as part of an appropriate OTT CAS processing output. In one aspect, the feedback loop control is provided based on a determination of the OTT CAS system that automatic intervention of surgical tool functionality is needed to prevent an improper cut, or harm to an anatomical structure within the OTT CAS surgical field.

In still further aspects, embodiments of the tactile feedback mechanism or other feedback mechanisms configured to utilize the outputs from the systems and methods described herein may be used to automatically or semi-automatically control one or more operating characteristics of an active element of a surgical tool utilizing an on tool tracking device. Still further an embodiment of the OTT CAS system may also be configured to control the operation of the surgical tool in response to a determination of the position of the surgical tool relative to the desired boundary. Specifically, if the system determines that the tool is positioned within the tissue to be resected that is not proximate the boundary (i.e. in the green zone), the system may allow the surgical tool to controlled as desired by the surgeon. If the system determines that the tool is positioned within the tissue to be resected that is proximate the boundary (i.e. the yellow zone), the system may reduce or attenuate the operation of the surgical tool. For instance, if the tool is a saw, and it enters the yellow zone, the system may slow down the reciprocation or revolution of the saw as it moves proximate the resection boundary. Further still, if the system detects that the tool is positioned at the boundary or on tissue that is not to be resected or operated on, the system may control the surgical tool by completely stopping the tool. Although the system may automatically control the operation of the surgical tool, the system includes an override function that allows the surgeon to override the control of the tool. In this way, if the surgeon determines that a portion of tissue should be resected that was not identified for resection during the pre-operative analysis; the surgeon can override the system and resect the tissue during the procedure.

Embodiments of the tactile feedback mechanism include a wide variety of tactile stimulus. For example, the stimulus could be as simple as enhanced vibration to indicate deviation of the surgical path from the intended resection. Tactile stimulus provides the opportunity for more sophisticated indications in accordance with the various modifications and outputs provided by the OTT CAS methods described herein.

In general, powered surgical tools are activated by means of a trigger and embodiments of the feedback based mechanisms described herein provide detectable and variable (increases and decreases under control of the OTT CAS computer) resistance on the trigger or pressure on the surgeon's finger actuating the tool in a manner to indicate to the surgeon when the surgical path or current use of the active element deviates from the intended resection or other action according to the OTT CAS surgical plan. It is to be appreciated that the variety of different configurations for providing tactile feedback may be used with an unmodified, modified or replaced trigger for actuating the surgical tool used with an OTT device. In some various alternative embodiments, a trigger based feedback assembly includes a dynamic member coupled to a scissor mechanism that is in turn coupled to a stationary base (usually mounted on the handle of the surgical tool. The position or stiffness of the assembly, typically as a result of interaction with a transmission shaft or cable is dictated by a control unit within the OTT. The control unit may be configured to provide a wide variety of OTT related feedback functions including, by way of example, an actuator to operate the transmission shaft which in turn changes the force to close the scissor mechanism, moves the trigger mechanism to a full extended position, move the trigger mechanism to a full contracted position, move to a position to impair operation of the trigger, or, optionally to stop operation of the active element of the tool. In one aspect, the transmission shaft or cable or element is Bowden cable. In still other embodiments, the transmission shaft that couples the scissor mechanism to the associated component in the OTT may be any suitable element such as a rod, spring, solenoid, chain, gear, or a mini pneumatic or hydraulic actuated system. Still further, it is to be appreciated that the actuator used for the controls described above may also be included within the feedback mechanism in proximity to the trigger. In one alternative of this aspect, the actuator may be connected to the OTT device via a wired or wireless connection to provide the appropriate OTT CAS process control signals to the actuator in furtherance of the above described OTT CAS techniques.

The control unit is also capable of receiving data from the computer system. When the system determines a deviation in excess of a specified threshold level exists between the surgical path and the surgical plan by comparing the position of the tool to the intended resection of the surgical plan, the control unit actuates the transmission, increasing the resistance required to pull the trigger. Indication can be provided in the form of preventing the depression of the trigger so that the surgeon cannot activate the tool. Alternatively, indication can take the form of increased resistance, which the surgeon can overcome by the application of more force.

The trigger and other tool control embodiments described with regard to FIGS. 37A-51 may also be utilized with an externally tracked tool such as those described in co-pending and commonly assigned application Ser. No. 11/764,505 filed on Jun. 18, 2007 and Ser. No. 11/927,429 filed on Oct. 29, 2007, each of these applications are incorporated herein by reference in its entirety.

FIGS. 52A and 52B are front and rear isometric views respectively of an on tool tracking and navigation device (OTT) that includes a display with OTT housing coupled to a surgical tool having a trigger based feedback mechanism coupled to the OTT. The view also shows an exemplary computer system in communication with the OTT.

FIG. 36 is a flowchart representing an exemplary OTT CAS process including modification of any of the above described OTT CAS processes to include associated surgical tool operational characteristics, parameters or other data related to the use of an active element in any OTT CAS process or procedure. The OTT CAS process 3600 includes many of the same processing steps described above with regard to OTT CAS process 3100 in FIG. 31A.

Figure 63:
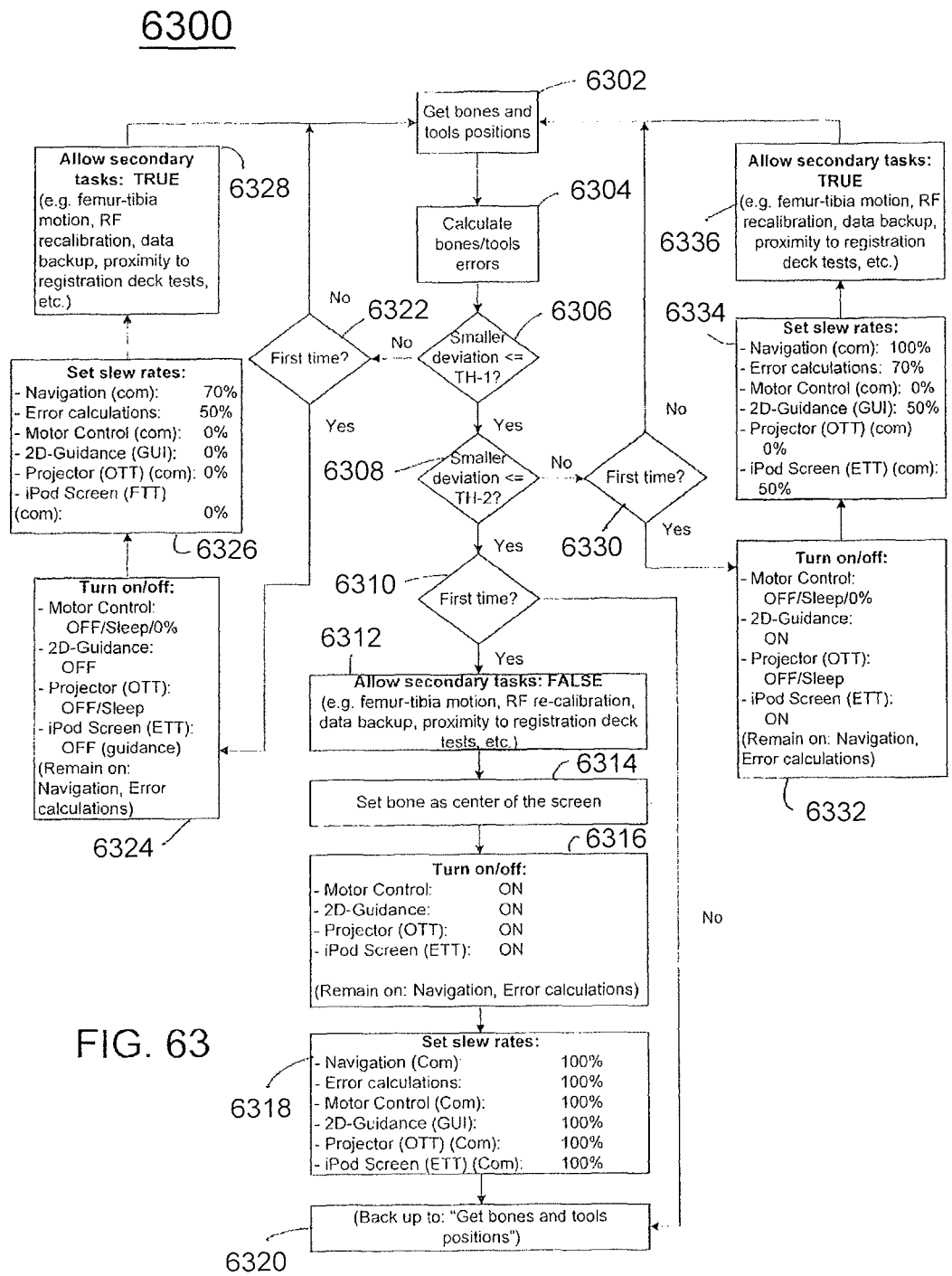
FIGS. 63, 64 and 65 are various flow charts related to various OTT CAS methods.

FIG. 63 illustrates a flowchart 6300 illustrating the various steps performed by the CAS guidance system when operating in hover mode. The steps start by getting bones and tool positions in registration at step 6302. Next, at step 6304 calculate deviations (i.e. bones and tools errors relative to the plan). Next at step 6306, determine whether the deviations calculated are less than or equal to TH-1. TH-1 is the outer threshold spacing. In this context, the outer threshold spacing is used to determine when the tool is at a distance spaced sufficiently far away from the point of surgery that certain aspects or secondary operations may be utilized with system resources, or that high tolerance tracking or control is not critical. If the answer at step 6306 is yes then the process proceeds to step 6308. At step 6308, the calculated errors are compared against a smaller deviation which is threshold TH-2. The threshold TH-2 is used as an inner threshold value to trigger when the system is close in to the surgical field. If the answer to step 6308 is yes then the method proceeds to step 6310 to determine whether this is the first time that the threshold TH-2 has been triggered. If the answer at 6310 is yes then the method proceeds to step 6312 where all secondary tasks are not permitted to operate, and FIG. 63 shows examples of those in box 6312. In step 6312 the system is essentially overriding all other operations so that maximum resources are made available for the tracking mode since the comparisons at step 6306 and step 6308 have determined that the system is near or is within cutting mode. Examples of secondary tasks that would not operate during this time include, for example, RF recalibration, data backup, proximity to registration and various data tests performed by the system. After step 6312, the next step 6314 sets the bone as the center of the screen on the display used by the OTT, unless overridden by the user or the user has preferences set to the contrary. Next at step 6316, additional control signals are sent within the system. In the illustrative steps of 6316, motor control is turned on, 2-D guidance is turned on, projector is turned on in the OTT embodiment. Again, here and from this point onwards, the description assumes that the user has not set options to the contrary of what is described here. If an ETT system is being used, the iPod screen is also turned on and a suitable user selectable default initial view shown. In addition, the navigation and error calculations functions remain in operation. Next at step 6318, various slew rates are set to 100%. In the illustrative step of 6318, navigation, error calculations, motor control and communications, 2-D guidance, projector, and iPod screen are all set to 100%. Next at step 6320, this mode of operational loop is repeated and the system continues to get bones and tool positions at step 6302.

Continuing on from 6302 to calculate bones and tools errors at 6304, next at step 6306, if the response at step 6306 is "no" then the system proceeds to step 6322 to determine whether or not this is the first time that the system has registered an error that is greater than the near threshold TH-1. If the answer is yes to step 6322 the method proceeds to step 6324 which permits some aspects of the system to be placed into different states. Next at step 6326, the slew rates are set to a variety of different levels in contrast to the slew rate settings found in step 6316. Next at step 6328, secondary tasks may be performed by the system. At step 6328, secondary tasks are allowed and system resources may be devoted to other activities since the system is likely not in cutting mode. Thereafter, the system returns to the base step of 6302 to get bone and tool position information. Returning down the method from 6302 to the calculation steps 6304 and the smaller deviation comparison for near threshold TH-1, if the answer at step 6306 is yes and the answer at the near field deviation TH-2 (step 6308) is no, the method then proceeds to decision step 6330. If the answer to the question first time at 6330 is no, indicating that this is not the first time that the near threshold error has been greater than the error threshold TH-2 then the method returns back to step 6302 to get bone and tool information. If, the answer to first time query at step 6330 is "yes", then the system proceeds to step 6332. In step 6332, various control functions are set to different values based upon the computer's determination of the tool position. Next at step 6334, various slew rates are set for navigation, error calculations and 2-D guidance. Thereafter, at step 6336 secondary tasks are also allowed to operate similar to step 6328. The secondary tasks are permitted because the system has determined that system resources may be used for other than critical navigation with motor control functions simultaneously. In each of the first time blocks, 6322 and 6330 and 6310, this is a simplification for a validation and latching process to prevent repeated switching of states when not necessary and adding some hysteresis to prevent toggling back and forth from one state to another based on random fulfillment of a condition. By setting the thresholds TH-1 and TH-2 to appropriate levels then the system may determine whether or not a user's movement of the OTT is intentional and directed away from the field of surgery or intentional towards the field of surgery or continuing on a step of cutting with only a minor adjustment, for example. Such intended hysteresis of course reduces the effect of digital noise and random errors especially near the boundaries of different states of the system.

In general, in the method 6300, the left hand steps (6328, 6326, and 6324) indicate a normal hover mode where the system liberates resources for secondary tasks when time sensitive tasks are not required. On the right hand side of the method 6300 (steps 6332, 6334 and 6336) are used when the system indicates that it is within a volume of interest relative to the target bone but still not in a position to cut the target bone (like a standby when the sensors and resources would be available to switch motor control on at short notice). Secondary tasks are still allowed in this condition, but time sensitive aspects are more closely monitored than in the previous case described above on the left hand side. In the bottom portion of the method 6300, these indicate the time-sensitive tasks are in action during active cutting. Method steps 6312, 6314, 6316, and 6318 are all used to insure that full slew rates are applied to all cut-related processes. During this time, system resources are not directed towards secondary resources or secondary activities are neglected all together.

In general, in the method 6300, the left hand steps (6328, 6326, and 6324) indicate a normal hover mode where the system primarily saves electric battery power and reduce heat generation and dissipation and liberates resources for secondary tasks when time sensitive tasks are not required. On the right hand side of the method 6300 (steps 6332, 6334 and 6336) are used when the system indicates that it is within a volume of interest relative to the target bone but still not in a position to cut the target bone (like a standby when the sensors and resources would be available to switch motor control on at short notice). In still another aspect, an additional factor or consideration in steps 6326, 6324, 6332, or 6334 is that one or more electronic devices may be shut down, placed in standby mode or otherwise adjusted to save power. As a result of this type of determination by the OTT CAS system, it is believed that battery life in an OTT module may be extended because high energy consuming devices like the projector, for example, may be placed in an energy conservation mode if the OTT CAS mode deems that a practical step.

Figure 64:
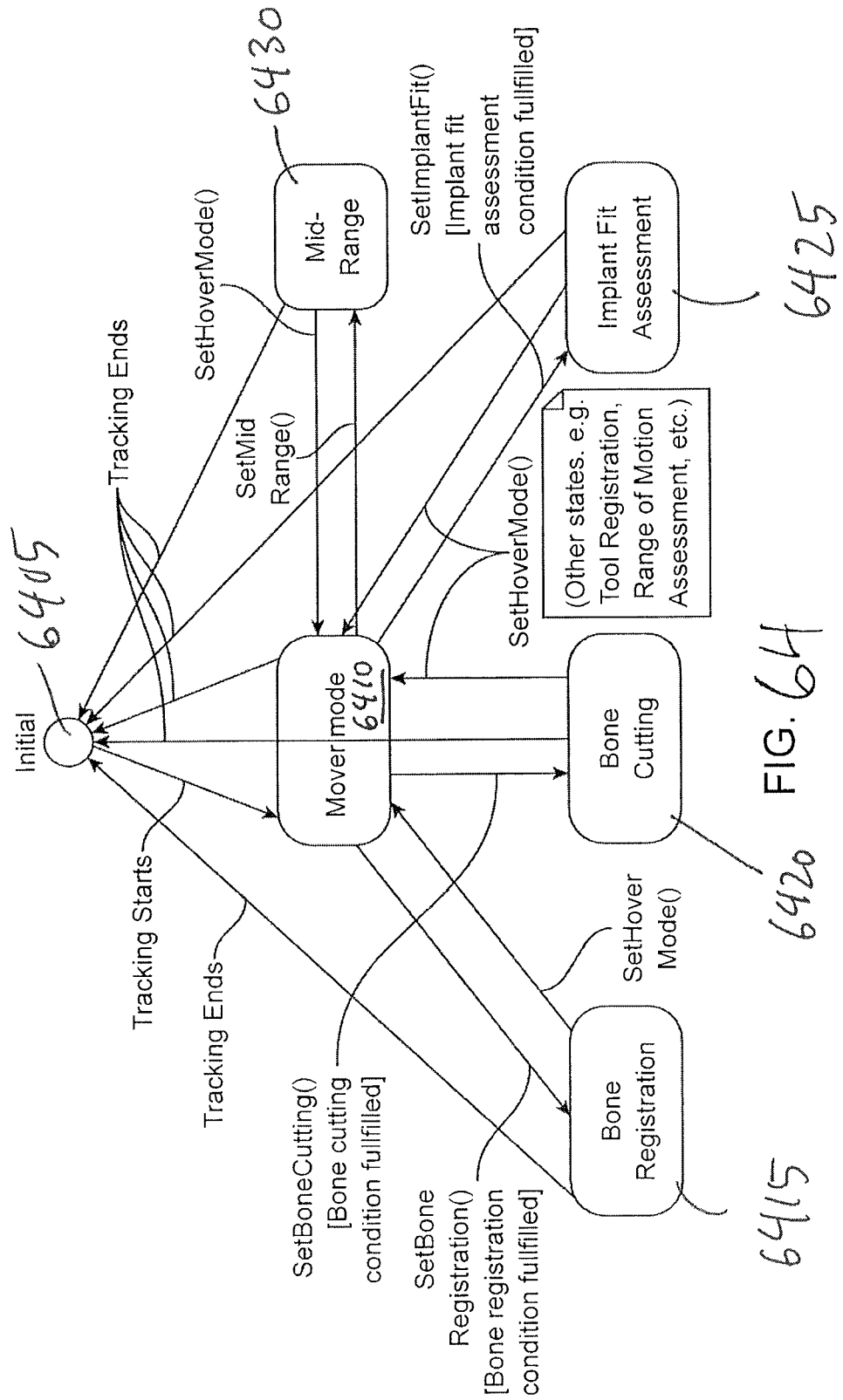

FIG. 64 illustrates a simplified hover mode state diagram. The mode state diagram begins at initiation at step 6405. Next, the system may enter into hover mode at step 6410. Thereafter, if system parameters indicate that bone registration is being performed the system will move into a bone registration mode at step 6415. At the completion of bone registration, the system may either end tracking or return to the initiation step 6405. Alternatively, at the conclusion of bone registration the system may set hover mode and return to the hover mode step 6410. In addition, from the hover mode step 6410, the system may detect bone cutting steps. In this case, the system will go into bone cutting mode as shown at step 6420. At the conclusion of the bone cutting step, the system may return to hover mode at step 6410, or cease tracking and return to initial mode 6405. Another option from hover mode 6410 is to move into a bone implant fit assessment at step 6425. At the conclusion of any implant fit assessment, the system may return to hover mode at 6410, or cease tracking and return to initial mode state 6405. One example of assessment (that is not shown in the diagram to avoid clutter) si to assess the quality of the cut with a navigated surface tester, with which a cut surface location and orientation are tested to assess their quality and suggest further cutting refinements if needed. Still another alternative path from hover mode 6410, is to go into mid-range tracking at step 6430. From the mid-range tracking step 6430, the system may cease tracking and return to the initial state 6405. Alternatively, the mid-range tracking step 6430 may conclude and return to the hover mode tracking step 6410.

Figure 65:
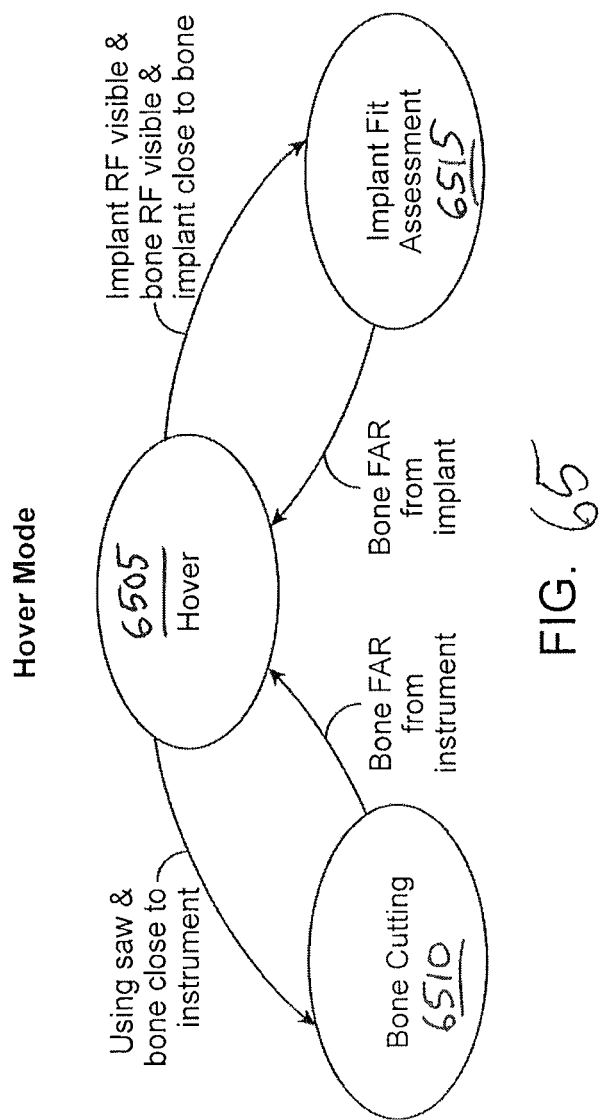
Figure 66A:
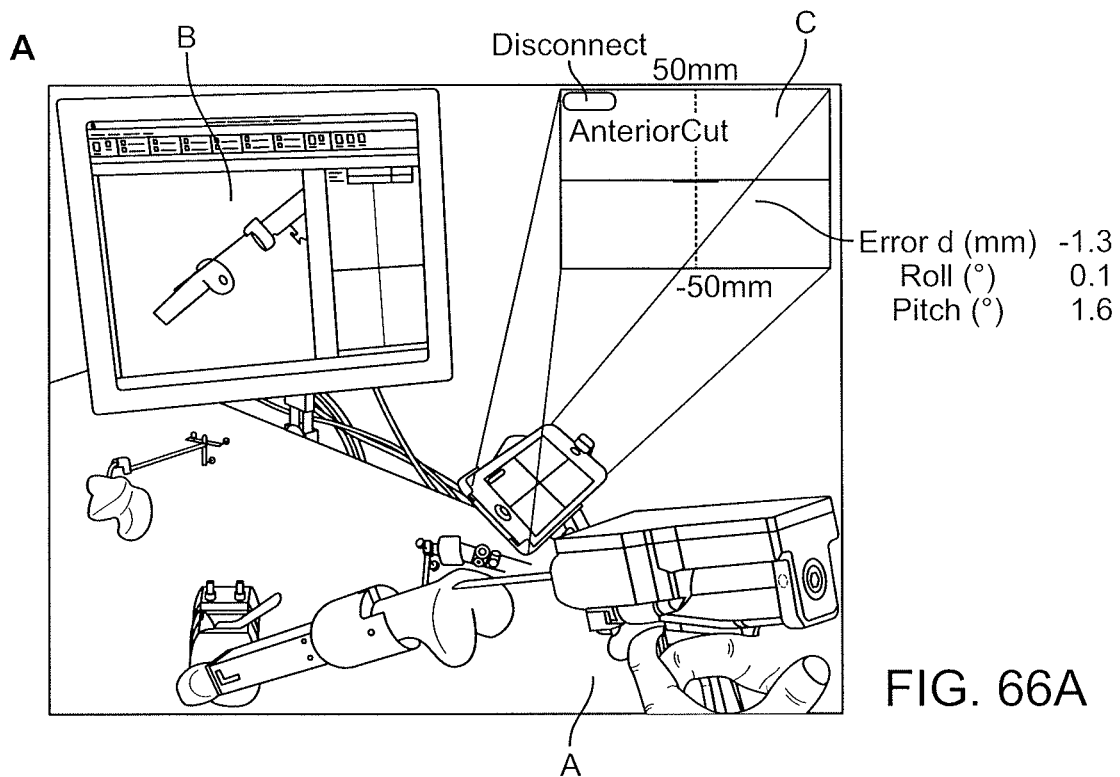
Figure 67:
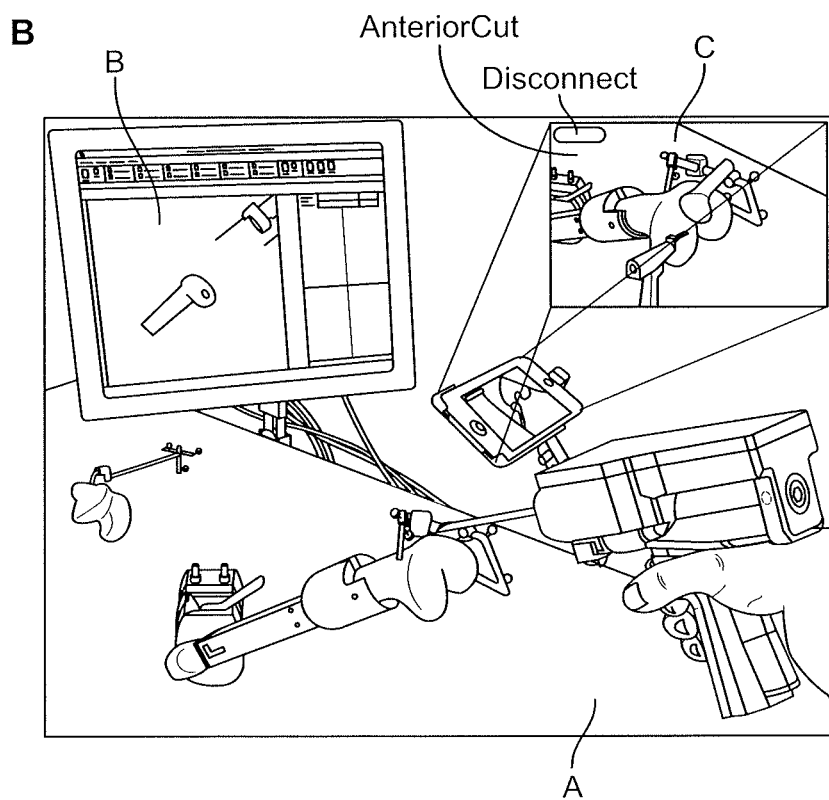

FIG. 65 illustrates another alternative view of the hover mode operation. In the sequence illustrated by FIG. 65, the system is shown moving between three modes; hover mode 6505, a bone cutting mode 6510 or in implant or cut fit assessment mode 6515. When in the hover mode 6505, using a saw and with the bone being close to an instrument will move the system into a bone cutting tracking mode 6510. Alternatively, as the bone is moved further away from the instrument, or vice versa, the saw away from the bone, the system will detect such movement and move from the bone cutting mode 6510 and back into a remote 6505 hover mode. Alternatively, if the system detects a navigated implant trial or navigated bone (cut) surface assessment tool are visible or implant trial or such tool is close to the bone, then the system will shift from hover mode 6505 into the implant fit or bone surface assessment step 6515. At the conclusion of the assessment above, as when the bone is now far from the trial implant or assessment tool, the system will return to hover mode 6505. FIGS. 66A, 66B and 67 illustrate various in-room display and on tool display or projector views depending on the operation of the OTT. Turning now to FIG. 66A, the in-room scene (A) illustrates an active cutting step. Since an active cutting step is involved, the on tool display (portion B of the view of FIG. 66A) is indicating the angular error (orientational deviation around two axes) or other cutting information about error rate or location of the blade relative to a surgical plan (offset) as described herein. In the view of FIG. 66B, the in-room display is showing the side view of the tool and blade in contact with the bone according to the surgical plan. Determining orientation for the 2D guidance display In various places of our graphical user interface (GUI) on the main CAS computer, we sometimes use our flight simulator like (2D) graphical guidance system 66B. This display guides the user to move the instrument so the plane (labeled) merges with the target surface plane (labeled) by tipping, or changing the pitch of, the saw downwards, and rolling, to make the two lines coincide with each other (hence saw pitch is correct) AND both lie along the horizon line (hence saw roll is correct). Whether the guidance lines should go up or down depends on whether the navigated saw was held normally or upside down—and latter is possible.

To determine if the guidance to go up or down, depending on whether the saw is upside down or normal, is for the computer which logs positions to store recent history (eg. a few ms or seconds) and examine the moving average. If upon reviewing the last one hundred or ten or say one second of tracking, the computer notes that it is telling the user to go up and yet we are going down, then it must be that we are holding the saw upside down. So if it finds that the user is getting further away while we they are trying to move towards the target, it switches the guidance by 180 degrees and tells you so verbally (by voice). If you want to oppose that function and override it, you can optionally stop that.

Also, the computer can tell if you are almost aligned (near the target in 3D) and within a few degrees. Then it knows that you are in the right orientation. But if you are almost 180 degree upside down to the target (i.e. parallel to the target but within almost 180 degrees) then it means that you are holding the saw upside down so it automatically switches its coordinate system to adjust. If it sees you persistently holding the saw at 180 degrees towards the target plane, (you are close to the target plane but you are holding it at about 180 degrees plus or minus a certain threshold, say plus or minus say 10 degrees) then it automatically switches the guidance to be the other way round so the guidance is effectively going in the correct direction.

The concept relies on a knowledge based system and the following proviso: The user almost knows what they are doing and they are almost right, but the system suffered a reversal of coordinate system sign due to the user flipping the device upside down. We can make this detect and correct automatically within a few milliseconds or much less than a second.

FIG. 67 shows the location of an OTT system relative to a bone on an approach or an evaluation step. In the view of FIG. 67A, the in-room view, the tool is shown approaching the surgical field. The in-room display B also shows the approach of the tool to the bone within a surgical field. The view of FIG. 67C shows the display on the on tool system which indicates the alignment of the tool relative to the bone. The view shown in FIG. 67C is adjustable using the smart views command as described herein and elsewhere.

In addition or alternatively, any of the OTT modules described herein may be modified to have additional functionality. For example, an OTT may be modified to include a display. Alternatively, the OTT may be adapted to work with a remote control to drive the main system, such as, for example, to run via an iPod, an iPad or other iOS or Android (or smart phone like) device that may be removeably mounted on the OTT. In other aspects, such an OTT may be described as an OTT tablet. In one embodiment, an OTT module may have a screen (eg. color LCD type) or other display incorporated into a surface of the OTT housing. In an alternative embodiment, a display is provided as a detachable item. In one embodiment, the display runs on an iOS implementation and runs on iPod, iPads, etc. In addition or alternatively, an iPod or other device can be used as a 'remote control' to drive the main system. That is, the remote control device can be on-board the OTT device, or just loose. In use, an iPod, iPad or smart phone like device for this purpose is placed in a sterile bag and put it in the surgical scene, so the surgeon and/or nurse can drive the system settings from there.

Portable Display Screen

The attached screen is currently embodied as an iPhone and could be any other similarly-sized smart phone, such as a Droid or Blackberry, or a custom built touch display.

Attached to the saw, the display is typically intended for use with an attitude and offset distance display. It can also utilize a 3D rendering engine software and show 3D surface or volumetric models and provide the same guidance and selection of viewing parameters as specified in the automatic selection of view.

Additionally, the user can move the model on the screen. Such changes are analogous to the view on the main OTT CAS screen with the advantage being the closer proximity of the attached screen compared to the terminal screen, and the implications of touching screens in the sterile environment versus main computer screens which may (optionally) or may not be sterile or conveniently close to the surgeon or assistant.

In another example, the view, or any parameters of the display, can be changed by using the touch screen interface.

The attached screen can also be removed and used as a detached display or as a remote control device.

In still another aspect, there is provided methods of using the pico-projector or other projector onboard the OTT for use in an automatic, or semi-automatic bone registration technique. In one aspect, there is provided a method for calculating or determining the bone registration matrix in the context of OTT using reference frames. This can be implemented as a combination of the 3D tracking described for OTT and a dynamic 3D scanning process such as those used in commercially available image processing and tracking processes.

In one aspect, such an OTT based registration process or technique includes the steps of:

a) Obtaining a 3D model of the anatomy (e.g. bone), usually during pre-surgical planning. For example, on an image-based setup, this can be done as 3D reconstruction from the patient's computer tomography (CT) or Magnetic resonance Imaging (MRI), data or through morphing (scaling) of a generalized bone from an atlas.

b) Attaching a tracking reference frame to the bone. The tracking reference frame is visible to the OTT cameras.

c) Performing a 3D scanning of the anatomy (e.g. bone) surface by using OTT's projector to project a pattern (e.g. point(s), line(s), grid(s), etc.) on the surface of interest and OTT's camera(s) system to capture and process the reflection of the lights on the surface of interest.

d) Simultaneously with c), the tracking in 3D the reference frame attached to the object of interest (e.g. bone), using any of the techniques described herein. While OTT cameras are used for both processes, 3D scanning and tracking, one example of how to coordinate the two processes is by switching from one function to another at high rate, and pairing each 3D scanning data sampling with a 3D tracking position/orientation.

e) Based on data from c) and d), obtaining a surface model of the anatomy (e.g. bone) surface positioned and oriented relative to the reference frame attached to the object of interest (e.g. bone).

f) Surface matching a) and c). This process calculates a transformation matrix that matches one surface into the other. The process can be done manually (with user graphical intervention or verification) or with various levels of automation. The latter harnesses image processing and pattern recognition and matching routines using correlation or other known techniques.

g) Calculating final anatomy (e.g. bone) registration matrix combining e) and f).

The process described above may be modified or enhanced using a number of different variations. Some variations of the steps outlined above include, by way of illustration and not limitation:

(a) using pico-projector for bone registration is similar to the steps above but optionally includes using different wavelengths filters to optimize step d); or (b) using pico-projector for bone registration is similar to the steps above but optionally includes using the known anatomy shape from a) to optimize 3D scanning process on c).

OTT Tracking without Reference Frames

In this alternative embodiment, an OTT system is adapted and configured for performing reference frame-free 3D tracking with OTT. In one aspect, there is the step of projecting a known pattern with the projector (e.g. mono- or multi-chrome, infrared, etc. point(s), line(s), grid(s), etc.) on a known geometry (e.g. bone), and applying image recognition and computer vision algorithms on the reflected light to track the position and orientation of the object of interest (e.g. bone) in 3D (e.g. relative to OTT's internal origin and coordinate system). This may be considered a form of using a projected grid for navigation. One method for implementing such a freehand surgical navigation technique includes, by way of example and not limitation:

a) Obtaining a 3D model of the anatomy (e.g. bone), usually during pre-surgical planning. For example, on an image-based setup, this can be done as 3D reconstruction from the patient's computer tomography (CT) data or other methods mentioned above.

b) Dynamically projecting a known pattern with the projector (e.g. mono- or multi-chrome, infrared, etc. point(s), line(s), grid(s), etc.) on the real patient's anatomy (e.g. bone).

c) Applying image recognition and computer vision algorithms (as well as techniques presented in 2.) on the images projected on the anatomy (e.g. bone) to calculate its position and orientation in space.

The process described above may be modified or enhanced using a number of different variations. Some variations of the steps outlined above include, by way of illustration and not limitation:

(a) using OTT's projector for both, 3D tracking and displaying information to guide the user during cutting, drilling, etc., the system uses different color schemes to two sets of images to avoid interfering with the image processing, as well as interfering with the users' interpretation of the projected guidance;

(b) using emitted infrared light for tracking patterns to avoid interfering with the users' interpretation of the visible light projected guidance; (c) using OTT's switches from grid to guidance at high rate to create a stroboscopic effect, but still preventing the two processes (object tracking and user guidance) from interfering with each other.

Multiple Reference Frames

For a particular surgical case there may not be a single location for the bone's reference frame where the instrument with the cameras can 'see' it from any location required for cutting (or drilling, or filing, etc.). In such cases, one can use a 'combination' reference frame (multi-faced): A single registration process (using any of the faces) allows the system to track the object afterwards regardless of which of the faces is visible at the time.

Notwithstanding, any element of the indicator subsystem could readily be used for any approach to computer assisted surgery wherein the computer assisted surgery system establishes both the location of the tool in three dimensions and calculates where, according to a surgical plan, the surgeon intends to make a resection. In one alternative aspect, the methods, systems and procedures described herein are modified to incorporate one or more of the techniques, devices or methods described in U.S. Non Provisional patent application Ser. No. 11/764,505 filed on Jun. 18, 2007 and published as US 2008/0009697 entitled "Method and Apparatus for Computer Aided Surgery," the entirety of which is incorporated herein for all purposes.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An on tool tracking and guidance device for use with a surgical tool, comprising:
 a housing having a surface configured to engage the surgical tool, the surface having a conforming shape to a portion of an exterior surface of the surgical tool;
 a first camera and a second camera within the housing in an arrangement where the first camera and the second camera are on opposite sides of an active element of the surgical tool while the surgical tool is engaged with the housing and where each of the first camera and the second camera provides an image output selected for viewing a surgical field selected for a computer assisted surgery procedure using the surgical tool while the surgical tool is engaged with the housing;
 a plurality of sensors mounted on a substrate within the housing wherein the substrate is positioned within the housing such that the plurality of sensors provide an indication of one or more of roll, pitch, yaw, orientation, or vibration information related to the surgical tool while the surgical tool is engaged with the housing; and
 a projector within the housing configured to provide an output at least partially within the surgical field of view, wherein the output from the projector is adapted for projection on a portion of the patient's anatomy or on or within the surgical field, and wherein the output from the projector comprises information to guide a user performing the computer assisted surgery procedure.

2. The on tool tracking and guidance device of claim 1 further comprising an electronic image processor within the housing configured to receive an output from each of the first and second cameras and perform an image processing operation using at least a portion of the output from each of the first and second cameras for use in the computer assisted surgery procedure.

3. The on tool tracking and guidance device of claim 1, wherein the plurality of sensors is selected from the group consisting of: an inclinometer, a gyroscope, a two axis gyroscope, a three axis gyroscope or other multiple axis gyroscope, a one-two-three or multiple axis accelerometer, a potentiometer, and a MEMS instrument.

4. The on tool tracking and guidance device of claim 1, wherein the surgical field includes an active element of the surgical tool, wherein the active element is a saw blade, a burr, or a drill.

5. The on tool tracking and guidance device of claim 1, wherein the portion of the anatomy is a bone.

6. The on tool tracking and guidance device of claim 1, further comprising: a display on the housing.

7. The on tool tracking and guidance device of claim 1, wherein the projector is a pico projector.

8. The on tool tracking and guidance device of claim 1, further comprising: a communication element within the housing configured to wirelessly provide information related to an output from one or more of the plurality of sensors mounted on the substrate within the housing.

9. The on tool tracking and guidance device of claim 1, wherein the communication element provides information wirelessly to and from the component separate from the housing.

10. The on tool tracking and guidance device of claim 1, wherein the communication element provides information via a wired connection to the component separate from the housing.

11. The on tool tracking and guidance device of claim 1, wherein the output from the projector comprises information visible to the user of the surgical tool to indicate at least one navigation or guidance parameter related to a positioning of the active element of the surgical tool within the surgical field.

12. The on tool tracking and guidance device of claim 1, wherein the output from the projector comprises information visible to the user of the surgical tool to indicate a portion of tissue to be resected.

13. The on tool tracking and guidance device of claim 1, wherein the output from the projector comprises information visible to the user of the surgical tool to indicate a portion of tissue that is not to be resected.

14. The on tool tracking and guidance device of claim 1, wherein the output from the projector comprises information visible to the user of the surgical tool to indicate a resection boundary.

* * * * *